US008551970B2

(12) United States Patent
Farrar et al.

(10) Patent No.: US 8,551,970 B2
(45) Date of Patent: *Oct. 8, 2013

(54) GENETIC SUPPRESSION AND REPLACEMENT

(75) Inventors: Gwenyth Jane Farrar, Monkstown (IE); Peter Humphries, Cabiuteeley (IE); Paul Francis Kenna, Dublin (IE)

(73) Assignee: Optigen Patents Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 12/710,343

(22) Filed: Feb. 22, 2010

(65) Prior Publication Data

US 2011/0190371 A1 Aug. 4, 2011

Related U.S. Application Data

(63) Continuation of application No. 10/651,754, filed on Aug. 29, 2003, now abandoned, which is a continuation-in-part of application No. 09/155,708, filed as application No. PCT/GB97/00929 on Apr. 2, 1997, now Pat. No. 7,138,378.

(60) Provisional application No. 60/407,389, filed on Aug. 30, 2002, provisional application No. 60/414,698, filed on Sep. 30, 2002.

(30) Foreign Application Priority Data

Apr. 2, 1996 (GB) .................................. 9606961.2

(51) Int. Cl.
*A61K 48/00* (2006.01)
*A61K 38/00* (2006.01)
*A01N 43/04* (2006.01)
*C07H 21/04* (2006.01)
*C12Q 1/68* (2006.01)

(52) U.S. Cl.
USPC ...................... 514/44 R; 435/91.1; 435/91.31; 435/320.1; 435/325; 435/375; 536/23.1; 536/23.2; 536/24.31; 536/24.5

(58) Field of Classification Search
None
See application file for complete search history.

(56) References Cited

U.S. PATENT DOCUMENTS

| 5,087,617 A | 2/1992 | Smith |
| 5,223,391 A | 6/1993 | Coen et al. |
| 5,240,846 A | 8/1993 | Collins et al. |
| 5,246,921 A | 9/1993 | Reddy et al. |
| 5,399,346 A | 3/1995 | Anderson et al. |
| 5,582,972 A | 12/1996 | Lima et al. |
| 5,814,500 A | 9/1998 | Dietz |
| 5,834,440 A | 11/1998 | Goldenberg et al. |
| 5,945,290 A | 8/1999 | Cowsert |
| 5,977,296 A | 11/1999 | Nielsen et al. |
| 5,977,391 A | 11/1999 | Gewald et al. |
| 6,025,127 A | 2/2000 | Sidransky |
| 6,077,705 A | 6/2000 | Duan et al. |
| 6,326,174 B1 | 12/2001 | Joyce et al. |
| 6,482,803 B1 | 11/2002 | Roth et al. |
| 6,713,457 B2 | 3/2004 | Farrar et al. |
| 7,138,378 B1 * | 11/2006 | Farrar et al. ................. 514/44 R |
| 2003/0069195 A1 | 4/2003 | Farrar et al. |
| 2004/0234999 A1 | 11/2004 | Farrar et al. |
| 2004/0254138 A1 | 12/2004 | Farrar et al. |
| 2006/0128648 A1 | 6/2006 | Farrar et al. |

FOREIGN PATENT DOCUMENTS

| EP | 0414134 B1 | 2/1991 |
| EP | 0475623 A1 | 3/1992 |
| WO | WO 92/12262 A1 | 7/1992 |
| WO | WO 93/12257 A1 | 6/1993 |
| WO | WO 93/21202 A1 | 10/1993 |
| WO | WO 94/03596 A1 | 2/1994 |
| WO | WO 94/11494 A1 | 5/1994 |
| WO | WO 94/22487 A1 | 10/1994 |
| WO | WO 94/26887 A1 | 11/1994 |
| WO | WO 95/03335 A1 | 2/1995 |
| WO | WO 95/19448 A1 | 7/1995 |
| WO | WO 95/34573 A1 | 12/1995 |
| WO | WO 97/11169 A1 * | 6/1997 |
| WO | WO 97/32024 A1 | 9/1997 |
| WO | WO97/37014 A1 * | 10/1997 |
| WO | WO 98/48027 A2 | 10/1998 |
| WO | WO 03/048362 A2 | 6/2003 |
| WO | WO 2004/020631 A2 | 3/2004 |

OTHER PUBLICATIONS

Akhtar et al., "In vivo Studies With Antisense Oligonucleotides," TiPS, 1997, 18: 12-18.
Allerson et al., "Fully 2'-Modified Oligonucleotide Duplexes with Improved in Vitro Potency and Stability Compared to Unmodified Small Interfering RNA" (2005) *J. Med. Chem.* 48:901-904.
Aniarzguioui et al., "Tolerance for mutations and chemical modifications in a siRNA" (2003) *Nucleic Acids Research* 31(2): 589-595.
Blaese et al., Strategies for Gene Therapy. Pathol. Biol. (Paris), 1993, 41(8): 672-6.

(Continued)

*Primary Examiner* — Janet Epps-Smith
(74) *Attorney, Agent, or Firm* — Wolf, Greenfield & Sacks, P.C.

(57) ABSTRACT

Methods and agents for suppressing expression of a mutant allele of a gene and providing a replacement nucleic acid are provided. The methods of the invention provide suppression effectors such as, for example, antisense nucleic acids, ribozymes, or RNAi, that bind to the gene or its RNA. The invention further provides for the introduction of a replacement nucleic acid with modified sequences such that the replacement nucleic acid is protected from suppression by the suppression effector. The replacement nucleic acid is modified at degenerate wobble positions in the target region of the suppression effector and thereby is not suppressed by the suppression effector. In addition, by altering wobble positions, the replacement nucleic acid can still encode a wild type gene product. The invention has the advantage that the same suppression strategy could be used to suppress, in principle, many mutations in a gene. Also disclosed is a transgenic mouse that expresses human rhodopsin (modified replacement gene) and a transgenic mouse that expresses a suppression effector targeting rhodopsin. Also disclosed in intraocular administration of siRNA.

21 Claims, 39 Drawing Sheets

(56) References Cited

OTHER PUBLICATIONS

Bordignon et al., "Transfer of the ADA Gene into Bone Marrow Cells and Peripheral Blood Lymphocytes for the Treatment of Patients Affected by ADA-Deficient SCID." Hum. Gene Ther., 1993, 4(4): 513-20.
Boutla et al., "Short 5'—phosphorylated double-stranded RNAs induce RNA interference in *Drosophila*" (2001) *Current Biology* 11:1776-1780.
Braasch et al., "RNA Interference in Mammalian Cells by Chemically-Modified RNA" (2003) *Biochemistry* 42:7967-7975.
Branch, A good antisense molecule is hard to find, TIBS 23, (1998), pp. 45-50.
Brummelkamp et al., Apr. 19, 2002, "A System for Stable Expression of Short Interfering RNAs in Mammalian Cells", Science, vol. 296:5567, pp. 550-553.
Burke, "Hairpin and Hammerhead Ribozymes: How Different Are They?," Biochemical Society Transactions, 2002, 30(6): 1116-1118.
Cameron et al., "Specific gene suppression by engineered ribozymes in monkey cells," Proc. Natl. Acad. Sci. USA (1989) vol. 86, pp. 9139-9143.
Carter et al., "Antisense Technology for Cancer Therapy: Does It Make Sense?" Cancer Res., 1993, 67: 869-876.
Cazenave et al., "Comparative Inhibition of Rabbit Globin mRNA Translation by Modified Antisense Oligodeoxynucleotides," Nuc. Acid Res., 1989, 17: 4255-4273.
Chertkov et al., "The Hematopoietic Stromal Microenvironment Promotes Retrovirus-Mediated Gene Transfer into Hematopoietic Stem Cells." Stem Cells, 1993, 11(3): 218-27.
Chiu and Rana "siRNA function in RNAi: A chemical modification analysis" (2003) *RNA* 9:1034-1048.
Ch'ng et al., "Antisense RNA Complementary to 3' Coding and Noncoding Sequences of Creatine Kinase is a Potent Inhibitor of Translation in vivo." Proc. Natl. Acad. Sci. USA, 1989, 86: 10006-10.
Chowrira et al., "In Vitro and in Vivo Comparison of Hammerhead, Hairpin, and Hepatitis Delta Virus Self-processing Ribozyme Cassettes," The Journal of Biological Chemistry (1994) vol. 269, No. 41, pp. 25856-25864.
Conget et al., "Adenoviral-Mediated Gene Transfer Into Ex Vivo Expanded Human Bone Marrow Mesenchymal Progenitor Cells," Experimental Hematology, 2000: 382-390.
Connell et al., "Molecular Cloning, Primary Structure, and Orientation of the Vertebrate Photoreceptor Cell Protein Peripherin in the Rod Outer Segment Disk Membrane," 1990, 29: 4691-4698.
Corey "RNA learns from antisense" (2007) *Nature Chemical Biology* 3(1):8-11.
Cotten et al., "Ribozyme mediated destruction of RNA in vivo," The EMBO Journal (1989) vol. 8, No. 12, pp. 3861-3866.
Cournoyer et al., "Gene Therapy of the Immune System." Ann. Rev. Immunol., 1993, 11: 297-329.
Couture et al., "Retroviral Vectors Containing Chimeric Promoter/Enhancer Elements Exhibit Cell-Type Specific Gene Expression." Hum. Gene Ther., 1994, 5(6): 667-77.
Crooke, Basic Principles of Antisense Therapeutics. Antisense Research and Application. 1998:1-50.
Czauderna et al., "Structural variations and stabilising modifications of synthetic siRNAs in mammalian cells" (2003) *Nucleic Acids Research* 31(11): 2705-2716.
D'Alessio et al, "Characterization of a COLIAI Splicing Defect in a Case of Ehlers-Danlos Syndrome Type VII: Further Evidence of Molecular Homogeneity," The American Society of Human Genetics, 1991, 49: 400-406.
Dalgleish et al., "Length polymorphism in the Pro a2(I) Collagen Gene: An Alternative Explanation in a Case of Marfan Syndrome," Human Genetics, 1986, 73: 91-92.
Dawson et al., "Hammerhead Ribozymes Selectively Suppress Mutant Type I Collagen mRNA in Osteogenesis Imperfecta Fibroblasts," Nucleic Acids Research, 2000, 28(20): 4013-4020.
Denman et al., "Ribozyme mediated degradation of p-amyloid peptide precursor mRNA in COS-7 cells," Nucleic Acids Research, Oxford University Press, (1994) vol. 22, No. 12, pp. 2375-2382.

Dosaka-Akita et al , "Inhibition of Proliferation by *L-myc* Antisense DNA for the Translational Initiation Site in Human Small Cell Lung Cancer," Cancer Res., 1995, 55: 1559-1564.
Dryja et al., "A Point Mutation of the Rhodopsin Gene in One Form of Retinitis Pigmentosa," Nature, 1990, 343: 364-366.
Duval-Valentin et al., "Specific Inhibition of Transcription by Triple Helix-Forming Oligonucleotides," Proc. Natl. Acad. Sci. USA, 1992, 89: 504-508.
Ellis et al., "Design and Specificity of Hammerhead Ribozymes Against Calretinin mRNA," Nuc. Acid Res., 1993, 21: 5171-5178.
Fairbanks et al., Biochemical and Immunological for Adenosine Deaminase (ADA) Deficiency. Status Following Gene Therapy and PEG-ADA Therapy Adv. Exp. Med. Biol., 1994, 370: 391-4.
Farrar et al., "A Three-Base-Pair Deletion in the Peripherin-RDS Gene in One Form of Retinitis Pigmentosa," Nature, 1991, 354: 478-480.
Farrar et al., "Autosomal Dominant Retinitis Pigmentosa: A Novel Mutation At the Peripherin/RDS Locus in the Original 6p-Linked Pedigree," Genomics, 1991, 14: 805-807.
Farrar et al., "Autosomal Dominant Retinitis Pigmentosa. Linkage to Rhodopsin and Evidence for Genetic Heterogeneity," Genomics, 1990, 8: 35-40.
Farrar et al., "On the Genetics of Retinitis Pigmentosa and on Mutation-Independent Approaches to Therapeutic Intervention," EMBO J., 2002, 21(5): 857-864.
Farrar et al., "Progress in Genetic Linkage for Retinitis Pigmentosa and Gene Delivery to Ocular Tissues," Invest. Ophthamol. Vis. Sci. (ARVO), 1995, 36(4).
Feng et al., "Neoplastic Reversion Accomplished by High Efficiency Adenoviral-Mediated Delivery of an Anti-Ras Ribozyme," Can. Res., 1995, 55: 2024-2028.
Filie et al., "A De Novo $G^{+1}$__,A Mutation at the A2(I) Exon 16 Splice Donor Site Causes Skipping of Exon 16 in the CDNA of One Allele of an 01 Type IV Proband," Human Mutation, 1993, 2: 380-388.
Friedmann, "Overcoming the Obstacles to Gene Therapy." Sci. Am. Jun. 1997, 96-101.
Gaughan et al., "Ribozyme Mediated Cleavage of Acute Phase Serum Amyloid A (A-SAA) Mrna in Vitro," FEBS Letters, 1995, 374: 241-245.
Gomez-Navarro et al., "Gene Therapy for Cancer," European Journal of Cancer (1999) vol. 35, No. 6, pp. 867-885.
Grossman et al., "Successful ex vivo Gene Hypercholesterolaemia." Nature Gen.1994, Therapy Directed to Liver in a Patient with Familial 6: 335-341.
Hamada et al., "Effects on RNA Interference in Gene Expression (RNAi) in Cultured Mammalian Cells of Mismatches and the Introduction of Chemical Modifications at the 3'—Ends of siRNAs" (2002) *Antisense and Nucleic Acid Drug Development* 12:301-309.
Hanvey et al., "Antisense and Antigene Properties of Peptide Nucleic Acids," Science, 1992, 258: 1481-1485.
Harborth et al., "Sequence, Chemical, and Structural Variation of Small Interfering RNAs and Short Hairpin RNAs and the Effect on Mammalian Gene Silencing" (2003) *Antisense and Nucleic Acid Drug Development* 13:83-105.
Hardenbol et al., "Sequence Specificity of Triplex DNA Formation: Analysis by a Combinatorial Approach, Restriction Endonuclease Protection Selection and Amplification," Proc. Natl. Acad. Sci. USA, 1996, 93: 2811-2816.
Hart et al., "The Introduction of Two Silent Mutations Into the CFTR Cdna Construct Allows Improved Detection of Exogenous Mma in Gene Transfer Experiments," Human Mol. Gen., 1995, 4(9): 1597-1602.
Herrmann, Cancer Gene Therapy: Principles, Problems, and Perspectives, J. Mol. Med. (1995) vol. 73: 157-163.
Herschlag et al., "An RNA Chaperone Activity of Non-Specific RNA Binding Proteins in Hammerhead Ribozyme Catalysis," EMBO, 1994, 13(12): 2913-2924.
Hershfield, PEG-ADA replacement therapy for Adenosine Deaminase Deficiency: an update after 8.5 years. Clin Immunol Immunopathol. 1995, 76:S228-32.
Herskowitz, "Functional Inactivation of Genes by Dominant Negative Mutations," Nature, 1987, 329: 219-222.

Holt et al., "Inducible Production of C-Fos Antisense RNA Inhibits 3T3 Cell Proliferation," Proc. Natl. Acad. Sci. USA, 1986, 83: 4794-4798.

Holt, "Antisense Rescue Defines Specialized and Generalized Functional Domains for C-Fos Protein," Molecular and Cellular Biology, 1993, 13(6): 3821-3830.

Horwitz, "Transplantability and Therapeutic Effects of Bone Marrow-Derived Mesenchymal Cells in Children With Osteogenesis Imperfecta," Nature Medicine, 1999, 5(3): 309-313.

Hughes et al., "Delivery of a Secretable Adenosine Deaminase Through Microcapsules—A Novel Approach to Somatic gene therapy." Hum. Gene Ther., 1994, 5(12): 1445-55.

Humphries et al., "On the Molecular Genetics of Retinitis Pigmentosa," Science, 1992, 1-5.

International Preliminary Examination Report for International Patent Application PCT/GB03/03793, dated Dec. 27, 2004, 8 pages.

International Preliminary Report on Patentability dated Jul. 3, 1998 in connection with PCT/GB97/00929.

International Search Report for International Patent Application No. PCT/GB96/02357, dated May 7, 1997, 4 pages.

International Search Report for International Patent Application No. PCT/GB03/03793, dated Jun. 14, 2004, 10 pages.

International Search Report mailed Aug. 29, 1997 in connection with PCT/GB97/00929.

Jankowsky et al., "Oligonucleotide Facilitators May Inhibit or Activate a Hammerhead Ribozyme," Nuc. Acid Res., 1996, 24(3): 423-429.

Jones et al., "Tagging Ribozyme Reaction Sites to Follow Trans-Splicing in Mammalian Cells," Nature Medicine, 1996, 2: 643-648.

Jordan et al., "Localization of an Autosomal Dominant Retinitis Pigmentosa Genc to Chromosome 7q," Nature Genetics, 1993, 4: 54-58.

Kajiwara et al., "Mutations in the Human Retinal Degeneration Slow Gene in Autosomal Dominant Retinitis Pigmentosa," Nature, 1991, 354: 480-483.

Kariko et al., "Lipofectin-aided cell delivery of ribozyme targeted to human urokinase receptor mRNA," FEBS Letter (1994) vol. 352, pp. 41-44.

Kashani-Sabet et al., "Suppression of Neoplastic Phenotype in Vivo by an Anti-ras Ribozyme," Cancer Research (1994), vol. 54, pp. 900-902.

Kawasaki et al., Selection of the best target site for ribozyme-mediated cleavage within a fusion gene for adenovirus E1A-associated 300 kDa protein (p300) and luciferase. Nucleic Acids Res. Aug. 1, 1996;24(15):3010-6.

Khillan et al., "Partial rescue of a lethal phenotype of fragile bones in transgenic mice with a chimeric antisense gene directed against a mutated collagen gene," Proc. Natl. Acad. Sci. USA (1994) vol. 91, pp. 6298-6302.

Knudsen et al., "Antisense Properties of Duplex- and Triplex-Forming PNAs," Nuc. Acid Res., 1996, 24(3): 494-500.

Kobayashi et al., "Specificity of Ribozyme Designed for Mutated DI-1FR mRNA," Biochemical Pharmacology (1994) vol. 47, No. 9, pp. 1607-1613.

Kuo et al., "Efficient Gene Transfer into Primary Murine Lymphocytes Obviating the Need for Drug Selection." Blood, 1993, 82(3): 845-52.

Lange et al., "In Vitro and in Vivo Effects of Synthetic Ribozymes Targeted Against BCRJABL mRNA," Leukemia, 1993, 7: 1786-1794.

Larsson et al., "Reduced 32-microglobulin mRNA levels in transgenic mice expressing a designed hammerhead ribozyme," Nucleic Acids Research (1994) vol. 22, No. 12, pp. 2242-2248.

Lewin et al., "Ribozyme Rescue of Photoreceptor Cells in a Transgenic Rat Model of Autosomal Dominant Retinitis Pigmentosa," Nature Medicine, 1998, 4(8): 967-971.

Lieber et al. "Adenovirus-Mediated Expression of Ribozymes in Mice," Journal of Virology (1996) vol. 70, No. 5, pp. 3153-8.

Lieber et al., Selection of efficient cleavage sites in target RNAs by using a ribozyme expression library. Molecular and Cellular Biology (1995) vol. 15, No. 1, pp. 540-551.

Liechty et al., "Human Mesenchymal Stem Cells Engraft and Demonstrate Site-Specific Differentiation After in Utero Transplantation in Sheep," Nature Medicine, 2000, 6(11): 1282-1286.

Little et al., "Generation of a Mammalian Cell Line Deficient in Glucose-regulated Protein Stress Induction through Targeted Ribozyme Driven by a Stress-inducible Promoter," The Journal of Biological Chemistry (1995) vol. 270, No. 16, pp. 9526-9534.

Lyons et al., "An Improved Retroviral Vector Encoding the Herpes Simplex Virus Thymidine Kinase Gene Increases Anitumor Efficacy in Vivo." Genetic Therapy, Inc, Gaithersburg, Maryland 20878, USA. Cancer Gene Ther., 1995, 2(4): 273-80.

Manoharan "RNA interference and chemically modified siRNAs" (2003) Nucleic Acids Research 3; 115-116.

Mansergh et al., "Evidence for Genetic Heterogeneity in Best's Vitelliform Macular Dystrophy," J. Med. Genet, 1995, 32: 855-858.

Marini et al., "Antisense Oligonucleotides Selectively Suppress Production in Mutant Alpha2(I) Collagen in Osteogenesis Imperfecta Type IV Fibroblasts: An Approach to Gene Therapy for a Dominant Disorder of Matrix Structural Protein." Pediatric Res., 1995, 37:150.

Marshall et al., Special News Report: "Gene Therapy's Growing Pains," Science (1995) vol. 269, pp. 1050-1055.

Mashhour et al., "In Vivo Adenovirus-Mediated Gene Transfer Into Ocular Tissues," Gene Therapy, 1994, 1: 122-126.

McKay et al., "Enhanced Activity of an Antisense Oligonucleotide Targeting Murine Protein Kinase C- [alpha] by the Incorporation of 2'-0-Propyl Modifications," Nuc. Acid Res., 1996, 24(3): 411-417.

McNally et al., "Structural and functional rescue of murine rod photoreceptors by human rhodopsin transgene," Human Molecular Genetics, 1999, 8(7): 1309-1312.

McWilliam et al., "Autosomal Dominant Retinitis Pigmentosa (ADRP): Localization of an ADRP Gene to the Long Arm of Chromosome 3," Genomics, 1989, 5: 619-622.

Mickisch et al., "From Laboratory Expertise to Clinical Practice: Multidrug-Resistance-Based Gene Therapy Becomes Available for Urologists." World J. Urol., 1994, 12(2): 104-11.

Millington-Ward et al., "A Mutation-Independent Therapeutic Strategem for Osteogenesis Imperfecta," Antisense & Nucleic Acid Drug Development, 1999, 9(6): 537-542.

Millington-Ward et al., "Strategems in Vitro for Gene Therapies Directed to Dominant Mutations," Human Molecular Genetics, 1997, 6(9): 1415-1426.

Millington-Ward et al., "Validation in Mesenchymal Progenitor Cells of a Mutation-Independent Ex Vivo Approach to Gene Therapy for Osteogenesis Imperfecta," Human Molecular Genetics, 2002, 11(19): 2201-2206.

Mitani et al., "Gene transfer therapy for heritable disease: cell and expression targeting," Philos Trans. R. Soc. Lond. B. Biol. Sci. 1993, 339:217-224.

Mitani et al., "Long-term Expression of Retroviral-Transduced Adenosine Deaminase in Human Primitive Hematopoietic Progenitors." Hum. Gene Ther., 1993, 4(1) 9-16.

Mitani et al., "Transduction of Human Bone 941-8. Morrow by Adenoviral Vector." Hum. Gene Ther., 1994, 5(8): 941-8.

Moritz et al., "Human Cord Blood Cells as Targets for Gene Transfer: Potential Use in Genetic Therapies of Severe Combined Immunodeficiency Disease." J. Exp. Med., 1993, 178(2): 529-36.

Nabel et al., "Direct Gene Transfer for Treatment of Human Cancer." Howard Hughes Medical Institute, Ann Arbor, Michigan, USA. Ann. N. Y. Acad. Sci., 1995, 772: 227-31.

Nathans et al., "Isolation, Sequence Analysis, and Intro-Exon Arrangement of the Gene Encoding Bovine Rhodopsin," Cell, 1983, 34: 807-814.

Nimgaonkar et al., "Long-term Expression of the Glucocerebrosidase Gene in Mouse and Human Hematopoietic Progenitors." Department of Medicine, University of Pittsburgh Medical Center, PA, USA. Leukemia, 1995, 9 Suppl 1: S38-42.

Ohkawa et al., "Ribozymes: From Mechistic Studies to Applications in Vivo," J. Biochem. (1995) vol. an Ribozyme 118, pp. 251-258.

Ohta et al., "Tissue-specific expression of an anti-ras ribozyme inhibits proliferation of human malignant melanoma cells," Nucleic Acids Research (1996) vol. 24, No. 5, pp. 938-942.

O'Neill et al., "Ribozyme-Based Therapeutic Approaches for Autosoinal Dominant Retinitis Pigmentosa," Invest. Ophthalmol. Vis. Sci., 2000, 41(10): 2863-2869.

Orkin et al., "Report and Recommendations of the Panel to Assess the NIH Investment in Research on Gene Therapy." http://www.nih.gov/news/panelrcp.html. Dec. 7, 1995.

Ott et al., "Localizing Multiple X Chromosome-Linked Retinitis Pigmentosa Loci Using Multilocus Homogeneity Tests," Pro. Natl. Acad. Sci., 1990, 87: 701-704.

Oyama et al., "N-ras Mutation of Thyroid Tumor With Special Reference to the Folicular Type," Pathol Int., 1995, 45: 45-50.

Oyama et al., "Retrovirally Transduced Bone Marrow Stromal Cells Isolated From a Mouse Model of Human Osteogenesis Imperfecta (oim) Persist in Bone and Retain the Ability to Form Cartilage and Bone After Extended Passaging," Gene Therapy, 1999, 6: 321-329.

Pereira et al., "Marrow Stromal Cells as a Source of Progenitor Cells for Nonhematopoietic Tissues in Transgenic Mice With a Phenotype of Osteogenesis Imperfecta," Pro. Natl. Acad. Sci. USA, 1998, 95: 1142-1147.

Phillips et al., "A Substitution At a Non-Glycine Position in the Triple-Helical Domain of Proa2(I) Collagen Chains Present in an Individual With a Variant of the Marfan Syndrome," The American Society for Clinical Investigation, Inc., 1990, 86: 1723-1728.

Pittenger et al., "Multilineage Potential of Adult Human Mesenchymal Stem Cells," Science, Apr. 2, 1999;284(5411):143-7.

Porumb et al., "Temporary Ex Vivo Inhibition of the Expression of the Human Oncogene HER2 (NEU) by a Triple Helix-Forming Oligonucleotide," Can. Res., 1996, 56: 515-522.

Postel et al., "Evidence that a Triplex-Forming Oligodeoxyribonucleotide Binds to the c-Myc Promoter in HeLa Cells, Thereby Reducing c-Myc mRNA Levels." Proc. Natl. Acad. Sci. USA, 1991, 88: 8227-8231.

Quattrone et al., "Reversion of the Invasive Phenotype of Transformed Human Fibroblasts by Anti-Messenger Oligonucleotide Inhibition of Urokinase Receptor Gene Expression," Can. Res., 1995, 55: 90-95.

Ramesh et al., "High-Level Expression from a Cytomegalovirus Promoter in Macrophage Cells." Hum Gene Ther., 1995, 6(10): 1323-7.

Ramesh et al., "High-Level Human Adenosine Deaminase Expression in Dog Skin Fibroblasts is not Sustained Following Transplantation." Hum. Gene Ther., 1993, 4(1): 3-7.

Ramsey et al., "Retrovirus Mediated Gene Transfer as Therapy for Adenosine Deaminase (ADA) deficiency." Leukemia., 1995, 9 Suppl 1: S70.

Reichenberger et al., "Genomic Organization and Full-Length cDNA Sequence of Human Collagen X," FEBS, 1992, 311(3): 305-310.

Rimsky et al., "Trans-Dominant Inactivation of HTLV-1 and HIV-1 Gene Expression by Mutation of the HTLV-1 Rex Transactivator," Nature, 1989, 341: 453-456.

Robinson-Benion et al., "Gene transplantation: Combined Antisense Inhibition and Gene Replacement Strategies," Leukemia, 1994, 8: S152-155.

Setoguchi et al., [Gene Transfer to Airway Epithelial Cells: Current Status and Future Direction] Nihon Kvobu Shikkan Gakkai Zasshi, 1994, 32 Suppl:8 6-95. Japanese; English abstract.

Stacey et al., "Rescue of Type I Collagen-Deficient Phenotype by Retroviral-Vector-Mediated Transfer of Human proα1 (I) Collagen Gene Into Mov-13 Cells," Journal of Virology, 1987, 61(8): 2549-2554.

Sullenger et al., "Ribozyme-Mediated Repair of Defective mRNA by Targeted Trans-Splicing." Nature 1994, 371: 619-622.

Sun et al., "Sequence-Specific Intercalating Agents: Intercalation at Specific Sequences on Duplex DNA Via Major Groove Recognition by Oligonucleotide-Intercalator Conjugations," Proc. Natl. Acad. Sci USA, 1989, 86: 9198-9202.

Takagi et al., "Mechanism of Action of Hammerhead Ribozymes and Their Applications in Vivo: Rapid Identification of Functional Genes in the Post-Genome Era by Novel Hybrid Rybozyme Libraries," Biochemical Society Transactions, 2002, 30(6): 1145-1149.

Takaku, [Recent Trends of Gene Therapy of Human Patients] Nippon Rinsho, 1993, 51(7): 1915-22. Japanese. English abstract.

Tolstoshev, "Gene Therapy, Concepts, Current Trials and Future Directions." Ann. Rev. Pharmacol. Toxicol. 1993, 33: 573-96.

Toudjarska et al, "Delivery of a Hammerhead Ribozyme Specifically Downregulates Mutant Type I Collagen mRNA in a Murine Model of Osteogenesis Imperfecta," Antisense & Nucleic Acid Drug Development, 2001, 11(5): 341-346.

Trauger et al., "Recognition of DNA by Designed Ligands at Subnanomolar Concentrations," Nature, 1996, 382: 559-561.

Valera et al., "Expression of GLUT-2 Antisense RNA in B Cells of Transgenic Mice Leads to Diabetes," J. Biol. Chem., 1994, 269: 28543-28546.

Van Soest et al., "Assignment of a Gene for Autosomal Recessive Retinitis Pigmentosa (RP12) to Chromosome 1q31-02.1 in an Inbred and Genetically Heterogeneous Disease Population," Genomics, 1994, 22: 499-504.

Vasan et al., "A Mutation in the Proct2(I) Gene (COLIA2) for Type I Procollagen in Ehlers-Danlos Syndrome Type VII: Evidence Suggesting That Skipping of Exon 6 in RNA Splicing May Be a Common Cause of the Phenotype," The American Society of Human Genetics, 1991, 48: 305-317.

Vaulont et al., "Disruption of the adenosine deaminase (ADA) gene using a dicistronic promoterless construct: production of an ADA-deficient homozygote ES cell line." Transgenic Res., 1995, 4(4): 247-55.

Verma et al. "Gene Therapy—Promises, Problems, and Prospects." Nature, 1987, 389: 239-242.

Wei et al., "Hybridization Properties of Oligodeoxynucleotide Pairs Bridged by Polyarginine Peptides," Nuc. Acid Res., 1996, 24:(4): 655-661.

Welsh et al., "Adenovirus-Mediated Gene Transfer for Cystic Fibrosis: Part A. Safety of Dose and Repeat Administration in the Nasal Epithelium. Part B. Clinical Efficacy in the Maxillary Sinus." Hum. Gene Ther., 1995, 6(2): 205-18.

Welsh et al., "Cystic Fibrosis Gene Therapy Using an Adenovirus Vector: In Vivo Safety and Efficacy in Nasal Epithelium." Hum. Gene Ther., 1994, 5(2): 209-19.

Westerhausen et al:, "A Sequence Polymorphism in the 3'-Nontranslated Region of the Proα1 Chain of Type I Procollagen," Nucleic Acids Research, 1990, 18: 4968.

Willing et al., "Molecular Heterogeneity in Osteogenesis Imperfecta Type I," American Journal of Medical Genetics, 1993, 45: 223-227.

Yu et al., "Liposome-Mediated in vivo E1 a Gene Transfer Suppressed Dissemination of Ovarian Cancer Cells that Overexpress HER-2/neu." Department of Tumor Biology, University of Texas MD Anderson Cancer Center, Houston 77030, USA. Oncogene, 1995, 11(7): 1383-8.

Zabner et al., "Adenovirus-Mediated Gene Transfer Transiently Corrects the Chloride Transport Defect in Nasal Epithelia of patients with cystic fibrosis." Cell., 1993, 75(2): 207-16.

Zabner et al., "Correction of cAMP-Stimulated Fluid Secretion in Cystic Fibrosis Airway Epithelia: Efficiency of Adenovirus-Mediated Gene Transfer in vitro." Hum. Gene Ther., 1994, 5(5): 585-93.

Zabner et al., "Safety and Efficacy of Repetitive Adenovirus-Mediated Transfer of CFTR cDNA to Airway Epithelia of Primates and Cotton Rats." Nature Gen 1994, 6: 75-83.

Zhao et al., "Generating Loss-of-Function Phenotypes of the Fushi Tarazu Gene with a Targeted Ribozyme in Drosophila." Nature, 1993, 365: 448-50.

Zhuang et al., "Direct Sequencing of PCR Products Derived From cDNAs for the Proα1 and Proα2 Chains of Type I Procollagen As a Screening Method to Detect Mutations in Patients With Osteogenesis Imperfecta," Human Mutation, 1996, 7: 89-99.

* cited by examiner

Restriction Map and Multiple Cloning Site (MCS) of pIRES2-EGFP Vector. Unique restriction sites are in bold. Note that the Eco47 III site has not been confirmed in the final construct.

*Col1a1R2 Target Sequence*
Base 3982- 39999 in Col1a1 NM 000088
GAT GCC ATC *AAA GTC TTC TGC AAC ATG GAG* ACT GGT GAG ACC TGC GTG T
Codon         Lys  leu  Phe Cys Asn Met Glu
*RNAi2MutagF*
GAT GAA ATC A*A*G GT*G* TT*T* TGT AA*T* AT*G* GA*G* ACT GGT GAG ACC
Codon         Lys  leu  Phe Cys Asn Met Glu
*RNAi2MutagR*
CAC ACC AGT *C*TC *C*AT A*T*T ACA *A*AA *C*AC *C*TT GAT GCA TCC AGG
Codon         Glu  Met Asn Cys Phe leu  Lys

*Col1a1R3 Target Sequence*
Base in 4020 – 4038 Col1a1 in NM 000088
GTGTACCCCACT *CAG CCC AGT GTG GCC CAG AAG* AACTGGTACAT
Codon          Gln Pro Ser Val Ala Gln Lys
*RNAi3MutagF*
TAC CCC ACT CA*A* CC*G* AG*C* GT*A* GC*T* CA*A* A*A*A AAC TGG TAC ATC
Codon          Gln Pro Ser Val  Ala Gln Lys
*RNAi3MutagF*
GTA CTA GTT *TTT* *TT*G *A*GC *T*AC *GC*T *C*GG *TT*G AGT GGG GTA CAC
Codon         Lys Gln Ala Val Ser Pro Gln

*Col1a14 Target Sequence*
Base 4331 – 4380 in NM 000088
 CCGCTTCACC TAC *AGC GTC ACT GTC GAT GGC T*GC ACGAGTCACACCGGAG
Codon             Ser Val Thr Val Asp Gly Cys
*RNAi4MutagF*
ACC TAC TAC AG*T* GT*A* AC*G* GT*G* GA*C* GG*A* TGT ACG AGT CAC CGG
Codon         Ser  Val Thr Val Asp Gly Cys
*RNAi4MutagR*
GTG ACT CGT *A*CA ACC *G*TC *C*AC *C*GT TAC *A*CT ATA GTA GGC GAA
Codon         Cys Gly Asp Val Thr Val Ser MM target:    5'          CTGGCAACCTCAAGAAGGC    3' (4261-4279 acc # NM 000088)
MM:
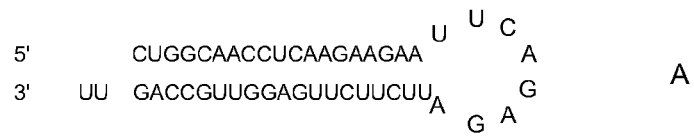

RNAi3 target: 5'          AGCCCAGTGTGGCCCAGAA    3' (4020-4038 acc # NM 000088)
RNAi3:
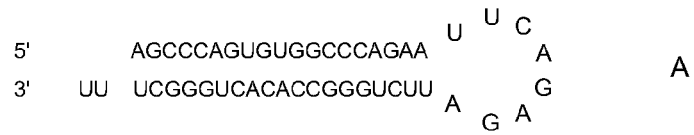

RNAi4 target: 5'          AGCGTCACTGTCGATGGCT    3' (4344-4362 acc # NM 000088)
RNAi4:
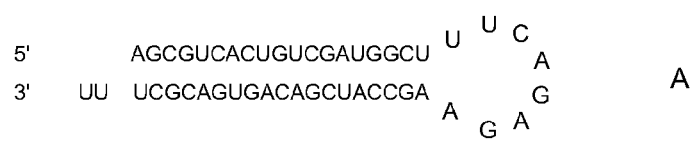

Rho (non-targeting control)

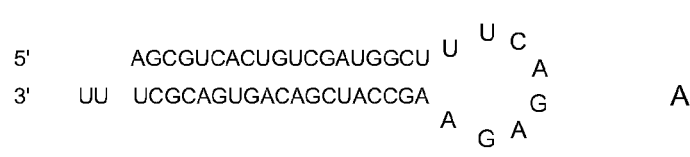

*Fig. 13B*

Stock Lines of Transgenic Mice:

rho-/-  RhoM  RhoRz40  RhoPro23His  RhoNhr

Mouse Breeding Programme:

*Fig. 19B*

Cycle 1: Matings with stock transgenic lines and rho-/- mice

| | |
|---|---|
| A Matings: | rho-/-  x  RhoM |
| Genotype produced | rho-/-RhoM+/- (1A) |
| (after a minimum of 2 generations of matings) | |
| | |
| B Matings: | rho-/-  x  Rz40 |
| Genotype produced | rho-/-Rz40+/- (1B) |
| (after a minimum of 2 generations of matings) | |
| | |
| C Matings: | rho-/-  x  RhoNhr |
| Genotype produced | rho-/-RhoNhr+/- (1C) |
| (after a minimum of 2 generations of matings) | |
| | |
| D Matings: | rho-/-  x  RhoP23Hr |
| Genotype produced | rho-/-RhoP23Hr+/- (1D) |
| (after a minimum of 2 generations of matings) | |

Cycle 2: Matings to assess the effects of the suppression agent and the replacement gene to undertake suppression of the target and replacement of the wild type gene

| | |
|---|---|
| A Matings: | rho-/-RhoM  x  rho-/-Rz40 (1A x 1B) |
| Desired genotypes produced | rho-/-RhoM+/-Rz40+/- (2A1) |
| | rho-/-RhoM+/- (2A2) |
| | |
| B Matings: | rho-/-RhoNhr  x  rho-/-Rz40 (1C x 1B) |
| Desired genotypes produced | rho-/-RhoNhr+/-Rz40+/- (2B1) |
| | rho-/-RhoNhr+/- (2B2) |
| | |
| C Matings: | rho-/-RhoM  x  rho-/-P23H (1A x 1D) |
| Desired genotypes produced | rho-/-RhoM+/-P23H+/- (2C1) |
| | rho-/-RhoM+/- (2C2) |

Cycle 3: Matings to assess effects of suppression agent and replacement gene bred onto a disease background (P23H)

| | |
|---|---|
| A Matings: | rho-/-RhoMRz40  x  rho-/-P23H (2A1 x 1D) |
| Desired genotypes produced | rho-/-RhoM+/-Rz40+/-RhoP23H+/- (3A1) |
| | rho-/-RhoM+/-RhoP23H+/- (3A2) |
| | |
| B Matings: | rho-/-RhoMP23H  x  rho-/-Rz40+/-RhoNhr+/- (2C1 x 2B1) |
| (can be used to produce the same desired | rho-/-RhoM+/-Rz40+/-RhoP23H+/- (3B1) |
| geotypes as A matings) | rho-/-RhoM+/-RhoP23H+/- (3B2) |

Cycle 4: Matings to assess effects of suppression agent and replacement gene bred onto a mice carrying a disease background (P23H) and also an additional copy of the wild type gene

| | |
|---|---|
| A Matings: | rho-/-RhoMRz40RhoP23H  x  rho-/-RhoNhr (3A1 x 1C) |
| Desired genotypes produced | rho-/-RhoM+/-Rz40+/-RhoP23H+/-RhoNhr+/- (4A1) |
| | rho-/-RhoM+/-RhoP23H+/-RhoNhr+/- (4A2) |

```
                            L   Y   V   T   V
Wild type       ATC AAC TTC CTC ACG CTC TAC GTC ACC GTC CAG CAC AA Replacement     ATC AAC TTC CTC ACG CTG TAT GTG ACG GTG CAG CAC AA
Amino acids                      L   Y   V   T   V siRNA Silencer A    ---------------------------- siRNA Silencer B            ----------------------------
```

Fig. 22

| Silencer | n | Mean | SD | SE |
|---|---|---|---|---|
| Control | 4 | 100.00 | 0.000 | 0.000 |
| A | 4 | 55.120 | 45.178 | 22.588 |
| B | 4 | 35.388 | 25.992 | 12.996 |

Fig. 23A

- Sub-retinal injection into rho+/- RhoNhr +/- transgenic mice
- 975ng of siRNA in 6µl volume; 50%PBS & 50% Xeragon buffer
- Left Eye: human rhodopsin siRNA; Right Eye: buffer control
- Extraction of retinal RNA 4 days post siRNA treatment
- Real-time PCR
- Right Eye control = 100% rhodopsin RNA
- Left Eye = 3.4% rhodopsin RNA with siRNA silencer B.
- Approximately 96.6% downregulation;

Fig. 23B

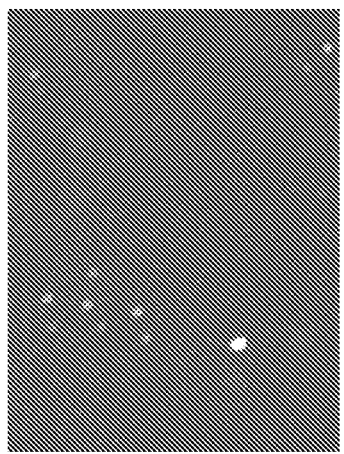
Modified human rhodopsin Cos-7 EGFP cells with oligofectamine alone
Fig. 24A
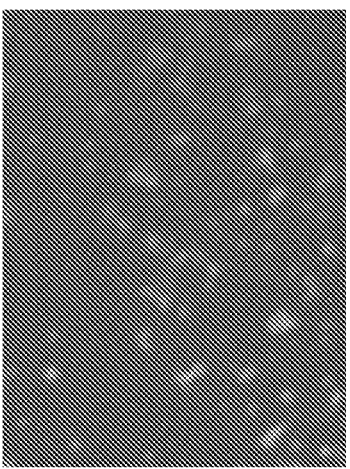
Modified human rhodopsin Cos-7 EGFP cells with silencer B
Fig. 24B
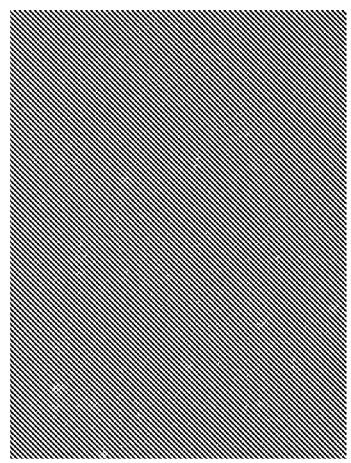
Modified human rhodopsin Cos-7 EGFP cells with EGFP siRNA : +ve down-regulation. (+ve control;)
Fig. 24C
Fig. 24

ATCAACTTCCTCACGCTGTATGTGACGGGTGCAGCACAAGAAGCTGCGCACGGCCTCTCAACT 250  260  270  280  290  300

↑ 40 M Site

Fig. 25

SEQUENCE LISTING

```
<160> NUMBER OF SEQ ID NOS: 185

<210> SEQ ID NO 1
<211> LENGTH: 617
<212> TYPE: DNA
<213> ORGANISM: Artificial Sequence
<220> FEATURE:
<223> OTHER INFORMATION: Description of Artificial Sequence: Synthetic
      human rhodopsin cDNA cloned in pDNA3
<220> FEATURE:
<221> NAME/KEY: modified_base
<222> LOCATION: (7)..(7)
<223> OTHER INFORMATION: a, c, g, t, unknown or other
<220> FEATURE:
<221> NAME/KEY: modified_base
<222> LOCATION: (10)..(10)
<223> OTHER INFORMATION: a, c, g, t, unknown or other
<220> FEATURE:
<221> NAME/KEY: modified_base
<222> LOCATION: (20)..(22)
<223> OTHER INFORMATION: a, c, g, t, unknown or other
<220> FEATURE:
<221> NAME/KEY: modified_base
<222> LOCATION: (33)..(33)
<223> OTHER INFORMATION: a, c, g, t, unknown or other
<220> FEATURE:
<221> NAME/KEY: modified_base
```

```
<222> LOCATION: (38)..(38)
<223> OTHER INFORMATION: a, c, g, t, unknown or other
<220> FEATURE:
<221> NAME/KEY: modified_base
<222> LOCATION: (79)..(79)
<223> OTHER INFORMATION: a, c, g, t, unknown or other
<220> FEATURE:
<221> NAME/KEY: modified_base
<222> LOCATION: (454)..(454)
<223> OTHER INFORMATION: a, c, g, t, unknown or other
<220> FEATURE:
<221> NAME/KEY: modified_base
<222> LOCATION: (478)..(478)
<223> OTHER INFORMATION: a, c, g, t, unknown or other
<220> FEATURE:
<221> NAME/KEY: modified_base
<222> LOCATION: (525)..(525)
<223> OTHER INFORMATION: a, c, g, t, unknown or other
<220> FEATURE:
<221> NAME/KEY: modified_base
<222> LOCATION: (542)..(542)
<223> OTHER INFORMATION: a, c, g, t, unknown or other
<220> FEATURE:
<221> NAME/KEY: modified_base
<222> LOCATION: (563)..(563)
<223> OTHER INFORMATION: a, c, g, t, unknown or other
<220> FEATURE:
<221> NAME/KEY: modified_base
<222> LOCATION: (570)..(570)
<223> OTHER INFORMATION: a, c, g, t, unknown or other
<220> FEATURE:
<221> NAME/KEY: modified_base
<222> LOCATION: (573)..(573)
<223> OTHER INFORMATION: a, c, g, t, unknown or other
<220> FEATURE:
<221> NAME/KEY: modified_base
<222> LOCATION: (589)..(589)
<223> OTHER INFORMATION: a, c, g, t, unknown or other
<220> FEATURE:
<221> NAME/KEY: modified_base
<222> LOCATION: (594)..(594)
<223> OTHER INFORMATION: a, c, g, t, unknown or other
<220> FEATURE:
<221> NAME/KEY: modified_base
<222> LOCATION: (597)..(597)
<223> OTHER INFORMATION: a, c, g, t, unknown or other

<400> SEQUENCE: 1
tcccttntgn tagattgcan nncccaataa aanaaggncc cgcttaaagg cttatcgaaa      60
ttaatacgac tcactatang gagacccaag cttagagtca tccagctgga gccctgagtg    120
gctgagctca ggccttcgca gcattcttgg gtgggagcag ccacgggtca gccacaaggg    180
ccacagccat gaatggcaca gaaggcccta acttctacgt gcccttctcc aatgcgacgg    240
gtgtggtacg cagccccttc gagtacccac agtactacct ggctgagcca tggcagttct    300
ccatgctggc cgcctacatg tttctgctga tcgtgctggg cttccccatc aacttcctca    360
cgctctacgt caccgtccag cacaagaagc tgcgcacgcc tctcaactac atcctggctc    420
aacctagccg tggctgaact cttcatggtc ctangtggct tcaccagcac ctctacanct    480
ctctgcatgg atactcgtct tcgggcccac aggatgcaat tgganggctc tttgcacctg    540
gngggaaatt gcctgtggtc ctngtggtcn ggncaccaac gtactggtng tgtntanccc    600
agaacaactc cgctccc                                                   617

<210> SEQ ID NO 2
<211> LENGTH: 639
<212> TYPE: DNA
<213> ORGANISM: Artificial Sequence
<220> FEATURE:
<223> OTHER INFORMATION: Description of Artificial Sequence: Synthetic
      human rhodopsin hybrid cDNA
<220> FEATURE:
```

```
<221> NAME/KEY: modified_base
<222> LOCATION: (3)..(6)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other
<220> FEATURE:
<221> NAME/KEY: modified_base
<222> LOCATION: (31)..(31)
<223> OTHER INFORMATION: a, c, g, t, unknown or other
<220> FEATURE:
<221> NAME/KEY: modified_base
<222> LOCATION: (34)..(34)
<223> OTHER INFORMATION: a, c, g, t, unknown or other
<220> FEATURE:
<221> NAME/KEY: modified_base
<222> LOCATION: (104)..(104)
<223> OTHER INFORMATION: a, c, g, t, unknown or other
<220> FEATURE:
<221> NAME/KEY: modified_base
<222> LOCATION: (326)..(326)
<223> OTHER INFORMATION: a, c, g, t, unknown or other
<220> FEATURE:
<221> NAME/KEY: modified_base
<222> LOCATION: (333)..(333)
<223> OTHER INFORMATION: a, c, g, t, unknown or other
<220> FEATURE:
<221> NAME/KEY: modified_base
<222> LOCATION: (366)..(366)
<223> OTHER INFORMATION: a, c, g, t, unknown or other
<220> FEATURE:
<221> NAME/KEY: modified_base
<222> LOCATION: (376)..(376)
<223> OTHER INFORMATION: a, c, g, t, unknown or other
<220> FEATURE:
<221> NAME/KEY: modified_base
<222> LOCATION: (392)..(392)
<223> OTHER INFORMATION: a, c, g, t, unknown or other
<220> FEATURE:
<221> NAME/KEY: modified_base
<222> LOCATION: (398)..(398)
<223> OTHER INFORMATION: a, c, g, t, unknown or other
<220> FEATURE:
<221> NAME/KEY: modified_base
<222> LOCATION: (430)..(430)
<223> OTHER INFORMATION: a, c, g, t, unknown or other
<220> FEATURE:
<221> NAME/KEY: modified_base
<222> LOCATION: (482)..(482)
<223> OTHER INFORMATION: a, c, g, t, unknown or other
<220> FEATURE:
<221> NAME/KEY: modified_base
<222> LOCATION: (485)..(485)
<223> OTHER INFORMATION: a, c, g, t, unknown or other
<220> FEATURE:
<221> NAME/KEY: modified_base
<222> LOCATION: (487)..(487)
<223> OTHER INFORMATION: a, c, g, t, unknown or other
<220> FEATURE:
<221> NAME/KEY: modified_base
<222> LOCATION: (503)..(503)
<223> OTHER INFORMATION: a, c, g, t, unknown or other
<220> FEATURE:
<221> NAME/KEY: modified_base
<222> LOCATION: (509)..(509)
<223> OTHER INFORMATION: a, c, g, t, unknown or other
<220> FEATURE:
<221> NAME/KEY: modified_base
<222> LOCATION: (544)..(544)
<223> OTHER INFORMATION: a, c, g, t, unknown or other
<220> FEATURE:
<221> NAME/KEY: modified_base
<222> LOCATION: (546)..(546)
<223> OTHER INFORMATION: a, c, g, t, unknown or other
<220> FEATURE:
<221> NAME/KEY: modified_base
<222> LOCATION: (563)..(563)
<223> OTHER INFORMATION: a, c, g, t, unknown or other
<220> FEATURE:
```

```
<221> NAME/KEY: modified_base
<222> LOCATION: (569)..(569)
<223> OTHER INFORMATION: a, c, g, t, unknown or other
<220> FEATURE:
<221> NAME/KEY: modified_base
<222> LOCATION: (574)..(574)
<223> OTHER INFORMATION: a, c, g, t, unknown or other
<220> FEATURE:
<221> NAME/KEY: modified_base
<222> LOCATION: (596)..(596)
<223> OTHER INFORMATION: a, c, g, t, unknown or other
<220> FEATURE:
<221> NAME/KEY: modified_base
<222> LOCATION: (600)..(600)
<223> OTHER INFORMATION: a, c, g, t, unknown or other
<220> FEATURE:
<221> NAME/KEY: modified_base
<222> LOCATION: (606)..(606)
<223> OTHER INFORMATION: a, c, g, t, unknown or other
<220> FEATURE:
<221> NAME/KEY: modified_base
<222> LOCATION: (620)..(621)
<223> OTHER INFORMATION: a, c, g, t, unknown or other
<220> FEATURE:
<221> NAME/KEY: modified_base
<222> LOCATION: (623)..(623)
<223> OTHER INFORMATION: a, c, g, t, unknown or other
<220> FEATURE:
<221> NAME/KEY: modified_base
<222> LOCATION: (626)..(626)
<223> OTHER INFORMATION: a, c, g, t, unknown or other
<220> FEATURE:
<221> NAME/KEY: modified_base
<222> LOCATION: (628)..(628)
<223> OTHER INFORMATION: a, c, g, t, unknown or other

<400> SEQUENCE: 2
ggnnnnttgg gtcgcgcatt naagaactca nggncccgca gcattcttgg gtgggagcag      60
ctacgggtca gccacaaggg ccacagccat gaatggcaca gaangccta acttctacgt     120 gcccttctcc aatgcgacgg gtgtggtacg cagcccctc gagtacccac agtactacct     180
ggctgagcca tggcagttct ccatgctggc cgcctacatg tttctgctga tcgtgctggg     240
cttccccatc aacttcctca cgctctacgt gaccgtccag cacaagaagc tgcgcacgcc     300
tctcaactac atcctgctca acctanccgt ggntgaactc ttcatggtcc taggtggctt     360
caccancaac ctctanacct ctctgcatgg anacttcntc ttccggccca caggatgcaa     420
tttggaaggn ttcctttaac acccgggggg ggaaaattgc ctgtggtcct tggtggtccg     480
gncancnaac ggtacttgtg gtntttaanc cataaacaat tccgcttcgg gaaaaacatg     540
ccancntggg gtttccttca ctnggttang ggcnggctgc ccccacccca atcccnggtn     600
gtcaantaat cccaagggcn nantgncntt ttaaacaaa                            639

<210> SEQ ID NO 3
<211> LENGTH: 686
<212> TYPE: DNA
<213> ORGANISM: Artificial Sequence
<220> FEATURE:
<223> OTHER INFORMATION: Description of Artificial Sequence: Synthetic
      human rhodopsin adRP
<220> FEATURE:
<221> NAME/KEY: modified_base
<222> LOCATION: (1)..(3)
<223> OTHER INFORMATION: a, c, g, t, unknown or other
<220> FEATURE:
<221> NAME/KEY: modified_base
<222> LOCATION: (10)..(10)
<223> OTHER INFORMATION: a, c, g, t, unknown or other
<220> FEATURE:
<221> NAME/KEY: modified_base
<222> LOCATION: (19)..(19)
<223> OTHER INFORMATION: a, c, g, t, unknown or other
```

-continued

```
<220> FEATURE:
<221> NAME/KEY: modified_base
<222> LOCATION: (31)..(31)
<223> OTHER INFORMATION: a, c, g, t, unknown or other
<220> FEATURE:
<221> NAME/KEY: modified_base
<222> LOCATION: (49)..(49)
<223> OTHER INFORMATION: a, c, g, t, unknown or other
<220> FEATURE:
<221> NAME/KEY: modified_base
<222> LOCATION: (387)..(387)
<223> OTHER INFORMATION: a, c, g, t, unknown or other
<220> FEATURE:
<221> NAME/KEY: modified_base
<222> LOCATION: (414)..(414)
<223> OTHER INFORMATION: a, c, g, t, unknown or other
<220> FEATURE:
<221> NAME/KEY: modified_base
<222> LOCATION: (427)..(427)
<223> OTHER INFORMATION: a, c, g, t, unknown or other
<220> FEATURE:
<221> NAME/KEY: modified_base
<222> LOCATION: (501)..(501)
<223> OTHER INFORMATION: a, c, g, t, unknown or other
<220> FEATURE:
<221> NAME/KEY: modified_base
<222> LOCATION: (508)..(508)
<223> OTHER INFORMATION: a, c, g, t, unknown or other
<220> FEATURE:
<221> NAME/KEY: modified_base
<222> LOCATION: (524)..(524)
<223> OTHER INFORMATION: a, c, g, t, unknown or other
<220> FEATURE:
<221> NAME/KEY: modified_base
<222> LOCATION: (549)..(549)
<223> OTHER INFORMATION: a, c, g, t, unknown or other
<220> FEATURE:
<221> NAME/KEY: modified_base
<222> LOCATION: (561)..(561)
<223> OTHER INFORMATION: a, c, g, t, unknown or other
<220> FEATURE:
<221> NAME/KEY: modified_base
<222> LOCATION: (563)..(563)
<223> OTHER INFORMATION: a, c, g, t, unknown or other
<220> FEATURE:
<221> NAME/KEY: modified_base
<222> LOCATION: (572)..(572)
<223> OTHER INFORMATION: a, c, g, t, unknown or other
<220> FEATURE:
<221> NAME/KEY: modified_base
<222> LOCATION: (606)..(606)
<223> OTHER INFORMATION: a, c, g, t, unknown or other
<220> FEATURE:
<221> NAME/KEY: modified_base
<222> LOCATION: (617)..(617)
<223> OTHER INFORMATION: a, c, g, t, unknown or other
<220> FEATURE:
<221> NAME/KEY: modified_base
<222> LOCATION: (628)..(628)
<223> OTHER INFORMATION: a, c, g, t, unknown or other
<220> FEATURE:
<221> NAME/KEY: modified_base
<222> LOCATION: (632)..(632)
<223> OTHER INFORMATION: a, c, g, t, unknown or other
<220> FEATURE:
<221> NAME/KEY: modified_base
<222> LOCATION: (656)..(656)
<223> OTHER INFORMATION: a, c, g, t, unknown or other
<220> FEATURE:
<221> NAME/KEY: modified_base
<222> LOCATION: (665)..(665)
<223> OTHER INFORMATION: a, c, g, t, unknown or other
<220> FEATURE:
<221> NAME/KEY: modified_base
<222> LOCATION: (670)..(670)
<223> OTHER INFORMATION: a, c, g, t, unknown or other
<220> FEATURE:
<221> NAME/KEY: modified_base
<222> LOCATION: (680)..(680)
<223> OTHER INFORMATION: a, c, g, t, unknown or other
```

```
<220> FEATURE:
<221> NAME/KEY: modified_base
<222> LOCATION: (682)..(683)
<223> OTHER INFORMATION: a, c, g, t, unknown or other

<400> SEQUENCE: 3
nnnttagggn cggatgtcna tataagcaga nctctctggg ctaactaana agaacccact      60
ggcttactgg cttatcgaaa ttaatacgac tcactatagg gagacccaag cttccggaaa    120
gcctgagctc agccacaagg gccacagcca tgaatggcac agaaagccct aacttctacg    180
tgcccttctc caatgcgacg ggtgtggtac gcagcctctt cgagtaccca cagtactacc    240
tggctgagcc atggcagttc tccatgctgg ccgcctacat gtttctgctg atcgtgctgg    300
gcttccccat caacttcctc acgctctacg tcaccgtcca gcacaagaag ctgcgcacgc    360
ctctcaacta catcctgctc aacctanccg tggctgaact cttcatggtc ctangtggct    420
tcaccancac cctctacacc tctctgcatg gatacttcgt cttccgggcc acaggatgca    480
atttggaagg cttctttgca ncctgggncg ggaaattgcc tgtngtcctg gtggtcctgg    540
ccatcaacng tacttgttgt ntnttaccca tnaacaattc cgctccggga aaacatgcac    600
atgggnttgc ctcactnggt ctggggcngg cnccccaccc caccccggt ggtcanttat     660
cccanggcgn aatgcctttn annaaa                                         686

<210> SEQ ID NO 4
<211> LENGTH: 787
<212> TYPE: DNA
<213> ORGANISM: Artificial Sequence
<220> FEATURE:
<223> OTHER INFORMATION: Description of Artificial Sequence: Synthetic
      hammerhead ribozyme (termed Rz10) cloned in pCDNA3
<220> FEATURE:
<221> NAME/KEY: modified_base
<222> LOCATION: (2)..(2)
<223> OTHER INFORMATION: a, c, g, t, unknown or other
<220> FEATURE:
<221> NAME/KEY: modified_base
<222> LOCATION: (5)..(5)
<223> OTHER INFORMATION: a, c, g, t, unknown or other
<220> FEATURE:
<221> NAME/KEY: modified_base
<222> LOCATION: (32)..(32)
<223> OTHER INFORMATION: a, c, g, t, unknown or other
<220> FEATURE:
<221> NAME/KEY: modified_base
<222> LOCATION: (39)..(39)
<223> OTHER INFORMATION: a, c, g, t, unknown or other
<220> FEATURE:
<221> NAME/KEY: modified_base
<222> LOCATION: (87)..(87)
<223> OTHER INFORMATION: a, c, g, t, unknown or other
<220> FEATURE:
<221> NAME/KEY: modified_base
<222> LOCATION: (142)..(142)
<223> OTHER INFORMATION: a, c, g, t, unknown or other
<220> FEATURE:
<221> NAME/KEY: modified_base
<222> LOCATION: (178)..(178)
<223> OTHER INFORMATION: a, c, g, t, unknown or other
<220> FEATURE:
<221> NAME/KEY: modified_base
<222> LOCATION: (254)..(254)
<223> OTHER INFORMATION: a, c, g, t, unknown or other
<220> FEATURE:
<221> NAME/KEY: modified_base
<222> LOCATION: (298)..(298)
<223> OTHER INFORMATION: a, c, g, t, unknown or other
<220> FEATURE:
<221> NAME/KEY: modified_base
<222> LOCATION: (305)..(305)
<223> OTHER INFORMATION: a, c, g, t, unknown or other
<220> FEATURE:
```

-continued

```
<221> NAME/KEY: modified_base
<222> LOCATION: (353)..(353)
<223> OTHER INFORMATION: a, c, g, t, unknown or other
<220> FEATURE:
<221> NAME/KEY: modified_base
<222> LOCATION: (358)..(358)
<223> OTHER INFORMATION: a, c, g, t, unknown or other
<220> FEATURE:
<221> NAME/KEY: modified_base
<222> LOCATION: (395)..(395)
<223> OTHER INFORMATION: a, c, g, t, unknown or other
<220> FEATURE:
<221> NAME/KEY: modified_base
<222> LOCATION: (403)..(403)
<223> OTHER INFORMATION: a, c, g, t, unknown or other
<220> FEATURE:
<221> NAME/KEY: modified_base
<222> LOCATION: (410)..(410)
<223> OTHER INFORMATION: a, c, g, t, unknown or other
<220> FEATURE:
<221> NAME/KEY: modified_base
<222> LOCATION: (414)..(414)
<223> OTHER INFORMATION: a, c, g, t, unknown or other
<220> FEATURE:
<221> NAME/KEY: modified_base
<222> LOCATION: (435)..(435)
<223> OTHER INFORMATION: a, c, g, t, unknown or other
<220> FEATURE:
<221> NAME/KEY: modified_base
<222> LOCATION: (469)..(469)
<223> OTHER INFORMATION: a, c, g, t, unknown or other
<220> FEATURE:
<221> NAME/KEY: modified_base
<222> LOCATION: (472)..(472)
<223> OTHER INFORMATION: a, c, g, t, unknown or other
<220> FEATURE:
<221> NAME/KEY: modified_base
<222> LOCATION: (496)..(497)
<223> OTHER INFORMATION: a, c, g, t, unknown or other
<220> FEATURE:
<221> NAME/KEY: modified_base
<222> LOCATION: (511)..(511)
<223> OTHER INFORMATION: a, c, g, t, unknown or other
<220> FEATURE:
<221> NAME/KEY: modified_base
<222> LOCATION: (516)..(516)
<223> OTHER INFORMATION: a, c, g, t, unknown or other
<220> FEATURE:
<221> NAME/KEY: modified_base
<222> LOCATION: (527)..(527)
<223> OTHER INFORMATION: a, c, g, t, unknown or other
<220> FEATURE:
<221> NAME/KEY: modified_base
<222> LOCATION: (548)..(548)
<223> OTHER INFORMATION: a, c, g, t, unknown or other
<220> FEATURE:
<221> NAME/KEY: modified_base
<222> LOCATION: (559)..(559)
<223> OTHER INFORMATION: a, c, g, t, unknown or other
<220> FEATURE:
<221> NAME/KEY: modified_base
<222> LOCATION: (569)..(569)
<223> OTHER INFORMATION: a, c, g, t, unknown or other
<220> FEATURE:
<221> NAME/KEY: modified_base
<222> LOCATION: (572)..(572)
<223> OTHER INFORMATION: a, c, g, t, unknown or other
<220> FEATURE:
<221> NAME/KEY: modified_base
<222> LOCATION: (583)..(583)
<223> OTHER INFORMATION: a, c, g, t, unknown or other
<220> FEATURE:
<221> NAME/KEY: modified_base
<222> LOCATION: (609)..(609)
<223> OTHER INFORMATION: a, c, g, t, unknown or other
<220> FEATURE:
<221> NAME/KEY: modified_base
<222> LOCATION: (617)..(617)
<223> OTHER INFORMATION: a, c, g, t, unknown or other
<220> FEATURE:
```

```
<221> NAME/KEY: modified_base
<222> LOCATION: (629)..(630)
<223> OTHER INFORMATION: a, c, g, t, unknown or other
<220> FEATURE:
<221> NAME/KEY: modified_base
<222> LOCATION: (632)..(632)
<223> OTHER INFORMATION: a, c, g, t, unknown or other
<220> FEATURE:
<221> NAME/KEY: modified_base
<222> LOCATION: (641)..(641)
<223> OTHER INFORMATION: a, c, g, t, unknown or other
<220> FEATURE:
<221> NAME/KEY: modified_base
<222> LOCATION: (645)..(645)
<223> OTHER INFORMATION: a, c, g, t, unknown or other
<220> FEATURE:
<221> NAME/KEY: modified_base
<222> LOCATION: (649)..(649)
<223> OTHER INFORMATION: a, c, g, t, unknown or other
<220> FEATURE:
<221> NAME/KEY: modified_base
<222> LOCATION: (651)..(651)
<223> OTHER INFORMATION: a, c, g, t, unknown or other
<220> FEATURE:
<221> NAME/KEY: modified_base
<222> LOCATION: (654)..(664)
<223> OTHER INFORMATION: a, c, g, t, unknown or other
<220> FEATURE:
<221> NAME/KEY: modified_base
<222> LOCATION: (666)..(669)
<223> OTHER INFORMATION: a, c, g, t, unknown or other
<220> FEATURE:
<221> NAME/KEY: modified_base
<222> LOCATION: (672)..(672)
<223> OTHER INFORMATION: a, c, g, t, unknown or other
<220> FEATURE:
<221> NAME/KEY: modified_base
<222> LOCATION: (674)..(674)
<223> OTHER INFORMATION: a, c, g, t, unknown or other
<220> FEATURE:
<221> NAME/KEY: modified_base
<222> LOCATION: (680)..(680)
<223> OTHER INFORMATION: a, c, g, t, unknown or other
<220> FEATURE:
<221> NAME/KEY: modified_base
<222> LOCATION: (707)..(707)
<223> OTHER INFORMATION: a, c, g, t, unknown or other
<220> FEATURE:
<221> NAME/KEY: modified_base
<222> LOCATION: (709)..(709)
<223> OTHER INFORMATION: a, c, g, t, unknown or other
<220> FEATURE:
<221> NAME/KEY: modified_base
<222> LOCATION: (721)..(721)
<223> OTHER INFORMATION: a, c, g, t, unknown or other
<220> FEATURE:
<221> NAME/KEY: modified_base
<222> LOCATION: (723)..(723)
<223> OTHER INFORMATION: a, c, g, t, unknown or other
<220> FEATURE:
<221> NAME/KEY: modified_base
<222> LOCATION: (731)..(731)
<223> OTHER INFORMATION: a, c, g, t, unknown or other
<220> FEATURE:
<221> NAME/KEY: modified_base
<222> LOCATION: (739)..(739)
<223> OTHER INFORMATION: a, c, g, t, unknown or other
<220> FEATURE:
<221> NAME/KEY: modified_base
<222> LOCATION: (742)..(745)
<223> OTHER INFORMATION: a, c, g, t, unknown or other
<220> FEATURE:
<221> NAME/KEY: modified_base
<222> LOCATION: (747)..(747)
<223> OTHER INFORMATION: a, c, g, t, unknown or other
<220> FEATURE:
<221> NAME/KEY: modified_base
<222> LOCATION: (765)..(766)
<223> OTHER INFORMATION: a, c, g, t, unknown or other
<220> FEATURE:
```

```
<221> NAME/KEY: modified_base
<222> LOCATION: (772)..(773)
<223> OTHER INFORMATION: a, c, g, t, unknown or other
<220> FEATURE:
<221> NAME/KEY: modified_base
<222> LOCATION: (775)..(775)
<223> OTHER INFORMATION: a, c, g, t, unknown or other
<220> FEATURE:
<221> NAME/KEY: modified_base
<222> LOCATION: (780)..(782)
<223> OTHER INFORMATION: a, c, g, t, unknown or other
<220> FEATURE:
<221> NAME/KEY: modified_base
<222> LOCATION: (784)..(786)
<223> OTHER INFORMATION: a, c, g, t, unknown or other

<400> SEQUENCE: 4
cngcncgttg aaatataagc agaccctctg gntaactana ataaccactg cttactggct      60
tatcgaaatt aatacgactc actatangga gaccaagctt ggtcggtctg atgagtccgt     120
gaggacgaaa cgtagagtct anagggcct attctatagt gtcacctaaa tgctaganct     180
cgctgatcag cctcgactgt gccttctagt tgccagccat ctgttgtttg cccctccccc     240
gtgccttcct tganccatgga aggtgccact cccactgtcc tttcctaata aaatgagnaa     300
ttgcntctca ttgtctgagt agtgtcatcc aatctggggg tgggtggggc agnacacnag     360
gggaagatgg gaaacatac aggcatgctg gggangccgt ggntctatgn ctcngaggcg     420
aaaaaacact ggggnctagg ggtacccac ccctgtacg gccataacnc gnggtttgtg     480
gtacccacta acgtanntgc accctacccg ncttcnttct cctcttncca tttccggttc     540
cctcaccnaa cgggccttng tcatatctng gnccaccaaa tanagtagtc tttgccccca     600
aagtccctna tgacctntaa gaccttcann anccccctt nttttnaaana nccnnnnnnn     660 nnnnannnnc cngnaaaaan aacaactaat tttgggaacc ccccccnana aaccctttcc     720
ntnttccccc natttaatnt tnnnntnccc cccccccccc cccnnttttt tnncnccccn     780 nnannng                                                              787

<210> SEQ ID NO 5
<211> LENGTH: 665
<212> TYPE: DNA
<213> ORGANISM: Artificial Sequence
<220> FEATURE:
<223> OTHER INFORMATION: Description of Artificial Sequence: Synthetic
      hammerhead ribozyme (termed Rz20) cloned in pCDNA3
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (11)..(11)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (19)..(19)
<223> OTHER INFORMATION: a, c, g, t, unknown or other
<220> FEATURE:
<221> NAME/KEY: modified_base
<222> LOCATION: (22)..(22)
<223> OTHER INFORMATION: a, c, g, t, unknown or other
<220> FEATURE:
<221> NAME/KEY: modified_base
<222> LOCATION: (25)..(25)
<223> OTHER INFORMATION: a, c, g, t, unknown or other
<220> FEATURE:
<221> NAME/KEY: modified_base
```

```
<222> LOCATION: (36)..(36)
<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (44)..(44)
<223> OTHER INFORMATION: a, c, g, t, unknown or other
<220> FEATURE:
<221> NAME/KEY: modified_base
<222> LOCATION: (67)..(67)
<223> OTHER INFORMATION: a, c, g, t, unknown or other
<220> FEATURE:
<221> NAME/KEY: modified_base
<222> LOCATION: (145)..(145)
<223> OTHER INFORMATION: a, c, g, t, unknown or other
<220> FEATURE:
<221> NAME/KEY: modified_base
<222> LOCATION: (147)..(147)
<223> OTHER INFORMATION: a, c, g, t, unknown or other
<220> FEATURE:
<221> NAME/KEY: modified_base
<222> LOCATION: (162)..(162)
<223> OTHER INFORMATION: a, c, g, t, unknown or other
<220> FEATURE:
<221> NAME/KEY: modified_base
<222> LOCATION: (304)..(304)
<223> OTHER INFORMATION: a, c, g, t, unknown or other
<220> FEATURE:
<221> NAME/KEY: modified_base
<222> LOCATION: (307)..(307)
<223> OTHER INFORMATION: a, c, g, t, unknown or other
<220> FEATURE:
<221> NAME/KEY: modified_base
<222> LOCATION: (312)..(312)
<223> OTHER INFORMATION: a, c, g, t, unknown or other
<220> FEATURE:
<221> NAME/KEY: modified_base
<222> LOCATION: (365)..(365)
<223> OTHER INFORMATION: a, c, g, t, unknown or other
<220> FEATURE:
<221> NAME/KEY: modified_base
<222> LOCATION: (369)..(369)
<223> OTHER INFORMATION: a, c, g, t, unknown or other
<220> FEATURE:
<221> NAME/KEY: modified_base
<222> LOCATION: (391)..(391)
<223> OTHER INFORMATION: a, c, g, t, unknown or other
<220> FEATURE:
<221> NAME/KEY: modified_base
<222> LOCATION: (397)..(397)
<223> OTHER INFORMATION: a, c, g, t, unknown or other
<220> FEATURE:
<221> NAME/KEY: modified_base
<222> LOCATION: (408)..(408)
<223> OTHER INFORMATION: a, c, g, t, unknown or other
<220> FEATURE:
<221> NAME/KEY: modified_base
<222> LOCATION: (422)..(422)
<223> OTHER INFORMATION: a, c, g, t, unknown or other
<220> FEATURE:
<221> NAME/KEY: modified_base
<222> LOCATION: (456)..(456)
<223> OTHER INFORMATION: a, c, g, t, unknown or other
<220> FEATURE:
<221> NAME/KEY: modified_base
<222> LOCATION: (482)..(482)
<223> OTHER INFORMATION: a, c, g, t, unknown or other
<220> FEATURE:
<221> NAME/KEY: modified_base
<222> LOCATION: (492)..(492)
<223> OTHER INFORMATION: a, c, g, t, unknown or other
<220> FEATURE:
<221> NAME/KEY: modified_base
<222> LOCATION: (526)..(526)
<223> OTHER INFORMATION: a, c, g, t, unknown or other
<220> FEATURE:
<221> NAME/KEY: modified_base
```

<222> LOCATION: (539)..(539)
<223> OTHER INFORMATION: a, c, g, t, unknown or other
<220> FEATURE:
<221> NAME/KEY: modified_base
<222> LOCATION: (548)..(548)
<223> OTHER INFORMATION: a, c, g, t, unknown or other
<220> FEATURE:
<221> NAME/KEY: modified_base
<222> LOCATION: (571)..(571)
<223> OTHER INFORMATION: a, c, g, t, unknown or other
<220> FEATURE:
<221> NAME/KEY: modified_base
<222> LOCATION: (590)..(590)
<223> OTHER INFORMATION: a, c, g, t, unknown or other
<220> FEATURE:
<221> NAME/KEY: modified_base
<222> LOCATION: (598)..(598)
<223> OTHER INFORMATION: a, c, g, t, unknown or other
<220> FEATURE:
<221> NAME/KEY: modified_base
<222> LOCATION: (636)..(636)
<223> OTHER INFORMATION: a, c, g, t, unknown or other
<220> FEATURE:
<221> NAME/KEY: modified_base
<222> LOCATION: (640)..(640)
<223> OTHER INFORMATION: a, c, g, t, unknown or other
<220> FEATURE:
<221> NAME/KEY: modified_base
<222> LOCATION: (653)..(653)
<223> OTHER INFORMATION: a, c, g, t, unknown or other
<220> FEATURE:
<221> NAME/KEY: modified_base
<222> LOCATION: (662)..(662)
<223> OTHER INFORMATION: a, c, g, t, unknown or other

<400> SEQUENCE: 5

```
nnccccgccc ntttnaaana anccnagcct ctggcnaact ananaaccac tgcttactgg      60
cttatcnaaa ttaatacgac tcactatagg gagacccaag ctttactcga actgatgagt    120
ccgtgaggac gaaaggctgc tctananggc cctattctat antgtcacct aaatgctaga    180
gctcgctgat cagcctcgac tgtgccttct aattgccagc catctgttgt ttgcccctcc    240
cccgtgcctt ccttgaccct ggaaggtgcc actcccactg tcctttccta ataaaatgaa    300
gatnttncat cncattgtct gagtaagtgt cattctattc tggggggtgg ggtggggcac    360
gacancaagg gggaagattg ggaaaaaata ncaggcntgc tggggatncc gtgggctcta    420
tngcttctga agcggaaaaa acaactgggg ctctangggg tatcccccccc ccctgtaac   480
gngcattaaa cncggggtg ttgtggttac cccaacttaa cgctancttg caacgcccna    540
acgccccncc tttcctttct cccttccttc ncccactttc cggggttcccn tcaacccnaa    600
tcggggcccc ttaggtccaa ttatgcttcg gccccncccn aaactaatag gtnggttctt    660
tngcc                                                                665
```

<210> SEQ ID NO 6
<211> LENGTH: 624
<212> TYPE: DNA
<213> ORGANISM: Artificial Sequence
<220> FEATURE:
<223> OTHER INFORMATION: Description of Artificial Sequence: Synthetic mouse rhodopsin cDNA cloned into pCDNA3
<220> FEATURE:
<221> NAME/KEY: modified_base
<222> LOCATION: (1)..(4)
<223> OTHER INFORMATION: a, c, g, t, unknown or other
<220> FEATURE:
<221> NAME/KEY: modified_base
<222> LOCATION: (8)..(8)
<223> OTHER INFORMATION: a, c, g, t, unknown or other
<220> FEATURE:
<221> NAME/KEY: modified_base
<222> LOCATION: (13)..(14)

<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (43)..(43)
<223> OTHER INFORMATION: a, c, g, t, unknown or other
<220> FEATURE:
<221> NAME/KEY: modified_base
<222> LOCATION: (77)..(77)
<223> OTHER INFORMATION: a, c, g, t, unknown or other
<220> FEATURE:
<221> NAME/KEY: modified_base
<222> LOCATION: (350)..(350)
<223> OTHER INFORMATION: a, c, g, t, unknown or other
<220> FEATURE:
<221> NAME/KEY: modified_base
<222> LOCATION: (367)..(367)
<223> OTHER INFORMATION: a, c, g, t, unknown or other
<220> FEATURE:
<221> NAME/KEY: modified_base
<222> LOCATION: (369)..(369)
<223> OTHER INFORMATION: a, c, g, t, unknown or other
<220> FEATURE:
<221> NAME/KEY: modified_base
<222> LOCATION: (431)..(431)
<223> OTHER INFORMATION: a, c, g, t, unknown or other
<220> FEATURE:
<221> NAME/KEY: modified_base
<222> LOCATION: (452)..(452)
<223> OTHER INFORMATION: a, c, g, t, unknown or other
<220> FEATURE:
<221> NAME/KEY: modified_base
<222> LOCATION: (454)..(454)
<223> OTHER INFORMATION: a, c, g, t, unknown or other
<220> FEATURE:
<221> NAME/KEY: modified_base
<222> LOCATION: (457)..(457)
<223> OTHER INFORMATION: a, c, g, t, unknown or other
<220> FEATURE:
<221> NAME/KEY: modified_base
<222> LOCATION: (503)..(503)
<223> OTHER INFORMATION: a, c, g, t, unknown or other
<220> FEATURE:
<221> NAME/KEY: modified_base
<222> LOCATION: (531)..(531)
<223> OTHER INFORMATION: a, c, g, t, unknown or other
<220> FEATURE:
<221> NAME/KEY: modified_base
<222> LOCATION: (568)..(569)
<223> OTHER INFORMATION: a, c, g, t, unknown or other
<220> FEATURE:
<221> NAME/KEY: modified_base
<222> LOCATION: (571)..(571)
<223> OTHER INFORMATION: a, c, g, t, unknown or other

<400> SEQUENCE: 6

```
nnnncttnct tanngcttgg taccganctc ggatccacta gtnaacggcc gccagtgtgc      60
tggaaattcc cagaggnact ctggggcaga caagatgaga cacccttttcc tttctttacc   120
taagggcctc cacccgatgt caccttggcc cctctgcaag ccaattaggc cccgtggca    180
gcagtgggat tagcgttagt atgatatctc gcggatgctg aatcagcctc tggcttaggg   240
agagaaggtc actttataag ggtctggggg ggtcagtgc ctggagttgc gctgtgggag    300
ccgtcagtgg ctgagctcgc caagcagcct tggtctctgt ctacgaaaan cccgtggggc   360
agcctcnana accgcagcca tgaacggcac agaaggcccc aatttttatg tgcccttctc   420
caacgtcaca ngcgtggtgc ggaaccccttt cnancanccg cagtactacc tggcggaacc   480
atggcagttc tccatgctgg cancgtacat gtcctgctca tcgtgctggg nttcccatca   540
actcctcacg ctctagttca ccgtaaanna naaaaaactg cgcaaccct caactaaatc     600
```
ctgctcaatt gggcgtgggt gaac                                            624

<210> SEQ ID NO 7
<211> LENGTH: 630
<212> TYPE: DNA
<213> ORGANISM: Artificial Sequence
<220> FEATURE:
<223> OTHER INFORMATION: Description of Artificial Sequence: Synthetic
      mouse rhodopsin hybrid cDNA
<220> FEATURE:
<221> NAME/KEY: modified_base
<222> LOCATION: (1)..(4)
<223> OTHER INFORMATION: a, c, g, t, unknown or other
<220> FEATURE:
<221> NAME/KEY: modified_base
<222> LOCATION: (11)..(11)
<223> OTHER INFORMATION: a, c, g, t, unknown or other
<220> FEATURE:
<221> NAME/KEY: modified_base
<222> LOCATION: (25)..(25)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (29)..(29)
<223> OTHER INFORMATION: a, c, g, t, unknown or other
<220> FEATURE:
<221> NAME/KEY: modified_base
<222> LOCATION: (33)..(34)
<223> OTHER INFORMATION: a, c, g, t, unknown or other
<220> FEATURE:
<221> NAME/KEY: modified_base
<222> LOCATION: (38)..(38)
<223> OTHER INFORMATION: a, c, g, t, unknown or other
<220> FEATURE:
<221> NAME/KEY: modified_base
<222> LOCATION: (40)..(40)
<223> OTHER INFORMATION: a, c, g, t, unknown or other
<220> FEATURE:
<221> NAME/KEY: modified_base
<222> LOCATION: (46)..(46)
<223> OTHER INFORMATION: a, c, g, t, unknown or other
<220> FEATURE:
<221> NAME/KEY: modified_base
<222> LOCATION: (91)..(91)
<223> OTHER INFORMATION: a, c, g, t, unknown or other
<220> FEATURE:
<221> NAME/KEY: modified_base
<222> LOCATION: (238)..(238)
<223> OTHER INFORMATION: a, c, g, t, unknown or other
<220> FEATURE:
<221> NAME/KEY: modified_base
<222> LOCATION: (240)..(240)
<223> OTHER INFORMATION: a, c, g, t, unknown or other
<220> FEATURE:
<221> NAME/KEY: modified_base
<222> LOCATION: (408)..(408)
<223> OTHER INFORMATION: a, c, g, t, unknown or other
<220> FEATURE:
<221> NAME/KEY: modified_base
<222> LOCATION: (413)..(413)
<223> OTHER INFORMATION: a, c, g, t, unknown or other
<220> FEATURE:
<221> NAME/KEY: modified_base
<222> LOCATION: (438)..(438)
<223> OTHER INFORMATION: a, c, g, t, unknown or other
<220> FEATURE:
<221> NAME/KEY: modified_base
<222> LOCATION: (448)..(448)
<223> OTHER INFORMATION: a, c, g, t, unknown or other
<220> FEATURE:
<221> NAME/KEY: modified_base
<222> LOCATION: (452)..(452)
<223> OTHER INFORMATION: a, c, g, t, unknown or other
<220> FEATURE:
<221> NAME/KEY: modified_base

```
<222> LOCATION: (454)..(454)
<223> OTHER INFORMATION: a, c, g, t, unknown or other
<220> FEATURE:
<221> NAME/KEY: modified_base
<222> LOCATION: (513)..(513)
<223> OTHER INFORMATION: a, c, g, t, unknown or other
<220> FEATURE:
<221> NAME/KEY: modified_base
<222> LOCATION: (564)..(564)
<223> OTHER INFORMATION: a, c, g, t, unknown or other
<220> FEATURE:
<221> NAME/KEY: modified_base
<222> LOCATION: (586)..(586)
<223> OTHER INFORMATION: a, c, g, t, unknown or other

<400> SEQUENCE: 7
nnnntcttcc nctttcgttt gttgnanant cannaaanan aggcgnccccg gaaggtgtca      60 gtgcctggag ttgcgctgtg ggacccgtca ntggctgagc tcgccaagca gccttggtct     120
ctgtctacga agagcccgtg gggcagcctc gagagccgca gccatgaacg gcacagaggg     180
ccccaatttc tatgtgccct tctccaacgt cacaggcgtg gtgcggagcc ccttcgancn     240
tccgcagtac tacctggcgg aaccatggca gttctccatg ctggcagcgt acatgttcct     300
gctcatcgtg ctgggcttcc ccatcaactt cctcacgctc tacgtcaccg tacagcacaa     360
gaagctgcgc acaccccctc aactacatcc tggctcaact tgggccgntg ggnttggaac     420
ctccttccca ttgggtcntt cccggaaggg antncaccaa ccaccctct aacacatcaa      480 ctcccatggg ctacttcgtt cttttgggc ccncaggctg ttaatctcga agggcttctt      540
tgccacacct tggaagtgaa atcnccctgt ggttccctgg tggtcntggc cattaacgct     600
acttgtggtc ctgcaaccca ataacaattc                                      630

<210> SEQ ID NO 8
<211> LENGTH: 649
<212> TYPE: DNA
<213> ORGANISM: Artificial Sequence
<220> FEATURE:
<223> OTHER INFORMATION: Description of Artificial Sequence: Synthetic
      hammerhead ribozyme (termed Rz33) cloned in pCDNA3
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (19)..(19)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (49)..(49)
<223> OTHER INFORMATION: a, c, g, t, unknown or other
<220> FEATURE:
<221> NAME/KEY: modified_base
<222> LOCATION: (52)..(52)
<223> OTHER INFORMATION: a, c, g, t, unknown or other
<220> FEATURE:
<221> NAME/KEY: modified_base
<222> LOCATION: (55)..(55)
<223> OTHER INFORMATION: a, c, g, t, unknown or other
<220> FEATURE:
<221> NAME/KEY: modified_base
<222> LOCATION: (57)..(57)
<223> OTHER INFORMATION: a, c, g, t, unknown or other
<220> FEATURE:
<221> NAME/KEY: modified_base
<222> LOCATION: (79)..(79)
<223> OTHER INFORMATION: a, c, g, t, unknown or other
<220> FEATURE:
```

```
<221> NAME/KEY: modified_base
<222> LOCATION: (81)..(81)
<223> OTHER INFORMATION: a, c, g, t, unknown or other
<220> FEATURE:
<221> NAME/KEY: modified_base
<222> LOCATION: (193)..(193)
<223> OTHER INFORMATION: a, c, g, t, unknown or other
<220> FEATURE:
<221> NAME/KEY: modified_base
<222> LOCATION: (212)..(212)
<223> OTHER INFORMATION: a, c, g, t, unknown or other
<220> FEATURE:
<221> NAME/KEY: modified_base
<222> LOCATION: (236)..(236)
<223> OTHER INFORMATION: a, c, g, t, unknown or other
<220> FEATURE:
<221> NAME/KEY: modified_base
<222> LOCATION: (240)..(240)
<223> OTHER INFORMATION: a, c, g, t, unknown or other
<220> FEATURE:
<221> NAME/KEY: modified_base
<222> LOCATION: (378)..(379)
<223> OTHER INFORMATION: a, c, g, t, unknown or other
<220> FEATURE:
<221> NAME/KEY: modified_base
<222> LOCATION: (407)..(407)
<223> OTHER INFORMATION: a, c, g, t, unknown or other
<220> FEATURE:
<221> NAME/KEY: modified_base
<222> LOCATION: (415)..(415)
<223> OTHER INFORMATION: a, c, g, t, unknown or other
<220> FEATURE:
<221> NAME/KEY: modified_base
<222> LOCATION: (417)..(417)
<223> OTHER INFORMATION: a, c, g, t, unknown or other
<220> FEATURE:
<221> NAME/KEY: modified_base
<222> LOCATION: (425)..(425)
<223> OTHER INFORMATION: a, c, g, t, unknown or other
<220> FEATURE:
<221> NAME/KEY: modified_base
<222> LOCATION: (441)..(441)
<223> OTHER INFORMATION: a, c, g, t, unknown or other
<220> FEATURE:
<221> NAME/KEY: modified_base
<222> LOCATION: (448)..(448)
<223> OTHER INFORMATION: a, c, g, t, unknown or other
<220> FEATURE:
<221> NAME/KEY: modified_base
<222> LOCATION: (464)..(464)
<223> OTHER INFORMATION: a, c, g, t, unknown or other
<220> FEATURE:
<221> NAME/KEY: modified_base
<222> LOCATION: (469)..(469)
<223> OTHER INFORMATION: a, c, g, t, unknown or other
<220> FEATURE:
<221> NAME/KEY: modified_base
<222> LOCATION: (478)..(478)
<223> OTHER INFORMATION: a, c, g, t, unknown or other
<220> FEATURE:
<221> NAME/KEY: modified_base
<222> LOCATION: (486)..(486)
<223> OTHER INFORMATION: a, c, g, t, unknown or other
<220> FEATURE:
<221> NAME/KEY: modified_base
<222> LOCATION: (500)..(500)
<223> OTHER INFORMATION: a, c, g, t, unknown or other
<220> FEATURE:
<221> NAME/KEY: modified_base
<222> LOCATION: (504)..(504)
<223> OTHER INFORMATION: a, c, g, t, unknown or other
<220> FEATURE:
<221> NAME/KEY: modified_base
<222> LOCATION: (509)..(509)
<223> OTHER INFORMATION: a, c, g, t, unknown or other
<220> FEATURE:
<221> NAME/KEY: modified_base
<222> LOCATION: (515)..(515)
<223> OTHER INFORMATION: a, c, g, t, unknown or other
<220> FEATURE:
```

```
<221> NAME/KEY: modified_base
<222> LOCATION: (524)..(524)
<223> OTHER INFORMATION: a, c, g, t, unknown or other
<220> FEATURE:
<221> NAME/KEY: modified_base
<222> LOCATION: (556)..(556)
<223> OTHER INFORMATION: a, c, g, t, unknown or other
<220> FEATURE:
<221> NAME/KEY: modified_base
<222> LOCATION: (566)..(566)
<223> OTHER INFORMATION: a, c, g, t, unknown or other
<220> FEATURE:
<221> NAME/KEY: modified_base
<222> LOCATION: (592)..(592)
<223> OTHER INFORMATION: a, c, g, t, unknown or other
<220> FEATURE:
<221> NAME/KEY: modified_base
<222> LOCATION: (595)..(595)
<223> OTHER INFORMATION: a, c, g, t, unknown or other
<220> FEATURE:
<221> NAME/KEY: modified_base
<222> LOCATION: (613)..(613)
<223> OTHER INFORMATION: a, c, g, t, unknown or other
<220> FEATURE:
<221> NAME/KEY: modified_base
<222> LOCATION: (633)..(633)
<223> OTHER INFORMATION: a, c, g, t, unknown or other
<220> FEATURE:
<221> NAME/KEY: modified_base
<222> LOCATION: (638)..(638)
<223> OTHER INFORMATION: a, c, g, t, unknown or other
<220> FEATURE:
<221> NAME/KEY: modified_base
<222> LOCATION: (641)..(641)
<223> OTHER INFORMATION: a, c, g, t, unknown or other
<220> FEATURE:
<221> NAME/KEY: modified_base
<222> LOCATION: (647)..(647)
<223> OTHER INFORMATION: a, c, g, t, unknown or other

<400> SEQUENCE: 8
tcccctnntt tttgtagcnc tgccaanaaa aaaggccagc tcacaggana antananaac    60
ccactgctta ctggcttanc naaattaata cgactcacta tagggagacc caagcttggc   120
acatctgatg agtccgtgag gacgaaaaaa ttggtctaca gggccctatt ctataatgtc   180
acctaaatgc tanagctcgc tgatcatcct cnactgtgcc ttctacttgc cagccntctn   240
ttgtttgccc ctccccgtg ccttccttga ccctggaagg tgccactccc actgtccttt    300
cctaataaaa tgaggaaatt gcatcgcatt gtctgagtaa gtgtcattct attctggggg   360
gtggggtggg gcaggacnnc aaaggggaag attgggaaat acaatancca aggancnctc   420
cccnggggta attgcggatt nggctctntc gcttccttaa ggcngaaana aacaactngg   480
gcgctncggg gtttccccn cccnccctnt tagcngcgca ttantcgccg cgggtgttgt    540
tgttactccc cacctnaacg ctacanttgc cagcgcctaa cgcccccct tnctnttctt    600 ccctcctttc tncacttcc ccggctttcc ccnccaancc naaatcngg             649

<210> SEQ ID NO 9
<211> LENGTH: 681
<212> TYPE: DNA
<213> ORGANISM: Artificial Sequence
<220> FEATURE:
<223> OTHER INFORMATION: Description of Artificial Sequence: Synthetic
      human peripherin cDNA cloned in pCDNA3
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (11)..(11)
<223> OTHER INFORMATION: a, c, g, t, unknown or other
```

-continued

```
<220> FEATURE:
<221> NAME/KEY: modified_base
<222> LOCATION: (16)..(16)
<223> OTHER INFORMATION: a, c, g, t, unknown or other
<220> FEATURE:
<221> NAME/KEY: modified_base
<222> LOCATION: (37)..(37)
<223> OTHER INFORMATION: a, c, g, t, unknown or other
<220> FEATURE:
<221> NAME/KEY: modified_base
<222> LOCATION: (52)..(52)
<223> OTHER INFORMATION: a, c, g, t, unknown or other
<220> FEATURE:
<221> NAME/KEY: modified_base
<222> LOCATION: (127)..(127)
<223> OTHER INFORMATION: a, c, g, t, unknown or other
<220> FEATURE:
<221> NAME/KEY: modified_base
<222> LOCATION: (251)..(251)
<223> OTHER INFORMATION: a, c, g, t, unknown or other
<220> FEATURE:
<221> NAME/KEY: modified_base
<222> LOCATION: (287)..(287)
<223> OTHER INFORMATION: a, c, g, t, unknown or other
<220> FEATURE:
<221> NAME/KEY: modified_base
<222> LOCATION: (297)..(297)
<223> OTHER INFORMATION: a, c, g, t, unknown or other
<220> FEATURE:
<221> NAME/KEY: modified_base
<222> LOCATION: (307)..(307)
<223> OTHER INFORMATION: a, c, g, t, unknown or other
<220> FEATURE:
<221> NAME/KEY: modified_base
<222> LOCATION: (310)..(310)
<223> OTHER INFORMATION: a, c, g, t, unknown or other
<220> FEATURE:
<221> NAME/KEY: modified_base
<222> LOCATION: (325)..(325)
<223> OTHER INFORMATION: a, c, g, t, unknown or other
<220> FEATURE:
<221> NAME/KEY: modified_base
<222> LOCATION: (349)..(349)
<223> OTHER INFORMATION: a, c, g, t, unknown or other
<220> FEATURE:
<221> NAME/KEY: modified_base
<222> LOCATION: (354)..(354)
<223> OTHER INFORMATION: a, c, g, t, unknown or other
<220> FEATURE:
<221> NAME/KEY: modified_base
<222> LOCATION: (358)..(358)
<223> OTHER INFORMATION: a, c, g, t, unknown or other
<220> FEATURE:
<221> NAME/KEY: modified_base
<222> LOCATION: (369)..(369)
<223> OTHER INFORMATION: a, c, g, t, unknown or other
<220> FEATURE:
<221> NAME/KEY: modified_base
<222> LOCATION: (395)..(395)
<223> OTHER INFORMATION: a, c, g, t, unknown or other
<220> FEATURE:
<221> NAME/KEY: modified_base
<222> LOCATION: (397)..(397)
<223> OTHER INFORMATION: a, c, g, t, unknown or other
<220> FEATURE:
<221> NAME/KEY: modified_base
<222> LOCATION: (413)..(413)
<223> OTHER INFORMATION: a, c, g, t, unknown or other
<220> FEATURE:
<221> NAME/KEY: modified_base
<222> LOCATION: (426)..(426)
<223> OTHER INFORMATION: a, c, g, t, unknown or other
<220> FEATURE:
<221> NAME/KEY: modified_base
<222> LOCATION: (441)..(441)
<223> OTHER INFORMATION: a, c, g, t, unknown or other
<220> FEATURE:
<221> NAME/KEY: modified_base
<222> LOCATION: (452)..(452)
<223> OTHER INFORMATION: a, c, g, t, unknown or other
```

```
<220> FEATURE:
<221> NAME/KEY: modified_base
<222> LOCATION: (465)..(466)
<223> OTHER INFORMATION: a, c, g, t, unknown or other
<220> FEATURE:
<221> NAME/KEY: modified_base
<222> LOCATION: (468)..(469)
<223> OTHER INFORMATION: a, c, g, t, unknown or other
<220> FEATURE:
<221> NAME/KEY: modified_base
<222> LOCATION: (471)..(471)
<223> OTHER INFORMATION: a, c, g, t, unknown or other
<220> FEATURE:
<221> NAME/KEY: modified_base
<222> LOCATION: (479)..(479)
<223> OTHER INFORMATION: a, c, g, t, unknown or other
<220> FEATURE:
<221> NAME/KEY: modified_base
<222> LOCATION: (489)..(489)
<223> OTHER INFORMATION: a, c, g, t, unknown or other
<220> FEATURE:
<221> NAME/KEY: modified_base
<222> LOCATION: (491)..(491)
<223> OTHER INFORMATION: a, c, g, t, unknown or other
<220> FEATURE:
<221> NAME/KEY: modified_base
<222> LOCATION: (498)..(498)
<223> OTHER INFORMATION: a, c, g, t, unknown or other
<220> FEATURE:
<221> NAME/KEY: modified_base
<222> LOCATION: (500)..(501)
<223> OTHER INFORMATION: a, c, g, t, unknown or other
<220> FEATURE:
<221> NAME/KEY: modified_base
<222> LOCATION: (505)..(505)
<223> OTHER INFORMATION: a, c, g, t, unknown or other
<220> FEATURE:
<221> NAME/KEY: modified_base
<222> LOCATION: (507)..(507)
<223> OTHER INFORMATION: a, c, g, t, unknown or other
<220> FEATURE:
<221> NAME/KEY: modified_base
<222> LOCATION: (514)..(514)
<223> OTHER INFORMATION: a, c, g, t, unknown or other
<220> FEATURE:
<221> NAME/KEY: modified_base
<222> LOCATION: (518)..(518)
<223> OTHER INFORMATION: a, c, g, t, unknown or other
<220> FEATURE:
<221> NAME/KEY: modified_base
<222> LOCATION: (538)..(538)
<223> OTHER INFORMATION: a, c, g, t, unknown or other
<220> FEATURE:
<221> NAME/KEY: modified_base
<222> LOCATION: (542)..(542)
<223> OTHER INFORMATION: a, c, g, t, unknown or other
<220> FEATURE:
<221> NAME/KEY: modified_base
<222> LOCATION: (568)..(568)
<223> OTHER INFORMATION: a, c, g, t, unknown or other
<220> FEATURE:
<221> NAME/KEY: modified_base
<222> LOCATION: (573)..(573)
<223> OTHER INFORMATION: a, c, g, t, unknown or other
<220> FEATURE:
<221> NAME/KEY: modified_base
<222> LOCATION: (588)..(588)
<223> OTHER INFORMATION: a, c, g, t, unknown or other
<220> FEATURE:
<221> NAME/KEY: modified_base
<222> LOCATION: (599)..(599)
<223> OTHER INFORMATION: a, c, g, t, unknown or other
<220> FEATURE:
<221> NAME/KEY: modified_base
<222> LOCATION: (613)..(614)
<223> OTHER INFORMATION: a, c, g, t, unknown or other
<220> FEATURE:
<221> NAME/KEY: modified_base
<222> LOCATION: (617)..(618)
<223> OTHER INFORMATION: a, c, g, t, unknown or other
```

```
<220> FEATURE:
<221> NAME/KEY: modified_base
<222> LOCATION: (626)..(626)
<223> OTHER INFORMATION: a, c, g, t, unknown or other
<220> FEATURE:
<221> NAME/KEY: modified_base
<222> LOCATION: (653)..(656)
<223> OTHER INFORMATION: a, c, g, t, unknown or other
<220> FEATURE:
<221> NAME/KEY: modified_base
<222> LOCATION: (659)..(659)
<223> OTHER INFORMATION: a, c, g, t, unknown or other
<220> FEATURE:
<221> NAME/KEY: modified_base
<222> LOCATION: (673)..(673)
<223> OTHER INFORMATION: a, c, g, t, unknown or other
<220> FEATURE:
<221> NAME/KEY: modified_base
<222> LOCATION: (680)..(680)
<223> OTHER INFORMATION: a, c, g, t, unknown or other

<400> SEQUENCE: 9
nnttgttggt ncagtnggat gtctatataa gcagagnctc tggctaacta gnagaaccca      60
ctgcttactg gcttatcgaa attaatacga ctcactatag ggagacccaa gcttggtacc     120
gagctcngat ccactagtaa cggccgccag tgtgctggaa ttcttcagcg cccacgacca     180
gtgactatcc cctgctcaag ctgtgattcc gagacccctg ccaccactac tgcattcacg     240
ggggatccca ngctaatggg actcgacatg ggttgccccc acggcanctc cctacanctt     300
gggccanctn cacttttccc aaagnccctaa atctccgcct ctcggctcnt taangttngg     360
ggtgggganc tgtgctgtgg gaaacaaccc agaananact tgggcagcat ggngctactg     420
aaagtncatt ttgaacagaa naaacggtcc antttggccc aaggnncnng ntcctaaant     480
ggttctccnt ntttggtngn ntccncnctt tccncctngg aatgttcctg aaaaattnaa     540
cnccaaaaaa gaacaaattg aaaaatantt ctnaaaaccc ttttgttncc cccccccna     600 aaagggaagg ggnnggnncc tttttnttcc cccccgggg ggggaaaatt ttnnnnaanc     660
cccccccccc ccnttttttn a                                               681

<210> SEQ ID NO 10
<211> LENGTH: 612
<212> TYPE: DNA
<213> ORGANISM: Artificial Sequence
<220> FEATURE:
<223> OTHER INFORMATION: Description of Artificial Sequence: Synthetic
      human peripherin hybrid DNA
<220> FEATURE:
<221> NAME/KEY: modified_base
<222> LOCATION: (7)..(7)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (85)..(85)
<223> OTHER INFORMATION: a, c, g, t, unknown or other
<220> FEATURE:
<221> NAME/KEY: modified_base
<222> LOCATION: (179)..(179)
<223> OTHER INFORMATION: a, c, g, t, unknown or other
<220> FEATURE:
<221> NAME/KEY: modified_base
<222> LOCATION: (270)..(270)
<223> OTHER INFORMATION: a, c, g, t, unknown or other
<220> FEATURE:
<221> NAME/KEY: modified_base
<222> LOCATION: (273)..(273)
<223> OTHER INFORMATION: a, c, g, t, unknown or other
<220> FEATURE:
```

```
<221> NAME/KEY: modified_base
<222> LOCATION: (360)..(360)
<223> OTHER INFORMATION: a, c, g, t, unknown or other
<220> FEATURE:
<221> NAME/KEY: modified_base
<222> LOCATION: (404)..(404)
<223> OTHER INFORMATION: a, c, g, t, unknown or other
<220> FEATURE:
<221> NAME/KEY: modified_base
<222> LOCATION: (408)..(408)
<223> OTHER INFORMATION: a, c, g, t, unknown or other
<220> FEATURE:
<221> NAME/KEY: modified_base
<222> LOCATION: (411)..(412)
<223> OTHER INFORMATION: a, c, g, t, unknown or other
<220> FEATURE:
<221> NAME/KEY: modified_base
<222> LOCATION: (418)..(418)
<223> OTHER INFORMATION: a, c, g, t, unknown or other
<220> FEATURE:
<221> NAME/KEY: modified_base
<222> LOCATION: (426)..(426)
<223> OTHER INFORMATION: a, c, g, t, unknown or other
<220> FEATURE:
<221> NAME/KEY: modified_base
<222> LOCATION: (434)..(434)
<223> OTHER INFORMATION: a, c, g, t, unknown or other
<220> FEATURE:
<221> NAME/KEY: modified_base
<222> LOCATION: (437)..(437)
<223> OTHER INFORMATION: a, c, g, t, unknown or other
<220> FEATURE:
<221> NAME/KEY: modified_base
<222> LOCATION: (445)..(445)
<223> OTHER INFORMATION: a, c, g, t, unknown or other
<220> FEATURE:
<221> NAME/KEY: modified_base
<222> LOCATION: (447)..(612)
<223> OTHER INFORMATION: a, c, g, t, unknown or other

<400> SEQUENCE: 10 ttatacncaca cactatangg agaccaagct tggtaccgag ctcggatcca ctagtaacgg      60
ccgccagtgt gctggaattc ttcancgccc aggaccagga ctatcccctg ctcaagctgt     120
gattccgaga cccctgccac cactactgca ttcacggggg atcccaggct agtgggacnc     180
gacatgggta tccccaggg cagctcccta cagcttgggc catctgcact tttcccaagg      240
ccctaagtct ccgcctctgg gctcgttaan gtntggggtg ggagctgtgc tgtgggaaac     300
aacccggact acacttggca agcatggcgc tgctgaaagt caagtttgaa cagaaaaaan     360
gggtcaagtt ggcccaaggg ctctggctca gggaaactgg gttnccncc nngttttngg      420 tttggntgca tcanctncca aaaanannnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nn                                                        612

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catggcgctg ctgaaagtca                                                  20

<210> SEQ ID NO 12
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catcttcagc ctgggactgt                                              20

<210> SEQ ID NO 13
<211> LENGTH: 610
<212> TYPE: DNA
<213> ORGANISM: Artificial Sequence
<220> FEATURE:
<223> OTHER INFORMATION: Description of Artificial Sequence: Synthetic
      human peripherin hybrid DNA
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (10)..(10)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (104)..(104)
<223> OTHER INFORMATION: a, c, g, t, unknown or other
<220> FEATURE:
<221> NAME/KEY: modified_base
<222> LOCATION: (377)..(377)
<223> OTHER INFORMATION: a, c, g, t, unknown or other
<220> FEATURE:
<221> NAME/KEY: modified_base
<222> LOCATION: (410)..(410)
<223> OTHER INFORMATION: a, c, g, t, unknown or other
<220> FEATURE:
<221> NAME/KEY: modified_base
<222> LOCATION: (414)..(414)
<223> OTHER INFORMATION: a, c, g, t, unknown or other
<220> FEATURE:
<221> NAME/KEY: modified_base
<222> LOCATION: (421)..(421)
<223> OTHER INFORMATION: a, c, g, t, unknown or other
<220> FEATURE:
<221> NAME/KEY: modified_base
<222> LOCATION: (437)..(437)
<223> OTHER INFORMATION: a, c, g, t, unknown or other
<220> FEATURE:
<221> NAME/KEY: modified_base
<222> LOCATION: (472)..(472)
<223> OTHER INFORMATION: a, c, g, t, unknown or other
<220> FEATURE:
<221> NAME/KEY: modified_base
<222> LOCATION: (483)..(483)
<223> OTHER INFORMATION: a, c, g, t, unknown or other
<220> FEATURE:
<221> NAME/KEY: modified_base
<222> LOCATION: (502)..(502)
<223> OTHER INFORMATION: a, c, g, t, unknown or other
<220> FEATURE:
<221> NAME/KEY: modified_base
<222> LOCATION: (526)..(526)
<223> OTHER INFORMATION: a, c, g, t, unknown or other
<220> FEATURE:
<221> NAME/KEY: modified_base
<222> LOCATION: (550)..(550)
<223> OTHER INFORMATION: a, c, g, t, unknown or other
<220> FEATURE:
<221> NAME/KEY: modified_base
```

```
<222> LOCATION: (556)..(556)
<223> OTHER INFORMATION: a, c, g, t, unknown or other
<220> FEATURE:
<221> NAME/KEY: modified_base
<222> LOCATION: (563)..(563)
<223> OTHER INFORMATION: a, c, g, t, unknown or other
<220> FEATURE:
<221> NAME/KEY: modified_base
<222> LOCATION: (585)..(585)
<223> OTHER INFORMATION: a, c, g, t, unknown or other
<220> FEATURE:
<221> NAME/KEY: modified_base
<222> LOCATION: (601)..(601)
<223> OTHER INFORMATION: a, c, g, t, unknown or other

<400> SEQUENCE: 13 ttttttntggn tntcnaatta atacgactca ctatagggag acccaagctt ggtaccgagc    60
tcggatccac tagtaacggc cgccagtgtg ctggaattct tcancgccca ggaccaggac   120
tatcccctgc tcaagctgtg attccgagac ccctgccacc actactgcat tcacggggat   180
cccaggctag tgggactcga catgggtagc ccccagggca gctccctaca gcttgggcca   240
tctgcacttt tcccaaggcc ctaagtctcc gcctctgggc tcgttaaggt ttggggtggg   300
agctgtgctg tgggaagcaa cccggactac acttggcaag catggcgcta ctgaaagtca   360
agtttgacca gaaaaacgg gtcaagttgg gcccaagggc tctgggctcn atgnaaacct    420
nggtttcccc cccctnttt gggctgggca tcatcatctt tcagcctggg antgttcctg    480
aanattgaac tcccaaagag ancgatgtga tgaataattc tgaaanccat tttgtgcccc   540
actcattgan aagganggggg tgnatcctgt ttcttcactc cctgntggaa aatgctacaa   600 nccctgaacc                                                           610

<210> SEQ ID NO 14
<211> LENGTH: 680
<212> TYPE: DNA
<213> ORGANISM: Artificial Sequence
<220> FEATURE:
<223> OTHER INFORMATION: Description of Artificial Sequence: Synthetic
      hammerhead ribozyme (termed Rz30) cloned in pCDNA3
<220> FEATURE:
<221> NAME/KEY: modified_base
<222> LOCATION: (2)..(2)
<223> OTHER INFORMATION: a, c, g, t, unknown or other
<220> FEATURE:
<221> NAME/KEY: modified_base
<222> LOCATION: (11)..(11)
<223> OTHER INFORMATION: a, c, g, t, unknown or other
<220> FEATURE:
<221> NAME/KEY: modified_base
<222> LOCATION: (19)..(19)
<223> OTHER INFORMATION: a, c, g, t, unknown or other
<220> FEATURE:
<221> NAME/KEY: modified_base
<222> LOCATION: (371)..(371)
<223> OTHER INFORMATION: a, c, g, t, unknown or other
<220> FEATURE:
<221> NAME/KEY: modified_base
<222> LOCATION: (376)..(376)
<223> OTHER INFORMATION: a, c, g, t, unknown or other
<220> FEATURE:
<221> NAME/KEY: modified_base
<222> LOCATION: (402)..(402)
<223> OTHER INFORMATION: a, c, g, t, unknown or other
<220> FEATURE:
<221> NAME/KEY: modified_base
<222> LOCATION: (449)..(449)
<223> OTHER INFORMATION: a, c, g, t, unknown or other
<220> FEATURE:
<221> NAME/KEY: modified_base
<222> LOCATION: (453)..(454)
<223> OTHER INFORMATION: a, c, g, t, unknown or other
<220> FEATURE:
```

-continued

```
<221> NAME/KEY: modified_base
<222> LOCATION: (464)..(464)
<223> OTHER INFORMATION: a, c, g, t, unknown or other
<220> FEATURE:
<221> NAME/KEY: modified_base
<222> LOCATION: (475)..(475)
<223> OTHER INFORMATION: a, c, g, t, unknown or other
<220> FEATURE:
<221> NAME/KEY: modified_base
<222> LOCATION: (485)..(486)
<223> OTHER INFORMATION: a, c, g, t, unknown or other
<220> FEATURE:
<221> NAME/KEY: modified_base
<222> LOCATION: (494)..(494)
<223> OTHER INFORMATION: a, c, g, t, unknown or other
<220> FEATURE:
<221> NAME/KEY: modified_base
<222> LOCATION: (496)..(497)
<223> OTHER INFORMATION: a, c, g, t, unknown or other
<220> FEATURE:
<221> NAME/KEY: modified_base
<222> LOCATION: (511)..(511)
<223> OTHER INFORMATION: a, c, g, t, unknown or other
<220> FEATURE:
<221> NAME/KEY: modified_base
<222> LOCATION: (519)..(519)
<223> OTHER INFORMATION: a, c, g, t, unknown or other
<220> FEATURE:
<221> NAME/KEY: modified_base
<222> LOCATION: (524)..(524)
<223> OTHER INFORMATION: a, c, g, t, unknown or other
<220> FEATURE:
<221> NAME/KEY: modified_base
<222> LOCATION: (526)..(527)
<223> OTHER INFORMATION: a, c, g, t, unknown or other
<220> FEATURE:
<221> NAME/KEY: modified_base
<222> LOCATION: (529)..(530)
<223> OTHER INFORMATION: a, c, g, t, unknown or other
<220> FEATURE:
<221> NAME/KEY: modified_base
<222> LOCATION: (533)..(538)
<223> OTHER INFORMATION: a, c, g, t, unknown or other
<220> FEATURE:
<221> NAME/KEY: modified_base
<222> LOCATION: (541)..(542)
<223> OTHER INFORMATION: a, c, g, t, unknown or other
<220> FEATURE:
<221> NAME/KEY: modified_base
<222> LOCATION: (548)..(549)
<223> OTHER INFORMATION: a, c, g, t, unknown or other
<220> FEATURE:
<221> NAME/KEY: modified_base
<222> LOCATION: (551)..(552)
<223> OTHER INFORMATION: a, c, g, t, unknown or other
<220> FEATURE:
<221> NAME/KEY: modified_base
<222> LOCATION: (554)..(554)
<223> OTHER INFORMATION: a, c, g, t, unknown or other
<220> FEATURE:
<221> NAME/KEY: modified_base
<222> LOCATION: (556)..(557)
<223> OTHER INFORMATION: a, c, g, t, unknown or other
<220> FEATURE:
<221> NAME/KEY: modified_base
<222> LOCATION: (560)..(561)
<223> OTHER INFORMATION: a, c, g, t, unknown or other
<220> FEATURE:
<221> NAME/KEY: modified_base
<222> LOCATION: (565)..(570)
<223> OTHER INFORMATION: a, c, g, t, unknown or other
<220> FEATURE:
<221> NAME/KEY: modified_base
<222> LOCATION: (572)..(572)
<223> OTHER INFORMATION: a, c, g, t, unknown or other
<220> FEATURE:
<221> NAME/KEY: modified_base
<222> LOCATION: (574)..(574)
<223> OTHER INFORMATION: a, c, g, t, unknown or other
<220> FEATURE:
```

-continued

```
<221> NAME/KEY: modified_base
<222> LOCATION: (576)..(578)
<223> OTHER INFORMATION: a, c, g, t, unknown or other
<220> FEATURE:
<221> NAME/KEY: modified_base
<222> LOCATION: (581)..(585)
<223> OTHER INFORMATION: a, c, g, t, unknown or other
<220> FEATURE:
<221> NAME/KEY: modified_base
<222> LOCATION: (587)..(588)
<223> OTHER INFORMATION: a, c, g, t, unknown or other
<220> FEATURE:
<221> NAME/KEY: modified_base
<222> LOCATION: (592)..(599)
<223> OTHER INFORMATION: a, c, g, t, unknown or other
<220> FEATURE:
<221> NAME/KEY: modified_base
<222> LOCATION: (601)..(605)
<223> OTHER INFORMATION: a, c, g, t, unknown or other
<220> FEATURE:
<221> NAME/KEY: modified_base
<222> LOCATION: (611)..(611)
<223> OTHER INFORMATION: a, c, g, t, unknown or other
<220> FEATURE:
<221> NAME/KEY: modified_base
<222> LOCATION: (613)..(616)
<223> OTHER INFORMATION: a, c, g, t, unknown or other
<220> FEATURE:
<221> NAME/KEY: modified_base
<222> LOCATION: (618)..(618)
<223> OTHER INFORMATION: a, c, g, t, unknown or other
<220> FEATURE:
<221> NAME/KEY: modified_base
<222> LOCATION: (622)..(623)
<223> OTHER INFORMATION: a, c, g, t, unknown or other
<220> FEATURE:
<221> NAME/KEY: modified_base
<222> LOCATION: (625)..(628)
<223> OTHER INFORMATION: a, c, g, t, unknown or other
<220> FEATURE:
<221> NAME/KEY: modified_base
<222> LOCATION: (631)..(631)
<223> OTHER INFORMATION: a, c, g, t, unknown or other
<220> FEATURE:
<221> NAME/KEY: modified_base
<222> LOCATION: (633)..(638)
<223> OTHER INFORMATION: a, c, g, t, unknown or other
<220> FEATURE:
<221> NAME/KEY: modified_base
<222> LOCATION: (640)..(642)
<223> OTHER INFORMATION: a, c, g, t, unknown or other
<220> FEATURE:
<221> NAME/KEY: modified_base
<222> LOCATION: (644)..(652)
<223> OTHER INFORMATION: a, c, g, t, unknown or other
<220> FEATURE:
<221> NAME/KEY: modified_base
<222> LOCATION: (654)..(654)
<223> OTHER INFORMATION: a, c, g, t, unknown or other
<220> FEATURE:
<221> NAME/KEY: modified_base
<222> LOCATION: (657)..(658)
<223> OTHER INFORMATION: a, c, g, t, unknown or other
<220> FEATURE:
<221> NAME/KEY: modified_base
<222> LOCATION: (664)..(667)
<223> OTHER INFORMATION: a, c, g, t, unknown or other
<220> FEATURE:
<221> NAME/KEY: modified_base
<222> LOCATION: (669)..(676)
<223> OTHER INFORMATION: a, c, g, t, unknown or other
<220> FEATURE:
<221> NAME/KEY: modified_base
<222> LOCATION: (678)..(678)
<223> OTHER INFORMATION: a, c, g, t, unknown or other
<220> FEATURE:
<221> NAME/KEY: modified_base
<222> LOCATION: (680)..(680)
<223> OTHER INFORMATION: a, c, g, t, unknown or other
```

<400> SEQUENCE: 14

| | | | | | |
|---|---|---|---|---|---|
| cnttggtggt | nctgtcggnt | gtctatataa | gcagagctct | ctggctaact | agaagaaccc | 60 |
| actgcttact | ggcttatcga | aattaatacg | actcactata | gggagaccca | agcttacttt | 120 |
| cagctgatga | gtccgtgagg | acgaaagcgc | catctagagg | gccctattct | atagtgtcac | 180 |
| ctaaatgcta | gagctcgctg | atcagcctcg | actgtgcctt | ctagttgcca | gccatctgtt | 240 |
| gtttgcccct | cccccgtgcc | ttccttgacc | ctggaaggtg | ccactcccac | tgtcctttcc | 300 |
| taataaaatg | atgaaattgc | atcgcattgt | ctgagtaggt | gtcattctat | tctgggggt | 360 |
| gggtggggca | ngacancaag | ggggaagatt | gggaaaacaa | tncccgcctg | ctggggatgc | 420 |
| ggtgggctct | atggcttctg | aggcgaaana | acnnctgggg | tctnggggt | tcccnccccc | 480 |
| ctgtnncggc | cttnanncgg | gggttttgtg | ntcccccnc | ttancnntnn | ttnnnnnncc | 540 |
| nnccccnnc | nntncnttn | ntccnnnnn | tncnnntt | nnnngnntc | cnnnnnnnt | 600 |
| nnnnngggc | ncnnnngntc | cnntnnnncc | ncnnnnncn | nncnnnnnn | nntntgnngg | 660 |
| cccnnnncnn | nnnnncncn | | | | | 680 |

<210> SEQ ID NO 15
<211> LENGTH: 691
<212> TYPE: DNA
<213> ORGANISM: Artificial Sequence
<220> FEATURE:
<223> OTHER INFORMATION: Description of Artificial Sequence: Synthetic
      hammerhead ribozyme (termed Rz31) cloned in pCDNA3
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (14)..(14)
<223> OTHER INFORMATION: a, c, g, t, unknown or other
<220> FEATURE:
<221> NAME/KEY: modified_base
<222> LOCATION: (25)..(25)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (44)..(44)
<223> OTHER INFORMATION: a, c, g, t, unknown or other
<220> FEATURE:
<221> NAME/KEY: modified_base
<222> LOCATION: (50)..(50)
<223> OTHER INFORMATION: a, c, g, t, unknown or other
<220> FEATURE:
<221> NAME/KEY: modified_base
<222> LOCATION: (53)..(54)
<223> OTHER INFORMATION: a, c, g, t, unknown or other
<220> FEATURE:
<221> NAME/KEY: modified_base
<222> LOCATION: (97)..(97)
<223> OTHER INFORMATION: a, c, g, t, unknown or other
<220> FEATURE:
<221> NAME/KEY: modified_base
<222> LOCATION: (153)..(153)
<223> OTHER INFORMATION: a, c, g, t, unknown or other
<220> FEATURE:
<221> NAME/KEY: modified_base
<222> LOCATION: (293)..(293)
<223> OTHER INFORMATION: a, c, g, t, unknown or other
<220> FEATURE:
<221> NAME/KEY: modified_base

```
<222> LOCATION: (311)..(312)
<223> OTHER INFORMATION: a, c, g, t, unknown or other
<220> FEATURE:
<221> NAME/KEY: modified_base
<222> LOCATION: (341)..(341)
<223> OTHER INFORMATION: a, c, g, t, unknown or other
<220> FEATURE:
<221> NAME/KEY: modified_base
<222> LOCATION: (368)..(368)
<223> OTHER INFORMATION: a, c, g, t, unknown or other
<220> FEATURE:
<221> NAME/KEY: modified_base
<222> LOCATION: (373)..(373)
<223> OTHER INFORMATION: a, c, g, t, unknown or other
<220> FEATURE:
<221> NAME/KEY: modified_base
<222> LOCATION: (400)..(400)
<223> OTHER INFORMATION: a, c, g, t, unknown or other
<220> FEATURE:
<221> NAME/KEY: modified_base
<222> LOCATION: (430)..(430)
<223> OTHER INFORMATION: a, c, g, t, unknown or other
<220> FEATURE:
<221> NAME/KEY: modified_base
<222> LOCATION: (433)..(433)
<223> OTHER INFORMATION: a, c, g, t, unknown or other
<220> FEATURE:
<221> NAME/KEY: modified_base
<222> LOCATION: (436)..(436)
<223> OTHER INFORMATION: a, c, g, t, unknown or other
<220> FEATURE:
<221> NAME/KEY: modified_base
<222> LOCATION: (439)..(439)
<223> OTHER INFORMATION: a, c, g, t, unknown or other
<220> FEATURE:
<221> NAME/KEY: modified_base
<222> LOCATION: (446)..(446)
<223> OTHER INFORMATION: a, c, g, t, unknown or other
<220> FEATURE:
<221> NAME/KEY: modified_base
<222> LOCATION: (456)..(456)
<223> OTHER INFORMATION: a, c, g, t, unknown or other
<220> FEATURE:
<221> NAME/KEY: modified_base
<222> LOCATION: (469)..(469)
<223> OTHER INFORMATION: a, c, g, t, unknown or other
<220> FEATURE:
<221> NAME/KEY: modified_base
<222> LOCATION: (474)..(475)
<223> OTHER INFORMATION: a, c, g, t, unknown or other
<220> FEATURE:
<221> NAME/KEY: modified_base
<222> LOCATION: (479)..(480)
<223> OTHER INFORMATION: a, c, g, t, unknown or other
<220> FEATURE:
<221> NAME/KEY: modified_base
<222> LOCATION: (487)..(487)
<223> OTHER INFORMATION: a, c, g, t, unknown or other
<220> FEATURE:
<221> NAME/KEY: modified_base
<222> LOCATION: (494)..(494)
<223> OTHER INFORMATION: a, c, g, t, unknown or other
<220> FEATURE:
<221> NAME/KEY: modified_base
<222> LOCATION: (496)..(496)
<223> OTHER INFORMATION: a, c, g, t, unknown or other
<220> FEATURE:
<221> NAME/KEY: modified_base
<222> LOCATION: (501)..(501)
<223> OTHER INFORMATION: a, c, g, t, unknown or other
<220> FEATURE:
<221> NAME/KEY: modified_base
<222> LOCATION: (505)..(505)
<223> OTHER INFORMATION: a, c, g, t, unknown or other
<220> FEATURE:
<221> NAME/KEY: modified_base
<222> LOCATION: (521)..(522)
<223> OTHER INFORMATION: a, c, g, t, unknown or other
<220> FEATURE:
<221> NAME/KEY: modified_base
```

```
<222> LOCATION: (525)..(525)
<223> OTHER INFORMATION: a, c, g, t, unknown or other
<220> FEATURE:
<221> NAME/KEY: modified_base
<222> LOCATION: (527)..(527)
<223> OTHER INFORMATION: a, c, g, t, unknown or other
<220> FEATURE:
<221> NAME/KEY: modified_base
<222> LOCATION: (532)..(532)
<223> OTHER INFORMATION: a, c, g, t, unknown or other
<220> FEATURE:
<221> NAME/KEY: modified_base
<222> LOCATION: (534)..(534)
<223> OTHER INFORMATION: a, c, g, t, unknown or other
<220> FEATURE:
<221> NAME/KEY: modified_base
<222> LOCATION: (537)..(537)
<223> OTHER INFORMATION: a, c, g, t, unknown or other
<220> FEATURE:
<221> NAME/KEY: modified_base
<222> LOCATION: (545)..(546)
<223> OTHER INFORMATION: a, c, g, t, unknown or other
<220> FEATURE:
<221> NAME/KEY: modified_base
<222> LOCATION: (551)..(553)
<223> OTHER INFORMATION: a, c, g, t, unknown or other
<220> FEATURE:
<221> NAME/KEY: modified_base
<222> LOCATION: (559)..(559)
<223> OTHER INFORMATION: a, c, g, t, unknown or other
<220> FEATURE:
<221> NAME/KEY: modified_base
<222> LOCATION: (584)..(584)
<223> OTHER INFORMATION: a, c, g, t, unknown or other
<220> FEATURE:
<221> NAME/KEY: modified_base
<222> LOCATION: (586)..(586)
<223> OTHER INFORMATION: a, c, g, t, unknown or other
<220> FEATURE:
<221> NAME/KEY: modified_base
<222> LOCATION: (590)..(590)
<223> OTHER INFORMATION: a, c, g, t, unknown or other
<220> FEATURE:
<221> NAME/KEY: modified_base
<222> LOCATION: (595)..(595)
<223> OTHER INFORMATION: a, c, g, t, unknown or other
<220> FEATURE:
<221> NAME/KEY: modified_base
<222> LOCATION: (604)..(604)
<223> OTHER INFORMATION: a, c, g, t, unknown or other
<220> FEATURE:
<221> NAME/KEY: modified_base
<222> LOCATION: (609)..(609)
<223> OTHER INFORMATION: a, c, g, t, unknown or other
<220> FEATURE:
<221> NAME/KEY: modified_base
<222> LOCATION: (626)..(626)
<223> OTHER INFORMATION: a, c, g, t, unknown or other
<220> FEATURE:
<221> NAME/KEY: modified_base
<222> LOCATION: (630)..(630)
<223> OTHER INFORMATION: a, c, g, t, unknown or other
<220> FEATURE:
<221> NAME/KEY: modified_base
<222> LOCATION: (633)..(633)
<223> OTHER INFORMATION: a, c, g, t, unknown or other
<220> FEATURE:
<221> NAME/KEY: modified_base
<222> LOCATION: (635)..(635)
<223> OTHER INFORMATION: a, c, g, t, unknown or other
<220> FEATURE:
<221> NAME/KEY: modified_base
<222> LOCATION: (637)..(637)
<223> OTHER INFORMATION: a, c, g, t, unknown or other
<220> FEATURE:
<221> NAME/KEY: modified_base
<222> LOCATION: (644)..(647)
<223> OTHER INFORMATION: a, c, g, t, unknown or other
<220> FEATURE:
<221> NAME/KEY: modified_base
```

```
<222> LOCATION: (650)..(650)
<223> OTHER INFORMATION: a, c, g, t, unknown or other
<220> FEATURE:
<221> NAME/KEY: modified_base
<222> LOCATION: (653)..(653)
<223> OTHER INFORMATION: a, c, g, t, unknown or other
<220> FEATURE:
<221> NAME/KEY: modified_base
<222> LOCATION: (657)..(657)
<223> OTHER INFORMATION: a, c, g, t, unknown or other
<220> FEATURE:
<221> NAME/KEY: modified_base
<222> LOCATION: (659)..(659)
<223> OTHER INFORMATION: a, c, g, t, unknown or other
<220> FEATURE:
<221> NAME/KEY: modified_base
<222> LOCATION: (661)..(661)
<223> OTHER INFORMATION: a, c, g, t, unknown or other
<220> FEATURE:
<221> NAME/KEY: modified_base
<222> LOCATION: (666)..(666)
<223> OTHER INFORMATION: a, c, g, t, unknown or other
<220> FEATURE:
<221> NAME/KEY: modified_base
<222> LOCATION: (669)..(669)
<223> OTHER INFORMATION: a, c, g, t, unknown or other
<220> FEATURE:
<221> NAME/KEY: modified_base
<222> LOCATION: (671)..(671)
<223> OTHER INFORMATION: a, c, g, t, unknown or other
<220> FEATURE:
<221> NAME/KEY: modified_base
<222> LOCATION: (673)..(674)
<223> OTHER INFORMATION: a, c, g, t, unknown or other
<220> FEATURE:
<221> NAME/KEY: modified_base
<222> LOCATION: (678)..(678)
<223> OTHER INFORMATION: a, c, g, t, unknown or other

<400> SEQUENCE: 15
nntttntcct acgnccgttt taaananaac cagaccctct gganaattan atnnccactg    60
cttactggct tatcgaaatc aatacgactc actatangga gacccaagct tacagtccct   120
gatgagtccg tgaggacgaa aggctgaatc tanagggccc tattctatag tgtcacctaa   180
atgctagagc tcgctgatca gcctcgactg tgccttctaa ttgccagcca tctgttgttt   240
gcccctcccc cgtgccttcc ttgaccctgg aaggtgccac tcccactgtc ctntcctaat   300
aaaatgatga nnttgcatcg cattgtctga gtaagtgtca ntctattctg ggggtgggg    360 tggggcanga cancaagggg gaagattggg aaaaacattn cacgcatgcc ggggatgcg    420 gtgggctctn ttngcntcng aaggcngaaa aaaacnactg gggccctang ggtnncccnn   480
tcccccntgt aacngnccct naacncgggg gtttgtggtt nnccnanctt ancnctnaac   540 ttccnnccc nnnccccnc tcttcccttt tcctccatc tccncntttn cccgntctcc     600
cttncactna aatgggggcc cctacngggn ctntntntct cttnnnnccn ccnccnana   660 natatnctng ntnnttcncc tctcggcccc t                                 691

<210> SEQ ID NO 16
<211> LENGTH: 805
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(1)
<223> OTHER INFORMATION: a, c, g, t, unknown or other
<220> FEATURE:
<221> NAME/KEY: modified_base
<222> LOCATION: (4)..(4)
```

-continued

```
<223> OTHER INFORMATION: a, c, g, t, unknown or other
<220> FEATURE:
<221> NAME/KEY: modified_base
<222> LOCATION: (7)..(7)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (25)..(25)
<223> OTHER INFORMATION: a, c, g, t, unknown or other
<220> FEATURE:
<221> NAME/KEY: modified_base
<222> LOCATION: (33)..(34)
<223> OTHER INFORMATION: a, c, g, t, unknown or other
<220> FEATURE:
<221> NAME/KEY: modified_base
<222> LOCATION: (41)..(41)
<223> OTHER INFORMATION: a, c, g, t, unknown or other
<220> FEATURE:
<221> NAME/KEY: modified_base
<222> LOCATION: (122)..(122)
<223> OTHER INFORMATION: a, c, g, t, unknown or other
<220> FEATURE:
<221> NAME/KEY: modified_base
<222> LOCATION: (153)..(153)
<223> OTHER INFORMATION: a, c, g, t, unknown or other
<220> FEATURE:
<221> NAME/KEY: modified_base
<222> LOCATION: (251)..(251)
<223> OTHER INFORMATION: a, c, g, t, unknown or other
<220> FEATURE:
<221> NAME/KEY: modified_base
<222> LOCATION: (308)..(308)
<223> OTHER INFORMATION: a, c, g, t, unknown or other
<220> FEATURE:
<221> NAME/KEY: modified_base
<222> LOCATION: (311)..(311)
<223> OTHER INFORMATION: a, c, g, t, unknown or other
<220> FEATURE:
<221> NAME/KEY: modified_base
<222> LOCATION: (346)..(346)
<223> OTHER INFORMATION: a, c, g, t, unknown or other
<220> FEATURE:
<221> NAME/KEY: modified_base
<222> LOCATION: (366)..(366)
<223> OTHER INFORMATION: a, c, g, t, unknown or other
<220> FEATURE:
<221> NAME/KEY: modified_base
<222> LOCATION: (416)..(416)
<223> OTHER INFORMATION: a, c, g, t, unknown or other
<220> FEATURE:
<221> NAME/KEY: modified_base
<222> LOCATION: (459)..(459)
<223> OTHER INFORMATION: a, c, g, t, unknown or other
<220> FEATURE:
<221> NAME/KEY: modified_base
<222> LOCATION: (497)..(497)
<223> OTHER INFORMATION: a, c, g, t, unknown or other
<220> FEATURE:
<221> NAME/KEY: modified_base
<222> LOCATION: (563)..(563)
<223> OTHER INFORMATION: a, c, g, t, unknown or other
<220> FEATURE:
<221> NAME/KEY: modified_base
<222> LOCATION: (567)..(567)
<223> OTHER INFORMATION: a, c, g, t, unknown or other
<220> FEATURE:
<221> NAME/KEY: modified_base
<222> LOCATION: (600)..(600)
<223> OTHER INFORMATION: a, c, g, t, unknown or other
<220> FEATURE:
<221> NAME/KEY: modified_base
<222> LOCATION: (616)..(616)
<223> OTHER INFORMATION: a, c, g, t, unknown or other
<220> FEATURE:
<221> NAME/KEY: modified_base
<222> LOCATION: (631)..(631)
```

-continued

```
<223> OTHER INFORMATION: a, c, g, t, unknown or other
<220> FEATURE:
<221> NAME/KEY: modified_base
<222> LOCATION: (641)..(641)
<223> OTHER INFORMATION: a, c, g, t, unknown or other
<220> FEATURE:
<221> NAME/KEY: modified_base
<222> LOCATION: (682)..(683)
<223> OTHER INFORMATION: a, c, g, t, unknown or other
<220> FEATURE:
<221> NAME/KEY: modified_base
<222> LOCATION: (685)..(685)
<223> OTHER INFORMATION: a, c, g, t, unknown or other
<220> FEATURE:
<221> NAME/KEY: modified_base
<222> LOCATION: (691)..(691)
<223> OTHER INFORMATION: a, c, g, t, unknown or other
<220> FEATURE:
<221> NAME/KEY: modified_base
<222> LOCATION: (695)..(695)
<223> OTHER INFORMATION: a, c, g, t, unknown or other
<220> FEATURE:
<221> NAME/KEY: modified_base
<222> LOCATION: (698)..(719)
<223> OTHER INFORMATION: a, c, g, t, unknown or other
<220> FEATURE:
<221> NAME/KEY: modified_base
<222> LOCATION: (732)..(732)
<223> OTHER INFORMATION: a, c, g, t, unknown or other
<220> FEATURE:
<221> NAME/KEY: modified_base
<222> LOCATION: (748)..(748)
<223> OTHER INFORMATION: a, c, g, t, unknown or other
<220> FEATURE:
<221> NAME/KEY: modified_base
<222> LOCATION: (750)..(751)
<223> OTHER INFORMATION: a, c, g, t, unknown or other
<220> FEATURE:
<221> NAME/KEY: modified_base
<222> LOCATION: (755)..(755)
<223> OTHER INFORMATION: a, c, g, t, unknown or other
<220> FEATURE:
<221> NAME/KEY: modified_base
<222> LOCATION: (757)..(757)
<223> OTHER INFORMATION: a, c, g, t, unknown or other
<220> FEATURE:
<221> NAME/KEY: modified_base
<222> LOCATION: (768)..(768)
<223> OTHER INFORMATION: a, c, g, t, unknown or other
<220> FEATURE:
<221> NAME/KEY: modified_base
<222> LOCATION: (773)..(773)
<223> OTHER INFORMATION: a, c, g, t, unknown or other
<220> FEATURE:
<221> NAME/KEY: modified_base
<222> LOCATION: (776)..(776)
<223> OTHER INFORMATION: a, c, g, t, unknown or other
<220> FEATURE:
<221> NAME/KEY: modified_base
<222> LOCATION: (783)..(783)
<223> OTHER INFORMATION: a, c, g, t, unknown or other
<220> FEATURE:
<221> NAME/KEY: modified_base
<222> LOCATION: (787)..(787)
<223> OTHER INFORMATION: a, c, g, t, unknown or other
<220> FEATURE:
<221> NAME/KEY: modified_base
<222> LOCATION: (792)..(792)
<223> OTHER INFORMATION: a, c, g, t, unknown or other
<220> FEATURE:
<221> NAME/KEY: modified_base
<222> LOCATION: (795)..(795)
<223> OTHER INFORMATION: a, c, g, t, unknown or other
<220> FEATURE:
<221> NAME/KEY: modified_base
<222> LOCATION: (802)..(805)
<223> OTHER INFORMATION: a, c, g, t, unknown or other

<400> SEQUENCE: 16
```

-continued

```
ntcncgncat ttaancaggc caggnctacc gcnnggtcca ngtaggccgg gagccccagc      60
aacgccggga aggccagcag cacccttggc accagtaagg ccgtttgctc caggattacc     120
angaggtcca acggggccgg agaggcctgg aanaccactt caccacgggg aaccggcggg     180
tccagtagga ccagcgttac caacagctcc aatttcaccc ttggggccag gggcacctgg     240
gaagcctgga nggccagcag accaatggga ccagcaggac cacggaccac acttccatca     300
ctgctttngc ncagctgggc aagggcacaa cacttctctc tcacangaac ccacggctcc     360
tgtttnactg aattccattt cacagggcac agttcacctt cacacaagaa cacggntgtc     420
cttcatcatc agacatgttt ccctaatgct tgagcagant cagattcagg aaacacacac     480
ctttgtccac atctctncac agtctcggtt tcaggtacac tcccacctgc agaggcactg     540
accaacctga gacattgaca ttncagncca cagtctgaac tgagcgggca cgccatggcn     600
agtcatacct gtcagnatca tcttctctta ncattcccaa ngggcagaat gaaagctgac     660
tccccaatgt cttattttta annangggttt naaanaannn nnnnnnnnnn nnnnnnnnnc     720
cccccccctt tngggtttat tatctatncn ncccntngga tatctttncc ccnttnccccc    780 ctnaaanttt tnttntttt tnnnn                                            805
```

<210> SEQ ID NO 17
<211> LENGTH: 797
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (13)..(13)
<223> OTHER INFORMATION: a, c, g, t, unknown or other
<220> FEATURE:
<221> NAME/KEY: modified_base
<222> LOCATION: (54)..(54)
<223> OTHER INFORMATION: a, c, g, t, unknown or other
<220> FEATURE:
<221> NAME/KEY: modified_base
<222> LOCATION: (67)..(67)
<223> OTHER INFORMATION: a, c, g, t, unknown or other
<220> FEATURE:
<221> NAME/KEY: modified_base
<222> LOCATION: (95)..(95)
<223> OTHER INFORMATION: a, c, g, t, unknown or other
<220> FEATURE:
<221> NAME/KEY: modified_base
<222> LOCATION: (140)..(140)
<223> OTHER INFORMATION: a, c, g, t, unknown or other
<220> FEATURE:
<221> NAME/KEY: modified_base
<222> LOCATION: (183)..(183)
<223> OTHER INFORMATION: a, c, g, t, unknown or other
<220> FEATURE:
<221> NAME/KEY: modified_base
<222> LOCATION: (246)..(246)
<223> OTHER INFORMATION: a, c, g, t, unknown or other
<220> FEATURE:
<221> NAME/KEY: modified_base
<222> LOCATION: (266)..(266)
<223> OTHER INFORMATION: a, c, g, t, unknown or other
<220> FEATURE:
<221> NAME/KEY: modified_base
<222> LOCATION: (296)..(296)
<223> OTHER INFORMATION: a, c, g, t, unknown or other
<220> FEATURE:
<221> NAME/KEY: modified_base
<222> LOCATION: (302)..(302)
<223> OTHER INFORMATION: a, c, g, t, unknown or other
<220> FEATURE:
<221> NAME/KEY: modified_base
<222> LOCATION: (343)..(343)
<223> OTHER INFORMATION: a, c, g, t, unknown or other -continued

```
<220> FEATURE:
<221> NAME/KEY: modified_base
<222> LOCATION: (356)..(356)
<223> OTHER INFORMATION: a, c, g, t, unknown or other
<220> FEATURE:
<221> NAME/KEY: modified_base
<222> LOCATION: (402)..(402)
<223> OTHER INFORMATION: a, c, g, t, unknown or other
<220> FEATURE:
<221> NAME/KEY: modified_base
<222> LOCATION: (435)..(435)
<223> OTHER INFORMATION: a, c, g, t, unknown or other
<220> FEATURE:
<221> NAME/KEY: modified_base
<222> LOCATION: (444)..(444)
<223> OTHER INFORMATION: a, c, g, t, unknown or other
<220> FEATURE:
<221> NAME/KEY: modified_base
<222> LOCATION: (518)..(518)
<223> OTHER INFORMATION: a, c, g, t, unknown or other
<220> FEATURE:
<221> NAME/KEY: modified_base
<222> LOCATION: (538)..(538)
<223> OTHER INFORMATION: a, c, g, t, unknown or other
<220> FEATURE:
<221> NAME/KEY: modified_base
<222> LOCATION: (541)..(541)
<223> OTHER INFORMATION: a, c, g, t, unknown or other
<220> FEATURE:
<221> NAME/KEY: modified_base
<222> LOCATION: (548)..(548)
<223> OTHER INFORMATION: a, c, g, t, unknown or other
<220> FEATURE:
<221> NAME/KEY: modified_base
<222> LOCATION: (554)..(554)
<223> OTHER INFORMATION: a, c, g, t, unknown or other
<220> FEATURE:
<221> NAME/KEY: modified_base
<222> LOCATION: (560)..(560)
<223> OTHER INFORMATION: a, c, g, t, unknown or other
<220> FEATURE:
<221> NAME/KEY: modified_base
<222> LOCATION: (565)..(565)
<223> OTHER INFORMATION: a, c, g, t, unknown or other
<220> FEATURE:
<221> NAME/KEY: modified_base
<222> LOCATION: (589)..(590)
<223> OTHER INFORMATION: a, c, g, t, unknown or other
<220> FEATURE:
<221> NAME/KEY: modified_base
<222> LOCATION: (598)..(598)
<223> OTHER INFORMATION: a, c, g, t, unknown or other
<220> FEATURE:
<221> NAME/KEY: modified_base
<222> LOCATION: (611)..(611)
<223> OTHER INFORMATION: a, c, g, t, unknown or other
<220> FEATURE:
<221> NAME/KEY: modified_base
<222> LOCATION: (613)..(613)
<223> OTHER INFORMATION: a, c, g, t, unknown or other
<220> FEATURE:
<221> NAME/KEY: modified_base
<222> LOCATION: (623)..(623)
<223> OTHER INFORMATION: a, c, g, t, unknown or other
<220> FEATURE:
<221> NAME/KEY: modified_base
<222> LOCATION: (627)..(637)
<223> OTHER INFORMATION: a, c, g, t, unknown or other
<220> FEATURE:
<221> NAME/KEY: modified_base
<222> LOCATION: (641)..(641)
<223> OTHER INFORMATION: a, c, g, t, unknown or other
<220> FEATURE:
<221> NAME/KEY: modified_base
<222> LOCATION: (644)..(644)
<223> OTHER INFORMATION: a, c, g, t, unknown or other
<220> FEATURE:
<221> NAME/KEY: modified_base
<222> LOCATION: (646)..(646)
<223> OTHER INFORMATION: a, c, g, t, unknown or other
```

```
<220> FEATURE:
<221> NAME/KEY: modified_base
<222> LOCATION: (653)..(653)
<223> OTHER INFORMATION: a, c, g, t, unknown or other
<220> FEATURE:
<221> NAME/KEY: modified_base
<222> LOCATION: (659)..(659)
<223> OTHER INFORMATION: a, c, g, t, unknown or other
<220> FEATURE:
<221> NAME/KEY: modified_base
<222> LOCATION: (662)..(662)
<223> OTHER INFORMATION: a, c, g, t, unknown or other
<220> FEATURE:
<221> NAME/KEY: modified_base
<222> LOCATION: (664)..(664)
<223> OTHER INFORMATION: a, c, g, t, unknown or other
<220> FEATURE:
<221> NAME/KEY: modified_base
<222> LOCATION: (667)..(667)
<223> OTHER INFORMATION: a, c, g, t, unknown or other
<220> FEATURE:
<221> NAME/KEY: modified_base
<222> LOCATION: (683)..(683)
<223> OTHER INFORMATION: a, c, g, t, unknown or other
<220> FEATURE:
<221> NAME/KEY: modified_base
<222> LOCATION: (686)..(686)
<223> OTHER INFORMATION: a, c, g, t, unknown or other
<220> FEATURE:
<221> NAME/KEY: modified_base
<222> LOCATION: (688)..(688)
<223> OTHER INFORMATION: a, c, g, t, unknown or other
<220> FEATURE:
<221> NAME/KEY: modified_base
<222> LOCATION: (700)..(700)
<223> OTHER INFORMATION: a, c, g, t, unknown or other
<220> FEATURE:
<221> NAME/KEY: modified_base
<222> LOCATION: (720)..(720)
<223> OTHER INFORMATION: a, c, g, t, unknown or other
<220> FEATURE:
<221> NAME/KEY: modified_base
<222> LOCATION: (741)..(742)
<223> OTHER INFORMATION: a, c, g, t, unknown or other
<220> FEATURE:
<221> NAME/KEY: modified_base
<222> LOCATION: (754)..(754)
<223> OTHER INFORMATION: a, c, g, t, unknown or other
<220> FEATURE:
<221> NAME/KEY: modified_base
<222> LOCATION: (758)..(758)
<223> OTHER INFORMATION: a, c, g, t, unknown or other
<220> FEATURE:
<221> NAME/KEY: modified_base
<222> LOCATION: (760)..(760)
<223> OTHER INFORMATION: a, c, g, t, unknown or other
<220> FEATURE:
<221> NAME/KEY: modified_base
<222> LOCATION: (762)..(763)
<223> OTHER INFORMATION: a, c, g, t, unknown or other
<220> FEATURE:
<221> NAME/KEY: modified_base
<222> LOCATION: (768)..(768)
<223> OTHER INFORMATION: a, c, g, t, unknown or other
<220> FEATURE:
<221> NAME/KEY: modified_base
<222> LOCATION: (777)..(779)
<223> OTHER INFORMATION: a, c, g, t, unknown or other
<220> FEATURE:
<221> NAME/KEY: modified_base
<222> LOCATION: (783)..(783)
<223> OTHER INFORMATION: a, c, g, t, unknown or other
<220> FEATURE:
<221> NAME/KEY: modified_base
<222> LOCATION: (790)..(790)
<223> OTHER INFORMATION: a, c, g, t, unknown or other

<400> SEQUENCE: 17 cccctttaaaa canggccagg aataccgcgg ggtccaggga ggccgggacc ccancaacgc    60
```

-continued

```
cgggaangcc cagcagcacc cttggcacca gtaangccgt ttgctccagg attaccagga    120
ggtccaacgg ggccggagan gcctggaaga ccacttcacc acgggaacg gcgggaccag     180 cangaccagc gttaccaaca gctccaattt caccettggg gccaggggca cctgggaagc    240 ctggangcc agcagaccaa tgggancagc aggaccacgg gaccacactt ccatcnctgc     300
cnctggcacc agctgggcaa gggcacaaca cttctctctc acnaagaacc cacggntcct    360
gtttaactga attccatttc acagggcaca gttcaccttc anacagaaca cgggtgtcct    420
tcatcatcaa acatntttcc tatnccttga gcagaatcag attcaggaac acacactttg    480
tcacatctcc tcacagtctc ggtttcaggt aacactcnca cctgcagagg cactgacnaa    540
nctcaganat ttanattccn ctccncagtt tgaacttagg cgggccctnn catttggntt    600
gtcctaacct ntnggggtt ttncttnnnn nnnnnnnttt nacnantccc aanggggana    660
ananagntga ctcctatgtc ttnttntnaa aaggtttttn aaaaattaac ccccccctn    720 ttgggttatt tattttttt nnccccctt ttgngaancn tnncccntt ttccccnnna      780 aantttttn tttttt                                                    797
```

```
<210> SEQ ID NO 18
<211> LENGTH: 697
<212> TYPE: DNA
<213> ORGANISM: Artificial Sequence
<220> FEATURE:
<223> OTHER INFORMATION: Description of Artificial Sequence: Synthetic
      hammerhead ribozyme (termed Rz907) cloned in pCDNA3
<220> FEATURE:
<221> NAME/KEY: modified_base
<222> LOCATION: (1)..(1)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (20)..(20)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (44)..(44)
<223> OTHER INFORMATION: a, c, g, t, unknown or other
<220> FEATURE:
<221> NAME/KEY: modified_base
<222> LOCATION: (46)..(46)
<223> OTHER INFORMATION: a, c, g, t, unknown or other
<220> FEATURE:
<221> NAME/KEY: modified_base
<222> LOCATION: (74)..(74)
<223> OTHER INFORMATION: a, c, g, t, unknown or other
<220> FEATURE:
<221> NAME/KEY: modified_base
<222> LOCATION: (301)..(301)
<223> OTHER INFORMATION: a, c, g, t, unknown or other
<220> FEATURE:
<221> NAME/KEY: modified_base
<222> LOCATION: (327)..(327)
<223> OTHER INFORMATION: a, c, g, t, unknown or other
<220> FEATURE:
```

```
<221> NAME/KEY: modified_base
<222> LOCATION: (361)..(361)
<223> OTHER INFORMATION: a, c, g, t, unknown or other
<220> FEATURE:
<221> NAME/KEY: modified_base
<222> LOCATION: (366)..(366)
<223> OTHER INFORMATION: a, c, g, t, unknown or other
<220> FEATURE:
<221> NAME/KEY: modified_base
<222> LOCATION: (386)..(386)
<223> OTHER INFORMATION: a, c, g, t, unknown or other
<220> FEATURE:
<221> NAME/KEY: modified_base
<222> LOCATION: (459)..(459)
<223> OTHER INFORMATION: a, c, g, t, unknown or other
<220> FEATURE:
<221> NAME/KEY: modified_base
<222> LOCATION: (473)..(473)
<223> OTHER INFORMATION: a, c, g, t, unknown or other
<220> FEATURE:
<221> NAME/KEY: modified_base
<222> LOCATION: (495)..(495)
<223> OTHER INFORMATION: a, c, g, t, unknown or other
<220> FEATURE:
<221> NAME/KEY: modified_base
<222> LOCATION: (518)..(518)
<223> OTHER INFORMATION: a, c, g, t, unknown or other
<220> FEATURE:
<221> NAME/KEY: modified_base
<222> LOCATION: (590)..(590)
<223> OTHER INFORMATION: a, c, g, t, unknown or other
<220> FEATURE:
<221> NAME/KEY: modified_base
<222> LOCATION: (615)..(615)
<223> OTHER INFORMATION: a, c, g, t, unknown or other
<220> FEATURE:
<221> NAME/KEY: modified_base
<222> LOCATION: (640)..(640)
<223> OTHER INFORMATION: a, c, g, t, unknown or other
<220> FEATURE:
<221> NAME/KEY: modified_base
<222> LOCATION: (642)..(642)
<223> OTHER INFORMATION: a, c, g, t, unknown or other
<220> FEATURE:
<221> NAME/KEY: modified_base
<222> LOCATION: (654)..(654)
<223> OTHER INFORMATION: a, c, g, t, unknown or other
<220> FEATURE:
<221> NAME/KEY: modified_base
<222> LOCATION: (669)..(669)
<223> OTHER INFORMATION: a, c, g, t, unknown or other

<400> SEQUENCE: 18
nctttcnntc tnatncatan aagcaggccc tctnnaaaaa ctananttc  cactgcttac      60 tggcttatcg aaancaatac gactcactat agggagaccc aagcttcggc ggctgatgag    120
tccgtgagga cgaaaccagc atctagaggg ccctattcta tagtgtcacc taaatgctag    180
agctcgctga tcagcctcga ctgtgccttc tagttgccag ccatctgttg tttgcccctc    240
ccccgtgcct tccttgaccc tggaaggtgc cactcccact gtcctttcct aataaaatga    300
ngaaattgca tcgcattgtc tgagtangtg tcattctatt ctgggggtg  gggtggggca    360 ngacancaag ggggaagatt gggaanacaa taacaggcat gctggggatg cggtgggctc    420
tatggcttct gaggcggaaa gaaccaactg gggctctang gggtatcccc acnccctgt     480 taccggcgca ttaancgcgg gggtgttgtg gttacccnca acttaacgct acacttgcca    540
cgcctaacgc ccctccttc  gcttcttcct tccttctccc acttcccgn  tttcccttca    600 actctaatcg gggcnccta  ggtccaatta atcttacggn cncacccaaa actnataggt    660
aagtccttnt ggcccccaa  aaaggttccc ctaaatg                             697

<210> SEQ ID NO 19
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tacgtcaccg tccag                                                          15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tacgtgaccg tccag                                                          15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aatttttatg tgccc                                                          15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aatttctatg tgccc                                                          15

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgctactga aagtc                                                          15

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcgctgctga aagtc                                                          15

<210> SEQ ID NO 25
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 25
agcctaggac tgttc                                                       15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agcctgggac tgttc                                                       15

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gctggtcccg ccggt                                                       15

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gctggacccg ccggt                                                       15

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggtcggtctg atgagtccgt gaggacgaaa cgtagag                               37

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tactcgaact gatgagtccg tgaggacgaa aggctgc                               37

<210> SEQ ID NO 31
<211> LENGTH: 37
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 31
ggcacatctg atgagtccgt gaggacgaaa aaattgg                                37

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
actttcagct gatgagtccg tgaggacgaa agcgcca                                37

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acagtccctg atgagtccgt gaggacgaaa ggctgaa                                37

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cggcggctga tgagtccgtg aggacgaaac cagca                                  35

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggaaactttg ctccccagct gtcttat                                           27

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggaaactttg cgccccagct gtcttat                                           27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 37
ggaaactttg ctccccagct gtcttat                                           27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggcaactttg cgccccagct ttcttat                                           27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggaaactttg ctccccagct gtcttat                                           27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggcaactttg cgccacagct ttcgtat                                           27

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aaggggcagg gggtcaagct att                                               23

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cggaattcag ggacccaagg gagaacact                                         29

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
```

```
cgggatccca tgggacctga agctccag                                   28
```

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
ggaaactttg cgccccagct gtcttat                                    27
```

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
ataagacagc tggggcgcaa agtttcc                                    27
```

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
ggcaactttg cgccccagct ttcttat                                    27
```

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
ataagaaagc tggggcgcaa agttgcc                                    27
```

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

```
ggcaactttg cgccacagct ttcgtat                                    27
```

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

```
atacgaaagc tgtggcgcaa agttgcc                                    27
```

```
<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cgggactttc caaaatgtcg                                                    20

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cctgactcga gtgacctcaa gagtgtgcca ct                                      32

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cgtatggatc cgggccacat cgatgctgg                                          29

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ctggcaacct caagaagaa                                                     19

<210> SEQ ID NO 54
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54 gatcccctg gcaacctcaa gaagaattca agagattctt cttgaggttg ccagttttttg        60 aaa                                                                      63

<210> SEQ ID NO 55
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agcttttcca aaaactggca acctcaagaa gaatctcttg aattcttctt gaggttgcca        60
```

```
gggg                                                                64
```

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56

```
aagtcttctg caacaatgg                                                19
```

<210> SEQ ID NO 57
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
gatccccaag tcttctgcaa caatgttcaa gagatccatg ttgcagaaga cttttttga    60 aa                                                                  62
```

<210> SEQ ID NO 58
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
agcttttcca aaaaagtct tctgcaacaa tgtctcttga atccatgttg cagaagactt    60
ggg                                                                 63
```

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
agcccagtgt ggcccagaa                                                19
```

<210> SEQ ID NO 60
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

```
gatccccagc ccagtgtggc ccagaattca agagattctg ggccacatgg gcttttttga   60
aa                                                                  62
```

<210> SEQ ID NO 61
<211> LENGTH: 63
<212> TYPE: DNA
<213> ORGANISM: Artificial Sequence
<220> FEATURE:

-continued

```
<223> OTHER INFORMATION: Description of Artificial Sequence: Synthetic
      primer

<400> SEQUENCE: 61
agcttttcca aaaagccca gtgtggccca gaatctcttg aattctgggc cacatgggct    60
ggg                                                                63

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agcgtcactg tcgatggct                                               19

<210> SEQ ID NO 63
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gatccccagc gtcactgtcg atggctttca agagaagcca tcgacagtga cgctttttg    60 aaa                                                                63

<210> SEQ ID NO 64
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
agcttttcca aaaagcgtc actgtcgatg gcttctcttg aaagccatcg acagtgacgc    60
tggg                                                               64

<210> SEQ ID NO 65
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ggatgcatca aggtgttttg taatatggag actggtgaga cc                     42

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cacaccagtc tccatattac aaaacacctt gatgcatcca gg                     42

<210> SEQ ID NO 67
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
taccccactc aaccgagcgt agctcaaaaa aactggtaca tc                            42

<210> SEQ ID NO 68
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtactagttt ttttgagcta cgctcggttg agtggggtac ac                            42

<210> SEQ ID NO 69
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ttcacctact atagtgtaac ggtggacggc ggttgcacgg taagt                         45

<210> SEQ ID NO 70
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
taccgtgcaa ccgccgtcca ccgttacact atagtaggcg aagcg                         45

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
atggtcctag gtggcttcac c                                                   21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
catgatggca tggttctccc c                                                   21

<210> SEQ ID NO 73
<211> LENGTH: 37
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 73 acuucagcu gaugaguccg ugaggacgaa agcgcca                                37

<210> SEQ ID NO 74
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ggucggucug augaguccgu gaggacgaaa cguagag                               37

<210> SEQ ID NO 75
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ggacggucug augaguccgu gaggacgaaa cguagag                               37

<210> SEQ ID NO 76
<211> LENGTH: 185
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 76
ggacggucug augaguccgu gaggacgaaa cguagaguuc aggcuaccua uccaugaacu      60
gaugaguccg ugaggacgaa aggucagccc aguuucgucg augguguacu gaugaguccg     120
ugaggacgaa agggugcuga ccuguauccc uccuucugau gagccguga ggacgaaacg      180 gugga                                                                185

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cgtaccactg gcatcgtg                                                    18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gtttcgtgga tgccacag                                                    18
```

```
<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgactgtgcc ttctagttgc                                              20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cacaccctaa ctgacacaca                                              20

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cggtctgatg agtccgtga                                               19

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
agaaggcaca gtcgaggct                                               19

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aagcagcctt ggtctctgtc                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cttaagcttg gtaccgaatc                                              20

<210> SEQ ID NO 85
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ttccaagcac actgtgggca                                                 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgtgacttcg ttcattctgc                                                 20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tctctcatga gcctaaagct                                                 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
atgcctggaa ccaatccgag                                                 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ttcaagccca agctttcgcg                                                 20

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
agtgctcgtg tgggatc                                                    17

<210> SEQ ID NO 91
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 91
caaatccctg aagtcctc                                                       18

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cattcttggg tgggagcag                                                      19

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggacaggaga agggagaagg                                                     20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ccacctagga ccatgaagag                                                     20

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ctctacgtca ccgtccagca caa                                                 23

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
cuacgucacc guccagcaca a                                                   21

<210> SEQ ID NO 97
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 97
gugcuggacg gugacguaga g                                                    21

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aacaacttcc tcacgctcta cgt                                                  23

<210> SEQ ID NO 99
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
caacuuccuc acgcucuacg uuu                                                  23

<210> SEQ ID NO 100
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
acguagagcg ugaggaaguu guu                                                  23

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cggcaagctg accctgaagt tcat                                                 24

<210> SEQ ID NO 102
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gcaagcugac ccugaaguuc au                                                   22

<210> SEQ ID NO 103
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 103
gaacuucagg gucagcuugc cg                                              22

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cagcctcaag atcatcagca                                                 20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
catgagtcct tccacgatac                                                 20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ctttcctgat ctgctgggtg                                                 20

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ggcaaagaac gctgggatg                                                  19

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
cagcctcaag atcatcagca                                                 20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109

```
catgagtcct tccacgatac                                             20

<210> SEQ ID NO 110
<211> LENGTH: 75
<212> TYPE: DNA
<213> ORGANISM: Artificial Sequence
<220> FEATURE:
<223> OTHER INFORMATION: Description of Artificial Sequence: Synthetic
      nucleotide
      construct

<400> SEQUENCE: 110
gctagcgcta ccggactcag atctcgagct caagcttcga attctgcagt cgacggtacc    60
gcgggcccgg gatcc                                                     75

<210> SEQ ID NO 111
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (10)..(30)

<400> SEQUENCE: 111 gatgccatc aaa gtc ttc tgc aac atg gag actggtgaga cctgcgtgt          49
          Lys Val Phe Cys Asn Met Glu
          1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Leu Phe Cys Asn Met Glu
1               5

<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (10)..(30)

<400> SEQUENCE: 113 gatgaaatc aag gtg ttt tgt aat atg gag actggtgaga cc                 42
          Lys Val Phe Cys Asn Met Glu
          1               5

<210> SEQ ID NO 114
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: CDS
<222> LOCATION: (10)..(30)

<400> SEQUENCE: 114 cacaccagt ctc cat att aca aaa cac ctt gatgcatcca gg         42

Leu His Ile Thr Lys His Leu
          1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Glu Met Asn Cys Phe Leu Lys
1               5

<210> SEQ ID NO 116
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (10)..(30)

<400> SEQUENCE: 116 gtgtacccc act cag ccc agt gtg gcc cag aagaactggt acat         44

Thr Gln Pro Ser Val Ala Gln
          1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Pro Ser Val Ala Gln Lys
1               5

<210> SEQ ID NO 118
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (10)..(30)

<400> SEQUENCE: 118 taccccact caa ccg agc gta gct caa aaa aactggtaca tc         42

Gln Pro Ser Val Ala Gln Lys
          1               5

<210> SEQ ID NO 119
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 119
gtactagttt ttttgagcta cgctcggttg agtggggtac ac                    42

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Lys Gln Ala Val Ser Pro Gln
1               5

<210> SEQ ID NO 121
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (14)..(34)

<400> SEQUENCE: 121
ccgcttcacc tac agc gtc act gtc gat ggc tgc acgagtcaca ccggag      50
            Ser Val Thr Val Asp Gly Cys
            1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Val Thr Val Asp Gly Cys
1               5

<210> SEQ ID NO 123
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (10)..(30)

<400> SEQUENCE: 123 acctactac agt gta acg gtg gac gga tgt acgagtcacc gg               42
          Ser Val Thr Val Asp Gly Cys
          1               5

<210> SEQ ID NO 124
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: CDS
<222> LOCATION: (10)..(30)

<400> SEQUENCE: 124
gtgactcgta caaccgtcca ccgttacact atagtaggcg aa                          42

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Cys Gly Asp Val Thr Val Ser
1               5

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
aagtcttctg caacatgga                                                   19

<210> SEQ ID NO 127
<211> LENGTH: 48
<212> TYPE: DNA
<213> ORGANISM: Artificial Sequence
<220> FEATURE:
<223> OTHER INFORMATION: Description of Artificial Sequence: Synthetic
      olionucleotide
<220> FEATURE:
<223> OTHER INFORMATION: DNA/RNA hybrid sequence

<400> SEQUENCE: 127
aagtcttctg caacatggau ucagagaacc auguugcaga agacuuuu                   48

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agcccagtgt ggcccagaa                                                   19

<210> SEQ ID NO 129
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
agcccagugu ggcccagaau ucagagaauu cugggccaca cugggcuuu                  49
```

<210> SEQ ID NO 130
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
agcgtcactg tcgatggct                                              19

<210> SEQ ID NO 131
<211> LENGTH: 49
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 131
agcgucacug ucgauggcuu ucagagaaag ccaucgacag ugacgcuuu            49

<210> SEQ ID NO 132
<211> LENGTH: 49
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 132
agcgucacug ucgauggcuu ucagagaaag ccaucgacag ugacgcuuu            49

<210> SEQ ID NO 133
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 133
cucuacguca ccgucc                                                 16

<210> SEQ ID NO 134
<211> LENGTH: 38
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 134
ggacggucug augaggccga aaggccggaa acguagag                        38

<210> SEQ ID NO 135
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 135
cuguagguga cggugc                                                 16

<210> SEQ ID NO 136
<211> LENGTH: 38

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ggacggucug augaggccga aaggccggaa acguagag                                 38

<210> SEQ ID NO 137
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (16)..(30)

<400> SEQUENCE: 137
atcaacttcc tcacg ctc tac gtc acc gtc cagcacaa                             38

Leu Tyr Val Thr Val
1               5

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Tyr Val Thr Val
1               5

<210> SEQ ID NO 139
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (16)..(30)

<400> SEQUENCE: 139
atcaacttcc tcacg ctg tat gtg acg gtg cagcacaa                             38

Leu Tyr Val Thr Val
1               5

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Leu Tyr Val Thr Val
1               5

<210> SEQ ID NO 141
<211> LENGTH: 61
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 141
atcaacttcc tcacgctgta tgtgacggtg cagcacaaga agctgcgcac gcctctcaac    60
t                                                                    61

<210> SEQ ID NO 142
<211> LENGTH: 398
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: a, c, g, t, unknown or other
<220> FEATURE:
<221> NAME/KEY: modified_base
<222> LOCATION: (5)..(5)
<223> OTHER INFORMATION: a, c, g, t, unknown or other
<220> FEATURE:
<221> NAME/KEY: modified_base
<222> LOCATION: (10)..(10)
<223> OTHER INFORMATION: a, c, g, t, unknown or other
<220> FEATURE:
<221> NAME/KEY: modified_base
<222> LOCATION: (17)..(18)
<223> OTHER INFORMATION: a, c, g, t, unknown or other
<220> FEATURE:
<221> NAME/KEY: modified_base
<222> LOCATION: (22)..(22)
<223> OTHER INFORMATION: a, c, g, t, unknown or other
<220> FEATURE:
<221> NAME/KEY: modified_base
<222> LOCATION: (24)..(24)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (31)..(33)
<223> OTHER INFORMATION: a, c, g, t, unknown or other
<220> FEATURE:
<221> NAME/KEY: modified_base
<222> LOCATION: (35)..(36)
<223> OTHER INFORMATION: a, c, g, t, unknown or other
<220> FEATURE:
<221> NAME/KEY: modified_base
<222> LOCATION: (38)..(38)
<223> OTHER INFORMATION: a, c, g, t, unknown or other
<220> FEATURE:
<221> NAME/KEY: modified_base
<222> LOCATION: (41)..(41)
<223> OTHER INFORMATION: a, c, g, t, unknown or other
<220> FEATURE:
<221> NAME/KEY: modified_base
<222> LOCATION: (47)..(47)
<223> OTHER INFORMATION: a, c, g, t, unknown or other
<220> FEATURE:
<221> NAME/KEY: modified_base
<222> LOCATION: (50)..(50)
<223> OTHER INFORMATION: a, c, g, t, unknown or other
<220> FEATURE:
<221> NAME/KEY: modified_base
<222> LOCATION: (105)..(106)
<223> OTHER INFORMATION: a, c, g, t, unknown or other
<220> FEATURE:
<221> NAME/KEY: modified_base
<222> LOCATION: (284)..(284)
<223> OTHER INFORMATION: a, c, g, t, unknown or other
<220> FEATURE:

```
<221> NAME/KEY: modified_base
<222> LOCATION: (286)..(286)
<223> OTHER INFORMATION: a, c, g, t, unknown or other
<220> FEATURE:
<221> NAME/KEY: modified_base
<222> LOCATION: (348)..(348)
<223> OTHER INFORMATION: a, c, g, t, unknown or other

<400> SEQUENCE: 142
cnttncaatn ttgcgcnntt tncntgnaag nnntnnanag ngggaangtn tcctaagcag    60
agctggttta gtgaaccgtc agatccgcta gcgctaccgg actcnnatct cgagtgacct   120
caagatgtgc cactctgact ggaagagtgg agagtactgg attgacccca accaaggctg   180
caacctggat gccatcaaag tcttctgcaa catggagact ggtgagacct cgtgtaccc    240 cactcagccc agtgtggccc agaagaatgg tacatcagca agancntttt ttgacaagag   300
gcatgtctgg ttcggcgaga gcatgaccga atggattcca gttcgagnat ggcggccagg   360
gctccgaccc tgccgatgtg gccatccagc tgaccttc                          398

<210> SEQ ID NO 143
<211> LENGTH: 397
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (7)..(7)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (23)..(23)
<223> OTHER INFORMATION: a, c, g, t, unknown or other
<220> FEATURE:
<221> NAME/KEY: modified_base
<222> LOCATION: (46)..(46)
<223> OTHER INFORMATION: a, c, g, t, unknown or other
<220> FEATURE:
<221> NAME/KEY: modified_base
<222> LOCATION: (49)..(49)
<223> OTHER INFORMATION: a, c, g, t, unknown or other
<220> FEATURE:
<221> NAME/KEY: modified_base
<222> LOCATION: (285)..(286)
<223> OTHER INFORMATION: a, c, g, t, unknown or other

<400> SEQUENCE: 143
ttgtaangaa ggccagtntt ctntaatacg actcactata gggcgnttng ggtaccgggc    60
cccccctcga ggtcgacggt atcgataagc ttttccaaaa aagcgtcact gtcgatggct   120
tctcttgaaa gccatcgaca gtgacgctgg ggatctgtgg tctcatacag aacttataag   180
attcccaaat ccaaagacat ttcacgttta tggtgatttc ccagaacaca tagcgacatg   240
caaatattgc agggcgccac tccctgtcc ctcacagcca tcttnntgcc agggcgcacg    300
cgcactgggt gttcccgcct agtgacactg gcccgcgat tccttggagc gggttgatga    360
cgtcagcgtt cgaattcctg cagcccgggg gatccac                          397

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                                    -continued
      oligonucleotide

<400> SEQUENCE: 144
aaactttgct ccccagctgt ctt                                           23

<210> SEQ ID NO 145
<211> LENGTH: 15
<212> TYPE: DNA
<213> ORGANISM: artificial sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 145 ctc tac gtc acc gtc                                                 15
Leu Tyr Val Thr Val
1               5

<210> SEQ ID NO 146
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 146 ctg tat gtg acg gtg                                                 15
Leu Tyr Val Thr Val
1               5

<210> SEQ ID NO 147
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 147
gatgccatca aagtcttctg caacatggag actggtgaga cctgcgtgt               49

<210> SEQ ID NO 148
<211> LENGTH: 7
<212> TYPE: PRT
<213> ORGANISM: Artificial Sequence
<220> FEATURE:
<223> OTHER INFORMATION: synthetic peptide

<400> SEQUENCE: 148

Lys Leu Phe Cys Asn Met Glu
1               5

<210> SEQ ID NO 149
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 149
gatgaaatca agttttgaaa tgagactggt gagacc                             36
```

```
<210> SEQ ID NO 150
<211> LENGTH: 7
<212> TYPE: PRT
<213> ORGANISM: Artificial Sequence
<220> FEATURE:
<223> OTHER INFORMATION: synthetic peptide

<400> SEQUENCE: 150

Lys Leu Phe Cys Asn Met Glu
1               5

<210> SEQ ID NO 151
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 151
cacaccagtc tcatttcaaa acttgatgca tccagg                              36

<210> SEQ ID NO 152
<211> LENGTH: 7
<212> TYPE: PRT
<213> ORGANISM: Artificial Sequence
<220> FEATURE:
<223> OTHER INFORMATION: synthetic peptide

<400> SEQUENCE: 152

Glu Met Asn Cys Phe Leu Lys
1               5

<210> SEQ ID NO 153
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 153
gtgtacccca ctcagcccag tgtggcccag aagaactggt acat                     44

<210> SEQ ID NO 154
<211> LENGTH: 7
<212> TYPE: PRT
<213> ORGANISM: Artificial Sequence
<220> FEATURE:
<223> OTHER INFORMATION: synthetic peptide

<400> SEQUENCE: 154

Gln Pro Ser Val Ala Gln Lys
1               5

<210> SEQ ID NO 155
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 155
taccccacta actggtacat c                                              21

<210> SEQ ID NO 156
<211> LENGTH: 7
<212> TYPE: PRT
<213> ORGANISM: Artificial Sequence
<220> FEATURE:
```

<223> OTHER INFORMATION: synthetic peptide

<400> SEQUENCE: 156

Gln Pro Ser Val Ala Gln Lys
1               5

<210> SEQ ID NO 157
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 157
gtactagttt tttggcacct ggtgagtggg gtacac                            36

<210> SEQ ID NO 158
<211> LENGTH: 7
<212> TYPE: PRT
<213> ORGANISM: Artificial Sequence
<220> FEATURE:
<223> OTHER INFORMATION: synthetic peptide

<400> SEQUENCE: 158

Lys Gln Ala Val Ser Pro Gln
1               5

<210> SEQ ID NO 159
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 159
ccgcttcacc tacagcgtca ctgtcgatgg ctgcacgagt cacaccggag             50

<210> SEQ ID NO 160
<211> LENGTH: 7
<212> TYPE: PRT
<213> ORGANISM: Artificial Sequence
<220> FEATURE:
<223> OTHER INFORMATION: synthetic peptide

<400> SEQUENCE: 160

Ser Val Thr Val Asp Gly Cys
1               5

<210> SEQ ID NO 161
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 161
acctactaca ggtacgtgag gtgtacgagt caccgg                            36

<210> SEQ ID NO 162
<211> LENGTH: 7
<212> TYPE: PRT
<213> ORGANISM: Artificial Sequence
<220> FEATURE:
<223> OTHER INFORMATION: synthetic peptide

<400> SEQUENCE: 162

Ser Val Thr Val Asp Gly Cys

-continued

<210> SEQ ID NO 163
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 163
gtgactcgta cacctcacgt acctatagta ggcgaa                                    36

<210> SEQ ID NO 164
<211> LENGTH: 7
<212> TYPE: PRT
<213> ORGANISM: Artificial Sequence
<220> FEATURE:
<223> OTHER INFORMATION: synthetic peptide

<400> SEQUENCE: 164

Cys Gly Asp Val Thr Val Ser
1               5

<210> SEQ ID NO 165
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 165
ctggcaacct caagaaggc                                                       19

<210> SEQ ID NO 166
<211> LENGTH: 48
<212> TYPE: RNA
<213> ORGANISM: Artificial Sequence
<220> FEATURE:
<223> OTHER INFORMATION: synthetic oligonucleotide

<400> SEQUENCE: 166
cuggcaaccu caagaagaau ucagagauuc uucuugaggu ugccaguu                       48

<210> SEQ ID NO 167
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 167
agcccagtgt ggcccagaa                                                       19

<210> SEQ ID NO 168
<211> LENGTH: 48
<212> TYPE: RNA
<213> ORGANISM: Artificial Sequence
<220> FEATURE:
<223> OTHER INFORMATION: synthetic oligonucleotide

<400> SEQUENCE: 168
agcccagugu ggcccagaau ucagagauuc ugggccacac ugggcuuu                       48

<210> SEQ ID NO 169
<211> LENGTH: 19
<212> TYPE: DNA
<213> ORGANISM: Artificial Sequence

```
<220> FEATURE:
<223> OTHER INFORMATION: synthetic oligonucleotide

<400> SEQUENCE: 169
agcgtcactg tcgatggct                                          19

<210> SEQ ID NO 170
<211> LENGTH: 48
<212> TYPE: RNA
<213> ORGANISM: Artificial Sequence
<220> FEATURE:
<223> OTHER INFORMATION: synthetic oligonucleotide

<400> SEQUENCE: 170
agcgucacug ucgauggcuu ucagagaagc cucgacagug acagcuuu          48

<210> SEQ ID NO 171
<211> LENGTH: 48
<212> TYPE: RNA
<213> ORGANISM: Artificial Sequence
<220> FEATURE:
<223> OTHER INFORMATION: synthetic oligonucleotide

<400> SEQUENCE: 171
agcgucacug ucgauggcuu ucagagaagc caucgacagu gacgcuuu          48

<210> SEQ ID NO 172
<211> LENGTH: 5
<212> TYPE: PRT
<213> ORGANISM: Artificial Sequence
<220> FEATURE:
<223> OTHER INFORMATION: synthetic peptide

<400> SEQUENCE: 172

Leu Tyr Val Thr Val
1               5

<210> SEQ ID NO 173
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 173
ctctacgtca ccgtc                                              15

<210> SEQ ID NO 174
<211> LENGTH: 5
<212> TYPE: PRT
<213> ORGANISM: Artificial Sequence
<220> FEATURE:
<223> OTHER INFORMATION: synthetic peptide

<400> SEQUENCE: 174

Leu Tyr Val Thr Val
1               5

<210> SEQ ID NO 175
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 175
ctgtatgtga cggtg                                              15
```

```
<210> SEQ ID NO 176
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 176
cucuacguca ccgucc                                                         16

<210> SEQ ID NO 177
<211> LENGTH: 38
<212> TYPE: RNA
<213> ORGANISM: Artificial Sequence
<220> FEATURE:
<223> OTHER INFORMATION: synthetic oligonucleotide

<400> SEQUENCE: 177
ggacggucug augaggccga aaggccggaa acguagag                                 38

<210> SEQ ID NO 178
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 178
cuguaggvga cggugc                                                         16

<210> SEQ ID NO 179
<211> LENGTH: 38
<212> TYPE: RNA
<213> ORGANISM: Artificial Sequence
<220> FEATURE:
<223> OTHER INFORMATION: synthetic oligonucleotide

<400> SEQUENCE: 179
ggacggucug augaggccga aaggccggaa acguagag                                 38

<210> SEQ ID NO 180
<211> LENGTH: 5
<212> TYPE: PRT
<213> ORGANISM: Artificial Sequence
<220> FEATURE:
<223> OTHER INFORMATION: synthetic peptide

<400> SEQUENCE: 180

Leu Tyr Val Thr Val
1               5

<210> SEQ ID NO 181
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 181
atcaacttcc tcacgctcta cgtcaccgtc cagcacaa                                 38

<210> SEQ ID NO 182
<211> LENGTH: 38
<212> TYPE: DNA
<213> ORGANISM: Artificial Sequence
<220> FEATURE:
```

```
<223> OTHER INFORMATION: synthetic oligonucleotide

<400> SEQUENCE: 182
atcaacttcc tcacgctgta tgtgacggtg cagcacaa                    38

<210> SEQ ID NO 183
<211> LENGTH: 5
<212> TYPE: PRT
<213> ORGANISM: Artificial Sequence
<220> FEATURE:
<223> OTHER INFORMATION: synthetic peptide

<400> SEQUENCE: 183

Leu Tyr Val Thr Val
1               5

<210> SEQ ID NO 184
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 184
atcaacttcc tcacgctgta tgtgacggtg cagcacaaga agctgcgcac gcctctcaac    60
t                                                                   61

<210> SEQ ID NO 185
<211> LENGTH: 75
<212> TYPE: DNA
<213> ORGANISM: Artificial Sequence
<220> FEATURE:
<223> OTHER INFORMATION: synthetic oligonucleotide

<400> SEQUENCE: 185
gctagcgcta ccggactcag atctcgagct caagcttcga attctgcagt cgacggtacc    60
gcgggcccgg gatcc                                                    75
```

GENETIC SUPPRESSION AND REPLACEMENT

RELATED APPLICATIONS

This application is a continuation of U.S. application Ser. No. 10/651,754, filed on Aug. 29, 2003, which is a continuation-in-part of U.S. application Ser. No. 09/155,708, filed Apr. 5, 1999, now U.S. Pat. No. 7,138,378, which claims priority to PCT/GB97/00929, filed Apr. 2, 1997 and GB9606961.2, filed Apr. 2, 1996; and claims priority to U.S. Provisional Application Ser. Nos. 60/407,389, filed Aug. 30, 2002 and 60/414,698, filed Sep. 30, 2002, the entire disclosures of which are incorporated herein by reference.

BACKGROUND OF THE INVENTION

Genetic linkage, together with techniques for mutational screening of candidate genes, have enabled identification of causative dominant mutations in the genes encoding rhodopsin and peripherin. Globally, about 100 rhodopsin mutations have been found in patients with RP or congenital stationary night blindness. Similarly, approximately 40 mutations have been characterised in the peripherin gene in patients with RP or macular dystrophies (Ott et al. 1990; McWilliam et al. 1989; Dryja et al. 1990; Farrar et al. 1991a,b; Kajiwara et al. 1991; Humphries et al. 1992; Van Soest et al. 1994; Mansergh et al. 1995). Knowledge of the molecular etiology of these retinopathies has stimulated the generation of animal models and the exploration of methods of therapeutic intervention (Farrar et al. 1995; Humphries et al. 1997; Millington-Ward et al. 1997, 1999, 2002; O'Neill et al. 2000).

Osteogenesis imperfecta (OI) is an autosomal dominantly inherited human disease whose molecular pathogenesis is also extremely genetically heterogeneous. OI is often referred to as 'brittle bone disease' although additional symptoms such as hearing loss, growth deficiency, bruising, loose joints, blue sclerae and dentinogenesis imperfecta are frequently observed (www.ncbi.nlm.nih.gov/omim). Mutations in the genes encoding the two type I collagen chains (collagen 1A1 and 1A2) comprising the type I collagen heterodimer have been implicated in OI. Indeed, hundreds of dominantly acting mutations in these two genes have been identified in OI patients. Many collagen IA1 and IA2 gene mutations are single point mutations, although a number of insertion and deletion mutations have been found (Willing et al. 1993; Zhuang et al. 1996). Mutations in these genes have also been implicated in Ehlers-Danlos and Marfan syndromes (Phillips et al. 1990; D'Alessio et al. 1991; Vasan N S et al. 1991).

Gene therapies utilizing viral and non-viral delivery systems have been used to treat or study inherited disorders, cancers and infectious diseases. However, many therapies and studies have focused on recessively inherited disorders, the rationale being that introduction and expression of the wild type gene may be sufficient to prevent or ameliorate the disease phenotype. In contrast, gene therapy for dominant disorders such as RP or OI, for example, requires suppression of the dominant disease allele. In addition, there are many polygenic disorders due to co-inheritance of a number of genetic components that together give rise to the disease state. Gene therapies for dominant or polygenic diseases may target the primary defect and require suppression of the disease allele while in many cases still maintaining the function of the normal allele. This is particularly relevant where disease pathology is due to a gain of function mutation rather than to reduced levels of wild type protein. Alternatively, suppression therapies may target secondary effects associated with the disease pathology such as programmed cell death or apoptosis, which has been observed in many inherited disorders.

Suppression effectors have been used previously to achieve specific suppression of gene expression. Modifications have been made to oligonucleotides (e.g., phosphorothioates) to increase resistance to nuclease degradation, binding affinity and uptake (Cazenave et al. 1989; Sun et al. 1989; McKay et al. 1996; Wei et al. 1996). In some instances, antisense and ribozyme suppression strategies have led to the reversal of a tumor phenotype by reducing expression of a gene product or by cleaving a mutant transcript at the site of the mutation (Carter and Lemoine 1993; Lange et al. 1993; Valera et al. 1994; Dosaka-Akita et al. 1995; Feng et al. 1995; Quattrone et al. 1995; Ohta et al. 1996; Lewin et al. 1998). For example, neoplastic reversion was obtained using a ribozyme targeted to an H-ras mutation in bladder carcinoma cells (Feng et al. 1995). Ribozymes have also been proposed as a means of both inhibiting gene expression of a mutant gene and of correcting the mutant by targeted trans-splicing (Sullenger and Cech 1994; Jones et al. 1996). Ribozymes can be designed to elicit autocatalytic cleavage of RNA targets, however, the inhibitory effect of some ribozymes may be due in part to an antisense effect due to the antisense sequences flanking the catalytic core which specify the target site (Ellis and Rodgers 1993; Jankowsky and Schwenzer 1996). Ribozyme activity may be augmented by the use of, for example, non-specific nucleic acid binding proteins or facilitator oligonucleotides (Herschlag et al. 1994; Jankowsky and Schwenzer 1996). Multitarget ribozymes (connected or shotgun) have been suggested as a means of improving efficiency of ribozymes for gene suppression (Ohkawa et al. 1993).

Triple helix approaches have also been investigated for sequence specific gene suppression. Triplex forming oligonucleotides have been found in some cases to bind in a sequence specific manner (Postel et al. 1991; Duval-Valentin et al. 1992; Hardenbol and Van Dyke 1996; Porumb et al. 1996). Similarly, peptide nucleic acids have been shown to inhibit gene expression (Hanvey et al. 1991; Knudson and Nielsen 1996; Taylor et al. 1997). Minor groove binding polyamides can bind in a sequence specific manner to DNA targets and hence may represent useful small molecules for future suppression at the DNA level (Trauger et al. 1996). In addition, suppression has been obtained by interference at the protein level using dominant negative mutant peptides and antibodies (Herskowitz 1987; Rimsky et al. 1989; Wright et al. 1989). In some cases suppression strategies have lead to a reduction in RNA levels without a concomitant reduction in proteins, whereas in others, reductions in RNA have been mirrored by reductions in protein.

A new tool for modulating or suppressing gene expression has also been described called RNA interference (RNAi) or small interfering RNA (siRNA) or double stranded RNA (dsRNA) (Fire, 1998). The silencing effect of complementary double stranded RNA was first observed in 1990 in petunias by Richard Joergensen and termed cosuppression (Jorgensen, 1996). RNA silencing was subsequently identified in *C. elegans* by Andrew Fire and colleagues (Fire, 1998) who coined the term RNA interference (RNAi). The applications for this biological tool have now been extended to many species as RNAi has been shown to be effective in both mammalian cells and animals (Caplen, 2001; Elbashir, 2001; Yang, 2001; Paddison, 2002; Krichevsky, 2002; Lewis, 2002; Miller et al. 2003). An important feature of dsRNA or siRNA or RNAi is the double stranded nature of the RNA and the absence of large overhanging pieces of single stranded RNA, although dsRNA with small overhangs and with intervening loops of RNA has been shown to effect suppression of a target gene.

The pathway for silencing gene expression involving long (>30 nucleotides) double stranded RNA molecules has been elucidated and is thought to work via the following steps (shown in *Drosophila melanogaster*) (Zamore, 2001). Firstly, the long dsRNA is cleaved into siRNA approximately 21 nucleotides in length. This siRNA targets complimentary mRNA sequence, which is degraded. However, in mammals it has been found that long dsRNA triggers a non-specific response causing a decrease in all mRNA levels. This general suppression of protein synthesis is mediated by a dsRNA dependent protein kinase (PKR) (Clemens, 1997). Elbashir et al. were able to specifically suppress target mRNA with 21 nucleotide siRNA duplexes. Notably, siRNA bypassed the non-specific pathway and allowed for gene-specific inhibition of expression (Elbashir, 2001; Caplen, 2001). dsRNA can be delivered as synthesized RNA and or by using a vector to provide a supply of endogenously generated dsRNA. dsRNA may be locally or systemically delivered (Lewis, 2002; Miyagishhi, 2002; Paul, 2002; Siu, 2002). Indeed functional siRNAs have been generated both in cells and in transgenic animals and have been delivered using a variety of vector systems including lentivirus (McCaffrey et al. 2003, McManus et al. 2003, Sharp et al. 2003).

Strategies for differentiating between normal and disease alleles and switching off the disease allele using suppression effectors that target the disease mutation are problematic because frequently disease and normal alleles differ by only a single nucleotide. For example, a hammerhead ribozyme that cleaves only at an NUX site is not effective for targeting all point mutations. A further difficulty inhibiting development of gene therapies is the heterogeneous nature of some dominant disorders—many different mutations in the same gene give rise to a similar disease phenotype. Indeed, certain mutations may occur in only one patient. Development of specific gene therapies for each of these mutations may be prohibitive in terms of cost. Examples in which multiple genes and/or multiple mutations within a gene can give rise to a similar disease phenotype include OI, familial hypercholesteremia, and RP. Disease mutations are often single nucleotide changes. As a result differentiating between the disease and normal alleles may be difficult. Some suppression effectors require specific sequence targets, for example, hammerhead ribozymes cleave at NUX sites and hence may not be able to target many mutations. Notably, the wide spectrum of mutations observed in many diseases adds additional complexity to the development of therapeutic strategies for such disorders—some mutations may occur only once in a single patient. A further problem associated with suppression is the high level of homology present in coding sequences between members of some gene families. This can limit the range of target sites for suppression which will enable specific suppression of a single member of such a gene family. A need therefore exists for compositions and methods for suppressing gene expression while also providing for the expression of a non-disease causing allele of the gene that avoids recognition by the suppression effector.

SUMMARY OF THE INVENTION

The invention relates to compositions and methods for gene suppression and replacement that exploit the degeneracy of the genetic code, thereby circumventing the difficulties and expenses associated with the need to specifically target disease mutations. In particular, the invention relates to suppression of the expression of mutated genes that give rise to a dominant or deleterious effect or contributes towards a disease. In one embodiment of the invention, a suppression effector targets either the disease allele or normal allele. In another embodiment, the suppression effector targets both the disease allele and normal allele. In a particular embodiment of the invention, a replacement nucleic acid is provided that is altered at one or more degenerate or wobble bases from the endogenous wild type gene but will code for the identical amino acids as the wild type gene. In another embodiment, the replacement nucleic acid encodes a beneficial replacement nucleic acid (e.g., which encodes a more active or stable product than that encoded by the wild-type gene). The replacement nucleic acid provides expression of the normal protein product when required to ameliorate pathology associated with reduced levels of wild type protein. The same replacement nucleic acid can be used in conjunction with the suppression of many different disease mutations within a given gene.

Suppression in coding sequence holds the advantage that such sequences are present in both precursor and mature RNAs, thereby enabling suppressor effectors to target all forms of RNA. A combined approach using a number of suppression effectors may also be used. For some disorders, it may be necessary to block expression of a disease allele completely to prevent disease symptoms whereas for others low levels of mutant protein may be tolerated.

The strategy circumvents the need for a specific therapy for every disease-causing mutation within a given gene. Notably, the invention has the advantage that the same suppression effector can be used to suppress many mutations in a gene. This is particularly relevant when any one of a large number of mutations within a single gene can cause disease pathology. The compositions and methods of the invention allow greater flexibility in choice of target sequence for suppression of expression of a disease allele.

Suppression and replacement can be undertaken in conjunction with each other or separately. Suppression and replacement utilizing the degeneracy of the genetic code may be undertaken in test tubes, in cells, in animals and or in plants and may be used for experimental research (e.g., for the study of development or gene expression) or for therapeutic purposes.

In one aspect, the invention provides methods for preparing and using a suppression effector and replacement nucleic acid by preparing a suppression effector that binds to a coding region of a mature RNA or DNA encoding a mutant allele, thereby to inhibit the expression of the mutant allele, and preparing a replacement nucleic acid that encodes a wild-type or non-disease causing allele and that comprises at least one degenerate/wobble nucleotide that is altered so that the replacement nucleic acid is not suppressed, or is only partially suppressed, by the suppression effector.

In another aspect, the invention provides a composition comprising a suppression effector that binds to the coding region of a mature RNA or DNA encoding a mutant allele, thereby to inhibit the expression of the mutant allele and a replacement nucleic acid that encodes a wild-type or non-disease causing allele and that comprises at least one degenerate/wobble nucleotide that is altered so that the replacement nucleic acid is not suppressed, or is only partially suppressed, by the suppression effector.

In another aspect, the invention provides a kit comprising a suppression effector that suppresses the expression of a mature RNA or DNA encoding a mutant allele and a replacement nucleic acid that encodes a wild-type or non-disease causing allele that is not suppressed, or is only partially suppressed, by the suppression effector and that differs from the mutant allele in at least one degenerate/wobble nucleotide.

In an embodiment, the suppression effector is a nucleic acid such as an antisense DNA or RNA, peptide nucleic acid (PNA), a nucleic acid that forms a triple helix with the mutant allele, or a single-stranded RNA, for example.

In another embodiment, the suppression effector is a ribozyme that cleaves a mature RNA encoding a mutant allele and the replacement nucleic acid encodes a wild-type or non-disease causing allele that comprises at least one degenerate/wobble nucleotide that is altered so that the replacement nucleic acid is not suppressed, or is only partially suppressed, by the ribozyme. In an embodiment, the suppression effector is a ribozyme that cleaves an RNA encoded by the mutant allele, e.g., at an NUX or UX ribozyme cleavage site. In an embodiment, the ribozyme comprises the nucleotide sequence of SEQ ID NO: 29, 30, 31, 32, 33, 34, 75, or 76. In an embodiment, the RNA targeted is an mRNA.

In another embodiment, the suppression effector is a dsRNA and the replacement nucleic acid encodes a wild-type or non-disease causing allele that comprises at least one degenerate/wobble nucleotide that is altered so that the replacement nucleic acid is not suppressed, or is only partially suppressed, by the siRNA.

In an embodiment, the replacement nucleic acid encodes mammalian rhodopsin, collagen 1A1, collagen 1A2, or peripherin.

In an embodiment, the suppression effector and or replacement nucleic acid are operatively linked to an expression vector, such as a bacterial or viral expression vector. In an embodiment, the suppression effector suppresses both alleles of an endogenous gene. In another embodiment, the suppression effector suppresses only one allele of an endogenous gene.

In another aspect, the invention provides cells expressing a ribozyme or a dsRNA, either transiently or stably, and their experimental or therapeutic use. In an embodiment, the siRNA targets COL1A1. In an embodiment, the cells express COL1A1-EGFP. In an embodiment, the cells express a replacement nucleic acid expressing COL1A1 that is not targeted by the siRNA. In another embodiment, the cells comprise a vector encoding at least one siRNA. In another embodiment, the ribozyme targets rhodopsin.

In another aspect, the invention provides transgenic animals and their experimental or therapeutic use. In an embodiment, the transgenic animal is a model for Retinitis Pigmentosa (Pro23His). In another embodiment, the transgenic animal expresses a ribozyme that targets human rhodopsin. In another embodiment, the transgenic animal expresses a replacement nucleic acid transgene that has been altered at a wobble position such that it escapes suppression by a ribozyme. In another embodiment, the replacement nucleic acid encodes a modified human rhodopsin protein. In another embodiment, the transgenic animal expresses a wild type human rhodopsin transgene. In yet another embodiment, the transgenic animal is a knockout of the endogenous mouse rhodopsin gene (rho−/−).

In yet another aspect, the invention provides methods for suppressing rhodopsin expression in an animal by intraocular (e.g., subretinal) injection of a suppression effector into the animal.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which:

FIG. 13B provides the design of siRNA driven from a plasmid using a H1 promoter and targeting human COL1A1 transcripts. The design of modified human replacement COL1A1 genes using the degeneracy of the genetic code such that modified replacement genes encode for the same amino acids as the wild type gene are also provided. In addition, diagrammatic representations of siRNAs are provided. The sequences provided correspond, from top to bottom, to SEQ ID NO: 147-171.

FIG. 19B provides a more detailed schedule of animal matings. Five transgenic mouse lines are used. Mice in which the endogenous mouse rhodopsin is absent, that is, rhodopsin knockout mice (rho–/–), mice carrying a mutant human rhodopsin transgene (Pro23His), mice carrying a wild type human rhodopsin transgene (RhoNHR), mice carrying a modified human rhodopsin gene (RhoM) with sequence changes at degenerate sites and mice carrying the suppression effector (Rz40).

FIG. 22 shows siRNAs designed to target human rhodopsin transcripts. siRNAs (termed Silencer A and B) were designed over one or more of the five base alterations present in the modified replacement human rhodopsin gene described in FIG. 17. siRNA designs are provided however any part of the transcript could be targeted by one or more suppression agents and any degenerate site(s) used to introduce sequence modifications in the replacement gene. The sequences provided correspond, from top to bottom, to SEQ ID NO: 180-183.

FIG. 23A shows siRNA-based suppression of expression of human rhodopsin in COS-7 cells stably expressing the target wild type human rhodopsin gene. siRNA suppression was evaluated using real-time RT PCR. An siRNA targeting EGFP was utilized as a non-targeting control. Levels of GAPDH expression were used as an internal control.

FIG. 23B demonstrates siRNA-based suppression of rhodopsin expression in a mouse carrying a single copy of the human rhodopsin gene and a single copy of the mouse rhodopsin gene (rho+/−, RhoNhr+/−). Silencer B was subretinally injected into this mouse and subsequently siRNA-based suppression of rhodopsin expression was evaluated in retinal RNA from the same mouse using real-time RT PCR.

FIG. 24 shows that Silencer B is unable to suppress transcripts from the modified human rhodopsin replacement gene. The replacement gene was cloned into the pIRES 2-EGFP vector from which fusion transcripts carrying both the target sequence (human rhodopsin) and a reporter gene (enhanced green fluorescent protein EGFP) sequence are transcribed. Suppression was evaluated using the enhanced green fluorescent protein as a marker—results suggest that Silencer B does not suppress expression of the replacement gene—the presence of sequence alterations at degenerate sites in transcripts from the modified human rhodopsin replacement gene protects transcripts from siRNA-mediated suppression.

FIG. 25 shows the DNA sequence of the modified human rhodopsin replacement gene. The sequence provided corresponds to SEQ ID NO: 184.

DETAILED DESCRIPTION OF THE INVENTION

Figures 1A, 1B:
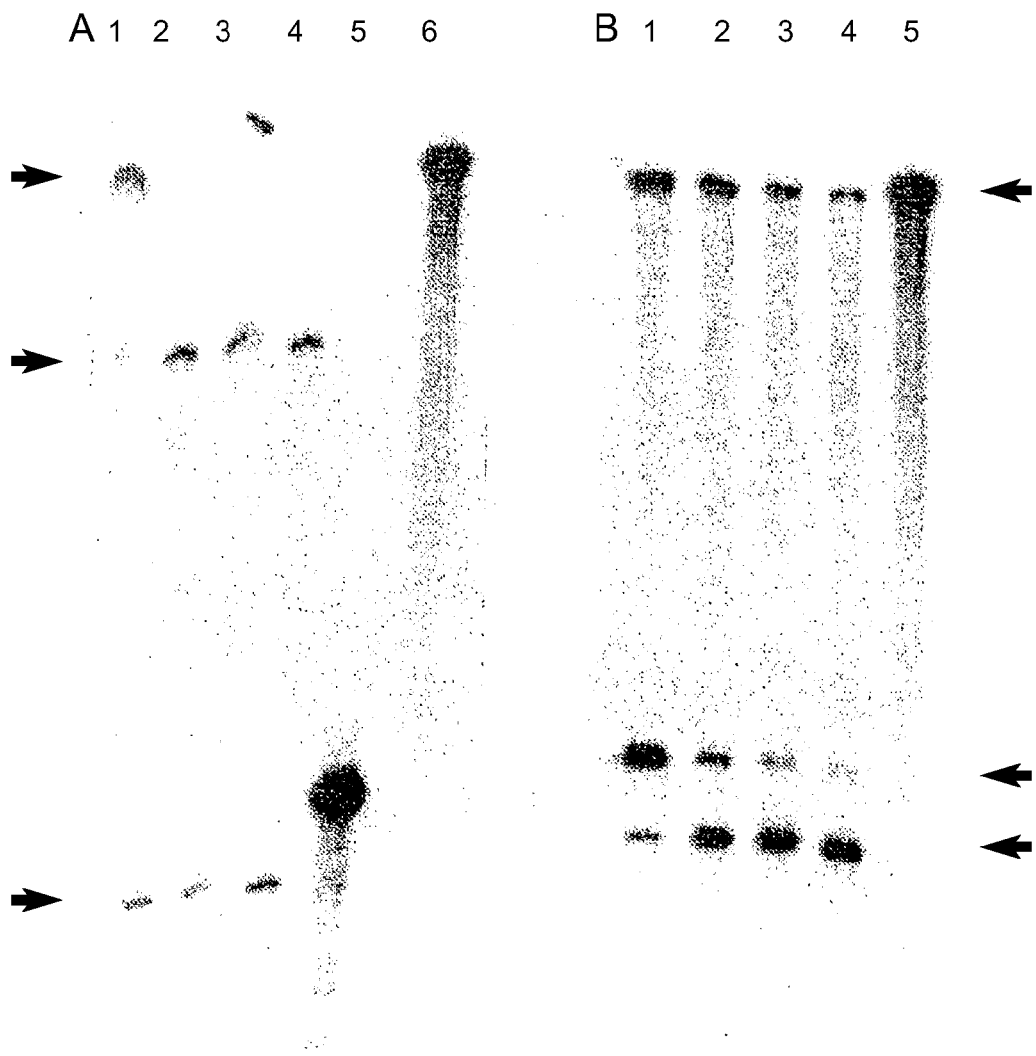
FIG. 1A shows human rhodopsin cDNA (SEQ ID NO:1) expressed from the T7 promoter to the BstEII site in the coding sequence.
FIG. 1B shows the unadapted human rhodopsin cDNA expressed from the T7 promoter to the FspI site in the coding sequence.

The invention provides compositions and methods for suppressing the expression of a nucleic acid such as an endogenous gene that has a deleterious mutation, using suppression effectors and replacing the mutant gene with a replacement nucleic acid that escapes recognition by the suppression effector. The invention provides methods and compositions for the treatment of a disease caused by a mutant endogenous gene.

Generally, the term 'suppression effector' means a molecule that can silence or reduce gene expression in a sequence specific matter. In an embodiment, the suppression effector targets (e.g., binds) coding sequence. The suppression effector can also target non-coding regions such as 5' or 3' untranslated regions, introns, control regions (e.g., promoter sequences), other sequences adjacent to a gene, or any combination of such regions. Binding of a suppression effector to its target nucleic acid prevents or lowers functional expression of the nucleic acid.

In an embodiment of the invention, the suppression effector is a ribozyme designed to elicit cleavage of target RNA. In another embodiment, the suppression effector is an antisense nucleic acid, a triple helix-forming DNA, a PNA, an RNAi, a peptide, an antibody, an aptamer, or a modified form thereof.

In an embodiment, the invention provides suppression effectors that bind specifically or partially specifically to coding sequences of a gene, RNA or protein encoded thereby to prevent or reduce the functional expression thereof, for the treatment of autosomal dominant disease, polygenic disease or infectious disease.

In an embodiment, the invention provides a strategy for suppressing a gene where the gene transcript or gene product interferes with the action of an administered compound. In one embodiment, the suppression effector and or replacement gene increases the effectiveness or action of a compound with which it is co-administered, e.g., by altering drug response. For example, one or more allelic variants of a drug metabolizing enzyme (DME) may either metabolize an administered drug too rapidly thereby limiting the bioavailability of the drug and therefore its efficacy or alternatively some allelic variants may metabolize an administered drug too slowly, leading to potential toxicity—i.e., too high levels of drug. Co-administration of the drug together with suppressing the gene encoding a DME and replacing it with an alternative variant of the DME may aid in optimizing the effectiveness of the co-administered drug and limit the associated toxicity. In another embodiment, the invention can be used to suppress and replace genes and gene products involved in either the absorption and transport of the drug and/or the receptor target for the drug itself. Some key categories of genes include those encoding drug metabolizing enzymes (for example, the cytochrome P450 genes, thiopurine methyl transferase amongst others), genes encoding receptor(s) for drugs (for example, dopamine receptors, β2-adrenergic receptor amongst others) and genes encoding products which alter drug absorption and transport (for example, P-glycoprotein amongst others). For example, the multi-drug resistance gene (MDR-1) encoding P glycoprotein, a member of the ABC transporter family, can significantly influence the bioavailability of chemotherapeutic drugs and over-expression of this gene is responsible for tumor resistance to chemotherapeutics in some cases (Gottesman et al. 1993). Similarly, well over 100 drugs are substrates for one of the cytochrome P450 genes (CYP2D6); various allelic variants have been defined in this gene that can result in significantly altered activity of the encoded protein, for example, allele CYP2D6*5 carries a deletion and hence encodes no enzyme (Skoda et al. 1988; Daly et al. 1996). Furthermore, studies with the β2-adrenergic receptor gene suggest that a single polymorphic variant at codon 16 (Gly/Arg) of the receptor gene significantly alters response (approximately a 5-fold difference) to bronchodilators such as albuterol (Martinez et al. 1997). The suppression and replacement of genes involved in altering drug response may aid in optimizing the utility of a broad range of drugs.

In an embodiment, the suppression effector comprises a nucleotide sequence complementary to at least a region of the sequence of the target nucleic acid. The suppression effector also functions to suppress or inhibit transcription or translation of the target nucleic acid. Both functions may be embodied in a single molecular structure, but the suppression effector may have distinct portions that provide a targeting function or a suppressor function. In an embodiment, the targeting function is provided by a nucleic acid that hybridizes under physiological conditions to a portion of the target nucleic acid. In an embodiment, the suppressing function is provided by a ribozyme or other suppression effector that restricts or cuts the target nucleic acid. If the suppression effector is a site-specific ribozyme or siRNA, it preferably is provided to a cell by transfection of an expression vector that encodes the ribozyme or siRNA, which upon transcription generates the RNA structure of the ribozyme or siRNA, complete with its targeting nucleotide sequence. Details of how to make and how to use such suppression effector expression constructs are disclosed herein. As a result of this transfection, expression of the target nucleic acid is inhibited, suppressed, or preferably eliminated, and its normally consequent phenotypic effects are blocked or at least diminished. In other instances, a replacement nucleic acid may be necessary. The replacement nucleic acid may be supplied to cells via coadministration on the same vector, or on a different vector but at the same time as the DNA encoding the suppression effector. Methods of introducing genes into organisms are described, for example, in U.S. Pat. Nos. 5,399,346, 5,087,617, 5,246,921, 5,834,440, the disclosures of which are incorporated herein by reference. Methods of making and transfecting such expression constructs into cells, and the methods for targeting the transfection to appropriate cells in a multicellular organism are known to those skilled in the art.

In an embodiment, the invention provides methods for suppressing the expression of an endogenous gene having a deleterious mutation(s) and, if required, introducing a replacement nucleic acid, the method having the steps of: (1) providing a suppressor effector that binds to the disease allele of a gene to be suppressed and (2) providing a replacement nucleic acid that is modified in at least one wobble base using the degeneracy of the genetic code, wherein the suppressor effector is unable to bind, or binds less efficiently to, the equivalent or homologous region in the replacement gene.

A suppressor effector that partially recognizes its target nucleic acid may not completely suppress the expression of its target nucleic acid. In a preferred embodiment a suppression effector achieves between about 5% and about 10%, about 10% and about 30%, about 30% and about 60% suppression of its target gene, more preferably between about 60% and about 80% suppression, more preferably between about 80% and about 90% suppression and still more preferably between about 90% and about 100% suppression.

The invention is useful where one or both alleles of the gene in question contain at least one mutation that affects the function or level of the gene product. For example, the alteration may result in an altered protein product from the wild-type gene or altered control of transcription and processing. Inheritance, or somatic acquisition of such a mutation gives rise to a disease phenotype or predisposes an individual to a disease phenotype. Alternatively, the gene of interest provides a wild-type or normal phenotype, but contributes to a disease state in another way such that the suppression of the gene would alleviate or improve the disease state or improve the effectiveness of an administered therapeutic compound. Notably, the invention has the advantage that the same suppression strategy could be used to suppress, in principle, many mutations in a gene. This is particularly relevant when large numbers of mutations within a single gene cause disease pathology.

In an embodiment, a suppression effector targets a characteristic of one allele of a gene such that suppression is specific or partially specific to one allele of a gene (see PCT/GB97/00574 which is incorporated by reference). The invention further provides for use of a replacement nucleic acid with altered coding sequences such that replacement nucleic acid is not recognized (or is recognized less effectively) by the suppression effector. A replacement nucleic acid provides a wild type gene product, a functionally equivalent gene product or a functionally improved gene product, but is protected completely or partially from suppression by the suppression effector. In an embodiment of the invention, the replacement nucleic acid has an altered nucleotide sequence in at least one coding region such that the replacement nucleic acid codes for a product with one or more altered amino acids. The product (the RNA and/or protein) encoded by the replacement gene is equivalent to or better than the wild type product.

In a further embodiment of the invention, replacement nucleic acids are provided that are not recognized by naturally occurring suppressors that inhibit or reduce gene expression in one or more individuals, animals or plants. The invention provides for replacement nucleic acids that have altered sequences around degenerate/wobble site(s) such that suppression by naturally occurring suppressors is completely or partially prevented. This may be due to partial or less efficient recognition, or selective or preferential binding, of a suppressor effector to the mutant allele vs. the replacement allele, and may refer to binding which is not stable, due to, for example, sequence dissimilarity or lack of complementarity of the sequences. Replacement genes may have naturally occurring or artificially introduced sequence changes at degenerate sites. The replacement nucleic acid provides (when necessary) additional expression of the normal protein product when required to ameliorate pathology associated with reduced levels of wild-type protein. The same replacement gene can be used in conjunction with the suppression of many different disease mutations within a given gene.

Nucleic acids encoding suppression effectors or replacement nucleic acids may be provided in the same vector or in separate vectors. Suppression effectors or replacement nucleic acids may be provided separately or as a combination of nucleic acids. The suppression effectors can be administered before, after, or simultaneously with a replacement nucleic acid. Multiple suppression effectors can be used to suppress one or more target nucleic acids or to optimise the efficiency of suppression. Suppression effectors may be administered as naked nucleic acids or nucleic acids in vectors or can be delivered with lipids, polymers, nucleic acids, or other derivatives that aid gene delivery or expression. Nucleotides may be modified to render them more stable, for example, resistant to cellular nucleases while still supporting RNaseH mediated degradation of RNA or with increased binding efficiencies, or uptake. Alternatively, antibodies, aptamers, or peptides can be generated to target the protein product of the gene to be suppressed. In an embodiment, replacement proteins or peptides may be used in place of a replacement nucleic acid.

The invention further provides vectors containing one or more suppression effectors in the form of nucleic acids that target coding sequence(s), or combinations of coding and non-coding sequences, of a target nucleic acid, and vector(s) containing a replacement nucleic acid sequence to which nucleic acids for suppression are unable to bind (or bind less efficiently), in the preparation of a combined medicament for the treatment of an autosomal dominant or polygenic disease. Vectors can be DNA or RNA vectors derived from, e.g., bacteria or viruses. Exemplary viral vectors that may be used in the practice of the invention include those derived from adenovirus (Ad) (Macejak et al. 1999); adenoassociated virus (AAV) (Horster et al. 1999); retroviral-C type such as MLV (Wang et al. 1999); lentivirus such as HIV or SIV (Takahashi et al. 1999); herpes simplex (HSV) (Latchman et al. 2000); and SV40 (Strayer et al. 2000). Exemplary, non-viral vectors that may be useful in the practice of the invention include bacterial vectors from *Shigella flexneri* (Sizemore et al. 1995 and Courvalin et al. 1995), such as the *S. flexneri* that is deficient in cell-wall synthesis and requires diaminopimeli-acid (DAP) for growth. In the absence of DAP, recombinant bacteria lyse in the host cytosol and release the plasmid. Another exemplary non-viral vector is the intergrase system from bacteriophage phiC31 (Ortiz-Urda S et al. 2001). Cat-ionic lipid mediated delivery of suppression effectors (Tam et al. 2000), soluble biodegradable polymer-based delivery (Maheshwari et al. 2000), or electroporation/ionthophoresis (Muramatsu et al. 2001; Rossi et al. 1983) may also be used.

The invention further provides a kit for use in the treatment of a disease caused by a deleterious mutation in a gene, the kit comprising at least one suppression effector able to bind to a gene or RNA to be suppressed and, optionally, a replacement nucleic acid to replace the mutant gene having a sequence that allows it to be expressed and to completely or partially escape suppression by the suppression effector.

In some cases it is possible that lowering RNA levels may lead to a parallel lowering of protein levels, however this is not always the case. In some situations mechanisms may prevent a significant decrease in protein levels despite a substantial decrease in levels of RNA. However, in many instances suppression at the RNA level has been shown to lower protein levels. In some cases it is thought that ribozymes elicit suppression not only by cleavage of RNA but also by an antisense effect due to the antisense arms in the ribozyme surrounding the catalytic core. Ribozyme activity may be augmented by the use of, for example, non-specific nucleic acid binding proteins or facilitator oligonucleotides (Herschlag et al., 1994; Jankowsky and Schwenzer, 1996). Multitarget ribozymes such as, for example, connected or shotgun ribozymes have been suggested as a means of improving the efficiency of ribozymes for gene suppression (Ohkawa et al., 1993). In addition, maxizymes which do not require NUX sites offer more flexibility in terms of selecting suitable target sites.

The strategies, compositions and methods described herein have applications for alleviating autosomal dominant diseases. Complete silencing of a disease allele may be difficult to achieve using certain suppression effectors or any combination thereof. However small quantities of mutant gene product may be tolerated in some autosomal dominant disorders. In others, a significant reduction in the proportion of mutant to normal product may result in an amelioration of disease symptoms. Hence this invention may be applied to any autosomal dominantly or polygenically inherited disease where the molecular basis of the disease has been established or is partially understood. The invention will enable the same therapy to be used to treat or study a range of different disease mutations within the same gene. The invention circumvents the need for a specific therapy for every mutation causing or predisposing to a disease. This is particularly relevant in some disorders, for example, rhodopsin linked autosomal dominant RP, in which to date about one hundred different mutations in the rhodopsin gene have been observed in adRP patients. Likewise, hundreds of mutations have been identified in the human type I Collagen 1A1 and 1A2 genes in autosomal dominant osteogenesis imperfecta.

The invention may be applied in gene therapy approaches for biologically important polygenic disorders affecting large proportions of the world's populations such as age-related macular degeneration, glaucoma, manic depression, cancers having a familial component and indeed many others, including infectious diseases (e.g., targeting genes for endogenous proteins required for infection of viruses, bacteria, parasites, or prions, for example). Polygenic diseases require inheritance of more than one mutation (component) to give rise to the disease state. Notably an amelioration in disease symptoms may require reduction in the presence of only one of these components, that is, suppression of one genotype which, together with others leads to the disease phenotype, may be sufficient to prevent or ameliorate symptoms of the disease. In some cases suppression of more than one component may be required to ameliorate disease symptoms. This invention provides interventive therapies for common polygenic diseases to suppress a particular genotype(s) or modifications of an aberrant drug response by using suppression and, when necessary, replacement nucleic acids or gene products.

In another embodiment, the suppression effector and replacement technology can be used to render a cell or individual which is genetically predisposed to infection by an infectious agent resistant to infection. Some infectious agents use defined molecular mechanisms to enter and infect cells. These mechanisms are specific to the infectious agent and indeed in some cases can vary between different serotypes of the same infectious agent (Davidson et al. 2000; Yotnda P et al. 2001). There is also evidence that small variations in the genes encoding products involved in these mechanisms of infection can have a substantial effect on the ability of the agent to be infectious. For example, there is evidence that HIV requires the CCR5 receptor for infection. The CCR5 gene encodes a cell surface receptor protein that binds HIV-suppressive β-chemokines. Some individuals are resistant to HIV (Samson et al. 1996) and this resistance has been linked to one allelic variant of the CCR5 gene that has a 32 bp deletion in the gene—individuals homozygous for this allele seem to be highly resistant to HIV infection. In the Caucasian population the frequency of this allele is about 0.1, suggesting that approximately 1 in 100 people may be homozygous for the allele. The other 99% of the population harbor one or two alleles of the CCR5 receptor gene that aid HIV infection. Similarly it has been established that the Haemaglobin C variant (β6Glu to Lys) can protect against malarial infection in individuals who are Haemoglobin C homozygous (HbCC). (Modlano D et al. 2001; Commentary in Science Magazine 2001 294: p 1439). Given this scenario there has been and will continue to be a natural evolution towards increased frequencies of the Haemaglobin C variant in populations where malaria is prevalent. Given knowledge of the molecular mechanisms of infection and resistance to infectious agents the suppression and replacement technologies described herein can be used in the prophylaxis and treatment of infectious agents/disorders such as those outlined above.

Ribozyme Suppression Effectors

Preferred antisense molecules are ribozymes designed to catalytically cleave target allele mRNA transcripts to prevent translation of mRNA and expression of a target allele (See, e.g., PCT International Publication WO 94/11364, published Oct. 4, 1990; Sarver et al., 1990). Ribozymes are enzymatic RNA molecules capable of catalyzing the specific cleavage of RNA. A ribozyme may be, for example, a hammerhead ribozyme (Haseloff et al. 1989); a hairpin ribozyme (Feldstein et al. 1989); a hepatitis delta virus RNA subfragment (Wu et al. 1989); a neurospora mitochondrial VA RNA (Saville et al. 1990); a connected or shotgun ribozyme (Chen et al. 1992); or a minizyme (or a transplicing ribozyme (Ayre et al. 1999) or a maxizyme (Kuwabara et al. 1998) (Kuwabara et al. 1996). In addition, the inhibitory effect of some ribozymes may be due in part to an antisense effect of the antisense sequences flanking the catalytic core which specify the target site. A hammerhead ribozyme may cleave an RNA at an NUX site in any RNA molecule, wherein N is selected from the group consisting of C, U, G, A and X is selected from the group consisting of C, U or A. Alternatively, other recognition sites may be used as appropriate for the ribozyme, such as 5'-UX -3', where X=A, C, or U. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include a catalytic sequence responsible for mRNA cleavage. For example, see U.S. Pat. No. 5,093,246, which is incorporated by reference herein in its entirety.

Other variables require consideration in designing a ribozyme, such as the two dimensional conformation of the RNA (e.g., loops) and the accessibility of a ribozyme for its target. The utility of an individual ribozyme designed to target an NUX site in an open loop structure of transcripts from one allele of a gene will depend in part on the robustness of the RNA open loop structure when various deleterious mutations are also present in the transcript. Robustness may be evaluated using an RNA-folding computer program such as RNA-PlotFold. A robust loop refers to the occurrence of the loop for most or all of the plotfolds with different energy levels. For example, data for six different adRP causing mutations in the rhodopsin gene were evaluated. For each of these mutations the large RNA open loop structure which is targeted by Rz40 was maintained in the mutant transcripts.

The ribozymes of the present invention also include RNA endoribonucleases (hereinafter "Cech-type ribozymes") such as the one that occurs naturally in Tetrahymena Thermophila (known as the IVS, or L-19 IVS RNA) and which has been extensively described by Thomas Cech and collaborators (Zaug, et al., 1984; Zaug and Cech, 1986; Zaug, et al., 1986; published International patent application No. WO88/04300 by University Patents Inc.; Been and Cech, 1986). The Cech-type ribozymes have an eight base pair active site which hybridizes to a target RNA sequence whereafter cleavage of the target RNA takes place. The invention encompasses those Cech-type ribozymes that target eight base-pair active site sequences that are present in a target allele. Hairpin, hammerhead, trans-splicing ribozymes and indeed any ribozyme could be used in the practice of the invention (Haseloff et al. 1989; Feldstein et al. 1989; Wu et al. 1989; Saville 1990; Chen et al. 1992; and Kuwabara et al 1996). In addition, any RNA inactivating or RNA cleaving agent which is capable of recognition of and/or binding to specific nucleotide sequences in an RNA is contemplated. For example, splicesome-mediated RNA trans-splicing (Puttaraju et al. 1999); double strand RNA (Fire et al. 1998; Bahramian et al. 1999); PNAs (Chinnery et al. 1999; Nielsen et al. 2000); antisense DNA (Reaves et al. 2000); antisense RNA (Chadwick et al. 2000); or triple helix forming oligonucleotides (Chan et al. 1997). All types of RNA may be cleaved in the practice of the invention, including, for example, mRNA, tRNA, rRNA and snRNPs.

Ribozymes can be composed of modified oligonucleotides (e.g., for improved stability, targeting, etc.) and should be delivered to cells that express the target allele. A preferred method of delivery involves using a DNA construct encoding the ribozyme under the control of a strong constitutive pol III or pol II promoter, so that transfected cells produce sufficient quantities of the ribozyme to destroy endogenous target allele messages and inhibit translation. Because ribozymes, unlike antisense molecules, are catalytic, a lower intracellular concentration of ribozymes may be required for efficient suppression.

Hammerhead ribozymes with antisense arms were used to elicit sequence specific cleavage of transcripts from genes implicated in dominant disorders but not of transcripts from replacement nucleic acids containing sequence modifications in wobble positions such that the replacement nucleic acid still codes for wild type protein. The present invention is exemplified using suppression effectors targeting sites in coding regions of the human and mouse rhodopsin, human peripherin and human collagen 1A2 genes. Rhodopsin expression is retina specific, whereas collagen 1A2 is expressed in a number of tissues, including skin and bond. While these four genes have been used as examples, there is no reason why the invention could not be deployed in the suppression of many other genes in which mutations cause or predispose to a deleterious effect. Many examples of mutant genes that give rise to disease phenotypes are known in the art—these genes all represent targets for the invention.

Although present invention is exemplified using RNAi and hammerhead ribozymes. There is no reason why other suppression effectors directed towards genes, gene transcripts or gene products could not be used to achieve gene suppression such as, for example, antisense RNA, antisense DNA, triple helix forming DNA, PNAs and peptides.

Antisense Suppression Effectors

Antisense suppression refers to administration or in situ generation of nucleic acid sequences or their derivatives that specifically hybridize or bind under cellular conditions, with the cellular mRNA and/or genomic DNA encoding one or more of the subject target alleles so as to inhibit expression of that target allele, e.g. by inhibiting transcription and/or translation. The binding may be by conventional base pair complementarity, or, for example, in the case of binding to DNA duplexes, through specific interactions in the major groove of the double helix. In general, antisense suppression refers to the range of techniques generally employed in the art, and includes any suppression which relies on specific binding to nucleic acid sequences. An antisense construct of the present invention can be delivered, for example, as an expression plasmid which, when transcribed in the cell, produces RNA that is complementary to at least a unique portion of the cellular mRNA that encodes a target sequence or target allele of an endogenous gene. Alternatively, the antisense construct is a nucleic acid that is generated ex vivo and which, when introduced into the cell, causes inhibition of expression by hybridizing with the mRNA and/or genomic sequences of a target allele of an endogenous gene. Such nucleic acids are preferably modified oligonucleotides that are resistant to endogenous nucleases, e.g., exonucleases and/or endonucleases, and are therefore stable in vivo. Modifications, such as phosphorothioates, have been made to nucleic acids to increase their resistance to nuclease degradation, binding affinity and uptake (Cazenave et al., 1989; Sun et al., 1989; McKay et al., 1996; Wei et al., 1996). Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al., 1988 and Stein et al., 1988.

Antisense approaches involve the design of oligonucleotides (either DNA or RNA) that are complementary to a target allele of a gene or its gene product. The antisense oligonucleotides may bind to the target allele mRNA transcripts and prevent translation. Absolute complementarity, although preferred, is not required. Antisense nucleic acids that are complementary to the 5' end of the message, e.g., the 5' untranslated sequence up to and including the AUG initiation codon, may work most efficiently at inhibiting translation. However, sequences complementary to the 3' untranslated sequences of mRNAs are also effective at inhibiting translation of mRNAs. (Wagner, R. 1994). Therefore, nucleic acids complementary to either the 5' or 3' untranslated, non-coding regions of a target allele of an endogenous gene could be used in an antisense approach to inhibit translation of the product of the target allele. Nucleic acids complementary to the 5' untranslated region of the mRNA should preferably include the complement of the AUG start codon. Antisense nucleic acids complementary to mRNA coding regions are less efficient inhibitors of translation but could be used in accordance with the invention. Whether designed to hybridize to the 5', 3' or coding region of the mRNA encoding a target allele, antisense nucleic acids should be about at least six nucleotides in length, and are preferably nucleic acids ranging from 6 to about 50 nucleotides in length. In certain embodiments, the nucleic acid is at least 10 nucleotides, at least 17 nucleotides, at least 25 nucleotides, or at least 50 nucleotides in length.

Suppression of RNAs that are not translated are also contemplated, such as, for example, snRNPs, tRNAs and rRNAs. For example, some genes are transcribed but not translated or the RNA transcript functions at the RNA level (i.e., the RNA of these genes may have a function that is separate from the function which its translated gene product (protein) may have). For example, in an Irish family suffering from retinitis pigmentosa in conjunction with sensorineural deafness, the mutation was identified to be a single base substitution in the second mitochondrial serine tRNA gene, a gene which is indeed transcribed but not translated (Mansergh et al. 1999). Other examples include Tsix and Xist (van Stijn et al. 1995; Rupert et al. 1995), H19 (Miyatake et al. 1996; Matsumoto et al. 1994; Redeker et al. 1993), IPW (imprinted gene in the Prader-Willi syndrome region) (Wevrick et al. 1994). The IPW RNA is spliced and polyadenylated, but its longest open reading frame is 45 amino acids. The RNA is widely expressed in adult and fetal tissues and is found in the cytoplasmic fraction of human cells, which is also the case for the H19 non-translated RNA, but differs from the Xist RNA which is found predominantly in the nucleus. Using a sequence polymorphism, exclusive expression from the paternal allele in lymphoblasts and fibroblasts has been demonstrated and monoallelic expression found in fetal tissues.

Regardless of the choice of target sequence, it is preferred that in vitro studies are first performed to quantitate the ability of the antisense nucleic acid to inhibit gene expression. It is preferred that these studies utilize controls that distinguish between antisense gene inhibition and nonspecific biological effects of the nucleic acids. It is also preferred that these studies compare levels of the target RNA or protein with that of an internal control RNA or protein.

The antisense nucleic acids can be DNA or RNA or chimeric mixtures or derivatives or "modified versions thereof", single-stranded or double-stranded. As referred to herein, "modified versions thereof" refers to nucleic acids that are modified, e.g., at a base moiety, sugar moiety, or phosphate backbone, for example, to improve stability or halflife of the molecule, hybridization, etc. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. The nucleic acid may include other appended groups such as peptides (e.g., for targeting host cell receptors in vivo), or agents facilitating transport across the cell membrane (see, e.g., Letsinger et al., 1989; Lemaitre et al., 1987; PCT Publication No. WO 88/09810, published Dec. 15, 1988) or the blood-brain barrier (see, e.g., PCT Publication No. WO 89/10134, published Apr. 25, 1988), hybridization-triggered cleavage agents, (See, e.g., Krol et al., 1988) or intercalating agents. (See, e.g., Zon, 1988). To this end, the oligonucleotide may be conjugated to another molecule, e.g., a peptide, hybridization triggered cross-linking agent, transport agent, hybridization-triggered cleavage agent, etc.

The antisense nucleic acid may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5oxyacetic acid methylester, uracil-5-oxyacetic acid (v), -5-methyl-2-thiouracil, 3-(3-amino-3-N-2-carboxypropyl)uracil, (acp3)w, and 2,6-diaminopurine.

The antisense nucleic acids may also comprise at least one modified sugar moiety selected from the group including but not limited to arabinose, 2-fluoroarabinose, xylulose, and hexose.

In yet another embodiment, the antisense nucleic acid comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense nucleic acid is an ə-anomeric oligonucleotide. An ə-anomeric oligonucleotide forms specific double-stranded hybrids with complementary RNA in which, contrary to the usual β-units, the strands run parallel to each other (Gautier et al., 1987). The oligonucleotide is a 2'-0-methylribonucleotide (Inoue et al., 1987), or a chimeric RNA-DNA analogue (Inoue et al., 1987).

The antisense molecules should be delivered to cells that express the target allele. A number of methods have been developed for delivering antisense DNA or RNA to cells; e.g., antisense molecules can be injected directly into a tissue site, or modified antisense molecules, designed to target the desired cells (e.g., antisense linked to peptides or antibodies that specifically bind receptors or antigens expressed on the target cell surface) can be administered systemically.

In an embodiment, a recombinant DNA construct in which the antisense nucleic acid is placed under the control of a strong promoter is used. The use of such a construct to transfect target cells results in the transcription of sufficient amounts of single stranded RNAs that form complementary base pairs with the endogenous target allele transcripts and thereby prevent translation of the target allele mRNA. For example, a vector is introduced such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981), the promoter contained in the 3' long terminal repeat of Rous sarcoma virus (Yamamoto et al., 1980), the herpes thymidine kinase promoter (Wagner et al., 1981), the regulatory sequences of the metallothionein gene (Brinster et al, 1982), the rhodopsin promoter (McNally et al. 1999; Zack et al., 1991), the collagen1A2 promoter (Akai et al. 1999; Antoniv et al. 2001), the collagen 1A1 promoter (Sokolov et al. 1995; Breault et al. 1997) and others. Any type of plasmid, cosmid, YAC or viral vector can be used to prepare the recombinant DNA construct which can be introduced directly into the tissue site; e.g., the bone marrow. Alternatively, viral vectors can be used which selectively infect the desired tissue; (e.g., for brain, herpesvirus vectors may be used), in which case administration may be accomplished by another route (e.g., systemically).

The antisense constructs of the present invention, by antagonizing the normal biological activity of the target allele proteins, can be used in the modulation (i.e., activation or stimulation, e.g., by agonizing or potentiating and inhibition or suppression, e.g., by antagonizing, decreasing or inhibiting) of cellular activity both in vivo and, likewise, for ex vivo tissue cultures.

The antisense techniques can be used to investigate the role of target allele RNA or protein product in developmental events, as well as the normal cellular function of target allele products in adult tissue. Such techniques can be utilized in cell culture, but can also be used in the creation of transgenic animals.

Triple Helix Suppression Effectors

Endogenous target allele gene expression can be reduced by targeting DNA sequences complementary to the regulatory region of the target allele (i.e., the target allele promoter and/or enhancers) to form triple helical structures that prevent transcription of the target allele in target cells in the body (Helene, 1991; Helene et al., 1992; Maher, 1992).

Nucleic acid molecules used in triple helix formation for the inhibition of transcription are preferably single stranded and composed of deoxyribonucleotides. The base composition of these oligonucleotides promotes triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex. Alternatively, other suppression effectors such as double stranded RNA could be used for suppression.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Oligonucleotides of the invention may be synthesized by standard methods known in the art, e.g. by use of an automated DNA synthesizer (e.g., such as are commercially available from Biosearch, Applied Biosystems, etc.). As examples, phosphorothioate oligonucleotides may be synthesized by the method of Stein et al., 1988, methylphosphonate oligonucleotides can be prepared by use of controlled pore glass polymer supports (Sarin et al., 1988).

Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

siRNA

RNAi can be used to suppress expression of the target nucleic acid. A replacement nucleic acid is provided that is altered around the RNAi target site at degenerate (wobble) positions such that it escapes suppression by the RNAi at least in part but the amino acid sequence it encodes is normal. Replacement nucleic acids thereby escape, at least in part, suppression by the RNAi. The sequence specificity of RNAi suppression may be dependent on the individual structures of siRNA molecules and their targets. Various studies exploring specific and non-specific siRNA suppression have been reported (Miller et al. 2003). It is notable that at times siRNA specificity may be at a single nucleotide level whereas in other cases multiple sequence differences between the target and the antisense strand of the siRNA may be required to eliminate suppression of the target by a given siRNA. The degeneracy of the genetic code is readily utilized to introduce such sequence differences.

Transgenic Animals

In another aspect, the invention provides transgenic animals, e.g., non-human animals, in which one or more of the cells of the animal contain heterologous nucleic acid introduced by way of human intervention, such as by transgenic techniques well known in the art. The nucleic acid is introduced into a cell, directly or indirectly by introduction into a precursor of a cell, by way of deliberate genetic manipulation, such as by microinjection or by infection with a recombinant virus. This molecule may be integrated within a chromosome, or it may be extrachromosomally replicating DNA. In the typical transgenic animals described herein, the transgene causes cells to express a recombinant form of a polypeptide, e.g. either agonistic or antagonistic forms. Moreover, transgenic animals may be animals in which gene disruption of one or more genes is caused by human intervention, including both recombination and antisense techniques. The transgenic animal could be used, as in humans, to develop therapies for animals. Alternatively, the transgenic animal could be used as research tools in the development of animal models mostly via transgenic techniques. For example, a transgenic animal expressing a suppression effector such as a ribozyme, that inhibits the expression of an endogenous gene may also express a replacement gene that is altered so as to not be recognized by the suppression effector. The transgenic animal therefore represents a rescued animal. In addition, the transgenic animal could be used to investigate the role/functions of various genes and gene products.

The "non-human animals" of the invention include mammals such as rodents, non-human primates, sheep, dog, cow, pig, chickens, as well as birds, marsupials, amphibians, reptiles, etc. Preferred non-human animals are selected from the primate family (e.g., macaque) or rodent family (e.g., rat and mouse) although transgenic amphibians, such as members of the *Xenopus* genus, and transgenic chickens are useful for understanding and identifying agents that affect, for example, embryogenesis, tissue formation, and cellular differentiation. The term "chimeric animal" is used herein to refer to animals in which a recombinant gene (e.g., suppression effector or replacement nucleic acid) is found, or in which a recombinant gene is expressed in some but not all cells of the animal. The term "tissue-specific chimeric animal" indicates that a recombinant gene is present and/or expressed or disrupted in some tissues but not others. As used herein, the term "transgene" means a nucleic acid sequence (encoding, e.g., human rhodopsin, or a ribozyme that targets mutant mouse rhodopsin) that has been introduced into a cell. A transgene could be partly or entirely heterologous, i.e., foreign, to the transgenic animal or cell into which it is introduced, or can be homologous to an endogenous gene of the transgenic animal or cell into which it is introduced, but which is inserted into the animal's genome in such a way as to alter the cell's genome (e.g., it is inserted at a location different from that of the natural gene, or its insertion results in a knockout). A transgene can also be present in a cell in the form of an episome. A transgene can include one or more transcriptional regulatory sequences and any other nucleic acid, such as 5' UTR sequences, 3' UTR sequences, or introns, that may be necessary for optimal expression of a selected nucleic acid.

The invention provides for transgenic animals that can be used for a variety of purposes, e.g., to identify human rhodopsin therapeutics. Transgenic animals of the invention include non-human animals containing a heterologous human rhodopsin gene or fragment thereof under the control of a human rhodopsin promoter or under the control of a heterologous promoter. Accordingly, the transgenic animals of the invention can be animals expressing a transgene encoding a wild-type human rhodopsin protein, for example, or fragment thereof or variants thereof, including mutants and polymorphic variants thereof. Such animals can be used, e.g., to determine the effect of a difference in amino acid sequence of human rhodopsin protein such as a polymorphic difference.

These animals can also be used to determine the effect of expression of human rhodopsin protein in a specific site or for identifying human rhodopsin therapeutics or confirming their activity in vivo. In a preferred embodiment, the human rhodopsin transgenic animal contains a human rhodopsin nucleic acid sequence that has been altered such that it cannot bind to a ribozyme such as it escapes suppression by the ribozyme Rz40. In another preferred embodiment, the transgenic animal of the invention expresses Rz40. In another preferred embodiment, the transgenic animal of the invention expresses both human rhodopsin and Rz40.

Transgenic animals in which the recombinant rhodopsin gene or the suppression effector is silent are also contemplated, as for example, the FLP or CRE recombinase dependent constructs described below or the use of promoters that are sensitive to chemicals or stimuli, for example, tetracycline inducible promoters.

In an embodiment, the transgenic animal contains a transgene, such as reporter gene, under the control of a human rhodopsin promoter or fragment thereof. These animals are useful, e.g., for identifying compounds that modulate production of human rhodopsin, such as by modulating human rhodopsin gene expression. A human rhodopsin gene promoter can be isolated, e.g., by screening of a genomic library with a human rhodopsin cDNA fragment and characterized according to methods known in the art. In a preferred embodiment of the invention, the transgenic animal containing a human rhodopsin reporter gene is used to screen a class of bioactive molecules known for their ability to modulate human rhodopsin protein expression.

In another embodiment, the transgenic animal is an animal in which the expression of the endogenous rhodopsin gene has been mutated or "knocked out". A "knock out" animal is one carrying a homozygous or heterozygous deletion of a particular gene or genes. These animals are useful for determining whether the absence of rhodopsin protein results in a specific phenotype, in particular whether the transgenic animal has or is likely to develop a specific disease, such as a high susceptibility to macular degeneration. Knockout transgenic animals are useful in screens for drugs that alleviate or attenuate the disease condition resulting from the mutation of a rhodopsin gene as outlined below. The animals are also useful for determining the effect of a specific amino acid difference, or allelic variation, in a rhodopsin gene. The rhodopsin knock out animals can be crossed with transgenic animals expressing, e.g., a mutated form or allelic variant of rhodopsin, thus resulting in an animal that expresses only the mutated protein or the allelic variant of rhodopsin and not the endogenous wild-type protein. In a preferred embodiment of the invention, a transgenic rhodopsin knock-out mouse, carrying the mutated rhodopsin locus on one or both of its chromosomes, is used as a model system for transgenic or drug treatment of the condition resulting from loss of rhodopsin expression.

Methods for obtaining transgenic and knockout non-human animals are well known in the art. Knock out mice are generated by homologous integration of a "knock out" construct into a mouse embryonic stem cell chromosome that encodes the gene to be knocked out. In one embodiment, gene targeting, which is a method of using homologous recombination to modify an animal's genome, is used to introduce changes into cultured embryonic stem cells (ES cells). By targeting a rhodopsin gene of interest in ES cells, these changes are introduced into the germlines of animals to generate chimeras. The gene targeting procedure is accomplished by introducing into tissue culture cells a DNA targeting construct that includes a segment homologous to a target rhodopsin locus, and that also includes an intended sequence modification to the rhodopsin genomic sequence (e.g., insertion, deletion, point mutation). The treated cells are then screened for accurate targeting to identify and isolate those that have been properly targeted.

In a preferred embodiment, the knock out mouse is generated by the integration of a suppression effector into the mouse genome, such that sufficient levels of the transgene are expressed and mouse rhodopsin (normal or mutant) expression is inhibited. Alternatively, the suppression effector is expressed in the cell or mouse but it is not integrated into the genome.

Gene targeting in ES cells is a means for disrupting a rhodopsin gene function through the use of a targeting transgene construct designed to undergo homologous recombination with one or more rhodopsin genomic sequences. The targeting construct can be arranged so that, upon recombination with an element of a rhodopsin gene, a positive selection marker is inserted into (or replaces) coding sequences of the gene. The inserted sequence functionally disrupts the rhodopsin gene, while also providing a positive selection trait. Exemplary rhodopsin targeting constructs are described in more detail below.

Generally, the ES cells used to produce the knockout animals are of the same species as the knockout animal to be generated. Thus for example, mouse embryonic stem cells can usually be used for generation of knockout mice. Embryonic stem cells are generated and maintained using methods well known to the skilled artisan. Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells is the 129J strain. Another ES cell line is murine cell line D3. Still another preferred ES cell line is the WW6 cell line. The cells are cultured and prepared for knockout construct insertion using methods well known to the skilled artisan.

A knock out construct refers to a uniquely configured fragment of nucleic acid that is introduced into a stem cell line and allowed to recombine with the genome at the chromosomal locus of the gene of interest to be mutated. Thus a given knock out construct is specific for a given gene to be targeted for disruption. Nonetheless, many common elements exist among these constructs and these elements are well known in the art. A typical knock out construct contains nucleic acid fragments of not less than about 0.5 kb nor more than about 10.0 kb from both the 5' and the 3' ends of the genomic locus which encodes the gene to be mutated. These two fragments are separated by an intervening fragment of nucleic acid that encodes a positive selectable marker, such as the neomycin resistance gene ($neo^R$). The resulting nucleic acid fragment, consisting of a nucleic acid from the extreme 5' end of the genomic locus linked to a nucleic acid encoding a positive selectable marker, which is in turn linked to a nucleic acid from the extreme 3' end of the genomic locus of interest, omits most of the coding sequence for the rhodopsin gene or other gene of interest to be knocked out. When the resulting construct recombines homologously with the chromosome at this locus, it results in the loss of the omitted coding sequence, otherwise known as the structural gene, from the genomic locus. A stem cell in which such a rare homologous recombination event has taken place can be selected for by virtue of the stable integration into the genome of the nucleic acid of the gene encoding the positive selectable marker and subsequent selection for cells expressing this marker gene in the presence of an appropriate drug (neomycin in this example).

Variations on this basic technique also exist and are well known in the art. For example, a "knock-in" construct refers to the same basic arrangement of a nucleic acid encoding a 5' genomic locus fragment linked to nucleic acid encoding a positive selectable marker that in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targeted gene, resulting in a transgenic animal that expresses a polypeptide of the targeted gene which is defective in one function, while retaining the function of other domains of the encoded polypeptide. This type of "knock-in" mutant frequently has the characteristic of a so-called "dominant negative" mutant because, especially in the case of proteins that homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. A marker gene is one that encodes an enzyme whose activity can be detected (e.g., β-galactosidase), the enzyme substrate can be added to the cells under suitable conditions and the enzymatic activity can be analyzed. One skilled in the art is familiar with other useful markers and the means for detecting their presence in a given cell. All such markers are contemplated as being included within the scope of the teaching of this invention.

As mentioned above, the homologous recombination of the above described "knock out" and "knock in" constructs is very rare and frequently such a construct inserts nonhomologously into a random region of the genome where it has no effect on the gene that has been targeted for deletion, and where it can potentially recombine so as to disrupt another gene that was otherwise not intended to be altered. Such nonhomologous recombination events can be selected against by modifying the above mentioned knock out and knock in constructs so that they are flanked by negative selectable markers at either end (particularly through the use of two allelic variants of the thymidine kinase gene, the polypeptide product of which can be selected against in expressing cell lines in an appropriate tissue culture medium well known in the art—i.e., one containing a drug such as 5-bromodeoxyuridine). Thus, a preferred embodiment of such a knock out or knock in construct of the invention consist of a nucleic acid encoding a negative selectable marker linked to a nucleic acid encoding a 5' end of a genomic locus linked to a nucleic acid of a positive selectable marker which in turn is linked to a nucleic acid encoding a 3' end of the same genomic locus which in turn is linked to a second nucleic acid encoding a negative selectable marker. Nonhomologous recombination between the resulting knock out construct and the genome usually result in the stable integration of one or both of these negative selectable marker genes and hence cells that have undergone nonhomologous recombination can be selected against by growth in the appropriate selective media (e.g., media containing a drug such as 5-bromodeoxyuridine for example). Simultaneous selection for the positive selectable marker and against the negative selectable marker results in a vast enrichment for clones in which the knock out construct has recombined homologously at the locus of the gene intended to be mutated. The presence of the predicted chromosomal alteration at the targeted gene locus in the resulting knock out stem cell line can be confirmed by means of Southern blot analytical techniques which are well known to those familiar in the art. Alternatively, PCR can be used.

Each knockout construct to be inserted into the cell must first be in the linear form. Therefore, if the knockout construct has been inserted into a vector, linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. For example, if the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knock out construct as described above. Where more than one construct is to be introduced into the ES cell, each knockout construct can be introduced simultaneously or one at a time.

After suitable ES cells containing the knockout construct in the proper location have been identified by the selection techniques outlined above, the cells can be inserted into an embryo. Insertion may be accomplished in a variety of ways known to the skilled artisan, however a preferred method is by microinjection. For microinjection, about 10-30 cells are collected into a micropipet and injected into embryos that are at the proper stage of development to permit integration of the foreign ES cell containing the knockout construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan.

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected carries the genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2-3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the rhodopsin gene knocked out in various tissues of the offspring by probing the Western blot with an antibody against the particular rhodopsin protein, or an antibody against the marker gene product, where this gene is expressed. Finally, in situ analysis (such as fixing the cells and labeling with antibody) and/or fluorescence activated cell sorting (FACS) analysis of various cells from the offspring can be conducted using suitable antibodies to look for the presence or absence of the knockout construct gene product.

Yet other methods of making knock-out or disruption transgenic animals are also generally known. Recombinase dependent knockouts can also be generated, e.g. by homologous recombination to insert target sequences, such that tissue specific and/or temporal control of inactivation of an rhodopsin gene can be controlled by recombinase sequences.

Animals containing more than one knockout construct and/or more than one transgene expression construct are prepared in any of several ways. The preferred manner of preparation is to generate a series of animals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

A rhodopsin transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a rhodopsin protein can be essential for many forms of lineage analysis and can additionally provide a means to assess the effects of, for example, lack of rhodopsin protein expression which might grossly alter the structure and integrity of retinal tissue. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques, which allow for the expression of transgenes can be regulated via site-specific genetic manipulation in vivo, are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject rhodopsin proteins. For example, excision of a target sequence which interferes with the expression of a recombinant rhodopsin gene, such as one which encodes an antagonistic homolog or an antisense transcript, can be designed to activate expression of that gene. This interference with expression of the protein can result from a variety of mechanisms, such as spatial separation of the rhodopsin gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence reorients the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description is given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 or the FLP recombinase system of *Saccharomyces cerevisiae* can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present; catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control results in genetic recombination of the target sequence only in cells where recombinase expression is mediated by the promoter element. Thus, the activation of expression of a recombinant rhodopsin protein can be regulated via control of recombinase expression.

Use of the cre/loxP recombinase system to regulate expression of a recombinant rhodopsin protein requires the construction of a transgenic animal containing transgenes encoding both the Cre recombinase and the subject protein. Animals containing both the Cre recombinase and a recombinant rhodopsin gene can be provided through the construction of "double" transgenic animals. A convenient method for providing such animals is to mate two transgenic animals each containing a transgene, e.g., an rhodopsin gene and recombinase gene.

One advantage derived from initially constructing transgenic animals containing an rhodopsin transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic rhodopsin transgene is silent allows the study of progeny from that founder in which disruption of rhodopsin protein mediated induction in a particular tissue or at certain developmental stages would result in, for example, a lethal phenotype.

Similar conditional transgenes can be provided using prokaryotic promoter sequences that require prokaryotic proteins to be simultaneous expressed in order to facilitate expression of the rhodopsin transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a rhodopsin transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA is incorporated into the host gene before the first cleavage. As a consequence, all cells of the transgenic animal carries the incorporated transgene. This in general is also reflected in the efficient transmission of the transgene to offspring of the founder since 50% of the germ cells are harbored in the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method is to incubate the embryos in vitro for about 1-7 days, depending on the species, and then reimplant them into the surrogate host.

For the purposes of this invention a zygote is essentially the formation of a diploid cell that is capable of developing into a complete organism. Generally, the zygote can be comprised of an egg containing a nucleus formed, either naturally or artificially, by the fusion of two haploid nuclei from a gamete or gametes. Thus, the gamete nuclei must be ones which are naturally compatible, i.e., ones that result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material that can be added to the nucleus of the zygote or to the genetic material that forms a part of the zygote nucleus. If no genetic material is removed, then the amount of exogenous genetic material that can be added is limited by the amount that is absorbed without being physically disruptive. Generally, the volume of exogenous genetic material inserted do not exceed about 10 picoliters. The physical effects of addition must not be so great as to physically destroy the viability of the zygote. The biological limit of the number and variety of DNA sequences vary depending upon the particular zygote and functions of the exogenous genetic material and are readily apparent to one skilled in the art, because the genetic material, including the exogenous genetic material, of the resulting zygote must be biologically capable of initiating and maintaining the differentiation and development of the zygote into a functional organism.

The number of copies of the transgene constructs that added to the zygote is dependent upon the total amount of exogenous genetic material added and is the amount that enables the genetic transformation to occur. Theoretically only one copy is required; however, generally, numerous copies are utilized, for example, 1,000-20,000 copies of the transgene construct, in order to insure that one copy is functional. There is often an advantage to having more than one functioning copy of each of the inserted exogenous DNA sequences to enhance the phenotypic expression of the exogenous DNA sequences.

Any technique that allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host varies according to species, but usually is comparable to the number of offspring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention includes exogenous genetic material. As set out above, the exogenous genetic material will, in certain embodiments, be a DNA sequence which results in the production of a rhodopsin protein (either agonistic or antagonistic), and antisense transcript, a rhodopsin mutant, or a suppression effector such as Rz40. Further, in such embodiments the sequence are attached to a transcriptional control element, e.g., a promoter, which preferably allows the expression of the transgene product in a specific type of cell.

Viral and non-viral transfection can also be used to introduce transgene into a non-human animal. The developing non-human embryo can be cultured in vitro to the blastocyst stage. During this time, the blastomeres can be targets, for example, for retroviral infection. Efficient infection of the blastomeres is obtained by enzymatic treatment to remove the zona pellucida. The viral vector system used to introduce the transgene is typically a replication-defective retrovirus carrying the transgene. Transfection is easily and efficiently obtained by culturing the blastomeres on a monolayer of virus-producing cells.

Alternatively, infection can be performed at a later stage. Virus or virus-producing cells can be injected into the blastocoele. Most of the founders are mosaic for the transgene since incorporation occurs only in a subset of the cells that formed the transgenic non-human animal. Further, the founder may contain various retroviral insertions of the transgene at different positions in the genome that generally segregate in the offspring. In addition, it is also possible to introduce transgenes into the germ line by intrauterine retroviral infection of the midgestation embryo.

A third type of target cell for transgene introduction is the embryonal stem cell (ES). ES cells are obtained from pre-implantation embryos cultured in vitro and fused with embryos. Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal.

Transgenic animal techniques using ES cells, microinjection into fertilized eggs and microinjection into mouse blastocysts have been used to generate five lines of transgenic mice that have been utilized to demonstrate the invention detailed in the application. Pro23His mice carrying a mutant human rhodopsin transgene, RhoNhr mice carrying a wild type human rhodopsin transgene, RhoM mice carrying a modified human rhodopsin transgene and Rz40 mice carrying a ribozyme targeting human rhodopsin and driven by a mouse rhodopsin promoter were generated utilizing microinjection of fertilized eggs and subsequent implantation of injected eggs into a surrogate mother mouse. Rhodopsin knockout mice (rho–/–) in which the endogenous mouse rhodopsin gene has been disrupted were generated utilizing ES cell technology and gene targeting by homologous recombination.

The invention is demonstrated herein by suppression effectors, hammerhead ribozymes and siRNA, targeting collagen and rhodopsin transcripts together with replacement genes engineered to have sequence alterations at degenerate sites such that they are protected from suppression. Detailed evaluation of hammerhead ribozymes targeting COL1A1 and rhodopsin transcripts have been undertaken in vitro as outlined in Example 1. Similarly the protection of transcripts expressed from modified replacement genes has also been demonstrated in vitro (Example 1). Furthermore evaluation of suppression of target genes using hammerhead ribozymes and siRNA has been undertaken in cells expressing the target sequences (Examples 2, 3, 5 and 9). In Example 2 ribozymes targeting human rhodopsin sequences were evaluated in stable COS-7 cell lines expressing the human rhodopsin gene. In Examples 2, 3, 5 and 9 siRNAs targeting either human COL1A1 or human rhodopsin transcripts were evaluated in COS-7 cells—both stable cell lines expressing the target genes and transient transfections were utilized in the study. Furthermore the ability of modified replacement genes (modified at degenerate sites) to encode functional wild type protein has been explored both in cells and in transgenic mice (Examples 1, 2, 3, 5, 6 and 9).

Practice of the invention will be still more fully understood from the following examples, which are presented herein for illustration only and should not be construed as limiting the invention in any way. Variations and alternate embodiments will be apparent to those of skill in the art. The contents of all cited references (including literature references, issued patents, published patent applications that may be cited throughout this application) are hereby expressly incorporated by reference. The practice of the present invention will employ, unless otherwise indicated, conventional techniques of molecular biology, cell biology, cell culture, microbiology, biochemistry, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al., eds.), the entire contents of which are hereby incorporated by reference.

EXEMPLIFICATION

Example 1

Materials and Methods cDNA templates and ribozymes were cloned into commercial expression vectors (pCDNA3, pZeoSV or pBluescript) that enable expression in a test tube from T7, T3 or SP6 promoters or expression in mammalian cells from CMV or SV40 promoters. DNA inserts were cloned into the multiple cloning site (MCS) of these vectors typically at or near the terminal ends of the MCS to delete most of the MCS and thereby prevent any possible problems with efficiency of expression subsequent to cloning. Clones containing template cDNAs and ribozymes were sequenced by ABI automated sequencing machinery using standard protocols.

RNA was obtained from clones by in vitro transcription using a commercially available Ribomax expression system (Promega) and standard protocols. RNA purifications were undertaken using the Bio-101 RNA purification kit or a solution of 0.3M sodium acetate and 0.2% SDS after isolation from polyacrylamide gels. Cleavage reactions were performed using standard protocols with varying $MgCl_2$ concentrations (0-15 mM) at 37° C., typically for 3 hours. Time points were performed at the predetermined optimal $MgCl_2$ concentrations for up to 5 hours. Radioactively labelled RNA products were obtained by incorporating $\alpha P^{32}$ rUTP (Amersham) in the expression reactions (Gaughan et al. 1995). Labelled RNA products were run on polyacrylamide gels before cleavage reactions were undertaken for the purpose of RNA purification and subsequent to cleavage reactions to establish if RNA cleavage had been achieved. Cleavage reactions were undertaken with 5 mM Tris-HCl pH8.0 and varying concentrations of $MgCl_2$ at 37° C.

Predictions of the secondary structures of human and mouse rhodopsin, human peripherin and human collagen 1A2 mRNAs were obtained using the RNAPlotFold program.

Ribozymes and antisense were designed to target areas of the RNA that were predicted to be accessible to suppression effectors, for example open loop structures. The integrity of open loop structures was evaluated from the 10 most probable RNA structures. Additionally, predicted RNA structures for truncated RNA products were generated and the integrity of open loops between full length and truncated RNAs compared.

The human rhodopsin cDNA (SEQ ID NO:1) was cloned into the HindIII and EcoRI sites of the MCS of pCDNA3 in a 5' to 3' orientation allowing subsequent expression of RNA from the T7 or CMV promoter in the vector. The full length 5'UTR sequence was inserted into this clone using primer driven PCR mutagenesis and a HindIII (in pCDNA3) to BstEII (in the coding sequence of the human rhodopsin cDNA) DNA fragment.

The human rhodopsin hybrid cDNA with a single base alteration (SEQ ID NO:2), a C—>G change (at nucleotide 271 of SEQ ID NO:2) was introduced into human rhodopsin cDNA, using a HindIII to BstEII PCR cassette, by primer directed PCR mutagenesis. This sequence change occurs at a silent position—it does not give rise to an amino acid substitution—however it eliminates the ribozyme cleavage site (GUX-->GUG). The hybrid rhodopsin was cloned into pCDNA3 in a 5' to 3' orientation allowing subsequent expression of RNA from the T7 or CMV promoter in the vector.

A human rhodopsin adRP mutation, a C-->T change (at codon 23; nucleotide 217 of SEQ ID NO:3) was introduced into human rhodopsin cDNA, using a HindIII to BstEII PCR cassette by primer directed PCR mutagenesis. This sequence change results in the substitution of a Proline for a Leucine residue. Additionally the nucleotide change creates a ribozyme cleavage site (CCC-->CTC) (nucleotide 216-218 of SEQ ID NO:3). The mutated rhodopsin nucleic acid sequence was cloned into the HindIII and EcoRI sites of pCDNA3 in a 5' to 3' orientation allowing subsequent expression of RNA from the T7 or CMV promoter in the vector (SEQ ID NO:3).

A hammerhead ribozyme (termed Rz10) (SEQ ID NO:29) designed to target a large conserved open loop structure in the RNA from the coding regions of the gene was cloned subsequent to synthesis and annealing into the HindIII and XbaI sites of pCDNA3 again allowing expression of RNA from the T7 or CMV promoter in the vector (SEQ ID NO:4). The target site was GUC (the GUX rule) at position 475-477 (nucleotides 369-371 of SEQ ID NO:1) of the human rhodopsin sequence. Note that there is a one base mismatch in one antisense arm of Rz10. A hammerhead ribozyme (termed Rz20) (SEQ ID NO:30) designed to target an open loop structure in RNA from the coding region of a mutant rhodopsin gene with a Pro23Leu mutation was cloned subsequent to synthesis and annealing into the HindIII and XbaI sites of pCDNA3 again allowing expression of RNA from the T7 or CMV promoter in the vector (SEQ ID NO:5). The target site was CTC (the NUX rule) at codon 23 (nucleotides 216-218 of SEQ ID NO:3) of the human rhodopsin sequence (Accession number: K02281). Antisense flanks are underlined.

```
Rz10:
                                    (SEQ ID NO: 29
GGTCGGTCTGATGAGTCCGTGAGGACGAAACGTAGAG;
nucleotides 101-137 of SEQ ID NO: 4)

Rz20:
                                    (SEQ ID NO: 30
TACTCGAACTGATGAGTCCGTGAGGACGAAAGGCTGC;
nucleotides 104-140 of SEQ ID NO: 5)
```

The full length mouse rhodopsin cDNA was cloned into the EcoRI sites of the MCS of pCDNA3 in a 5' to 3' orientation allowing subsequent expression of RNA from the T7 or CMV promoter in the vector (SEQ ID NO:6).

The mouse rhodopsin hybrid cDNA with a single base alteration, a T-->C change (at position 1460) (nucleotide 190 of SEQ ID NO:7) was introduced into mouse rhodopsin cDNA, using a HindIII to Eco47III PCR cassette, by primer directed PCR mutagenesis. This sequence change occurs at a silent position—it does not give rise to an amino acid substitution—however it eliminates the ribozyme cleavage site (TTT-->TCT) (nucleotides 189-191 of SEQ ID NO:7). The hybrid rhodopsin was cloned into pCDNA3 in a 5' to 3' orientation allowing subsequent expression of RNA from the T7 or CMV promoter in the vector (SEQ ID NO:7).

A hammerhead ribozyme (termed Rz33) (SEQ ID NO:31) designed to target a large robust open loop structure in the RNA from the coding regions of the gene was cloned subsequent to synthesis and annealing into the HindIII and XbaI sites of pCDNA3 again allowing expression of RNA from the T7 or CMV promoter in the vector (SEQ ID NO:8). The target site was TTT (the NUX rule) at position 1459-1461 (nucleotides 405-407 of SEQ ID NO:6) of the mouse rhodopsin sequence. (Accession number: M55171). Antisense flanks are underlined.

```
Rz33:
                                    (SEQ ID NO: 31
GGCACATCTGATGAGTCCGTGAGGACGAAAAAATTGG;
nucleotides 118-154 of SEQ ID NO: 8)
```

The full length human peripherin cDNA was cloned into the EcoRI sites of the MCS of pCDNA3 in a 5' to 3' orientation allowing subsequent expression of RNA from the T7 or CMV promoter in the vector (SEQ ID NO:9).

A human peripherin hybrid DNA with a single base alteration, a A-->G change (at position 257) (nucleotide 332 of SEQ ID NO:10) was introduced into human peripherin DNA by primer directed PCR mutagenesis (forward 257 mutation primer—5'CATGGCGCTGCTGAAAGTCA3' (SEQ ID NO:11)—the reverse 257 primer was complementary to the forward primer). This sequence change occurs at a silent position—it does not give rise to an amino acid substitution—however it eliminates the ribozyme cleavage site (CTA-->CTG) (nucleotides 330-332 of SEQ ID NO:10). A second human peripherin hybrid DNA with a single base alteration, a A-->G change (at position 359) (nucleotide 468 of SEQ ID NO:13) was introduced into human peripherin DNA, again by primer directed PCR mutagenesis (forward 359 mutation primer—5'CATCTTCAGCCTGGGACTGT3' (SEQ ID NO:12)—the reverse 359 primer was complementary to the forward primer) (SEQ ID NO:12). Similarly this sequence change occurs at a silent position—it does not give rise to an amino acid substitution—however again it eliminates the ribozyme cleavage site (CTA-->CTG) (nucleotides 466-468 of SEQ ID NO:13). The ribozyme cleavage sites at 255-257 (nucleotides 330-332 of SEQ ID NO:10) and 357-359 (nucleotides 466-468 of SEQ ID NO:13) occur at different open loop structures as predicted by the RNAPlotFold program. Hybrid peripherin DNAs included the T7 promoter sequence allowing subsequent expression of RNA.

Hammerhead ribozymes (termed Rz30 and Rz31 (SEQ ID NOs:32 and 33, respectively)), designed to target robust open loop structures in the RNA from the coding regions of the gene, were cloned subsequent to synthesis and annealing into the HindIII and XbaI sites of pCDNA3 again allowing expression of RNA from the T7 or CMV promoter in the vector (SEQ ID NOS:14 and 15, respectively). The target sites were both CTA (the NUX rule) at positions 255-257 and 357-359 respectively of the human peripherin sequence. (Accession number: M73531). Antisense flanks are underlined.

```
Rz30:
                                         (SEQ ID NO: 32
ACTTTCAGCTGATGAGTCCGTGAGGACGAAAGCGCCA;
nucleotides 116-153 of SEQ ID NO: 14)

Rz31:
                                         (SEQ ID NO: 33
ACAGTCCCTGATGAGTCCGTGAGGACGAAAGGCTGAA;
nucleotides 112-148 of SEQ ID NO: 15)
```

A human type I collagen 1A2 cDNA was obtained from the ATCC (Accession No: Y00724). A naturally occurring polymorphism has previously been found in collagen 1A2 at positions 907 of the gene involving a T-->A nucleotide change (Filie et al. 1993). The polymorphism occurs in a predicted open loop structure of human collagen 1A2 RNA. Polymorphic variants of human collagen 1A2 were generated by PCR directed mutagenesis, using a HindIII to XbaI PCR cassette. Resulting clones contained the following polymorphism: collagen 1A2 (A) has a T nucleotide at position 907 (A nucleotide 176 of SEQ ID NO:17, reverse strand). In contrast human collagen 1A2 (B) has an A nucleotide at position 907 (T nucleotide 181 of SEQ ID NO:16, reverse strand). In collagen 1A2 (A) there is a ribozyme target site, that is a GTC site (906-908) (nucleotides 175-177 of SEQ ID NO:17, reverse strand), however this cleavage site is lost in collagen 1A2 (B) as the sequence is altered to GAC (906-908) (nucleotides 180-182 of SEQ ID NO:16, reverse strand), thereby disrupting the ribozyme target site.

A hammerhead ribozyme (termed Rz907) (SEQ ID NO:34)was designed to target a predicted open loop structure in the RNA from the coding region of the polymorphic variant of the human collagen 1A2 gene. Rz907 oligonucleotide primers were synthesized, annealed and cloned into the HindIII and XbaI sites of pCDNA3 again allowing subsequent expression of RNA from the T7 or CMV promoter in the vector (SEQ ID NO:18). The target site was a GUX site at position 906-908 of the human type I collagen 1A2 sequence (Accession number: Y00724). Antisense flanks are underlined.

```
Rz907:
                                         (SEQ ID NO: 34
CGGCGGCTGATGAGTCCGTGAGGACGAAACCAGCA;
nucleotide 107-141 of SEQ ID NO: 18)
```

FIG. 1A shows Human rhodopsin cDNA (SEQ ID NO:1) expressed from the T7 promoter to the BstEII site in the coding sequence. Resulting RNA was mixed with Rz10RNA in 15 mM MgCl$_2$ and incubated at 37° C. for varying times. Lanes 1-4: Human rhodopsin RNA and Rz10RNA after incubation at 37° C. with 15 mM MgCl$_2$ for 0, 1 2 and 3 hours respectively. Sizes of the expressed RNAs and cleavage products are as expected (Table 1). Complete cleavage of human rhodopsin RNA was obtained with a small residual amount of intact RNA present at 1 hour. Lane 6 is intact unadapted human rhodopsin RNA (BstEII) alone. Lane 5 is unadapted human rhodopsin RNA (FspI) alone and refers to FIG. 1B. From top to bottom, human rhodopsin RNA and the two cleavage products from this RNA are highlighted with arrows.

FIG. 1B shows the unadapted human rhodopsin cDNA expressed from the T7 promoter to the FspI site in the coding sequence. The adapted human rhodopsin cDNA was expressed from the T7 promoter to the BstEII site in the coding sequence. Lanes 1-4: Resulting RNAs were mixed together with Rz10 and 15 mM MgCl$_2$ and incubated at 37° C. for varying times (0, 1, 2 and 3 hours respectively). The smaller unadapted rhodopsin transcripts were cleaved by Rz10 while the larger adapted transcripts were protected from cleavage by Rz10. Cleavage of adapted protected transcripts would have resulted in products of 564 bases and 287 bases—the 564 bases product clearly is not present—the 287 bp product is also generated by cleavage of the unadapted human rhodopsin transcripts and hence is present (FspI). After 3 hours the majority of the unadapted rhodopsin transcripts has been cleaved by Rz10. Lane 5 contains the intact adapted human rhodopsin RNA (BstEII) alone. From top to bottom adapted uncleaved human rhodopsin transcripts, residual unadapted uncleaved human rhodopsin transcripts and the larger of the cleavage products from unadapted human rhodopsin transcripts are highlighted by arrows. The smaller 22 bases cleavage product from the unadapted human rhodopsin transcripts has run off the gel.

Figures 2A, 2B:
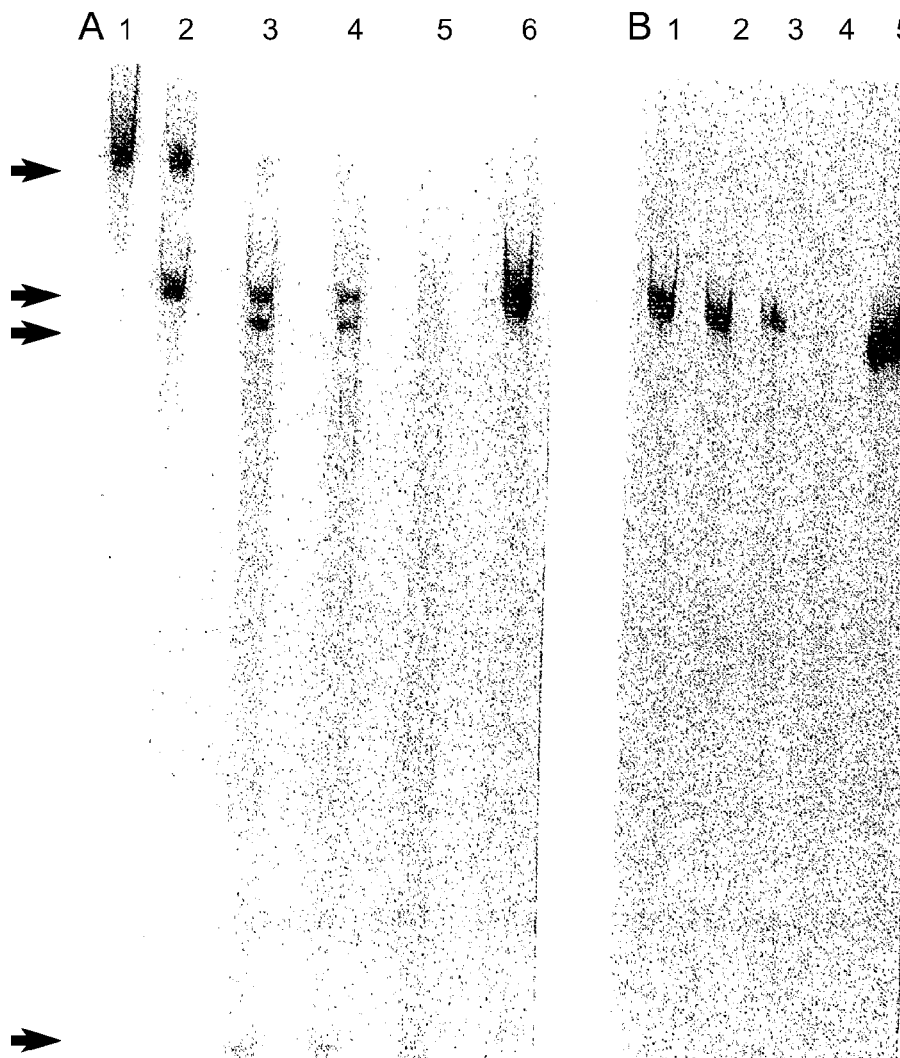
FIG. 2A shows unadapted (SEQ ID NO:1) and adapted (SEQ ID NO:2) human rhodopsin cDNAs expressed from the T7 promoter to the AcyI after the coding sequence and the BstEII site in the coding sequence, respectively.
FIG. 2B shows the adapted human rhodopsin cDNA expressed from the T7 promoter to the BstEII site in the coding sequence.

FIG. 2A shows unadapted (SEQ ID NO:1) and adapted (SEQ ID NO:2) human rhodopsin cDNAs expressed from the T7 promoter to the AcyI after the coding sequence and the BstEII site in the coding sequence, respectively. Sizes of expressed RNAs and cleavage products were as predicted (Table 1). Resulting RNAs were mixed together with Rz10RNA at varying MgCl$_2$ concentrations and incubated at 37° C. for 3 hours. Lane 1: Intact unadapted human rhodopsin RNA (AcyI) alone. Lanes 2-5: Unadapted and adapted human rhodopsin RNAs and Rz10 RNA after incubation at 37° C. with 0, 5, 10 and 15 mM MgCl$_2$ respectively. Almost complete cleavage of the larger unadapted human rhodopsin RNA was obtained with a small residual amount of intact RNA present at 5 mM MgCl$_2$. In contrast the adapted human rhodopsin RNA remained intact. From top to bottom, the unadapted and adapted rhodopsin RNAs, and two cleavage products from the unadapted human rhodopsin RNA are highlighted by arrows. Lane 6 is intact adapted human rhodopsin RNA (BstEII) alone.

FIG. 2B shows the adapted human rhodopsin cDNA expressed from the T7 promoter to the BstEII site in the coding sequence. Lanes 1-4: Resulting RNA was mixed together with Rz10 and 0, 5, 10 and 15 mM MgCl$_2$ and incubated at 37° C. for 3 hours respectively. The adapted rhodopsin transcripts were not cleaved by Rz10. Cleavage of adapted transcripts would have resulted in cleavage products of 564 bases and 287 bases which clearly are not present. Lane 5: intact adapted human rhodopsin RNA (BstEII) alone. Lane 4: RNA is absent—due to a loading error or degradation. The adapted uncleaved human rhodopsin RNA is highlighted by an arrow.

Figure 2C:
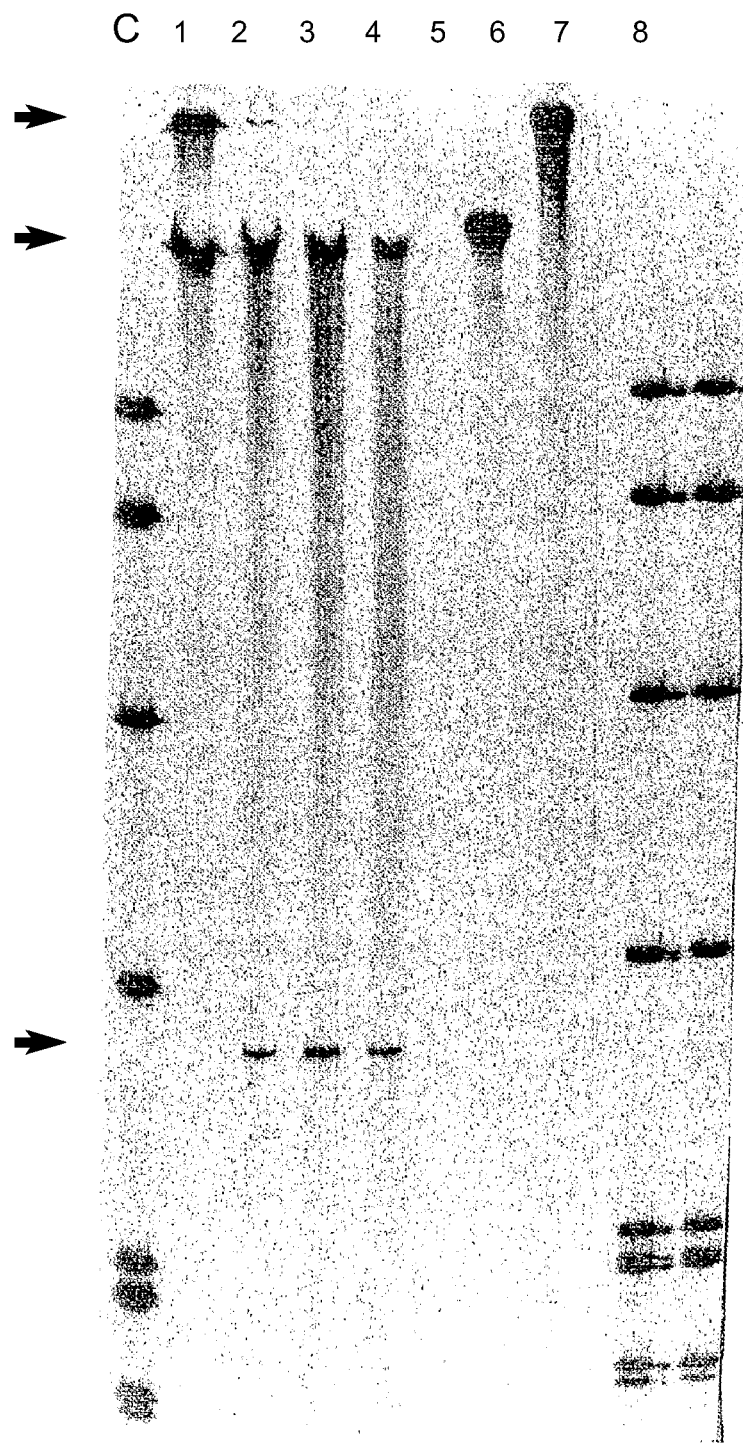
FIG. 2C shows unadapted (SEQ ID NO:1) and adapted (SEQ ID NO:2) human rhodopsin cDNAs expressed from the T7 promoter to the AcyI after the coding sequence and the BstEII site in the coding sequence respectively.

FIG. 2C shows unadapted (SEQ ID NO:1) and adapted (SEQ ID NO:2) human rhodopsin cDNAs expressed from the T7 promoter to the AcyI after the coding sequence and the BstEII site in the coding sequence respectively. Sizes of expressed RNAs and cleavage products were as predicted (Table 1). Resulting RNAs were mixed together with Rz10 RNA at varying MgCl$_2$ concentrations and incubated at 37° C. for 3 hours. Lane 1: DNA ladder. Lanes 2-5: Unadapted and adapted human rhodopsin RNAs and Rz10 RNA after incubation at 37° C. with 0, 5, 10 and 15 mM MgCl$_2$ respectively. Almost complete cleavage of the larger unadapted human rhodopsin RNA was obtained with a small residual amount of intact RNA present at 5 and 10 mM MgCl$_2$. In contrast the adapted human rhodopsin RNA remained intact. Lane 6: Adapted human rhodopsin RNA (BstEII) alone. Lane 7: Unadapted human rhodopsin RNA (AcyI) alone. Lane 8: DNA ladder. From top to bottom, the unadapted and adapted rhodopsin RNAs, and two cleavage products from the unadapted human rhodopsin RNA are highlighted by arrows. Separation of the adapted human rhodopsin RNA (851 bases) and the larger of the cleavage products from the unadapted RNA (896 bases) is incomplete in this gel (further running of the gel would be required to achieve separation)-however the separation of these two RNAs is demonstrated in FIG. 2A.

Figure 3:
FIG. 3 shows the mutant (Pro23Leu) (SEQ ID NO:3) human rhodopsin cDNA expressed from the T7 promoter to the BstEII in the coding sequence.

FIG. 3 shows the mutant (Pro23Leu) (SEQ ID NO:3) human rhodopsin cDNA expressed from the T7 promoter to the BstEII in the coding sequence. Likewise the Rz20 clone was expressed to the XbaI site. Resulting RNAs were mixed together with 10 mM $MgCl_2$ concentrations at 37° C. for varying times. Sizes of expressed RNAs and cleavage products were as predicted (Table 1). Lane 1: DNA ladder. Lanes 2: Pro23Leu human rhodopsin RNA alone. Lanes 3-7 Pro23Leu human rhodopsin RNA and Rz20RNA after incubation at 37° C. with 10 mM $MgCl_2$ for 0 mins, 30 mins, 1 hr, 2 hrs and 5 hrs respectively. Almost complete cleavage of mutant rhodopsin transcripts was obtained with a residual amount of intact RNA left even after 5 hours. Lane 8: DNA ladder. From the top to bottom, intact mutant rhodopsin RNA and the two cleavage products from the mutant human rhodopsin RNA are highlighted by arrows.

Figure 4:
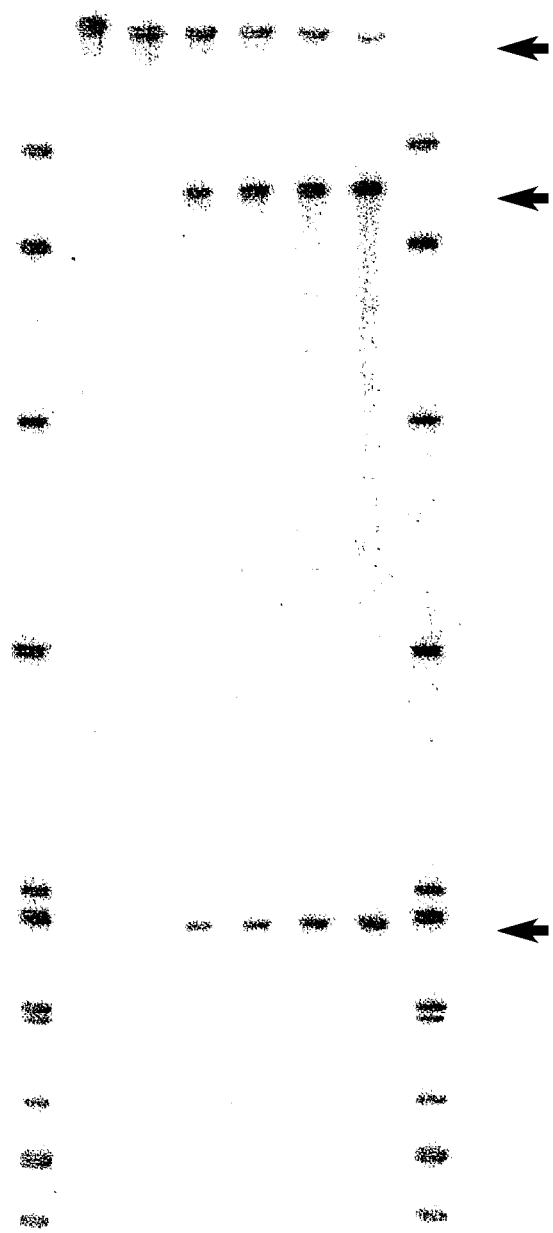
FIG. 4 shows the mutant (Pro23Leu) (SEQ ID NO:3) human rhodopsin cDNA expressed from the T7 promoter to the BstEII in the coding sequence.

FIG. 4 shows the mutant (Pro23Leu) (SEQ ID NO:3) human rhodopsin cDNA expressed from the T7 promoter to the BstEII in the coding sequence. Likewise the Rz10 clone (SEQ ID NO:4) was expressed to the XbaI site. Resulting RNAs were mixed together with 10 mM $MgCl_2$ concentrations at 37° C. for varying times. Sizes of expressed RNAs and cleavage products were as predicted (Table 1). Lane 1: DNA ladder. Lanes 2: Pro23Leu human rhodopsin RNA alone. Lanes 3-7 Pro23Leu human rhodopsin RNA and Rz10 RNA after incubation at 37° C. with 10 mM $MgCl_2$ for 0 mins, 30 mins, 1 hr, 2 hrs and 5 hrs respectively. Almost complete cleavage of mutant human rhodopsin RNA was obtained with a residual amount of intact RNA remaining even after 5 hours (Lane 7). Lane 8: DNA ladder. From top to bottom, intact mutant rhodopsin RNA and the two cleavage products from the mutant human rhodopsin RNA are highlighted by arrows.

FIG. 5 shows the mouse rhodopsin cDNA clone was expressed in vitro from the T7 promoter to the Eco47III site in the coding sequence. Likewise the Rz33 clone was expressed to the XbaI site. A: Resulting RNAs were mixed together with 10 mM $MgCl_2$ at 37° C. for varying times. Sizes of expressed RNAs and cleavage products were as predicted (Table 1). DNA ladder. Lane 1: mouse rhodopsin RNA alone. Lanes 2-5 Mouse rhodopsin RNA and Rz33RNA after incubation at 37° C. with 10 mM $MgCl_2$ at 0, 5, 7.5 and 10 mM $MgCl_2$ respectively for 3 hours. Cleavage of mouse rhodopsin RNA was obtained after addition of divalent ions (Lane 3). Residual uncleaved mouse rhodopsin RNA and the two cleavage products from the mouse rhodopsin RNA are highlighted by arrows. B: The adapted mouse rhodopsin cDNA clone with a base change at position 1460 (nucleotide 190 of SEQ ID NO:7) was expressed in vitro from the T7 promoter to the Eco471II site in the coding sequence. Likewise the Rz33 clone was expressed to the XbaI site. Resulting RNAs were mixed together with various $MgCl_2$ concentrations at 37° C. for 3 hours. Sizes of expressed RNAs and cleavage products were as predicted (Table 1). Lane 1: DNA ladder. Lane 2: Adapted mouse rhodopsin RNA alone. Lanes 3-6: Adapted mouse rhodopsin RNA and Rz33 RNA after incubation at 37° C. with 0, 5, 7.5 and 10 mM $MgCl_2$ for 3 hours at 37° C. No cleavage of the adapted mouse rhodopsin RNA was observed. The intact adapted mouse rhodopsin RNA is highlighted by an arrow.

Figures 6A, 6B:
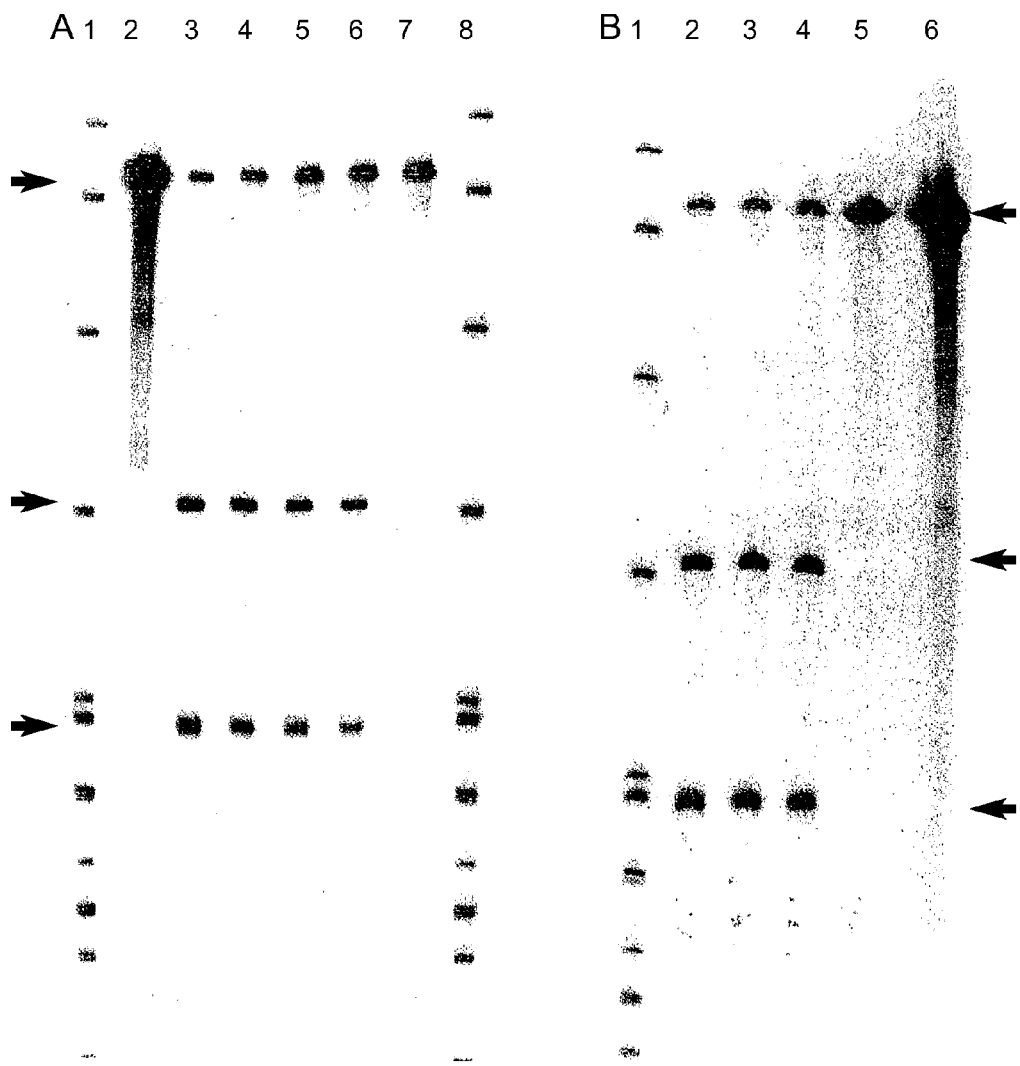
FIG. 6A shows the human peripherin cDNA clone expressed in vitro from the T7 promoter to the BglII site in the coding sequence and mixed with Rz30 and 10 mM $MgCl_2$ for 0 mins., 3 mins., 1 hour, 2 hours, and 3 hours.
FIG. 6B shows the human peripherin cDNA clone expressed in vitro from the T7 promoter to the BglII site in the coding sequence and mixed with Rz30 and 0, 5, 7.5, or 10 mM $MgCl_2$ for 3 hours.
Figure 6C:
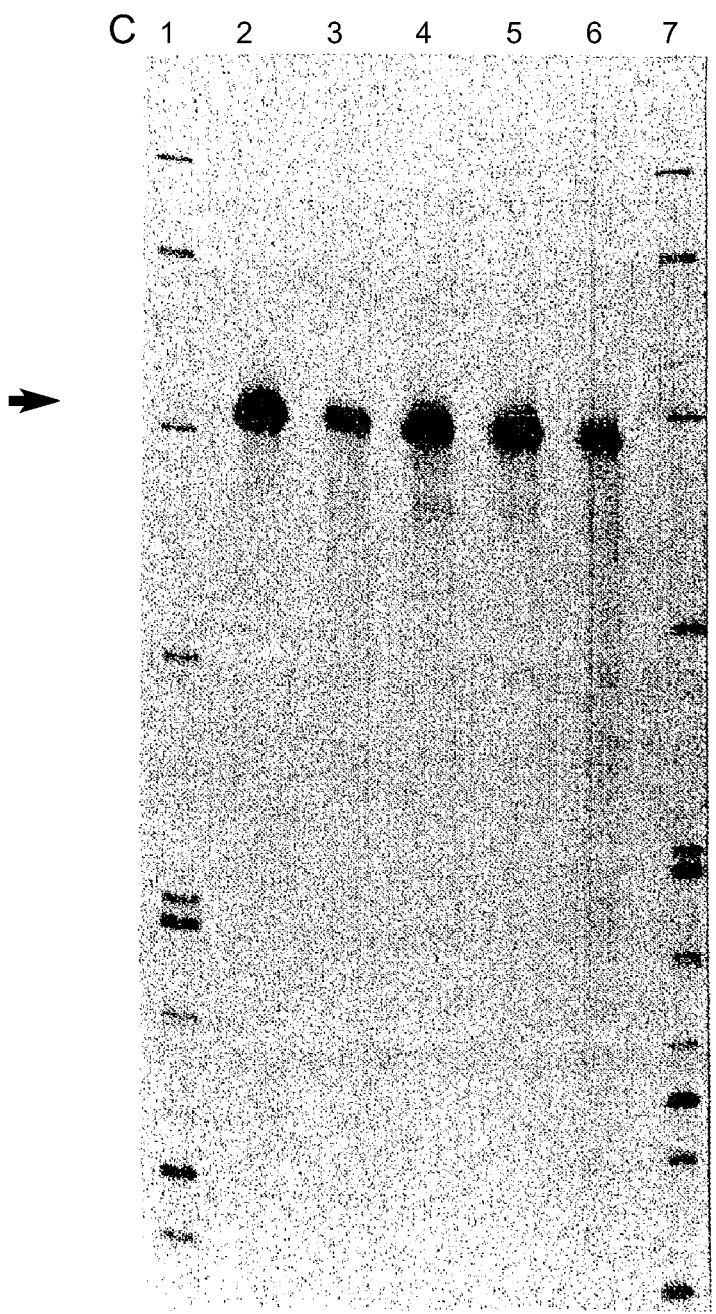
FIG. 6C shows the human peripherin cDNA clone with a base change at position 257, expressed in vitro from the T7 promoter to the BglII site in the coding sequence and mixed with Rz30 and 0, 5, 7.5, or 10 mM $MgCl_2$ for 3 hours.
Figure 6D:
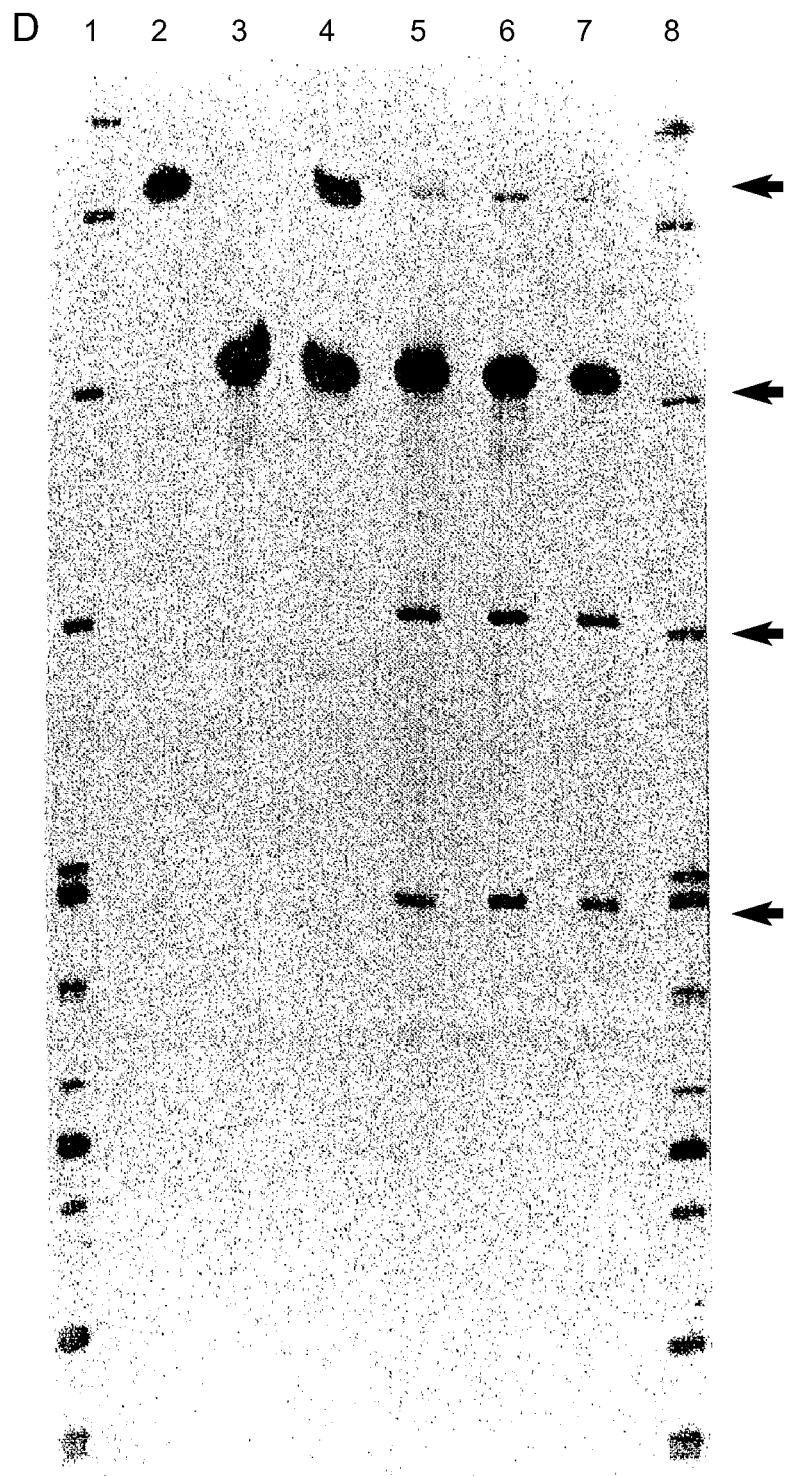
FIG. 6D shows the human peripherin cDNA clone or adapted human peripherin cDNA clone with a base change at position 257, expressed in vitro from the T7 promoter to the BglII site in the coding sequence and mixed with Rz30 and 0, 5, 7.5, or 10 mM $MgCl_2$ for 3 hours.

FIG. 6 shows was the human peripherin cDNA clone expressed in vitro from the T7 promoter to the BglII site in the coding sequence. Likewise Rz30 (targeting a cleavage site at 255-257) was expressed to the XbaI site. A: Resulting RNAs were mixed together with 10 mM $MgCl_2$ at 37° C. for varying times. Lane 1: DNA ladder. Lane 2: Intact human peripherin RNA alone. Lanes 3-7: Human peripherin RNA and Rz30 RNA after incubation at 37° C. with 10 mM $MgCl_2$ for 3 hrs, 2 hrs, 1 hr, 30 mins and 0 mins respectively. Lane 8: DNA ladder. From top to bottom, intact human peripherin RNA and the two cleavage products from the human peripherin RNA are highlighted by arrows. B: Resulting RNAs were mixed with Rz30 RNA at varying $MgCl_2$ concentrations and incubated at 37° C. for 3 hrs. Lane 1: DNA ladder. Lanes 2-5: Human peripherin RNA and Rz30 after incubation at 37° C. with 10, 7.5, 5 and 0 mM $MgCl_2$ respectively for 3 hrs. Lane 6: Intact human peripherin RNA alone. Sizes of the expressed RNAs and cleavage products are as expected (Table 1). Significant cleavage of human peripherin RNA was obtained with a residual amount of intact RNA present at each $MgCl_2$ concentration. From top to bottom, human peripherin RNA and the two cleavage products from this RNA are highlighted with arrows. C: The adapted human peripherin DNA with a single base change at position 257 was expressed from the T7 promoter to the AvrII site in the coding sequence. Resulting RNA was mixed with Rz30 at various $MgCl_2$ concentrations and incubated at 37° C. for 3 hrs. Lane 1: DNA ladder. Lane 2: Intact adapted human peripherin RNA alone. Lanes 3-6: Adapted human peripherin RNA and Rz30 after incubation at 37° C. with 0, 5, 7.5 and 10 mM $MgCl_2$ respectively for 3 hrs. Lane 7: DNA ladder. D: The unadapted human peripherin cDNA and the adapted human peripherin DNA fragment with a single base change at position 257 were expressed from the T7 promoter to the BglII and AvrII sites respectively in the coding sequence. Resulting RNAs were mixed with Rz30 at various $MgCl_2$ concentrations and incubated at 37° C. for 3 hrs. Lane 1: DNA ladder. Lane 2: Intact unadapted human peripherin RNA alone. Lane 3: Intact adapted human peripherin RNA alone. Lanes 4-7: Unadapted and adapted human peripherin RNAs and Rz30 after incubation at 37° C. with 0, 5, 7.5 and 10 mM $MgCl_2$ respectively for 3 hrs at 37° C. No cleavage of the adapted human peripherin RNA was observed even after 3 hours whereas a significant reduction in the unadapted RNA was observed over the same time frame. Lane 8: DNA ladder. From top to bottom, residual unadapted human peripherin RNA, adapted human peripherin RNA and the two cleavage products are highlighted by arrows.

Figures 7A, 7B:
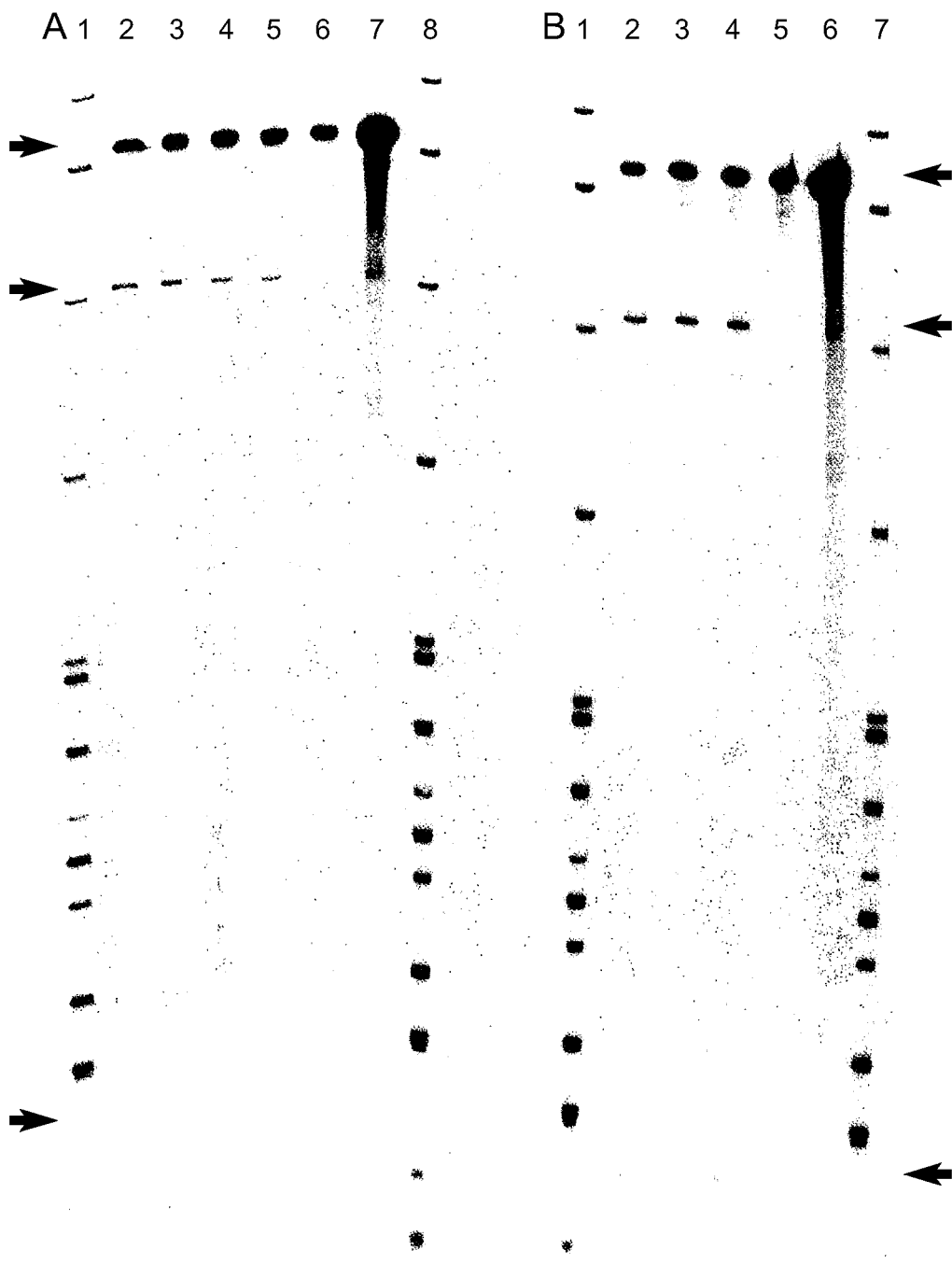
FIG. 7A shows human peripherin cDNA clone expressed in vitro from the T7 promoter to the BglII site in the coding sequence and mixed with Rz31 and 10 mM $MgCl_2$ for 0 mins., 3 mins., 1 hour, 2 hours, and 3 hours.
FIG. 7B shows human peripherin cDNA clone expressed in vitro from the T7 promoter to the BglII site in the coding sequence and mixed with Rz31 and 0, 5, 7.5, or 10 mM $MgCl_2$ for 3 hours.
Figure 7C:
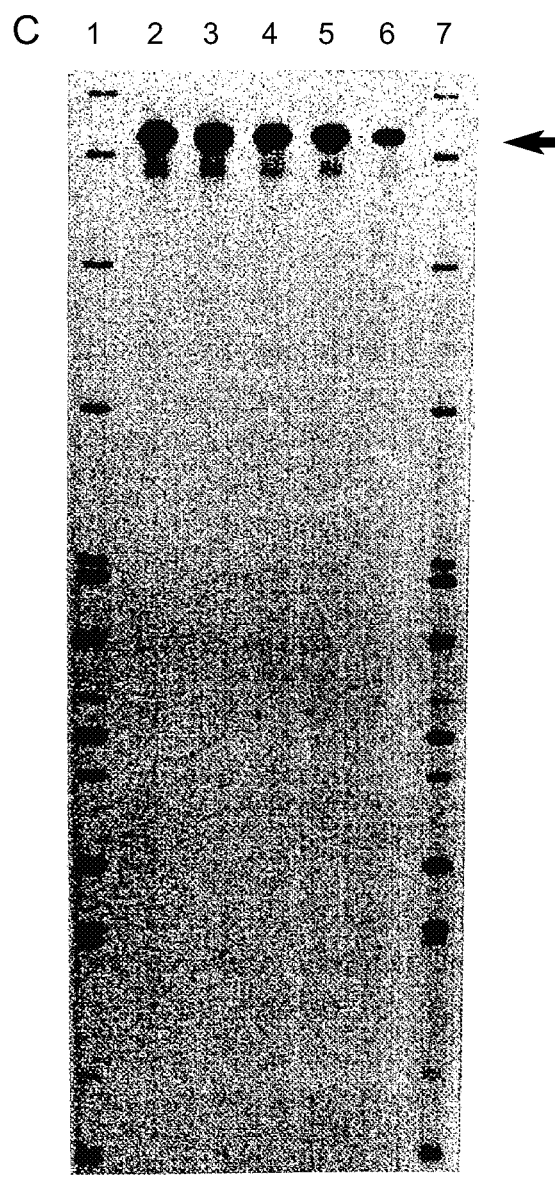
FIG. 7C shows human peripherin cDNA clone with an altered base at position 359, expressed in vitro from the T7 promoter to the BglII site in the coding sequence and mixed with Rz31 and 0, 5, 7.5, or 10 mM $MgCl_2$ for 3 hours.

FIG. 7 shows human peripherin cDNA clone expressed in vitro from the T7 promoter to the BglII site in the coding sequence. Likewise the Rz31 (targeting a cleavage site at 357-359) (nucleotides 466-468 of SEQ ID NO:13) was expressed to the XbaI site. A: Resulting RNAs were mixed together with 10 mM $MgCl_2$ at 37° C. for varying times. Lane 1: DNA ladder. Lanes 2-6: Human peripherin RNA and Rz31 RNA after incubation at 37° C. with 10 mM $MgCl_2$ for 3 hrs, 2 hrs, 1 hr, 30 mins and 0 mins respectively. Increased cleavage of mouse rhodopsin RNA was obtained over time—however significant residual intact RNA remained even after 3 hours (Lane 2). Lane 7: Intact human peripherin RNA alone. Lane 8: DNA ladder. From top to bottom, intact human peripherin RNA and the two cleavage products from the human peripherin RNA are highlighted by arrows. B: Resulting RNAs were mixed with Rz31 RNA at varying $MgCl_2$ concentrations and incubated at 37° C. for 3 hrs. Lane 1: DNA ladder. Lanes 2-5: Human peripherin RNA and Rz31 after incubation at 37° C. with 10, 7.5, 5 and 0 mM $MgCl_2$ respectively for 3 hrs. Sizes of the expressed RNAs and cleavage products are as expected (Table 1). Significant cleavage of human peripherin RNA was obtained with a residual amount of intact RNA present at each MgCl$_2$ concentration (Lanes 2-4). Lane 6: Intact human peripherin RNA alone. Lane 7: DNA ladder. From top to bottom, human peripherin RNA and the two cleavage products from this RNA are highlighted with arrows. C: The adapted human peripherin DNA with a single base change at position 359 (nucleotide 468 of SEQ ID NO:13) was expressed from the T7 promoter to the BglII site in the coding sequence. Resulting RNA was mixed with Rz31 at various MgCl$_2$ concentrations and incubated at 37° C. for 3 hrs. Lane 1: DNA ladder. Lane 2: Intact adapted human peripherin RNA alone. Lanes 3-6: Adapted human peripherin RNA and Rz31 after incubation at 37° C. with 0, 5, 7.5 and 10 mM MgCl$_2$ respectively for 3 hrs. No cleavage of the adapted human peripherin RNA was observed even after 3 hours. Lane 7: DNA ladder.

Figures 8A, 8B:
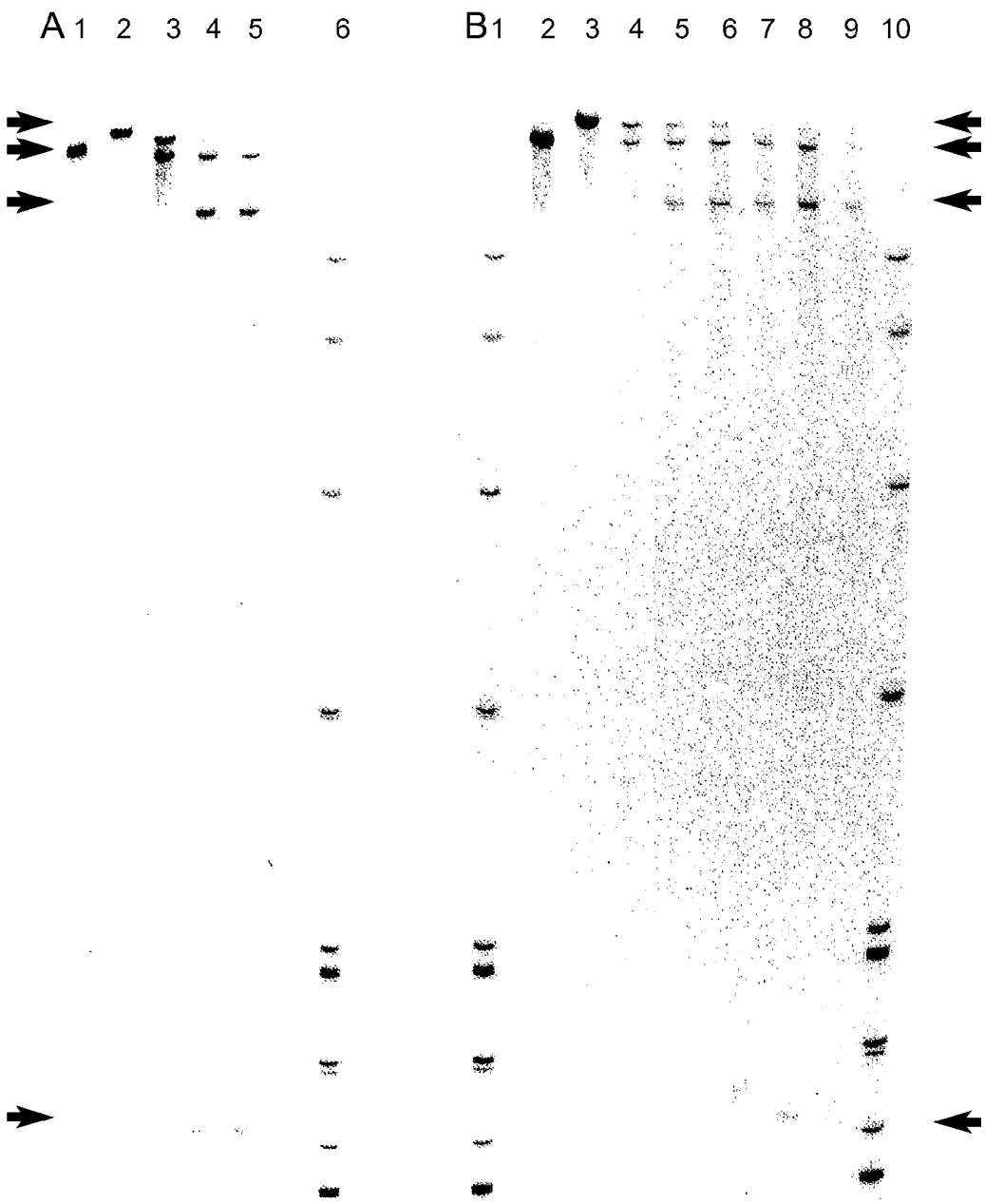
FIG. 8A shows the human collagen 1A2 cDNA clones containing the A and T alleles of the polymorphism at position 907 expressed from the T7 promoter to the MvnI and XbaI sites in the insert and vector respectively.
FIG. 8B shows the human collagen 1A2 cDNA (A)+(B) clones containing the A and T alleles of the polymorphism at 907 expressed from the T7 promoter to the MvnI and XbaI sites in the insert and vector respectively.

FIG. 8A shows the human collagen 1A2 cDNA clones containing the A and T alleles of the polymorphism at position 907 expressed from the T7 promoter to the MvnI and XbaI sites in the insert and vector respectively. Resulting RNAs were mixed together with Rz907 and various MgCl$_2$ concentrations and incubated at 37° C. for 3 hours. Lane 1: intact RNA from the human collagen 1A2 (A) containing the A allele of the 907 polymorphism. Lane 2: intact RNA from the human collagen 1A2 (B) containing the T allele of the 907 polymorphism. Lanes 3-5: Human collagen 1A2 (A) and (B) representing the A and T allele RNAs and Rz907 incubated with 0, 5, and 10 mM MgCl$_2$ at 37° C. for 3 hours. RNA transcripts from the T allele containing the 906-908 target site are cleaved by Rz907 upon addition of divalent ions—almost complete cleavage is obtained with a residual amount of transcript from the T allele remaining (Lane 5). In contrast transcripts expressed from the A allele (which are smaller in size to distinguish between the A (MvnI) and T (XbaI) alleles) were not cleaved by Rz907— no cleavage products were observed. From top to bottom, RNA from the T allele, the A allele and the two cleavage products from the T allele are highlighted by arrows. Lane 6: DNA ladder.

FIG. 8B shows the human collagen 1A2 cDNA (A)+(B) clones containing the A and T alleles of the polymorphism at 907 expressed from the T7 promoter to the MvnI and XbaI sites in the insert and vector respectively. Resulting RNAs were mixed together with Rz907 and 10 mM MgCl$_2$ and incubated at 37° C. for varying times. Lane 1: DNA ladder. Lane 2: intact RNA from the human collagen 1A2 (A) with the A allele of the 907 polymorphism. Lane 3: intact RNA from the human collagen 1A2 (B) with the T allele of the 907 polymorphism. Lanes 4-9: Human collagen 1A2 A and T allele RNA and Rz907 incubated with 10 mM MgCl$_2$ at 37° C. for 0, 30 mins, 1 hour, 2 hours, 3 hours and 5 hours respectively. RNA transcripts from the T allele containing the 906-908 target site are cleaved by Rz907—almost complete cleavage is obtained after 5 hours. In contrast transcripts expressed from the A allele (which are smaller in size to distinguish between the A (MvnI) and T (XbaI) alleles) were not cleaved by Rz907—no cleavage products were observed. From top to bottom, RNA from the T allele, the A allele and the two cleavage products from the T allele are highlighted by arrows.

Results:

Human and mouse rhodopsin, human peripherin and human collagen 1A2 cDNA clones were expressed in vitro. Ribozymes targeting specific sites in the human and mouse rhodopsin, human peripherin and human collagen 1A2 cDNAs were also expressed in vitro. cDNA clones were cut with various restriction enzymes resulting in the production of differently sized transcripts after expression. This aided in differentiating between RNAs expressed from unadapted and adapted cDNAs. Restriction enzymes used to cut each clone, sizes of resulting transcripts and predicted sizes of products after cleavage by target ribozymes are given below in Table 1. Exact sizes of expression products may vary by a few bases from that estimated as there may be some ambiguity concerning inter alia the specific base at which transcription starts.

A: Human Rhodopsin

The unadapted human rhodopsin cDNA (SEQ ID NO:1) and the human rhodopsin cDNA with a single nucleotide substitution in the coding sequence (SEQ ID NO:2) were cut with BstEII and expressed in vitro. The single base change occurs at the third base position or wobble position of the codon (at position 477) (nucleotide 271 of SEQ ID NO:2) and therefore does not alter the amino acid coded by this triplet. The Rz10 clone was cut with XbaI and expressed in vitro. Resulting ribozyme and human rhodopsin RNAs were mixed with varying concentrations of MgCl$_2$ to optimize cleavage of template RNA by Rz10. A profile of human rhodopsin RNA cleavage by Rz10 over time is given in FIG. 1A. The MgCl$_2$ curve profile used to test if adapted human rhodopsin transcripts could be cleaved by Rz10 is given in FIG. 2B. Unadapted and adapted human rhodopsin cDNAs were cut with FspI and BstEII respectively, expressed and mixed together with Rz10 RNA to test for cleavage (FIG. 1B) over time. Likewise, unadapted and adapted human rhodopsin cDNAs were cut with AcyI and BstEII respectively, both were expressed in vitro and resulting transcripts mixed with Rz10 RNA at varying MgCl$_2$ concentrations to test for cleavage (FIG. 2A, 2C). In all cases expressed RNAs were the predicted size. Similarly in all cases unadapted transcripts were cleaved into products of the predicted size. Cleavage of unadapted human rhodopsin RNA was almost complete— little residual uncleaved RNA remained. In all cases adapted human rhodopsin RNAs with a single base change at a silent site remained intact, that is, they were not cleaved by Rz10. Clearly, transcripts from the unadapted human rhodopsin cDNA are cleaved by Rz10 while transcripts from the adapted replacement nucleic acid which has been modified in a manner which exploits the degeneracy of the genetic code are protected from cleavage. It is worth noting that AcyI enzyme cuts after the stop codon and therefore the resulting RNA includes the complete coding sequence of the gene.

Rz20 was cut with XbaI and expressed in vitro. Similarly the rhodopsin cDNA containing a Pro23Leu mutation was cut with BstEII and expressed in vitro. Resulting RNAs were mixed and incubated at 37° C. with 10 mM MgCl$_2$ for varying times. Rz20 was designed to elicit mutation specific cleavage of transcripts containing a Pro23Leu rhodopsin mutation. All expressed products and cleavage products were the correct size. FIG. 3 demonstrates mutation specific cleavage of the mutant RNA over time incubated at 37° C. with 10 mM MgCl$_2$. Cleavage of mutant rhodopsin transcripts by Rz10 which targets a ribozyme cleavage site 3' of the site of the Pro23Leu mutation in rhodopsin coding sequence was explored. The mutant rhodopsin cDNA and Rz10 clones were cut with BstEII and XbaI respectively and expressed in vitro. Resulting RNAs were mixed and incubated with 10 mM MgCl$_2$ for varying times (FIG. 4). All expressed products and cleavage products were the correct size. Rz10 cleaved mutant rhodopsin transcripts. Using a replacement nucleic acid with a sequence change around the Rz10 cleavage site which is at a wobble position we demonstrated in Example 1A that transcripts from the replacement nucleic acid remain intact due to absence of the Rz10 target site (FIGS. 1B, 2A and 2B). Hence Rz10 could be used to cleave mutant transcripts in a manner independent of the disease mutation itself (that is, using this site) while transcripts from the replacement nucleic acid which code for the correct protein would remain intact and therefore could supply the wild type protein.

B. Mouse Rhodopsin

Figure 5A:
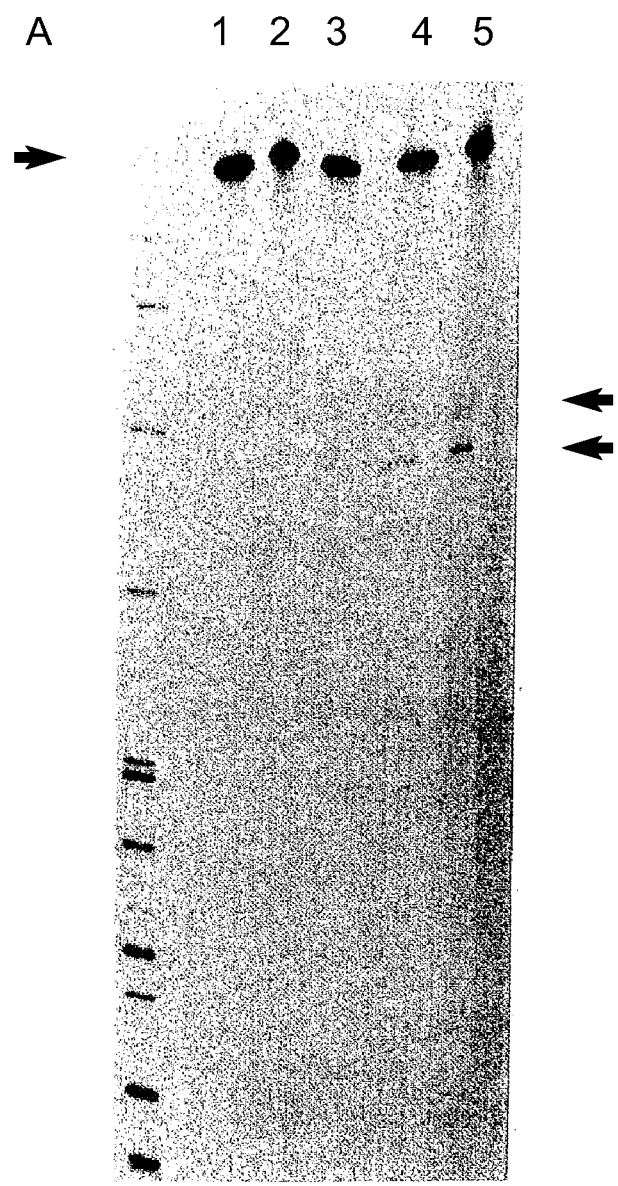
FIG. 5A shows the mouse rhodopsin cDNA clone was expressed in vitro from the T7 promoter to the Eco47III site in the coding sequence and mixed with Rz33 and 0, 5, 7.5, or mM $MgCl_2$ for 3 hours.
Figure 5B:
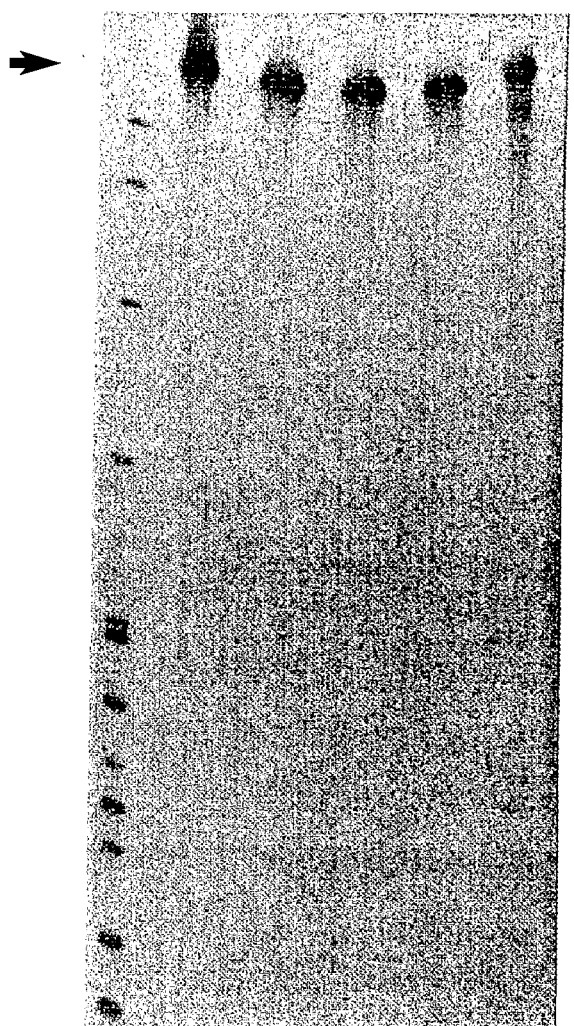
FIG. 5B shows the mouse rhodopsin cDNA clone containing an altered base at position 1460, expressed in vitro from the T7 promoter to the Eco47III site in the coding sequence and mixed with Rz33 and 0, 5, 7.5, or 10 mM $MgCl_2$ for 3 hours.

Rz33 was cut with XbaI and expressed in vitro. Similarly, the mouse rhodopsin cDNA was cut with Eco47III and expressed in vitro. Resulting RNAs were mixed and incubated with varying concentrations of $MgCl_2$. All expressed products and cleavage products were the correct size. FIG. 5A demonstrates specific cleavage of the mouse rhodopsin RNA over various $MgCl_2$ concentrations incubated at 37° C. for 3 hours. Using a replacement nucleic acid with a sequence change around the Rz33 cleavage site (TTT-->TCT) (nucleotides 189-191 of SEQ ID NO:7) which is at a wobble position we demonstrated that transcripts from the replacement nucleic acid remain intact due to absence of the Rz33 target site (FIG. 5B). Hence Rz33 could be used to cleave mutant transcripts in a manner independent of the disease mutation itself (that is, using this site) while transcripts from the replacement nucleic acid which code for the correct protein would remain intact and therefore could supply the wild type protein.

C. Human Peripherin

The unadapted human peripherin cDNA and two human peripherin DNA fragments generated by PCR mutagenesis with a single nucleotide substitution in the coding sequence were cut with BglII and AvrII respectively and expressed in vitro. The single base changes in the adapted DNAs occur at third base positions or wobble positions of the codon (at position 257 and 359) (nucleotide 468 of SEQ ID NO:13 and nucleotide 332 of SEQ ID NO:10, respectively) and therefore do not alter the amino acid coded by these triplets. The Rz30 and Rz31 clones were cut with XbaI and expressed in vitro. Resulting ribozymes and unadapted human rhodopsin RNAs were mixed with varying concentrations of $MgCl_2$ to optimize cleavage of template RNA by Rz30 and Rz31. Profiles of human peripherin RNA cleavage by Rz30 over various $MgCl_2$ concentrations and over time are given in FIG. 6. Similarly profiles of human peripherin RNA cleavage by Rz31 over various $MgCl_2$ concentrations and over time are given in FIG. 7. In all cases expressed RNAs were the predicted size. Similarly in all cases unadapted transcripts were cleaved into products of the predicted size. Adapted human rhodopsin RNAs were mixed together with Rz30 and Rz31 RNA over various $MgCl_2$ concentrations to test if adapted human peripherin transcripts could be cleaved by Rz30 and Rz31 (FIGS. 6+7). Expressed RNAs were the predicted size. In all cases adapted human peripherin RNAs with single base changes at silent sites remained intact, that is, they were not cleaved by Rz30 or Rz31. Clearly, transcripts from the unadapted human peripherin cDNA are cleaved by Rz30 and Rz31 while transcripts from the adapted replacement DNAs which have been modified in a manner which exploits the degeneracy of the genetic code are protected from cleavage.

D. Human Collagen 1A2

Rz907 clones targeting a polymorphic site in human collagen 1A2 sequence was cut with XbaI and expressed in vitro. The human collagen 1A2 cDNA clones (A and B) containing two allelic forms of a polymorphism in the coding sequence of the gene at positions 907 were cut with MvnI and XbaI respectively, expressed in vitro and RNAs mixed together with Rz907 RNA to test for cleavage of transcripts by this ribozyme. All expressed transcripts were of the predicted sizes. RNAs were mixed with varying concentrations of $MgCl_2$ to optimize cleavage of RNAs by Rz907 (FIG. 8). Notably the majority of the RNA transcripts from human collagen 1A2 (A) which has a T nucleotide at position 907 (A nucleotide 176 of SEQ ID NO:17, reverse strand) is cleaved by Rz907 (FIG. 8). This allelic form of the gene has a ribozyme cleavage site at 906-908. Notably the situation is reversed with transcripts from human collagen 1A2 (B) where in this allelic form of the gene due to the nature of the polymorphism present at position 907 the ribozyme cleavage site has been lost. In contrast to transcripts from human collagen (A), transcripts from human collagen (B) were protected from cleavage by Rz907 due to the alteration in the sequence around the ribozyme cleavage site (FIG. 8). Cleavage of collagen 1A2 (A) by Rz907 was efficient which is consistent with 2-D predictions of RNA open loop structures for the polymorphism—in the allele containing the Rz907 ribozyme cleavage site, the target site is found quite consistently in an open loop structure. This polymorphism found in an open loop structure of the transcript clearly demonstrates the feasibility and utility of using the degeneracy of the genetic code in the suppression of an endogenous gene (either suppressing both alleles or a single allele at a polymorphic site) and restoration of gene expression using a gene which codes for the same protein but has sequence modifications at third base wobble positions which protect the replacement nucleic acid from suppression.

TABLE 1

| | Restriction Enzyme | Estimated RNA Size | Cleavage Products |
|---|---|---|---|
| Human rhodopsin | BstEII | ~851 bases | 287 + 564 bases (Rz10) |
| | AcyI | ~1183 bases | 287 + 896 bases (Rz10) |
| | FspI | ~309 bases | 287 + 22 bases (Rz10) |
| Human rhodopsin artificial polymorphism | BstEII | ~851 bases | |
| Human rhodopsin Pro-Leu | BstEII | ~851 bases | 170 + 681 (Rz20) |
| Human rhodopsin Pro-Leu | BstEII | ~851 bases | 287 + 564 (Rz10) |
| Rz10 | XbaI | ~52 bases | |
| Rz20 | XbaI | ~52 bases | |
| Mouse rhodopsin | Eco47III | ~774 bases | 400 + 374 bases |
| Mouse rhodopsin artificial polymorphism | Eco47III | ~774 bases | |
| Rz33 | XbaI | ~52 bases | |
| Human peripherin | BglII | ~545 bases | 315 + 230 (Rz30) |
| Human peripherin | BglII | ~545 bases | 417 + 128 (Rz31) |
| Human peripherin artificial polymorphism | AvrII | ~414 bases | |
| Human peripherin artificial polymorphism | BglII | ~545 bases | |
| Rz30 | XbaI | ~52 bases | |
| Rz31 | XbaI | ~52 bases | |
| Human Collagen 1A2 (A) | MvnI | ~837 bases | |
| Human Collagen 1A2 (B) | XbaI | ~888 bases | 690 + 198 bases |
| Rz907 | XbaI | ~52 bases | |

(RNA sizes are estimates)

TABLE 2

A: Rhodopsin mutations tested to assess if the predicted open loop RNA structure containing the Rz10 target site (475-477) remains intact in mutant transcripts.

| Rhodopsin mutation | RNA open loop targeted by Rz10 |
|---|---|
| Pro 23 Leu | Intact |
| Gly 51 Val | Intact |
| Thr 94 Ile | Intact |
| Gly 188 Arg | Intact |
| Met 207 Arg | Intact |
| Ile del 255 | Intact |

B: Utilization of the degeneracy of the genetic code. Ribozyme cleavage sites are underlined

Human rhodopsin

| | |
|---|---|
| Unadapted sequence | 475-477<br>TAC <u>GTC</u> ACC GTC CAG<br>(SEQ ID NO: 19)<br>Val |
| Adapted sequence | 475-477<br>TAC GTG ACC GTC CAG<br>(SEQ ID NO: 20)<br>Val |

Mouse rhodopsin

| | |
|---|---|
| Unadapted sequence | 1459-1461<br>AAT <u>TTT TAT</u> GTG CCC<br>(SEQ ID NO: 21)<br>Phe |
| Adapted sequence | 1459-1461<br>AAT TTC TAT GTG CCC<br>(SEQ ID NO: 22)<br>Phe |

Human peripherin

| | |
|---|---|
| Unadapted sequence | 255-257<br>GCG <u>CTA</u> CTG AAA GTC<br>(SEQ ID NO: 23)<br>Leu |
| Adapted sequence | 255-257<br>GCG CTG CTG AAA GTC<br>(SEQ ID NO: 24)<br>Leu |
| Unadapted sequence | 357-359<br>AGC <u>CTA</u> GGA CTG TTC<br>(SEQ ID NO: 25)<br>Leu |
| Adapted sequence | 357-359<br>AGC CTG GGA CTG TTC<br>(SEQ ID NO: 26)<br>Leu |
| Human type I collagen 1A2<br>Sequence (A) | 906-908<br>GCT <u>GGT</u> CCC GCC GGT<br>(SEQ ID NO: 27)<br>Gly |
| Sequence (B) | 906-908<br>GCT GGA CCC GCC GGT<br>(SEQ ID NO: 28)<br>Gly |

In the examples outlined above, RNA was expressed from cDNAs coding for four different proteins: human and mouse rhodopsin, human peripherin and human type I collagen 1A2. Rhodopsin and peripherin have been used to exemplify the invention for retinopathies such as adRP—suppression effectors have been targeted to the coding sequences of these genes. In the case of the human collagen 1A2 gene, a naturally occurring polymorphism has been used to demonstrate the invention and the potential use of the invention for disorders such as OI—however non-polymorphic regions of the collagen 1A2 gene could be used to achieve suppression. The suppression effectors of choice in the invention have been hammerhead ribozymes with antisense flanks to define sequence specificity. Hammerhead ribozymes require NUX cleavage sites in open loop structures of RNA. Notably, other suppression effectors could be utilized in the invention and may lead to a more flexible choice of target sequences for suppression. Transcripts expressed from all four genes have been significantly attacked in vitro using suppression effectors directed towards target cleavage sites. In all four examples the ribozymes directed to cleavage sites were successful in cleaving target RNAs in the predicted manner. Antisense complementary to sequences surrounding the cleavage sites was used successfully to elicit binding and cleavage of target RNAs in a sequence specific manner. Additionally, transcripts from replacement nucleic acids, modified using the degeneracy of the genetic code so that they code for wild type protein, were protected fully from cleavage by ribozymes.

The utility of an individual ribozyme designed to target an NUX site in an open loop structure of transcripts from a gene will depend in part on the robust nature of the RNA open loop structure when various deleterious mutations are also present in the transcript. To evaluate this, we analyzed RNAPlotFold data for six different adRP causing mutations in the rhodopsin gene. For each of these, the large RNA open loop structure which is targeted by Rz10 was predicted to be maintained in the mutant transcripts (Table 2A). This is clearly demonstrated in example 1B (FIG. 3) using a Pro23Leu rhodopsin mutation. Rz10 clearly cleaves the mutant transcript effectively in vitro. The Pro23Leu mutation creates a ribozyme cleavage site and can be cleaved in vitro by Rz20 a ribozyme specifically targeting this site—however this is not the case for many mutations. In contrast we have shown that the Rz10 ribozyme cleavage site is available for different mutant rhodopsins and could potentially be used to suppress multiple mutations using a suppression and replacement approach.

In some cases lowering RNA levels may lead to a parallel lowering of protein levels however this may not always be the case. In some situations mechanisms may prevent a significant decrease in protein levels despite a substantial decrease in levels of RNA. However in many instances suppression at the RNA level has been shown to be effective. In some cases it is thought that ribozymes elicit suppression not only by cleavage of RNA but also by an antisense effect due to the antisense arms of the ribozyme surrounding the catalytic core.

In all examples provided ribozymes were designed to cleave at specific target sites. Target sites for four of the ribozymes utilized were chosen in open loop structures in the coding regions of transcripts from three retinal genes (human and mouse rhodopsin and human peripherin). In all cases, sequence specific cleavage was obtained at the target cleavage sites (FIGS. 1-7). Target sites were chosen in open loop structures to optimize cleavage. Additionally, target sites were chosen such that they could be obliterated by single nucleotide changes at third base wobble positions and therefore would code for the same amino acid (Table 2B). In turn this enabled the generation of replacement nucleic acids with single nucleotide alterations which code for wild type protein. In all cases tested transcripts from replacement nucleic acids were protected from cleavage by ribozymes. Further modifications could be made to replacement nucleic acids in wobble positions, for example, to limit the binding ability of the antisense arms flanking the ribozyme catalytic core. The examples provided for rhodopsin and peripherin involve suppression of expression of both disease and wild type alleles of a retinal gene and restoration of the wild type protein using a replacement nucleic acid. However, there may be situations where single alleles can be targeted specifically or partially specifically (PCT/GB97/00574).

In one example, human collagen 1A2, Rz907 was used to target a naturally occurring polymorphic site at amino acid 187, (GGA (glycine)-->GGT (glycine), located in an open loop structure from the predicted 2-D conformations of the transcript (FIG. 8, Table 2B). The ribozyme Rz907 cleaved transcripts containing the GGT sequence but transcripts with GGA were protected from cleavage. Transcripts from both alleles of individuals homozygous for the GGT polymorphism could be cleaved by Rz907 whereas in the case of heterozygotes, cleavage could be directed to single alleles (in particular to alleles containing deleterious mutations PCT/GB97/00574). In both situations replacement nucleic acids could have the sequence GGA and therefore would be protected from cleavage by Rz907. The presence of many such naturally occurring silent polymorphisms highlights that replacement nucleic acids could be modified in a similar fashion in wobble positions and should produce in most cases functional wild type protein. Multiple modifications could be made to replacement nucleic acids at wobble positions which would augment protection from suppression effectors. For example, in situations where antisense nucleic acids were used for suppression, transcripts from replacement nucleic acids with multiple modifications at third base positions would be protected partially or completely from antisense binding.

In all four examples provided, transcripts from cDNA clones were cleaved in vitro in a sequence specific manner at ribozyme cleavage sites. Additionally one base of the ribozyme cleavage site occurs at a wobble position and moreover can be altered so as to eliminate the cleavage site. Ribozyme cleavage sites in the examples given were destroyed by changing nucleotide sequences so that the consensus sequence for ribozyme cleavage sites was broken. However it may be that in some cases the cleavage site could be destroyed by altering the nucleotide sequence in a manner that alters the 2-D structure of the RNA and destroys the open loop structure targeted by the ribozyme. cDNAs or DNA fragments with altered sequences in the regions targeted by ribozymes were generated. RNAs expressed from these cDNAs or DNA fragments were protected entirely from cleavage due to the absence of the ribozyme cleavage site for each of the ribozymes tested. Of particular interest is the fact that a single nucleotide alteration can obliterate a ribozyme target site, thereby preventing RNA cleavage. Although ribozymes have been used in the demonstration of the invention, other suppression effectors could be used to achieve gene silencing. Again replacement nucleic acids with altered sequences (at third base wobble positions) could be generated so that they are protected partially or completely from gene silencing and provide the wild type (or beneficial) gene product.

The above method of suppression and, where necessary, gene replacement may be used as a therapeutic approach for treating diseases caused by many different mutations within a given gene. Given the continuing elucidation of the molecular pathogenesis of dominant and polygenic diseases the number of targets for this invention is rapidly increasing.

Example 2

Use of siRNA to Modulate COL1A1 Gene Expression

Figure 9:
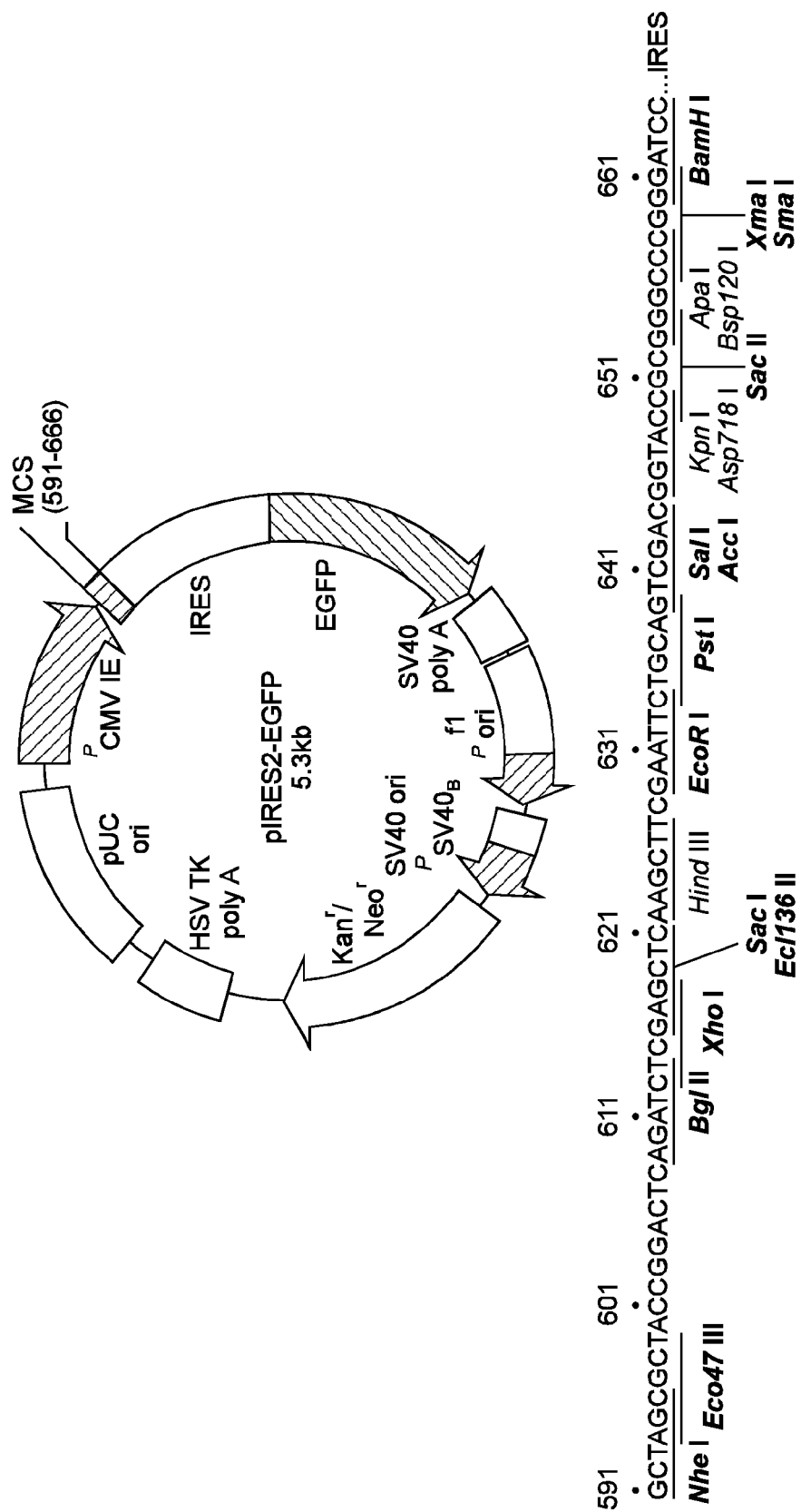
FIG. 9 shows the vector pIRES2-EGFP from Clontech (CA). The pIRES2-EGFP vector is a bicistronic vector in which two different proteins can be expressed from a single transcribed transcript (using an IRES). The sequence provided corresponds to SEQ ID NO: 185.

Duplexes of approximately 21 nucleotide RNAs, known as short interfering RNAs (siRNAs), inhibit gene expression of a target RNA in a sequence specific manner by RNA interference (RNAi). siRNAs targeting the human COL1A1 gene, a gene implicated in OI, were designed and evaluated in vitro. In addition, modified replacement genes altered such that transcripts from these genes avoid siRNA suppression, were generated. The siRNAs were commercially synthesized by Xeragon (Alabama, USA). These materials were then tested in COS-7 cells using reduction in EGFP fluorescence as a marker for suppression. Experiments evaluating down-regulation of a COL1A1 target nucleic acid were carried out by co-transfecting COS-7 cells with an siRNA targeting COL1A1 and a COL1A1-EGFP construct (FIG. 9). Further down-regulation experiments were also carried out on stable COS-7 cell lines expressing a partial COL1A1-EGFP construct. Stable lines were transiently transfected with COL1A1-specific RNAi. RNAi in both sets of experiments suppressed the target COL1A1 (by approximately 80-100%). Furthermore modified human COL1A1 targets with a single base, three and five base changes at degenerate sites escaped suppression by RNAi. Results from these studies show the usefulness of RNAi as a suppression effector in combination with the degeneracy of the genetic code to protect sequence modified targets from suppression.

A COL1A1 target region and replacement gene were cloned into pIRES2-EGFP (Clontech) (FIG. 9). The target was made using primers designed to give a 320 bp COL1A1 fragment surrounding the siRNA recognition site (Table 4). A replacement construct was made by introducing point mutation(s) at wobble sites via primer-directed PCR mutagenesis (Table 4). siRNA sequences together with the sequences of modified replacement constructs are provided in Tables 3 and 4.

The COL1A1 gene sequence was scanned for RNAi target sequences. The sequence AA(N19)TT with a 50% GC content was chosen for the COL1A1 RNAi—however it has been demonstrated that flexibility in RNAi designs can be tolerated and can result in efficient suppression of the target. The sequence chosen as the siRNA target was BLASTed (www.ncbi.nlm.nih.gov) to ensure it was not homologous to other known genes. The siRNA targeting region was checked for any known polymorphisms. Selected siRNA was synthesized by Xeragon. Sense and anti-sense strands were pre-annealed.

TABLE 3

Sequence of COL1A1 and COL7A1 siRNAs & COL1A1 wild type and replacement targets

| | | | | | | | | | |
|---|---|---|---|---|---|---|---|---|---|
| COL1A1siRNA | A | AAC | TTT | GCT | CCC | CAG | CTG | TCT | T |
| Amino acid No: | 157 | 158 | 159 | 160 | 161 | 162 | 163 | 164 | 165 |
| Wild type target | GGA | AAC | TTT | GCT | CCC | CAG | CTG | TCT | TAT (SEQ ID NO: 35) |
| Modified target | GGA | AAC | TTT | GCG (Ala) | CCC | CAG | CTG | TCT | TAT (SEQ ID NO: 36) |
| Wild type target | GGA | AAC | TTT | GCT | CCC | CAG | CTG | TCT | TAT (SEQ ID NO: 37) |
| Modified target | GGC (Gly) | AAC | TTT | GCG (Ala) | CCC | CAG | CTT (Leu) | TCT | TAT (SEQ ID NO: 38) |
| Wild type target | GGA | AAC | TTT | GCT | CCC | CAG | CTG | TCT | TAT (SEQ ID NO: 39) |
| Modified target | GGC (Gly) | AAC | TTT | GCG (Ala) | CCA (Pro) | CAG | CTT (Leu) | TCG (Ser) | TAT (SEQ ID NO: 40) |
| Col7A1 siRNA | AAG | GGG | CAG | GGG | GTC | AAG | CTA | TT | (SEQ ID NO: 41) |

TABLE 4

Oligonucleotides used to generate COL1A1 targets (both wild type and modified targets) and to sequence resulting constructs

| Name | Sequence |
|---|---|
| Col1A1RNAiF | CGGAATTCAGGGACCCAAGGGAGAACACT (SEQ ID NO: 42) |
| Col1A1RNAiR | CGGGATCCCATGGGACCTGAAGCTCCAG (SEQ ID NO: 43) |
| Col1A1Rep1F | GGAAACTTTGCGCCCCAGCTGTCTTAT (SEQ ID NO: 44) |
| Col1A1Rep1R | ATAAGACAGCTGGGGCGCAAAGTTTCC (SEQ ID NO: 45) |
| Col1A1Rep3F | GGCAACTTTGCGCCCCAGCTTTCTTAT (SEQ ID NO: 46) |
| Col1A1Rep3R | ATAAGAAAGCTGGGGCGCAAAGTTGCC (SEQ ID NO: 47) |
| Col1A1Rep5F | GGCAACTTTGCGCCACAGCTTTCGTAT (SEQ ID NO: 48) |
| Col1A1Rep5R | ATACGAAAGCTGTGGCGCAAAGTTGCC (SEQ ID NO: 49) |
| EGFPseqF | CGGGACTTTCCAAAATGTCG (SEQ ID NO: 50) |

Col1A1RNAiF and Col1A1RNAiR DNA primers were used to amplify the human COL1A1 target that was cloned in to the pIRES2-EGFP vector. The Col1A1Rep1F, Col1A1Rep1R, Col1A1Rep3F, Col1A1Rep3R, Col1A1Rep5F and Col1A1Rep5R primers were used for primer directed mutagenesis to incorporate sequence alterations at degenerate sites in the COL1A1 target (Tables 3 and 4). The EGFPseqF primer was used to sequence all constructs in the pIRES2-EGFP plasmid.

COS-7 cells were used both for transient transfection experiments and to create stable cell lines expressing the COL1A1 target using the COLIA1 pIRES2-EGFP vector. Stable cell lines were generated by selecting with G418 using standard techniques. In transient co-transfection experiments Lipofectamine-2000 (Invitrogen) was used to transfect $10^5$ cells with 0.8 µg of DNA and 0.20 µg of siRNA. In transient transfection experiments of stable lines, Oligofectamine (Invitrogen) was used to transfect $0.5 \times 10^5$ cells with 0.8 µg (50 nmoles) of siRNA.

Fluorescence was measured using a Picofluor (Turner Designs) on the blue channel (excitation 475±15 nm, emission 515±20 nm) with a minicell adaptor. Cells were trypsinized, pelleted and pellets resuspended in PBS before measuring fluorescence in a 200 µl volume. Light microscopy was used to visualize EGPF cell fluorescence in transfected and control cells using GFP filters.

Transient Co-transfection of Target and RNAi in COS-7 Cells

Figure 10:
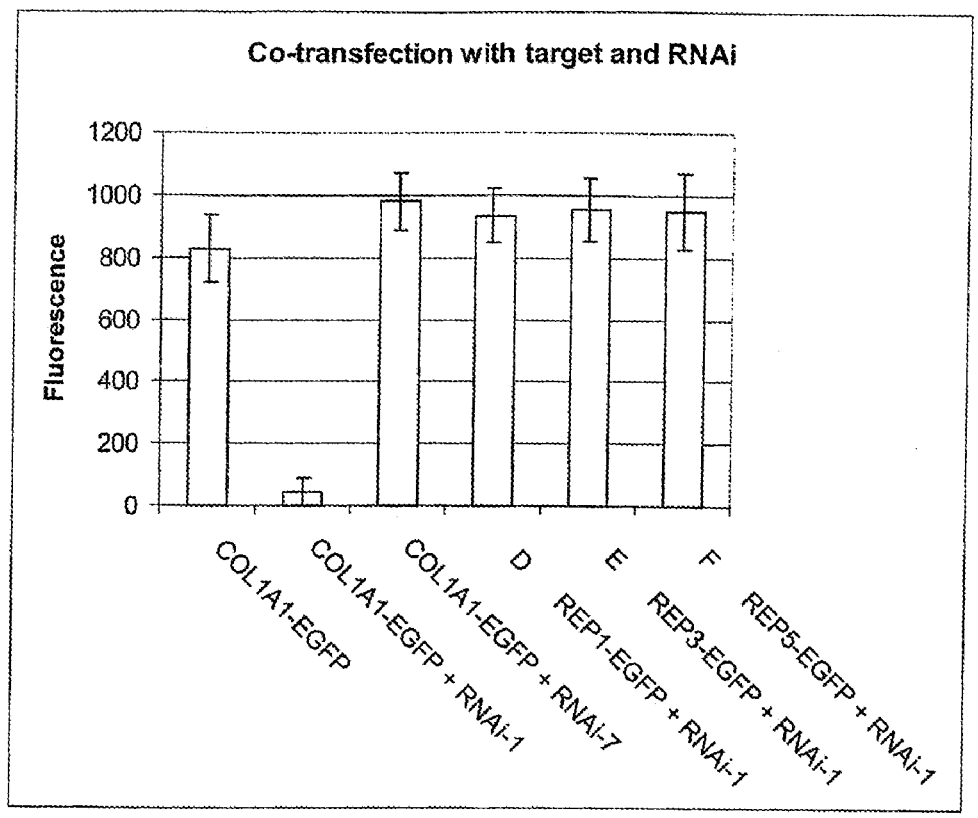
FIG. 10 shows COS-7 cells transiently co-transfected with the human COL1A1 targets (cloned into pIES2-EGFP) and siRNA targeting COL1A1 or a control siRNA (targeting human COL7A1). (RNAi-1=COL1A1 RNAi and RNAi-7=COL7A1).

FIG. 10 shows results from the co-transfection of the COL1A1 target (in the pIRES2-EGFP vector) and siRNA targeting COL1A1. Suppression of target COL1A1 transcripts was initially evaluated by co-transfection of COS-7 cells with siRNA targeting human COL1A1 and the COL1A1-EGFP construct using Lipofectamine2000. The pIRES2-EGFP vector enabled co-expression of the target and enhanced green fluorescent protein (EGFP) as a single transcript. Subsequent to transfection EGFP fluorescence was measured using a Picofluor (Turner Designs) using excitation optics with a blue. LED at 475 nm (+/−15), emission optics at 515 nm (+/−20).Cells transfected with siRNA showed substantial reduction in COL1A1-EGFP levels as assessed by EGFP fluorescence (column 2) when compared to cells without siRNA (column 1). In contrast, a non-complimentary control siRNA targeting COL7A1 showed no down-regulation (column 3). The sequence specificity of siRNA suppression was further explored using a modified COL1A1-EGFP construct carrying a single base change in the sequence targeted by siRNA. This alteration at codon 160 of COL1A1 is at a wobble site and hence both the wild type GCT and modified GCG sequences code for an alanine residue in the protein. The modified construct showed no down-regulation by siRNA targeting wild type COL1A1 sequence (Lane D). Thus, in this case a single base change at a degenerate site was sufficient to eliminate siRNA inhibition. Additional studies incorporating three and five base changes at degenerate sites in the COL1A1 sequence targeted by siRNA were assessed for suppression (Lanes E and F). Similarly, COL1A1-EGFP constructs with multiple sequence modifications avoided suppression by siRNA targeting wild type COL1A1 sequence. Although siRNA has been used in the demonstration of the invention, other suppression effectors could be used to achieve gene silencing. Again replacement nucleic acids with altered sequences (at wobble positions) could be generated so that transcripts from these constructs are protected partially or completely from gene silencing and provide the wild type (or beneficial) gene product.

Figure 11A:
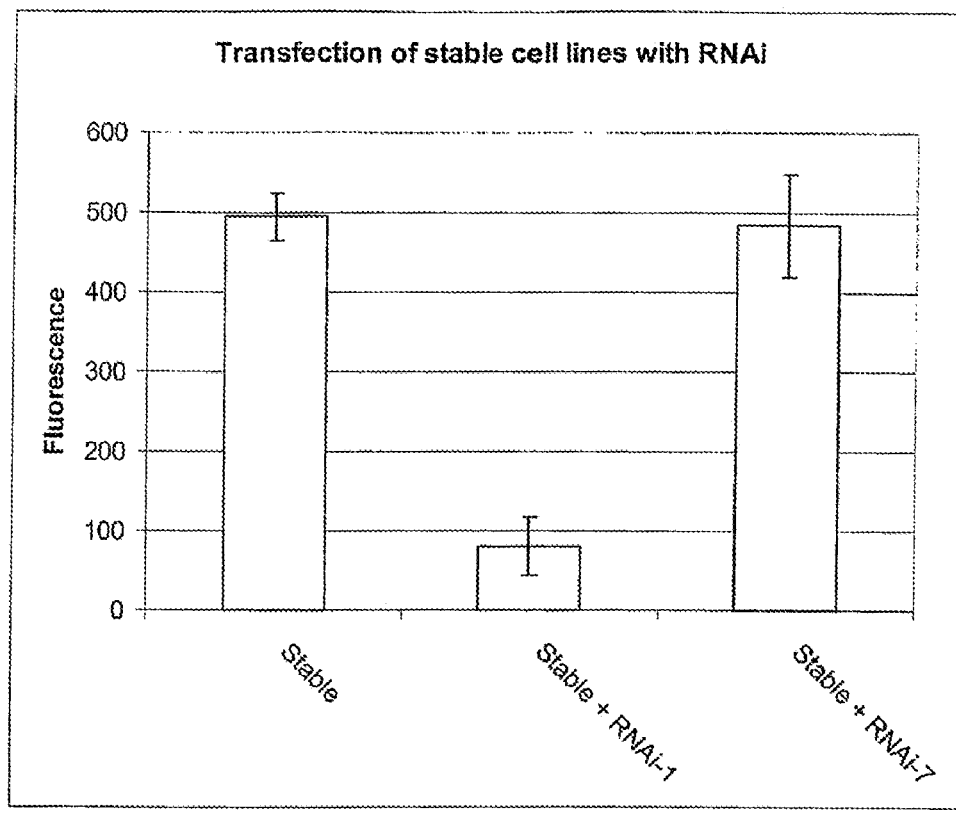
FIG. 11A shows EGFP expression in COS-7 cells stably expressing the human COL1A1-EGFP target (from the pIRES2-EGFP vector) and transfected with siRNA targeting COL1A1. (RNAi-1=COL1A1 RNAi and RNAi-7=COL7A1).
Figure 12:
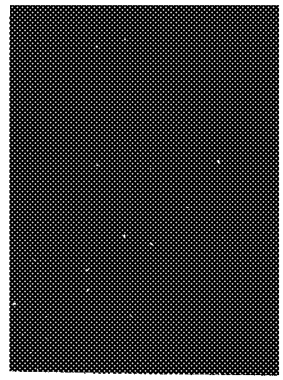
FIG. 12A shows EGFP fluorescence in COS-7 cells transiently transfected with the human COL1A1 target COL1A1-EGFP construct.
FIG. 12B shows EGFP fluorescence in COS-7 cells transiently transfected with the human COL1A1 target COL1A1-EGFP construct and siRNA-1 targeting wild-type COL1A1.
FIG. 12C shows EGFP fluorescence in COS-7 cells transiently transfected with the human COL1A1 target COL1A1-EGFP construct and control siRNA.
FIG. 12D shows EGFP fluorescence in COS-7 cells transiently transfected with the modified COL1A1-EGFP construct and siRNA-1 targeting wild-type COL1A1.
Figure 12:
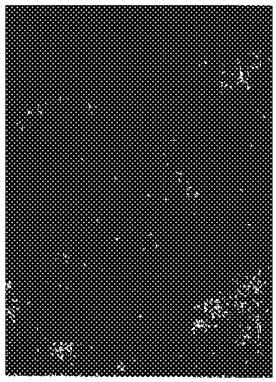
Figure 12:
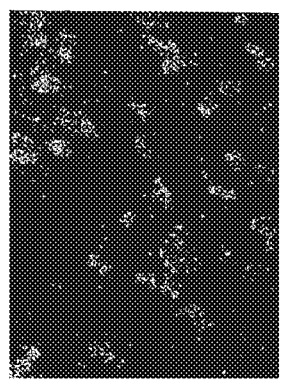

Transient Transfection of Stable COS-7 Cell Lines Expressing COL1A1-EGFP with RNAi FIG. 11A shows results from studies of siRNA-based suppression of COL1A1 in stable COS-7 cell lines expressing the COL1A1-EGFP target. Stable COS-7 cells expressing the COL1A1-EGFP construct (in pIRES2-EGFP) transfected (using Oligofectamine as a transfection agent) with siRNA complementary to COL1A1 showed a level of down-regulation/silencing partially dependent on transfection efficiency. As with the co-transfection results, the presence of complimentary siRNA in cells resulted in significant reduction of COL1A1-EGFP mRNA levels as assessed by EGFP protein fluorescence (FIG. 11A). Similarly non-complementary siRNA (designed to target COL7A1) did not suppress the COL1A1 target (FIG. 11A). EGFP fluorescence was measured using a Picofluor (Turner Designs). As seen in co-transfection experiments above the presence of complimentary siRNA in cells resulted in a significant reduction of COL1A1-EGFP levels. Non-complimentary siRNA (COL7A1 siRNA) did not suppress the COL1A1 target. Fluorescence microscopy of COS-7 cells transiently transfected with the COL1A1-EGFP construct and siRNAs Fluorescence microscopy was used to visualize EGFP fluorescence in cells (FIG. 12). EGFP fluorescence was evaluated in cells transfected with the COL1A1-EGFP construct, the COL1A1-EGFP construct and siRNA-1 targeting wild type COL1A1, the COL1A1-EGFP construct and siRNA-2 (control targeting COL7A1) and the modified COL1A1-EGFP construct and siRNA-1 targeting wild type COL1A1. Suppression with siRNA-1 (targeting COL1A1) was only effective when the wild type COL1A1 sequence was present. Notably no suppression was observed when a COL target with a single base change at a degenerate site was used. Results obtained with the Picofluor were confirmed with the Zeiss Axioplan 2 microscope (FIG. 12).

Timepoint Analysis of EGFP Levels after Addition of siRNA

Figure 11B:
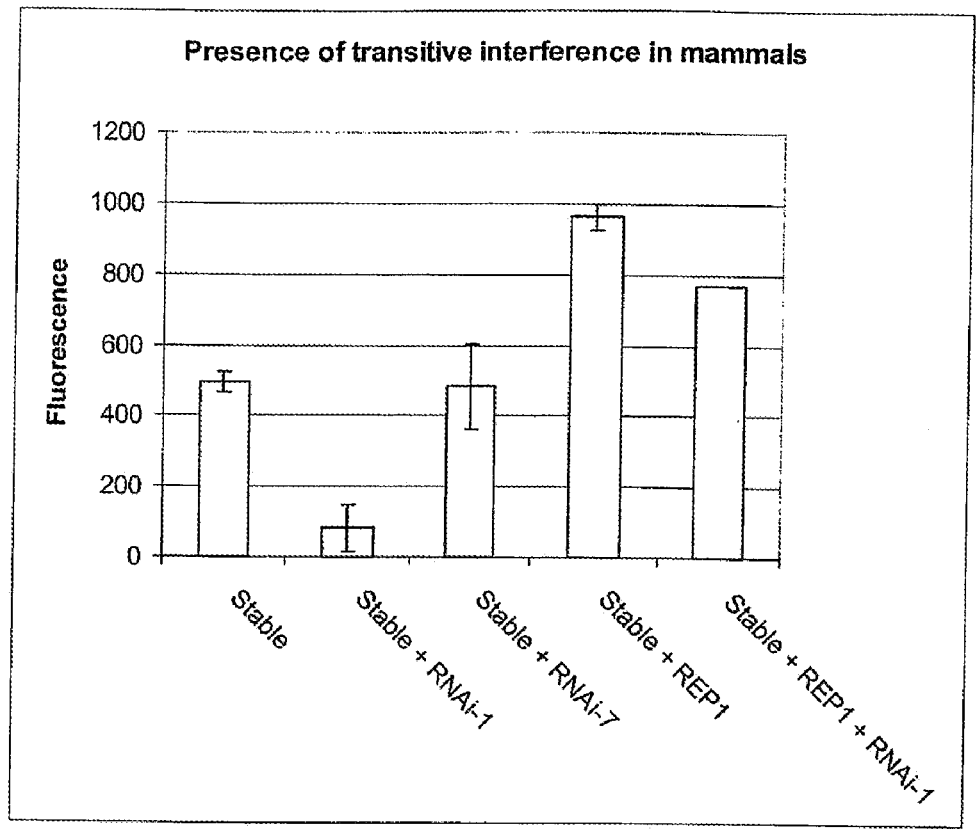
FIG. 11B shows EGFP expression in COS-7 cells stably expressing the COL1A1 target from the pIRES2-EGFP vector and transiently transfected with a vector expressing the replacement COL1A1 target (in pIRES2-EGFP) and siRNA targeting COL1A1 to study the presence/absence of transitive interference in mammalian cells. (RNAi-1=COL1A1 RNAi and RNAi-7=COL7A1).
Figure 13A:
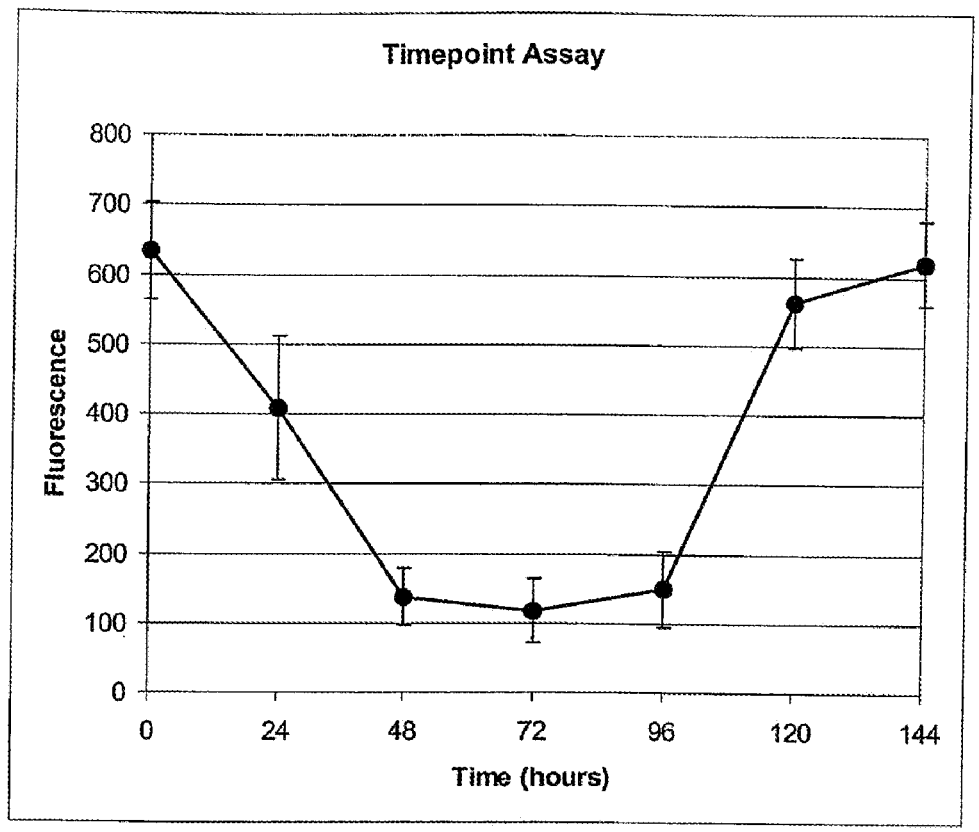
FIG. 13A shows COL1A1-EGFP expression in COS-7 cells stably expressing the COL1A1-EGFP target and transiently transfected with siRNA targeting COL1A1 evaluated over time.

FIG. 13 depicts the results from a time point assay of COL1A1 siRNA-based suppression in COS-7 cells. COS-7 cell lines stably expressing COL1A1-EGFP were used to establish timepoints for down-regulation using COL1A1 siRNA. Levels of down-regulation were determined at various time points by assessing levels of fluorescence generated by the cells. Fluorescence was assessed between 24 and 120 hours post transfection (in 4 separate tests). Down-regulation of EGFP protein levels was observed after 24 hours and persisted for up to 120 hours subsequent to treatment with COL1A1 targeting siRNA. EGFP fluorescence was measured using a Picofluor (Turner Designs). Presence/absence of Transitive Interference in Mammals FIG. 11B presents results from the study of the presence/absence of transitive interference in mammalian cells. Prior studies have suggested that in invertebrates, such as *C. elegans*, dsRNA can stimulate production of additional siRNAs 5' of the original targeted sequence termed transitive interference. Suppression using siRNA and replacement with a gene modified at a wobble position is only possible if this RNA amplification mechanism does not occur in mammalian systems. If such a mechanism were in operation in mammals siRNA generated 5' of the original target sequence would inhibit expression of both the wild type and modified replacement genes. This phenomenon was assessed in COS-7 cells containing three components—wild type COL1A1-EGFP transcripts (stably expressed), modified COL1A1-EGFP transcripts with one altered base at a degenerate site termed REP-1 (transiently expressed) and thirdly with siRNA targeted to wild type human COL1A1 sequence (transiently transfected). If siRNAs were generated 5' of the original target, significant inhibition of both wild type and modified COL1A1 transcripts might be expected. The modified COL1A1-EGFP transcript will be protected from suppression at the original siRNA target site using a wobble modification, however, no modifications were made 5' of this. If siRNA were generated 5' of the original target site the modified COL1A1-EGFP transcript would not be protected against these. Notably such inhibition was not observed. The data suggest that the mechanism of transitive interference observed in invertebrates may be absent in mammals and that siRNA 5' of the original trigger sequence may not be generated. Other research groups have since confirmed these findings and hence it would appear that transitive interference does not occur in mammalian systems. This information is important in optimizing the designs of replacement genes (using the degeneracy of the genetic code such that transcripts from replacement genes avoid suppression) when using siRNA as the suppression agent. Had transitive interference occurred in mammals the design of replacement constructs would be radically different and would require alteration of many of the degenerate sites 5' of the target siRNA sequence.

Example 3

Plasmid Generated siRNA Targeting Human COL1A1

Plasmid Generated Human COL1A1 siRNA
COL1A1 suppression using commercially synthesized siRNA (Xeragon) targeting COL1A1 transcripts was demonstrated in COS-7 cells expressing the target as described above. In addition the use of plasmid vectors to express siRNA targeting human COL1A1 is demonstrated in COS-7 cells.

Figure 13C:
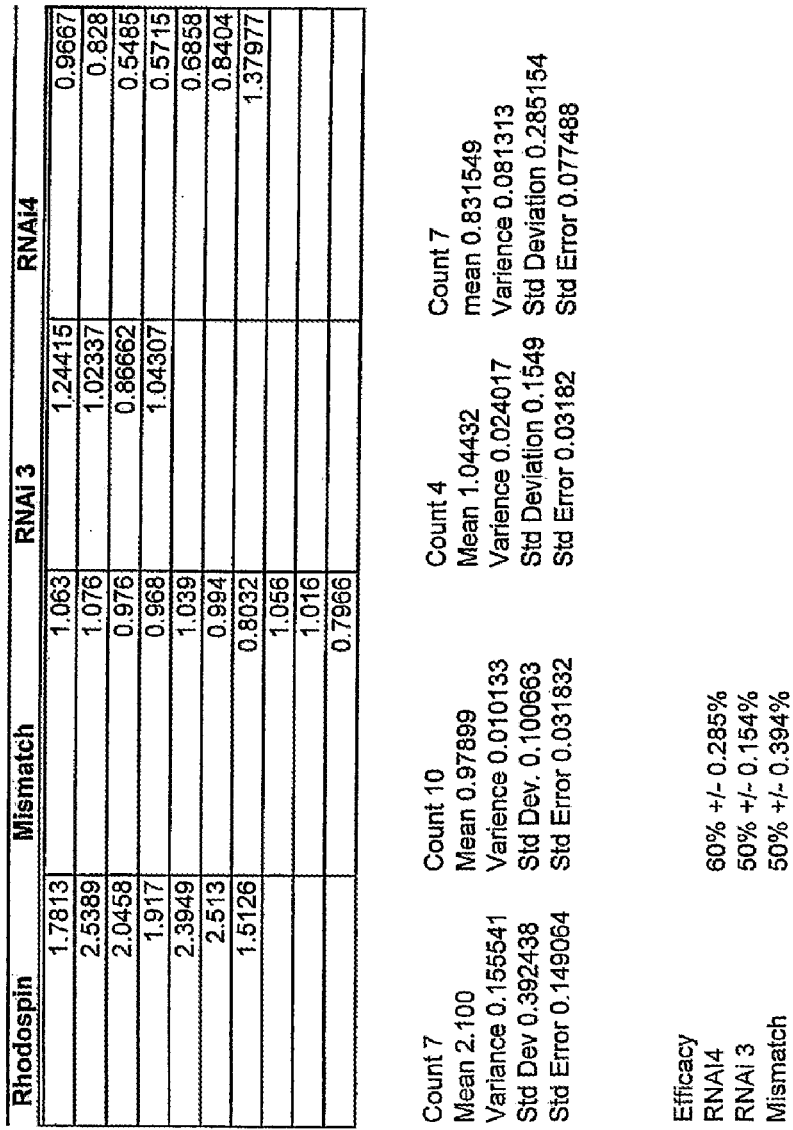
FIG. 13C shows the levels of suppression of the target COL1A1 achieved using siRNA generated from a plasmid vector using the H1 promoter to drive expression of siRNA. siRNAs target the coding sequence of the COL1A1 gene facilitating generation of a replacement COL1A1 gene with sequence modifications at degenerate sites.
Figure 14:
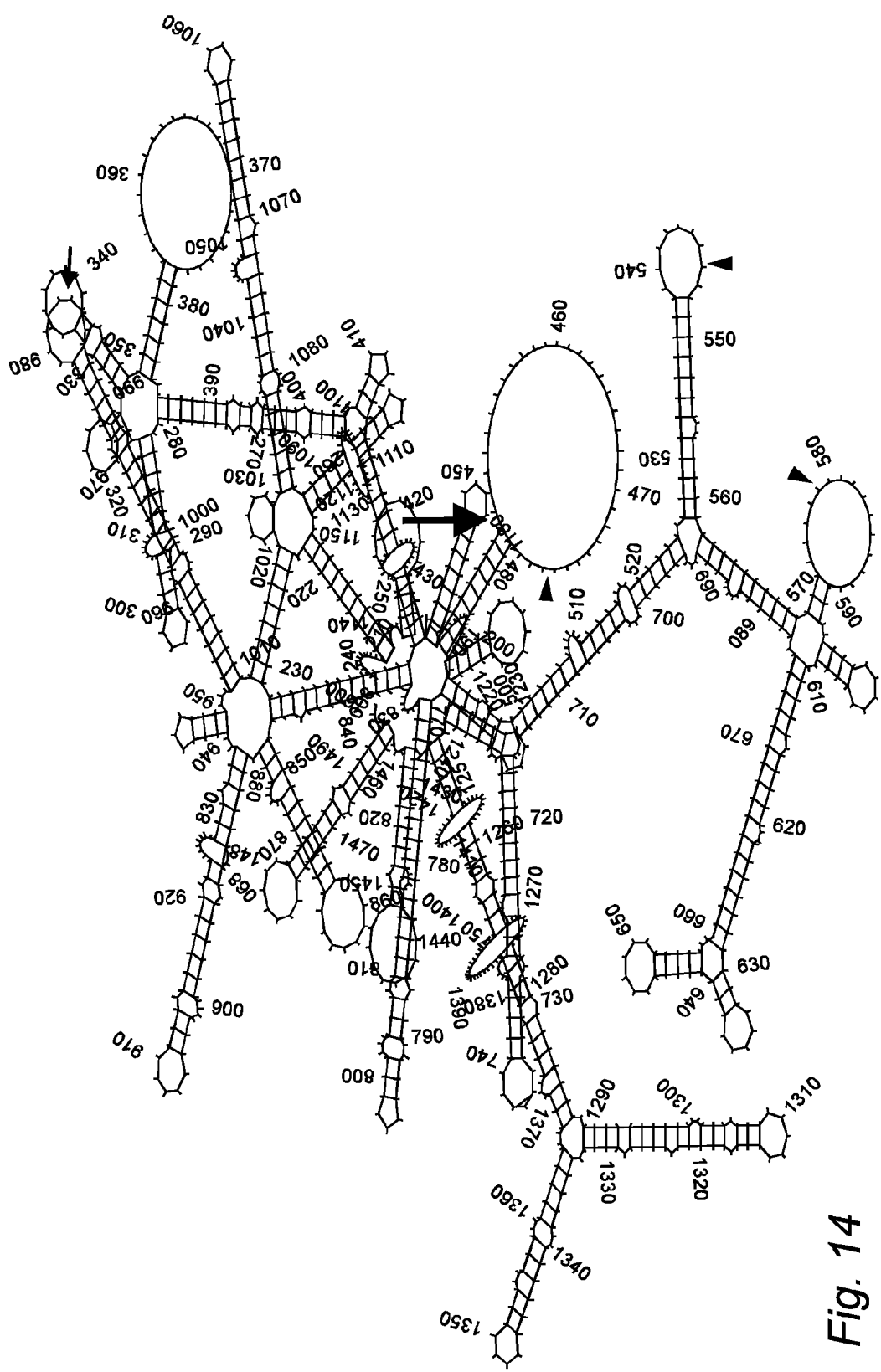
FIG. 14 shows the predicted 2-D structure of human rhodopsin RNA (using PlotFold) presented together with the choice of target site for ribozyme cleavage (for Rz10 and Rz40). The design is not limited to the use of this target site, other target sites within human rhodopsin can be used with ribozyme(s) and or suppression agents such as antisense and dsRNA.

Target Human COL1A1 Constructs
In order to test the efficacy of RNAi plasmid constructs targeting COL1A1to suppress the target, a stable cell line expressing a 547 bp fragment of the COL1A1 gene that encompasses four siRNA target regions chosen was established. FIG. 13B shows the design of four siRNAs targeting coding regions in human COL1A1 transcripts. The human COL1A1 DNA fragment was generated via PCR, the PCR fragment gel excised, digested with BamH1 and XhoI restriction enzymes and then cloned into the BamH1 and XhoI sites of the pIRES2-EGFP vector (Clontech see FIG. 9, PCR primers for COL1A1 PCR amplification are provided in Table 5A). Stable cell lines were established via transfection of COS-7 cells with the COL1A1-EGFP construct carrying the COL1A1 target sequence using Lipofectamine Plus (Invitrogen) as a transfection agent and subsequent selection of transfected cells using G418. Stable cell lines could be monitored by fluorescent microscopy (assaying for EGFP fluorescence). Stable cell lines were subsequently transiently transfected with COL1A1 RNAi constructs. RNA was extracted from COS-7 cells 48 hours post transfection and COL1A1 mRNA levels analyzed via real time RT PCR (FIG. 13C). Significant suppression of the COL1A1 target transcripts was observed with siRNA generated from the H1 promoter in the pKS vector. siRNA targeting human rhodopsin was utilized as a negative control in the study. Levels of expression of GAPDH were used as an internal control for real-time RT PCR reactions. The most effective siRNA targeting COL thus generated and evaluated was found to be RNAi4 which achieved approximately 60% suppression of the target. Sequence for the COL1A1-EGFP target construct is provided in SEQ ID NO: 142.

Constructs with RNAi/siRNA Targeting Human COL1A1
RNAi constructs were designed following the approach outlined in Brummelkamp et al. (2002). In a similar manner to the selection of synthetic siRNAs, the target sequence is about 16-24 nucleotides in length and should be flanked in the mRNA by AA at the 5' and TT at the 3'—although flexibility in the presence/absence of flanking sequences and in the nature of the flanking sequences can be afforded. Regions of the mRNA to select the target sequence from are preferably in the coding region although are not limited to the coding region and can include non-coding and or intronic sequences. Target sites may preferably be approximately 100 by from the start and termination of translation although flexibility again may be afforded. In addition given that the H1 promoter is being used to drive expression it is preferable that the target sequence selected does not contain a stretch of four or more adenines or thymidines as this may result in premature termination of the transcript. Four RNAi constructs were cloned into the pBluescript-KS vector (Stratagene), under the control of the polymerase III H1 promoter as described below (Table 5B). Each primer contains restriction enzyme overhangs (BglII and HindIII) to enable cloning, followed by the target siRNA sense strand a loop structure of between 1 and 20 bases, the target antisense siRNA strand, a termination signal for the H1 promoter and a restriction site overhang. Sequence for the H1 driven siRNA COL1A1 siRNA construct is provided in SEP ID NO: 143.

Replacement Human COL1A1 Constructs
Primer directed PCR-based mutagenesis was used to introduce sequence alterations into the replacement human COL1A1 target sequences using standard methods. PCR primers contain sequences changes from the wild type human COL1A1 sequence located at wobble/degenerate sites in the COL1A1 gene as detailed in Table 5C. Primer sequences in 5C include sequences 5' and 3' which are 100% complementary to the target to aid primer-binding together with sequence containing bases that have been modified from the human COL1A1 sequence at degenerate/wobble sites (sequence in italics) such that replacement sequences encodes for wild type human COL protein (FIG. 13B).

TABLE 5A

Primer sequences for PCR of COL1A1 target

RNAiTargtF bases 3894-3918 in Col1a1 sequence NM 000088

CCTGACTCGAGTGACCCTCAAGAGTGTGCCACT (SEQ ID NO: 51)

RNAiTargtR bases 4432-4450 in Col1a1 sequence NM000088

CGTATGGATCCGGGCCACATCGATGCTGG (SEQ ID NO: 52)

TABLE 5B

Primer sequences for siRNA targets
siRNA sequences are given in uppercase and italics, the sequences of loop regions are provided in bold and lower case and the leader sequences are provided in uppercase and bold.

Target siRNA sequence Col1a1MM base 4261-4279 in Col1a1 NM 000088

CTGGCAACCTCAAGAAGAA
(SEQ ID NO: 53)

Forward primer

GATCCCC*CTGGCAACCTCAAGAAG*AAttcaagaga*TTCTTCTTGAGGTTGCCAG*TTTTTGAAA
(SEQ ID NO: 54)

TABLE 5B-continued

Primer sequences for siRNA targets
siRNA sequences are given in uppercase and italics, the sequences of loop regions are provided in bold and lower case and the leader sequences are provided in uppercase and bold.

Reverse primer

AGCTTTTCCAAAAACTGGCAACCTCAAGAAGAAtctcttgaa *TTCTTCTTGAGGTTGCCAGGGG*
(SEQ ID NO: 55)
NOTE-MM = Mismatch last 2 bases of construct "AA" are mismatched.

*Target siRNA sequence Col1a1R2 base 3982-39999 in Col1a1 NM 000088*

AAGTCTTCTGCAACAATGG
(SEQ ID NO: 56)

Forward primer

GATCCCCAAGTCTTCTGCAACAATG ttcaagagaTCCATGTTGCAGAAGACTTTTTTTGAAA
(SEQ ID NO: 57)

Reverse primer

AGCTTTTCCAAAAAAAGTCTTCTGCAACAATG tctcttgaa TCCATGTTGCAGAAGACTT GGG
(SEQ ID NO: 58)

*Target siRNA sequence Col1a1R3 base in 4020-4038 Col1a1 in NM 000088*

AGCCCAGTGTGGCCCAGAA
(SEQ ID NO: 59)

Forward primer

GATCCCCAGCCCAGTGTGGCCCAGAAttcaagagaTTCTGGGCCACATGGGCTTTTTTGAAA
(SEQ ID NO: 60)

Reverse

AGCTTTTCCAAAAAAGCCCAGTGTGGCCCAGAAtctcttgaaTTCTGGGCCACATGGGCTGGG
(SEQ ID NO: 61)

*Target siRNA sequence Col1a1R4 base 4344-4362 in Col1a1 NM 000088*

AGCGTCACTGTCGATGGCT
(SEQ ID NO: 62)

Forward primer

GATCCCCAGCGTCACTGTCGATGGCT ttcaagagaAGCCATCGACAGTGACGCTTTTTTGAAA
(SEQ ID NO: 63)

Reverse primer

AGCTTTTCCAAAAAAGCGTCACTGTCGATGGCT tctcttgaaAGCCATCGACAGTGACGCTGGG
(SEQ ID NO: 64)

TABLE 5C

Primer sequences for replacement human COL1A1 constructs

RNAi2MutagF

GGA TGC ATC A*AG GTG TTT TGT AAT ATG GAG ACT GGT GAG ACC
(SEQ ID NO: 65)

*RNAi2MutagR*

CAC ACC AGT CTC CAT ATT ACA AAA CAC CTT GAT GCA TCC AGG
(SEQ ID NO: 66)

RNAi3MutagF

TAC CCC ACT CAA CCG ACC GTA GCT CAA AAA AAC TGG TAC ATC
(SEQ ID NO: 67)

TABLE 5C-continued

Primer sequences for replacement human COL1A1 constructs

RNAi3MutagF

GTA CTA GTT TTT TTG AGC TAC GCT CGG TTG AGT GGG GTA CAC
(SEQ ID NO: 68)

RNAi4MutagF

TTC ACC TAC TAT AGT GTA ACG GTG GAC GCC GGT TGC ACG GTA AGT
(SEQ ID NO: 69)

RNAi4MutagR

TAC CGT GCA ACC GCC GTC CAC CGT TAC ACT ATA GTA GGC GAA GCG
(SEQ ID NO: 70)

Example 4

Methods of Cell Culture, Cell Transfection, DNA and RNA Preparation and Handling Seeding Cells Cells were defrosted on ice and transferred to sterile tubes with 10 ml DMEM. Cells were then pelleted at 1000 rpm (IEC Centra-3c bench top centrifuge) for 5 minutes. The supernatant was removed and the pellet resuspended in 5 ml DMEM+. A millilitre of this mix containing $0.5 \times 10^6$ cells was placed into a 9 cm tissue culture dish and made up to 10 mls with DMEM+. Plates were incubated at 37° C. and 6% $CO_2$.

Splitting Cells (10 cm Dish)

Medium was removed form cells and cells washed with PBS. A millilitre of trypsin was added to the plate and the plate was placed at 37° C. for 5 minutes. The plate was tapped to lift cells. DMEM+ was added to bring the volume to 10 ml. An aliquot of 2 ml was added to each new plate and again made up to 10 ml with DMEM+. Plates were incubated at 37° C. and 6% $CO_2$.

Counting Cells (10 cm Dish)

DMEM+ was removed and the cells washed with 10 mls PBS. Two millilitres of trypsin was added and the plate was placed at 37° C. for 5 minutes. The plate was tapped to lift cells. DMEM+ was added to bring the volume to 10 ml. The mix was placed in a sterile tube and spun at 1000 rpm (IEC Centra-3c bench top centrifuge) for 5 minutes. The supernatant was removed and pellet resuspended in 1 ml DMEM+. Equal volumes of cell suspension and trypan blue were mixed (usually 10 µl of each) and placed on a haemocytometer. Sixteen squares were counted and the quantity of cells per millilitre calculated.

Freezing Down Cell Stocks

Freezing ampoules were placed in a pre-cooled Mr. Frosty box. Cells were diluted so that 500 µl contained approximately $2 \times 10^7$ cells. Equal volumes of cells and 2× freezing medium (500 µl of each) were added to an ampoule. The ampoules were then frozen at –80° C. or place in liquid nitrogen.

Transfection with LipofectAMINE PLUS

Cells were counted and seeded at a density to give 50-90% confluency on the day of transfection. Volumes of DNA, reagents and media varied depending on the plate format used. On the day of transfection the DNA was diluted in serum free DMEM. LipofectAMINE PLUS reagent was added, mixed and incubated at room temperature for 15 minutes. Meanwhile the LipofectAMINE reagent was diluted in serum free DMEM and after the 15 minutes incubation added to the DNA/LipofectAMINE PLUS mixture. This was then mixed and left at room temperature for a further 15 minutes. The media was then taken off the cells and was replaced by serum free DMEM and the DNA/LipofectAMINE PLUS/LipofectAMINE mixture. The plates were incubated at 37° C. and 6% $CO_2$ for 3 to 5 hours. DMEM+ with 30% FCS was added to bring the concentration of FCS on the cells to 30% FCS.

Transfection with Lipofectamine 2000 (Gibco/BRL)

Cells were counted and seeded at a density to give 90-95% confluency on the day of transfection. The volumes of DNA, (and siRNA), reagents and media varied depending on the plate format used. On the day of transfection the medium in the plates was replaced with antibiotic free DMEM+. The DNA was diluted in Opti-MEM I reduced serum medium. Lipofectamine 2000 reagent was diluted in Opti-MEM I reduced serum medium and after mixing was incubated for 5 minutes at room temperature. After this time the diluted DNA was added to the diluted Lipofectamine 2000 and left for a further 20 minutes at room temperature. Opti-MEM was used to bring the mixture up to its final volume. DNA/Lipofectamine 2000 complexes were added to the medium and cells. Plates were then mixed by gentle rocking and incubated at 37° C. and 6% $CO_2$ for 24 hours.

Transfection with Oligofectamine

Cells were counted and seeded at a volume to give 30-50% confluence on the day of transfection. The volumes of siRNA, reagents and media varied depending on the plate format being used. On the day of transfection the medium in the plates was changed for antibiotic free DMEM+. The siRNA was diluted in Opti-MEM I reduced serum medium. Oligofectamine reagent was diluted in Opti-MEM I reduced serum medium and after mixing was incubated for 10 minutes at room temperature. After this time the diluted siRNA was added to the diluted Oligofectamine and left for a further 25 minutes at room temperature. Opti-MEM was used to bring the mixture up to its final volume. siRNA/Oligofectamine complexes were added to the medium and cells. Plates were then mixed by gentle rocking and left at 37° C. and 6% $CO_2$ for 24 hours.

Generation of Stable Cells

Transfections were carried out using standard techniques with either LipofectAMINE PLUS or Lipofectamine 2000. Two days after transfection G418 selection was initiated. Media was then changed every 24 hours for 3 days. G418 selection was continued for at least 4 weeks after which cells were grown without G418.

Transient Co-transfection with Target COl1A1 Sequence (in a Plasmid) and RNAi

Co-transfections were carried out using Lipofectamine 2000 (GIBCO/BRL) in a 24 well format. Cells where transfected with 0.8 µg of DNA and 0.2 µg of siRNA.

Transient Transfection of Stable Cell Lines Expressing COL1A1 Sequence with RNAi Transfections were carried out using Oligofectamine in a 24 well format. Typically COS-7 cells where transfected with 0.8 µg of siRNA.

Measuring EGFP Production by Cells Using Fluorimetry 72 hours post transfection wells were rinsed with PBS and incubated for 5 minutes at 37° C. with 100 µl of trypsin. Cells were dislodged and 400 µl of PBS added. Cells were transferred to eppendorfs and spun at 1000 rpm (IEC Micromax bench top centrifuge) for 5 minutes. The supernatant was discarded and the cells resuspended in 200 µl PBS. A Picofluor from Turner Designs was used to measure fluorescence. The minicell adaptor was used so volumes of 75-200 µl would be measurable. The fluorimeter was first blanked with PBS. Readings were taken on the blue channel (excitation 475±15 nm, emission 515±20 nm).

Fluorescence Microscopy

Fluorescence microscopy was undertaken using a Zeiss Axioplan 2 with a UV light source and filters. Images were analyzed by computer using the KS300 imaging system from Zeiss.

Cloning of COL1A1 Constructs

Primers were designed for PCR amplification of a fragment of the human COL1A1 gene around the dsRNA target site. Primers Col1A1RNAiF and Col1A1RNAiR amplified a 320 bp fragment. The primers had EcoRI and BamHI restriction enzyme sites incorporated into them. These sites were used to clone the PCR generated fragment of COL1A1 into the pIRES2-EGFP plasmid. Primers were designed to PCR amplify replacement fragments of the human COL1A1 gene incorporating one, three or five altered bases at degenerate sites. Primers Col1A1Rep1F and Col1A1Rep1R were used to introduce a single base change, primers Col1A1Rep3F and Col1A1Rep3R used to introduce three base changes and primers Col1A1Rep5F and Col1A1Rep5R used to introduce five base changes. All COL1A1 replacement DNA fragments were cloned into pIRES2-EGFP using the EcoRI and BamHI restriction enzyme sites. Ligations, transformations and DNA minipreps were carried out for all constructs. DNA minipreps were tested by PCR to screen for those containing the appropriate inserts. Clones carrying the inserted fragment gave a PCR product of the expected size. Sequencing was carried out on these DNA minipreps to ensure that the correct inserts were present.

RNA Isolation from COS-7 Cells.

RNAs were isolated using Trizol (Gibco/BRL) and standard procedures.

Real Time RT PCR Analysis

Real time RT PCR was performed using the Quantitect Sybr Green RT-PCR kit. (Qiagen GmBH, Hilden). GAPDH or β-actin was used as an internal control. All primers for real time RT PCR were HPLC purified. The ROCHE lightcycler real time RT PCR machine was used in all analyses. Real time RT PCR reactions involved a denaturing step at 95° C., annealing at 55° C. and extension step at 72° C. for 34 cycles. PCR products were analyzed by electrophoresis on a 2% agarose gel.

Examples herein show the power of RNAi as a means of suppressing a target gene for, e.g., investigating the biological function of the gene(s), the generation of transgenic animals and/or plants and in the design and/or implementation of potential therapeutic agents. Notably, the target recognition of RNAi is specific and is sensitive to even a single base change. Generation of replacement constructs with one, three and five base changes using the degeneracy of the genetic code to avoid RNAi suppression and at the same time providing wild type sequence are also demonstrated. Both synthesized siRNA and plasmid generated siRNA has been used to successfully suppress the target human gene in COS-7 cells.

Notably, the approach adopted enables suppression of a target nucleic acid in a manner that is independent of the individual mutation(s) present in COLIA1. Furthermore, COLIA1 can be modified using the degeneracy of the genetic code such that transcripts from the replacement construct avoid siRNA suppression but can provide the wild type protein sequence. The same approach may be utilized for many applications including many other disorders where mutational heterogeneity represents a substantial obstacle.

Example 5

Expression of Rhodopsin and Rhodopsin Ribozymes in COS-7 Cells

Translating ribozyme cleavage efficiencies observed in vitro to in vivo situations, primarily requires the availability of suitable model systems to test ribozyme functionality. Cell culture systems offer an ideal semi-natural and therapeutically relevant environment in which to test ribozymes. However target photoreceptor cell specific transcripts such as rhodopsin are problematic, since photoreceptor cells are non-dividing they do not propagate in cell culture. Therefore, COS-7 cells, derived from African Green monkey kidneys and cells and known to divide well in culture, were stably transfected with rhodopsin using LipofectAMINE PLUS (Invitrogen) and art known protocols. Selection was carried out using 600 µg/ml G418. Rhodopsin expression levels were analyzed by Northern blotting and RT-PCR (with Primer F: 5' ATGGTCCTAGGTGGCTTCACC 3' (SEQ ID NO: 71) in exon 3 of rhodopsin and Primer R: 5' CATGATGGCATGGT-TCTCCCC 3' SEQ ID NO: 72 in exon 5 of rhodopsin).

Subsequently, stable cell lines were transiently transfected with Rz30, Rz10, Rz40 and RzMM (see below for sequence).

Rz30
(SEQ ID NO: 73)
5' <u>ACUUUCAG</u>CUGAUGAGUCCGUGAGGACGAA<u>AGCGCCA</u> 3'

Rz10
(SEQ ID NO: 74)
5' <u>GGUCGGU</u>CUGAUGAGUCCGUGAGGACGAA<u>ACGUAGAG</u> 3'

Rz40
(SEQ ID NO: 75)
5' <u>GGACGGU</u>CUGAUGAGUCCGUGAGGACGAA<u>ACGUAGAG</u> 3'

RzMM
(SEQ ID NO: 76)
5'
<u>GGACGGU</u>CUGAUGAGUCCGUGAGGACGAA<u>ACGUAGAG</u>*UUCAGGCUACCU*A

*UCCAUGAA*CUGAUGAGUCCGUGAGGACGAA<u>AGGUCAGC</u>*CCAGUUUCGUCG*

*AUGGUGUA*CUGAUGAGUCCGUGAGGACGAA<u>AGGGUGCU</u>*GACCUGUAUC*<u>CC</u>

<u>UCCUUC</u>CUGAUGAGUCCGUGAGGACGAA<u>ACGGUGGA</u> 3'

The antisense arms are underlined. A single base mismatch in Rz10 is highlighted in bold print. In RzMM conserved ribozyme core sequence is regular type and random intervening sequence is italicized. Rz30 is an inactive ribozyme. Rz10 and Rz40 are identical except for one base mismatch in one of the antisense arms of Rz10 that is highlighted in bold print in Rz10 (see FIG. 1 for ribozyme target site). Notably, RzMM is a connected multimeric ribozyme, which consists of Rz40, Rz41, Rz42 and Rz43 in tandem. All ribozymes target degenerate sites (wobble) of human rhodopsin (Table 6).

TABLE 6

| Ribozyme | Motif | Amino acid | Position in Rhodopsin |
| --- | --- | --- | --- |
| Rz10 | GUC | Val | 475-477 |
| Rz40 | GUC | Val | 475-477 |
| Rz41 | CTC | Leu | 544-546 |
| Rz42 | CTC | Leu | 577-579 |
| Rz43 | GTC | Val | 982-984 |

Transient transfections were carried out as follows: 1.5-8.0×10$^5$ cells were plated in 3 cm tissue culture dishes and grown to 50-80% confluency. Each dish was transfected with 8 µl LipofectAMINE, 30 µg DNA and 7 µl PLUS reagent according to the manufacturer's protocols.

Figure 15A:
FIG. 15A shows a Northern Blot of RNA from COS-7 cells that stably express human rhodopsin and that have been transiently transfected with a range of ribozymes. The blot was probed for rhodopsin transcripts. Lanes 1 and 2 represent RNAs extracted from cells transfected with inactive ribozyme Rz30. Lanes 3 and 4 represent RNAs extracted from cells transfected with Rz10. Lanes 5 and 6 represent RNAs extracted from cells transfected with Rz40. Lanes 7 and 8 represent RNAs extracted from cells transfected with RzMM.
Figure 15B:
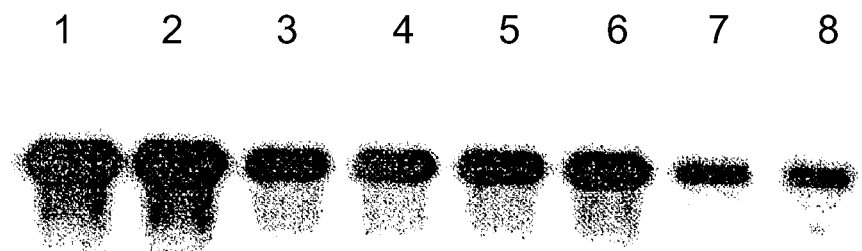
FIG. 15B shows the same Northern Blot as in FIG. 2A of RNA from cell lines, that have been transiently transfected with a range of ribozymes. The blot was probed for β-actin transcript, as a control for equal loading. Lanes 1 and 2 represent RNAs extracted from cells transfected with inactive ribozyme Rz30. Lanes 3 and 4 represent RNAs extracted from cells transfected with Rz10. Lanes 5 and 6 represent RNAs extracted from cells transfected with Rz40. Lanes 7 and 8 represent RNAs extracted from cells transfected with RzMM.
Figure 15C:
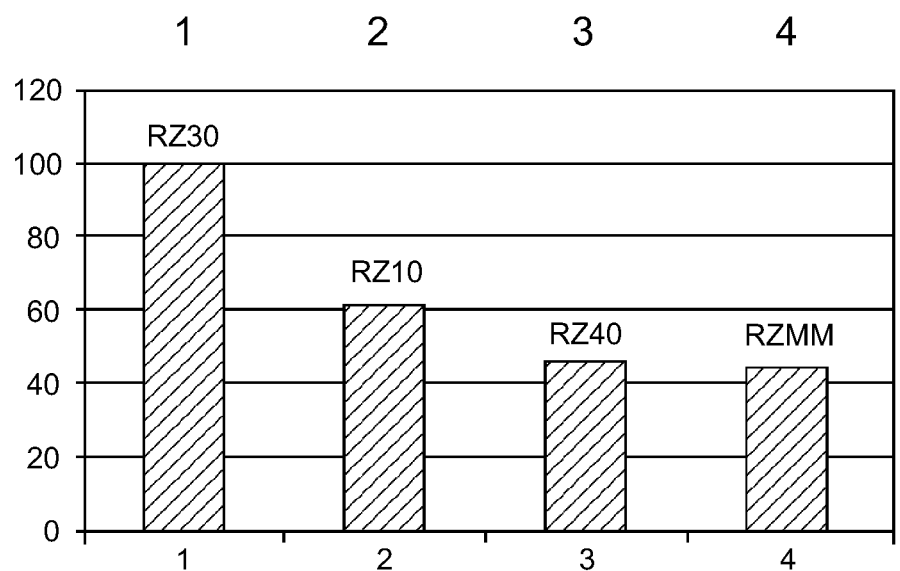
FIG. 15C shows a graphical representation of the decrease in rhodopsin mRNA levels observed in COS-7 cells that were transiently transfected with Rz30, Rz10, Rz40 or RzMM. Down-regulation of human rhodopsin expression of 62%, 46% and 45% was observed in cells transfected with Rz10, Rz40 or RzMM, respectively.
Figure 16:
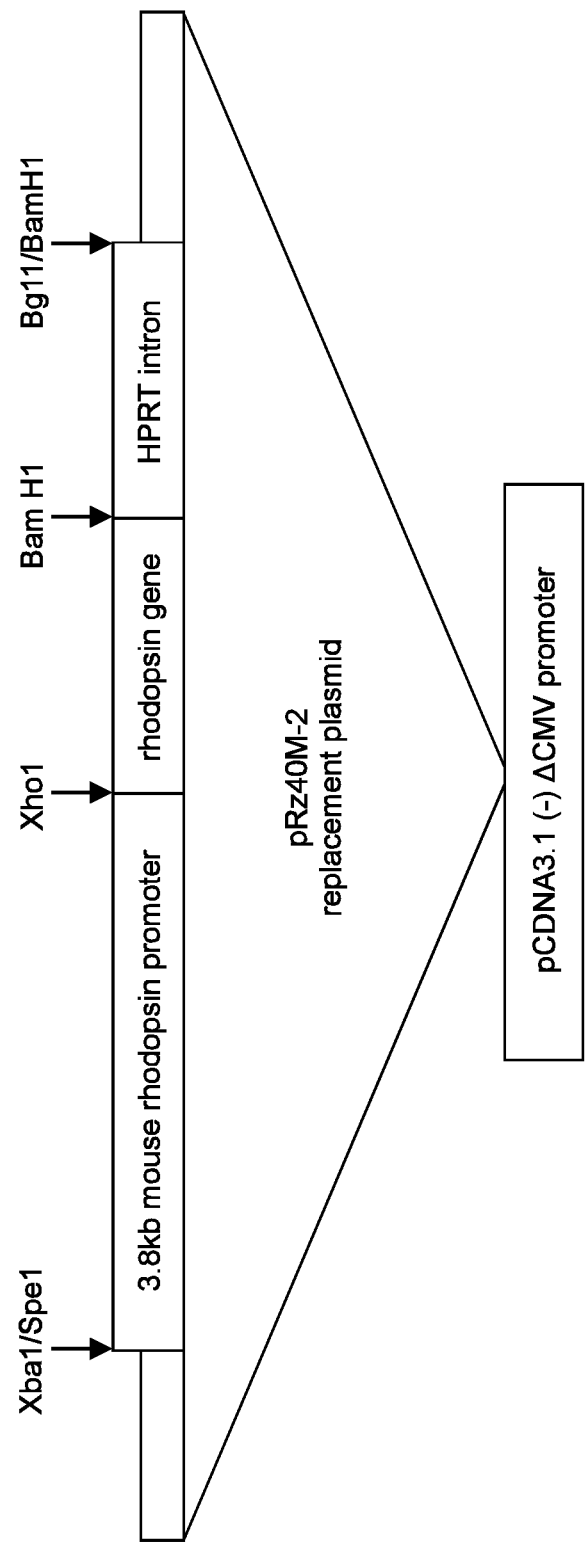
FIG. 16 shows a generic description of one design for replacement constructs. In principle any degenerate site(s) within a target sequence could be modified such that the encoded protein remains the same as wild type.
Figure 17:
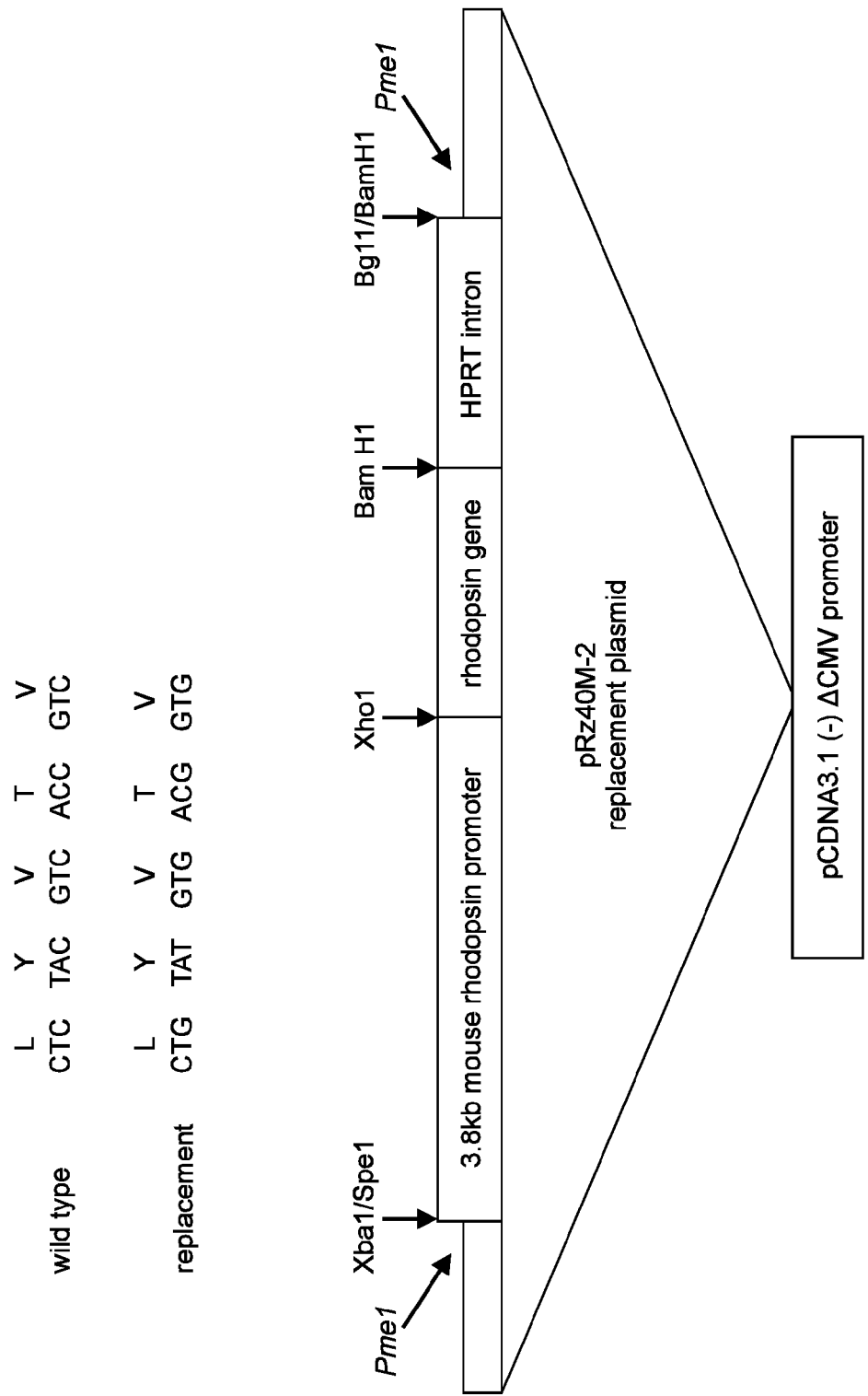
FIG. 17 shows an exemplary replacement rhodopsin construct. The replacement rhodopsin construct includes the incorporation of sequence alterations at the ribozyme target site and therefore transcripts from this gene should avoid cleavage and or binding at least in part by ribozyme(s). The replacement gene uses the target site depicted in FIG. 2 but is not limited to the use of this target site. The sequences provided correspond, from top to bottom, to SEQ ID NO: 172-175.

Poly (A) RNA was extracted 48 h post transfection from cells using standard procedures. Levels of rhodopsin expression in the stable cell lines, which had been transfected with Rz10, Rz40 and RzMM, were compared with levels in cells that had been transfected with inactive Rz30 by Northern blotting. The housekeeping gene β-actin was used as the internal control of loading levels. The β-actin probe for Northern blots was generated by PCR and the following primers: F Primer 5' CGTACCACTGGCATCGTG 3' (SEQ ID NO: 77) and R Primer 5' GTTTCGTGGATGCCACAG 3' (SEQ ID NO: 78). [α$^{32}$P] dCTP was included in the reaction. A human rhodopsin probe was generated by random labeling a plasmid with the gene using art known methods. Levels of expressions, represented by amount of radioactivity on the probed Northern blot, were determined by Instant Imaging (Packard). Levels of down-regulation, carried out in duplicate were substantial. Down-regulation of rhodopsin in COS-7 cells transiently transfected with Rz10, Rz40 and RzMM were 62%, 46% and 45%, respectively (FIG. 15).

Example 6

Transgenic Animal Expressing Modified Human Rhodopsin Gene

Five mouse models were generated. The first mouse is a model for the disorder Retinitis Pigmentosa (RP) (Pro23His). The second mouse carries a hammerhead ribozyme, Rz40, which targets human rhodopsin at a wobble site (Rz40). The third mouse carries a modified replacement human rhodopsin gene, which has been altered at wobble/degenerate positions such that it escapes suppression by Rz40 (RhoM) (FIGS. 16-19). The fourth mouse model carries the wild type human rhodopsin transgene (RhoNhr). The fifth mouse model is a knockout of the endogenous mouse rhodopsin gene (rho−/−).

Figure 19A:
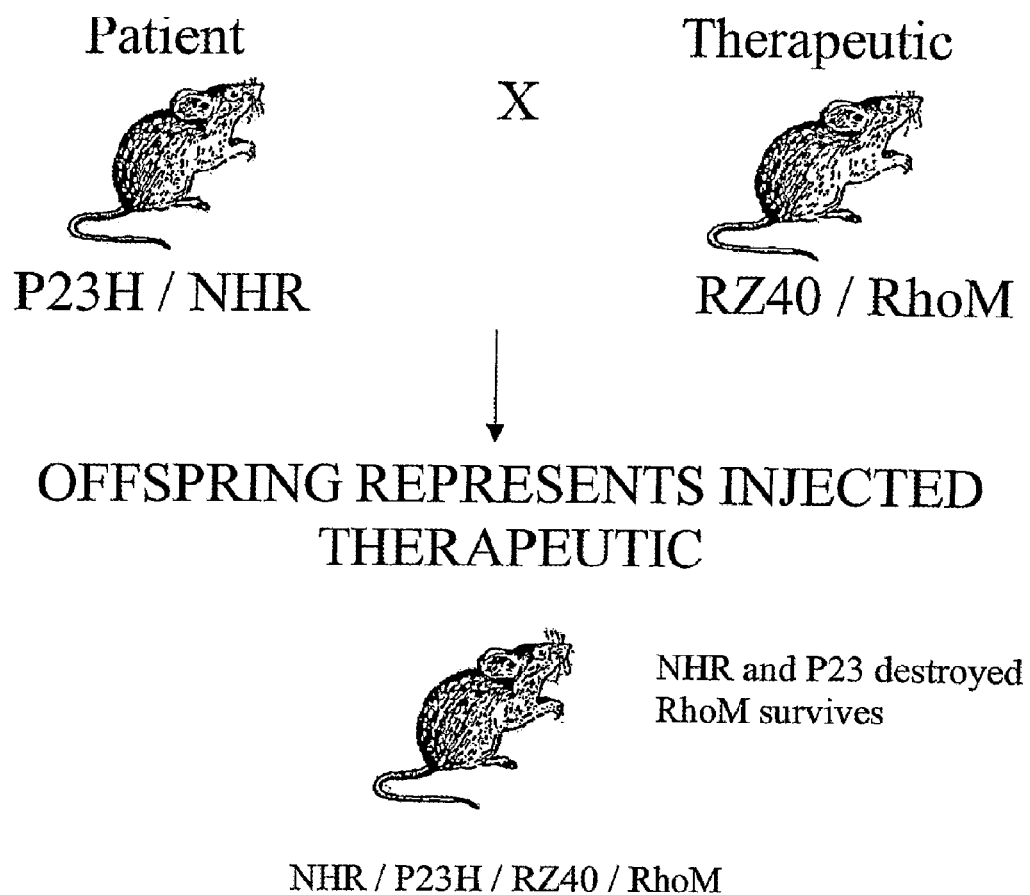
FIG. 19A shows an overview of schedule of animal mating to demonstrate suppression and replacement using rhodopsin-based disease as an example.
Figure 20A:
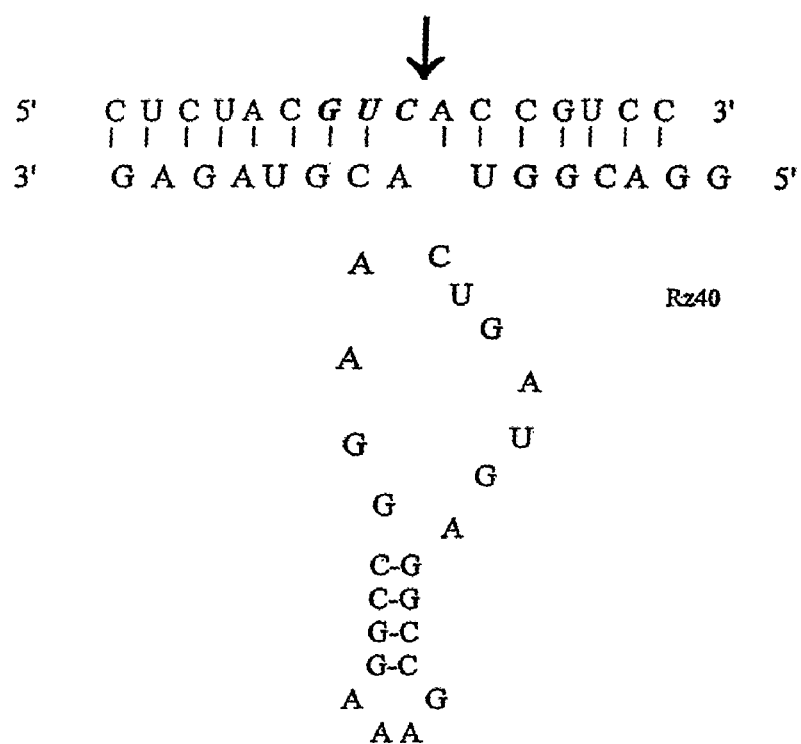
FIG. 20A shows Rz40 hybridized (indicated with vertical lines) to human rhodopsin mRNA. The NUX cleavage site is highlighted in bold print. The exact site of cleavage in the rhodopsin mRNA is indicated by an arrow. The sequences provided correspond, from top to bottom, to SEQ ID NO: 176-177.
Figure 20B:
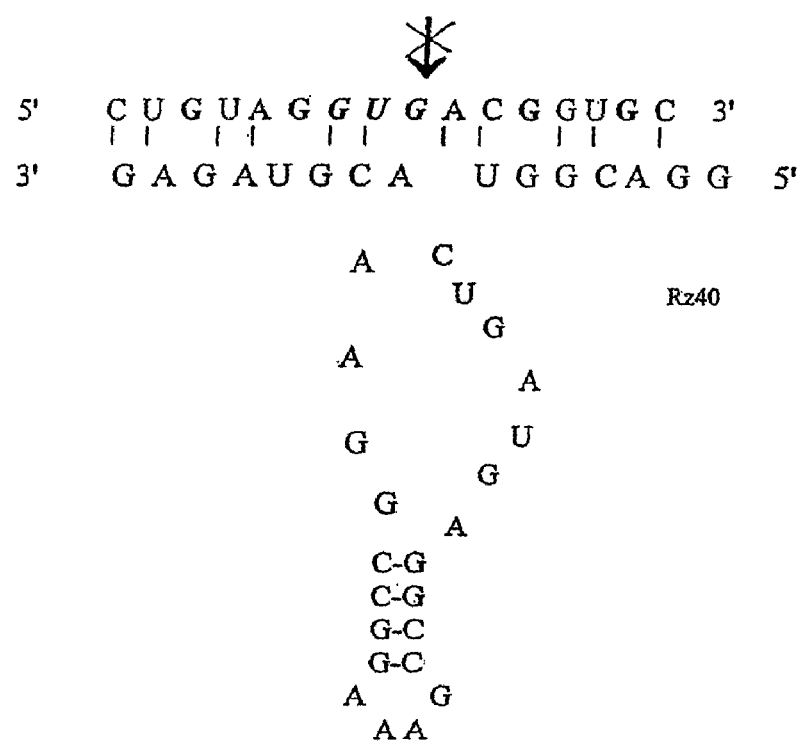
FIG. 20B shows the five base alterations in the replacement human rhodopsin mRNA indicated in bold print. Rz40 is unable to hybridize efficiently (indicated with absence of vertical lines) to replacement human rhodopsin mRNA. In addition, the NUX target site has been altered into an uncleavable NUG site. The sequences provided correspond, from top to bottom, to SEQ ID NO: 178-179.

One transgenic mouse with a human rhodopsin transgene, which harbors the common Pro23His mutation (Olsson J E et al. Neuron 1992 9(5): 815-30) has been constructed previously. The Pro23His transgenic mouse, which presents with a retinal degeneration akin to human RP, has been bred onto a null mouse rhodopsin background (rho−/− mice; Humphries et al. 1997), in preparation for testing ribozymes, inter alia Rz40. An additional transgenic mouse line has been generated that carries 3.8 kb of the mouse rhodopsin promoter followed by Rz40 and the small T1 intron (approximately 65 bp in length). This mouse has been shown by RT-PCR to express the ribozyme and splice out the intron. An additional line of transgenic mice has been generated that carries the 3.8 kb mouse rhodopsin promoter, the full length human rhodopsin cDNA with both the 5' and 3' untranslated regions (UTRs) and intron 9 of the HPRT gene, which is approximately 1.9 kb. The human rhodopsin cDNA in this transgenic mouse carries 5 base alterations at the site of Rz40 binding and cleavage. However, these alterations all occur at wobble/degenerate positions in the gene, which means that wild type protein should be generated from the altered rhodopsin gene. The alterations, however, ensure that Rz40 will not cleave mRNA arising from this altered rhodopsin gene and in addition will not bind or will bind the mRNA from this modified gene less efficiently (FIGS. 20A and 20B). Additionally, a transgenic mouse carrying the wild type human rhodopsin gene without any sequence changes at degenerate sites has previously been generated (Olsson et al 1992). Mouse breeding programs interbreeding these various transgenic lines have been established (FIG. 19).

Figure 18A:
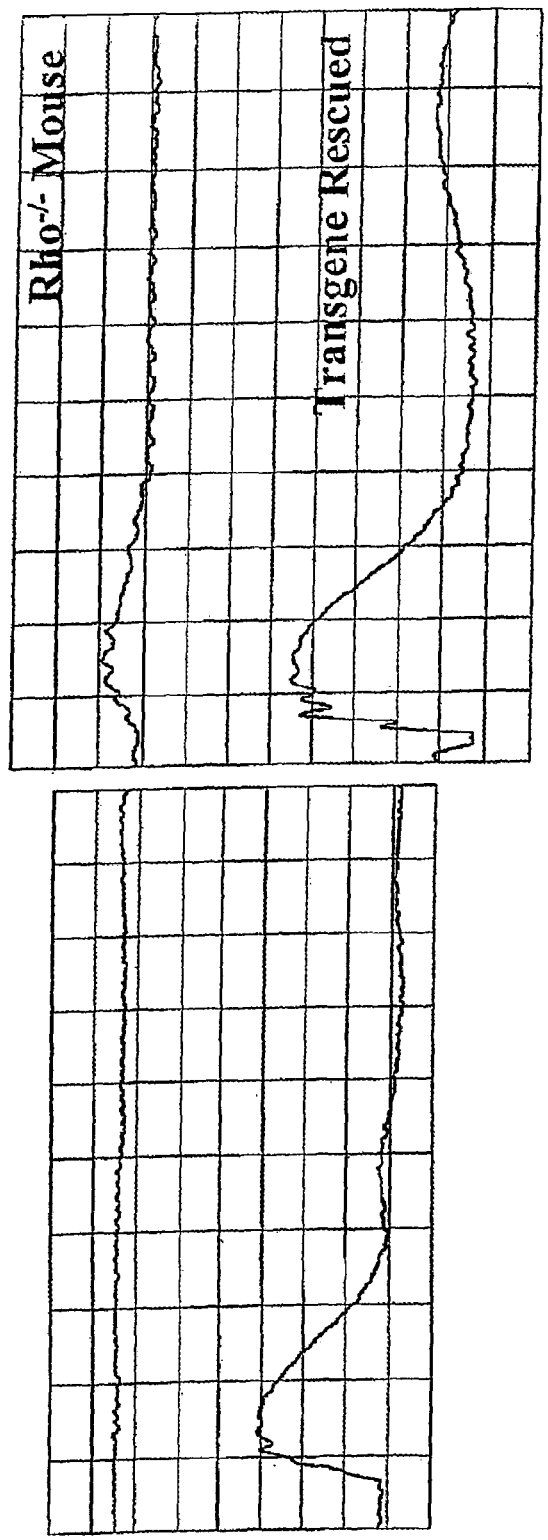
FIG. 18A shows a rod-isolated (left) and mixed rod/cone (right) electroretinogram (ERG) responses from (top) a Rho$^{-/-}$ mouse without the modified rhodopsin transgene and (bottom) a Rho$^{-/-}$ mouse with the modified rhodopsin transgene (rho–/– RhoM mice). The animal without the transgene has no recordable rod-isolated responses and grossly decreased amplitude mixed responses whereas the mouse with the transgene generates responses that are equivalent in timing and amplitudes to the wild-type animal.
Figure 18B:
FIG. 18B: A more detailed ERG showing transgenic rescue with the modified human rhodopsin transgene in rho–/– RhoM mice is presented. Again good electrical responses were recorded from the eyes of rho–/– RhoM mice.
Figure 18B:
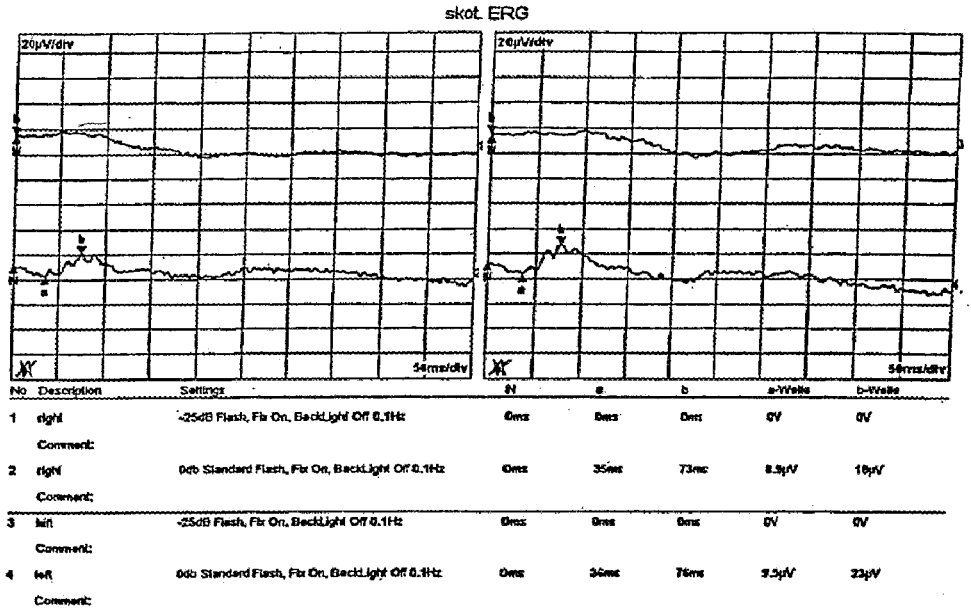
Figure 18B:
Figure 18B:
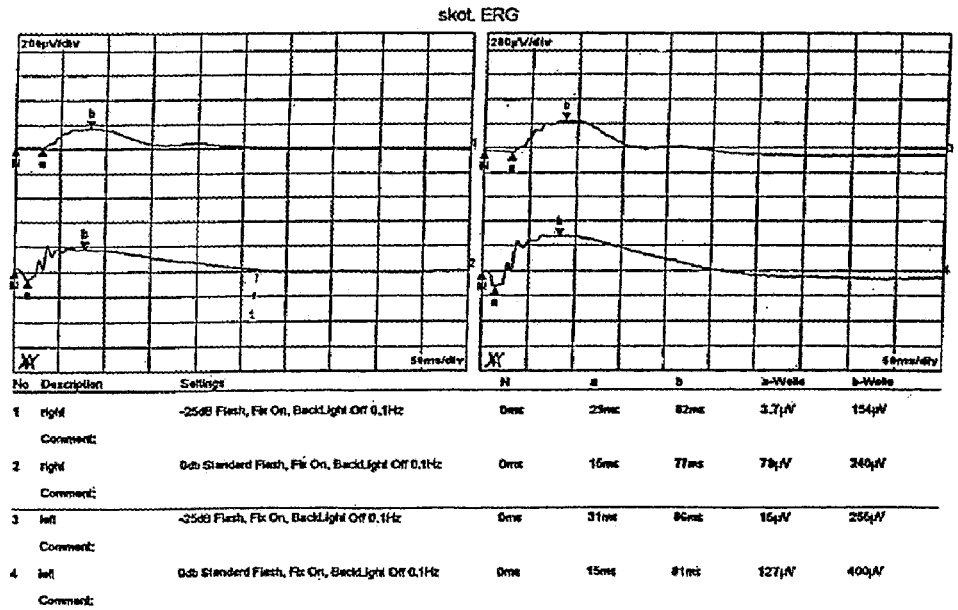
Figure 18C:
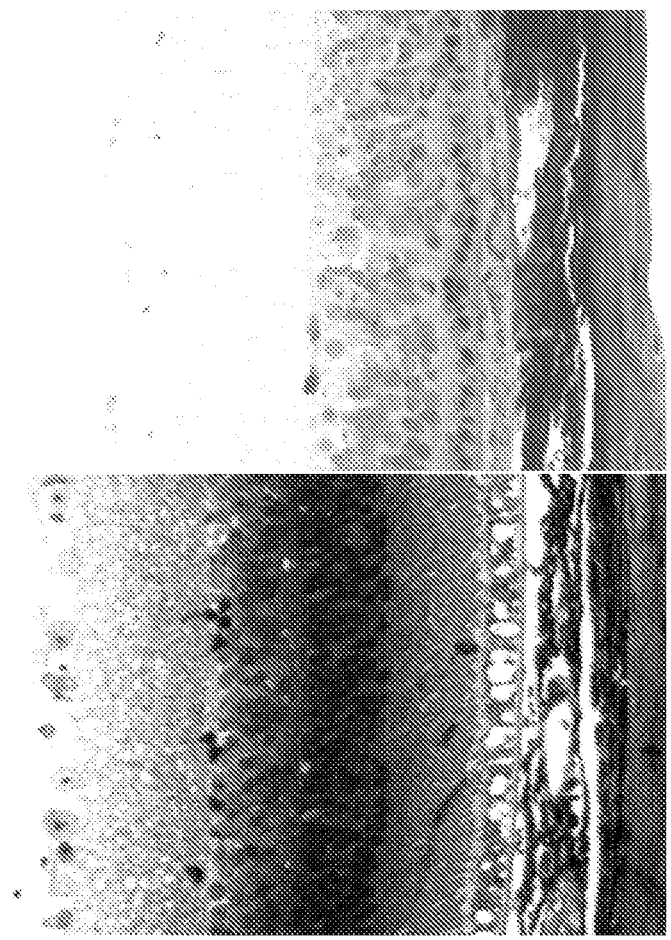
FIG. 18C shows that the significant retinal pathology present in rho–/– mice (B) has been rescued in mice expressing the modified human rhodopsin transgene-rho–/– RhoM mice (A).

Here we show that the modified human rhodopsin gene carrying sequence alterations at degenerate sites in the replacement transgenic mouse can substitute for the endogenous mouse rhodopsin gene—the modified replacement transgene produces rhodopsin protein that can function like wild type protein. Mice carrying a human rhodopsin transgene (modified to carry altered sequence at degenerate sites; RhoM mice) were mated to mice that lack endogenous mouse rhodopsin (rho−/− mice). Mice lacking mouse rhodopsin (rho−/−) present with a retinal degeneration, for example, rho−/− mice present with an abnormal electroretinogram (ERG) and a severe retinal pathology (Humphries et al. 1997). Notably, rho−/− mice that have been designed to also carry the modified human rhodopsin transgene have ERGs akin to those found in wild type/normal mice (rho−/−; RhoM) (FIGS. 18A & 18B). FIG. 18A demonstrates the electroretinographic responses of the dark-adapted rho$^{−/−}$ animal (upper panels) to a low intensity flash stimulus designed to elicit a pure rod response (left hand panel) and a maximal intensity flash designed to elicit a mixed rod/cone response (right hand panel). The equivalent responses from the modified human rhodopsin transgene animal are shown in the lower panels. No rod-isolated response could be recorded from the rho$^{−/−}$ mouse (upper left) whereas the responses from the transgenic animal (rho−/− RhoM) are entirely normal (lower left). The rho$^{−/−}$ animal shows only the cone contribution to the maximal intensity flash (upper right) whereas the transgenic animal (rho−/− RhoM) shows the normal combination of rod and cone contributions to the waveform (lower right). FIG. 18B contrasts the extinguished rod-isolated responses from the right and left eyes of a rho$^{−/−}$ mouse (1$^{st}$ panel) with the normal equivalent responses from a modified human rhodopsin transgene rescued animal (3$^{rd}$ panel). The responses to a maximal intensity flash designed to stimulate both rods and cones are shown in the 2$^{nd}$ panel (rho$^{−/−}$ mouse) and in the 4$^{th}$ panel (modified human rhodopsin transgene rescued animal) In the rhodopsin knockout animal only the cone contribution to this response is evident compared to the larger amplitude mixed rod and cone response from the transgene rescued mouse. Furthermore retinal histology from these mice (rho−/−, RhoM) suggests that the photoreceptor degeneration present in rho−/− has been rescued by the presence of the modified human rhodopsin transgene (FIG. 18C)—the human rhodopsin transgene carrying sequence alterations at degenerate sites in the rhodopsin gene was able to rescue the retinal disease present in rho−/− mice (FIG. 18C). FIG. 18C A showing a retinal section from rho−/− RhoM mice is compared to a retinal section from rho−/− mice (FIG. 18C B). Notably, the outer segments of the photoreceptor cells are entirely absent in rho−/− mice but are present in rho−/− RhoM mice.

Example 7

Transgenic Animal Expressing a Suppression Effector Targeting Rhodopsin

Figure 21A:
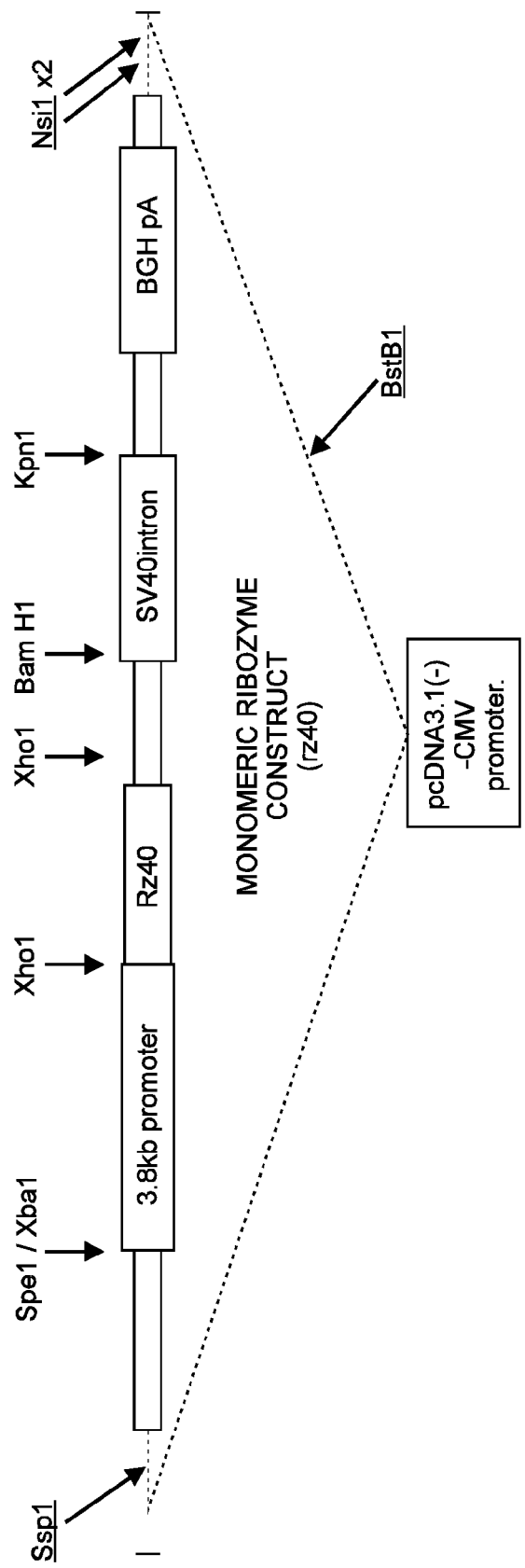
FIG. 21A provides a diagrammatic representation of the construct used to generate the Rz40 transgenic mouse. The Rz40 construct is driven by 3.8 kb of the mouse rhodopsin promoter to drive expression in photoreceptor cells.
Figure 21B:
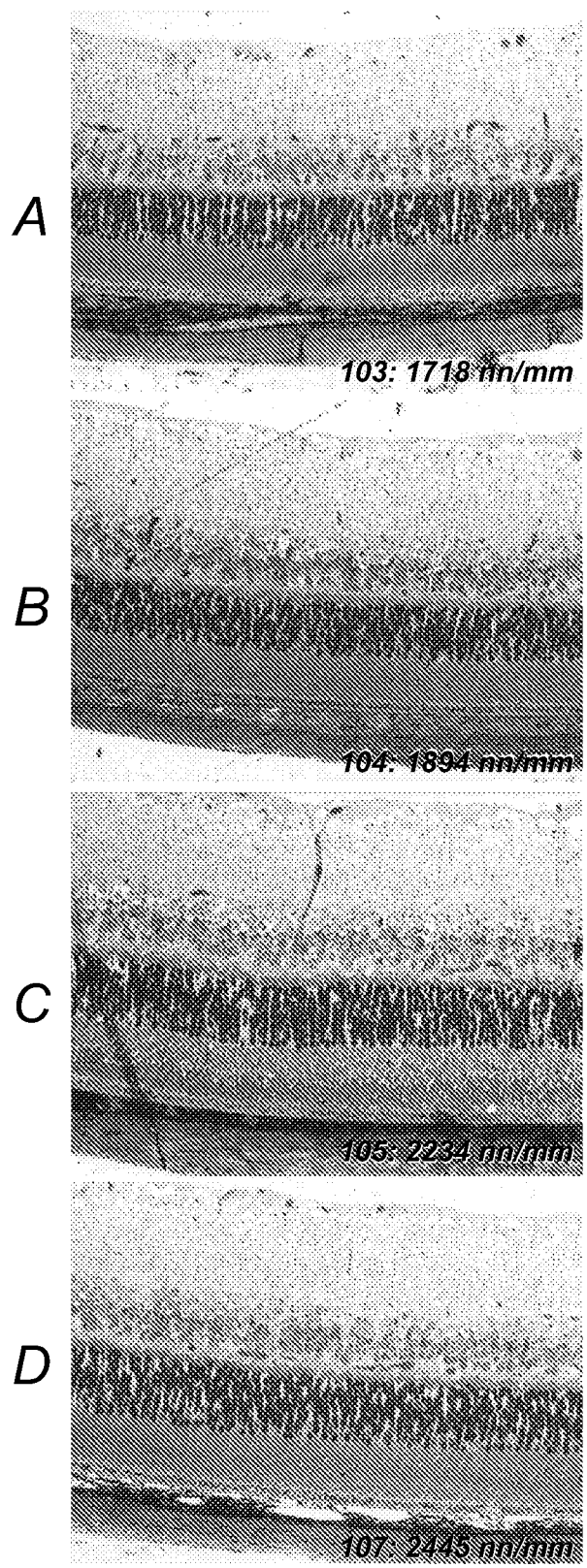
FIG. 21B shows that the retinal histologically from rho−/− mice with a single copy of the human wild type rhodopsin transgene (rho−/− RhoNhr+/− mice) is compared to that from rho−/− mice RhoNhr+/− mice carrying the Rz40 ribozyme targeting human rhodopsin. The retinas of mice with the Rz40 transgene were thinner (A&B) than from those without Rz40 (C&D) as assessed by retinal histology (using ultra thin retinal sections and H+E staining).

In addition transgenic mice carrying a suppression effector targeting human rhodopsin transcripts was generated (FIGS. 21A and 21B). The suppression effector, a hammerhead ribozyme Rz40 is expressed from a human rhodopsin promoter (3.8 kb) (FIG. 21A). The Rz40 construct was generated as follows: The CMV promoter was first removed from the mammalian expression vector pCDNA3.1(−) (Invitrogen) using Nru1 and Nhe1. Restriction ends were Klenow filled and the vector blunt ligated. Using Spe1 and Xho1, a 3.8 kb mouse rhodopsin promoter fragment (bases 4792-8640) was isolated from a 17.1 kb mouse rhodopsin genomic clone in pBluescript. The promoter fragment was subsequently cloned into the Xba1 and Xho1 sites of pcDNA3.1(−). Hammerhead ribozyme, Rz40, targeting a degenerative site in human rhodopsin mRNA was synthesised and inserted into the Xho1 site of the vector. Lastly, the SV40 derived small-t-antigen intron was PCR amplified (66 bases) and cloned into the BamH1 and Kpn1 sites of the above plasmid to increase expression and intracellular trafficking of the ribozyme. The sequence and restriction details of pcDNA3.1(−) can be obtained from the Invitrogen website at www.invitrogen.com.

Transgenic mice carrying Rz40 were mated onto rhodopsin knockout mice (rho−/−) and then mated onto mice carrying a single copy of the wild type human rhodopsin transgene (RhoNhr+/−) to generate the following combination of transgenes in a single mouse (rho−/−, RhoNhr+/−, Rz40+/−). Retinal sections from mice carrying the suppression effector Rz40 (rho−/−RhoNHr+/−Rz 40+/−) were compared to retinal sections from mice that do not carry the suppression effector (rho−/−, RhoNhr+/−). Thickness of the outer nuclear layers of the retinas from these mice were compared (in resin embedded retinal sections). Retinas from mice carrying the suppression effector (FIG. 21B A&B) were thinner than retinas from mice without the suppression effector (FIG. 21B C&D). This is likely due to a reduction in levels of rhodopsin in the retinas of mice carrying the suppression effector Rz40. While a ribozyme, Rz40, has been utilized for suppression of the target other suppression agents such as siRNA or antisense may be utilized in the invention. In summary, the functionality of the modified human rhodopsin replacement construct and the suppression agent were demonstrated in vivo using transgenic mice.

The Rz40 construct described in FIG. 21A has been subsequently used to generate a RzMM vector for use in the development of transgenic mice expressing the rhodopsin-specific connected-type multimeric ribozyme carrying four ribozymes targeting human rhodopsin (details of the RzMM multimeric ribozyme are provided in Example 5). Rz40 was removed from the Rz40 ribozyme construct by digestion with Xho1. Xho1 restriction ends were end-filled with Klenow. Following isolation of the RzMM fragment from pcDNA3 using Xho1 and Xba1 and end-filling both restriction ends, RzMM was blunt-ended into the end-filled Xho1 site of the Rz40 transgenic vector. Rz40 and RzMM DNA fragments used for micro-injection into fertilized mouse eggs were obtained as follows.

Isolation of DNA Fragments for Micro-injection into Mouse Eggs

For example: Digestion of the Rz40 clone with Ssp1 and Nsi1 produces two fragments of 5.183 Kb and 3.512 Kb respectively. The former fragment is required for micro-injection whereas the latter fragment is the vector backbone. In order to optimally separate the fragments on a gel to isolate the desired 5.1 kb fragment, digestion with BstB1 was undertaken. BstB1 digests the 3.5 kb vector fragment into two smaller fragments of 2.4 Kb and 1.1 kb (restriction enzymes available from New England BioLabs). The Ssp1 site is at position 8575 of the clone and the two Nsi1 sites are present at positions 5067 and 5139 respectively. Additionally, the BstB1 site occurs at nucleotide 6209. All DNA fragments for micro-injection were isolated in a similar fashion. Transgenic mice were generated using techniques known in the art and described in the description of the invention above.

PCR-based Assays for Presence of Transgenes in DNA from Transgenic Mice

The presence/absence of transgenes in mice subsequent to generation of transgenic mice and interbreeding of various lines of transgenic mice were monitored using PCR-based assays and DNA extracted from mouse tails.

```
Rz40 Assay (Rz40)
RzF:
                                       (SEQ ID NO: 79)
5'- CGA CTG TGC CTT CTA GTT GC -3'

RzR:
                                       (SEQ ID NO: 80)
5'- CAC ACC CTA ACT GAC ACA CA -3'

Rz40F:
                                       (SEQ ID NO: 81)
5'- CGG TCT GAT GAG TCC GTG A -3'

Rz40R:
                                       (SEQ ID NO: 82)
5'- AGA AGG CAC AGT CGA GGC T -3'

Rz40 Assay F:
                                       (SEQ ID NO: 83)
5'- AAG CAG CCT TGG TCT CTG TC -3'

Rz40 Assay R:
                                       (SEQ ID NO: 84)
5'- CTT AAG CTT GGT ACC GAA TC -3'

RhoNHR Assay: Accession NO: K02281, U49742
(RhoNhr)
NHRAssay(F)
                                       (SEQ ID NO: 85)
5'- TTC CAA GCA CAC TGT GGG CA -3'
(5114-5133)

NHRAssay(R)
                                       (SEQ ID NO: 86)
5'- TGT GAC TTC GTT CAT TCT GC -3'
(5371-5390).

Murine Rhodopsin Assay (rho-/-)
FEx2Rho:
                                       (SEQ ID NO: 87)
5'- TCT CTC ATG AGC CTA AAG CT -3'

REx2Rho:
                                       (SEQ ID NO: 88)
5'- ATG CCT GGA ACC AAT CCG AG -3'

P2N -
                                       (SEQ ID NO: 89)
5'- TTC AAG CCC AAG CTT TCG CG -3'
```

```
-continued
Modified Human Rhodopsin Assay (RhoM)
Rho551F
                              (SEQ ID NO: 90)
5'- AGT GCT CGT GTG GGA TC -3'

HPRTR1
                              (SEQ ID NO: 91)
5'- CAA ATC CCT GAA GTC CTC -3'

Pro23His Assay (RhoP23H)
Pro23HisF
                              (SEQ ID NO: 92)
5'- CAT TCT TGG GTG GGA GCA G -3'

Pro23HisR
                              (SEQ ID NO: 93)
5'- GGA CAG GAG AAG GGA GAA GG -3'

Pro23HisR2
                              (SEQ ID NO: 94)
5'- CCACCTAGGACCATGAAGAG -3'
```

Mice with a retinal degeneration akin to human RP, that is Pro23His mice are interbred with the transgenic mouse lines described above (FIG. 19). To demonstrate suppression of the mutant human rhodopsin target and replacement with a modified human rhodopsin gene a mouse with a retinal pathology is used (Pro23His mice). Mice carrying the following genotypes are generated: rho−/−, Pro23His, Rz40, RhoM using standard mouse breeding techniques and PCR-based tail assays to track the presence/absence of transgenes in interbred mice. Retinal histology and retinal function are compared between rho−/−, pro23His, rhoM mice with and without the suppression effector Rz40 using protocols outlined below. In the same way that Rz40 has been used to suppress the target gene (rhodopsin) any suppression effector(s) could be utilized for the same purpose.

Example 8

Protocols for Mouse Electroretinolgraphy and Mouse Retinal Histology

The electroretinogram (ERG) is a mass potential recorded from the corneal surface of the eye. The ERG generated by a brief flash includes an initial cornea-negative a-wave, the early portion of which reflects photo-transduction activity of rod and cone photoreceptors and the later portion of which reflects inner retinal negative components. The a-wave is followed by components that arise from post-receptor processes. Among these components is the b-wave, a cornea-positive potential that in the mammalian eye reaches a peak at ~60-100 ms after a moderately intense flash and, over a wide range of stimulus conditions, far exceeds the a-wave in absolute peak amplitude. Several new developments have vastly increased the value of the ERG as a research tool for studying abnormal photoreceptor function in inherited retinal degenerations.

The protocol for rodent Ganzfeld electroretinography is as follows: The animal is dark adapted for 12 hours and prepared for electroretinography under dim red light. The subject is anaesthetized by means of Ketamine and Xylazine. Pupillary dilatation is achieved by instillation of Atropine 0.1% and Phenylephrine HCL 2.5%. The subject is held steady by means of a bite-bar and nose-clamp and placed on a heating pad to maintain body temperature.

Standardized flashes of light are presented to the mouse in a Ganzfeld bowl to ensure uniform retinal illumination. The ERG responses are recorded simultaneously from both eyes by means of small contact lens electrodes placed on the corneas, using Amethocaine 1% as topical anaesthesia and Methylcellulose to maintain corneal hydration. A gold reference electrode is positioned subcutaneously approximately 1 mm from the temporal canthus and the ground electrode is clipped to the ear. The responses are analyzed using RetiScan Reti-Port electrophysiology equipment (Roland Consulting Gmbh).

In the standard protocol (based on that approved by the International Clinical Standards Committee for human electroretinography) rod-isolated responses are recorded using a dim blue flash presented in the dark-adapted state. The maximal combined rod/cone response to the maximal intensity flash is then recorded. Following light adaptation for 10 minutes to a background light of 30 candelas per $m^2$ presented in the Ganzfeld bowl the cone-isolated responses are recorded. a-waves are measured from the baseline to the trough and b-waves from the baseline (in the case of rod-isolated responses) or from the a-wave trough.

This protocol is the same as that used for electroretinography on human patients. In the case of human subjects general anaesthesia is not required, the procedure being conducted entirely under topical corneal anaesthesia.

Protocol for Mouse Retinal Histology—Resin Embedding

The mouse was euthanased under $CO_2$ and the superior pole of cornea marked with a small cautery burn. The mouse eye was then enucleated. For fixation the eye was placed in 2% Paraformaldehyde/2.5% Glutaraldehyde/0.1M Phosphate Buffer at pH7.2. A small bubble of air was injected into the anterior chamber to maintain the shape of the globe during fixation. The eye was fixed overnight at 4° C. For washing: the fixed eye washed ×6 in 0.1M PBS and the globe bisected through the optic nerve and the corneal cautery burn; lens removed. A small wedge of cornea was excised in the region of the cautery mark to indicate superior/inferior orientation of subsequent histological sections. For resin embedding—the hemi-globes were incubated in 1% Osmium $O_4$/0.1M Phosphate Buffer for 1 hour at room temperature and then washed in 50% Ethanol for 1 hour, washed in 75% Ethanol for 1 hour, washed in 95% Ethanol for 1 hour, followed by X3 washes in 100% Ethanol for 1 hour each. Subsequently X3 washes in Propylene Oxide for 1 hour each were undertaken. Samples were incubated in 50:50 Propylene Oxide/Agar™ Resin overnight followed by incubation in full strength Agar™ Resin for 4 hours. Freshly made Agar™ Resin was degassed under vacuum. Conical end of capped former shaved off; cap closed; former filled with degassed Agar™ Resin. The hemi-globes were positioned with the cut end of the hemi-globe flush with the cap of the former. The resin-filled former containing the hemi-globe was degassed under vacuum. The position of hemi-globe was checked and re-positioned if necessary and samples were then baked overnight at 65° C. 5 μm sections were cut from resin embedded sample using a microtome and sections then stained with Toluidene Blue or H&E.

Example 9 siRNA-based Suppression of Human Rhodopsin siRNAs targeting the human rhodopsin gene were designed and commercially synthesized by Xeragon (FIG. 22, Table 7). siRNAs were designed such that they covered one or more of the degenerate sites engineered into the construct that was used to generate the RhoM transgenic mouse (FIG. 22).The human rhodopsin cDNA was cloned into pcDNA3.1 vector (Invitrogen) and used to generate a COS-7 stable cell line expressing human rhodopsin using G418 selection and standard protocols (detail on generation of stable COS-7 cells expressing human rhodopsin are provided in Examples 4 & 5). 5×10⁵ COS-7 cells were transfected with 100 pMol siRNA using Oligofectamine as a transfection agent (Invitrogen). siRNA targeting EGFP was used as a non-targeting siRNA control. RNA was extracted from COS-7 cells 48 hours subsequent to addition of the siRNA/ Oligofectamine mix. Significant reductions in levels of human rhodopsin RNA were found in cells treated with siRNA Silencer A and Silencer B but not in cells treated with the non-targeting siRNA EGFP control as assessed by real-time RT PCR (FIG. 23A, Table 7) (all real-time RT PCR assays used GAPDH expression levels as an internal control). DNA primers utilized for real-time RT PCRs are also provided in Table 7.

TABLE 7

| siRNA | | SEQUENCE |
|---|---|---|
| Silencer A | DNA target | CTCTACGTCACCGTCCAGCACAA (SEQ ID NO: 95) |
| | Sense strand | CUACGUCACCGUCCAGCACAA (SEQ ID NO: 96) |
| | Anti-sense | GUGCUGGACGGUGACGUAGAG (SEQ ID NO: 97) |
| SilencerB | DNA target | AACAACTTCCTCACGCTCTACGT (SEQ ID NO: 98) |
| | Sense strand | CAACUUCCUCACGCUCUACGUUU (SEQ ID NO: 99) |
| | Anti-sense | ACGUAGAGCGUGAGGAAGUUGUU (SEQ ID NO: 100) |
| SilencerGFP | DNA target | CGGCAAGCTGACCCTGAAGTTCAT (SEQ ID NO: 101) |
| | Sense strand | GCAAGCUGACCCUGAAGUUCAU (SEQ ID NO: 102) |
| | Anti-sense | GAACUUCAGGGUCAGCUUGCCG (SEQ ID NO: 103) |

| PRIMER | SEQUENCE |
|---|---|
| GapdH F | CAGCCTCAAGATCATCAGCA (SEQ ID NO: 104) |
| GapdH R | CATGAGTCCTTCCACGATAC (SEQ ID NO: 105) |
| Rho1037F | CTTTCCTGATCTGCTGGGTG (SEQ ID NO: 106) |
| Rho1179R | GGCAAAGAACGCTGGGATG (SEQ ID NO: 107) |

The human rhodopsin replacement gene with sequence modifications at degenerate sites was cloned into the pIRES-2 EGFP vector (FIG. 9). This modified rhodopsin gene contains the same sequence alterations that are found in the transgenically engineered RhoM mouse. The pIRES-2 EGFP vector can be used to transcribe fusion transcripts containing both the target gene sequence and the sequence for EGFP separated by an IRES. This system enables evaluation of siRNA-based suppression of the target gene, in this case the human rhodopsin gene (modified at degenerate sites), using the EGFP protein as a read-out. Transient transfections of the pIRES-2 vector carrying the target modified human rhodopsin gene into COS-7 cells were undertaken using Lipofectamine 2000 as a transfection agent. Significant down-regulation of EGFP levels was observed using a positive siRNA control targeting EGFP. In contrast Silencer B did not result in down-regulation of the modified replacement rhodopsin target as assessed by EGFP fluorescence using light microscopy (FIG. 24; see Examples 2 and 3 for details of protocols). The presence of sequence alterations at degenerate sites can protect against siRNA-based suppression.

Protocol for Cells Transfections

Cell transfections involved standard techniques know in the art and detailed in Example 5.

Real Time RT PCR Analysis

Real time RT PCR was performed using the Quantitect Sybr Green RT-PCR kit. (Qiagen GmBH, Hilden). PCR amplification primers for the human rhodopsin cDNA sequence were designed to include nucleotides 1037 to 1047 (forward primer) and 1179 to 1199 (reverse primer): Gapdh was used as an internal control with primers designed also to give a 100 bp PCR product (Forward primer: CAGCCTCAA-GATCATCAGCA (SEQ ID NO: 108); Reverse primer: CAT-GAGTCCTTCCACGATAC (SEQ ID NO: 109)). All primers for real time RT PCR were HPLC purified and designed to flank an intron to identify potential DNA contamination. The ROCHE lightcycler real time RT PCR machine was used in all analyses. Real time RT PCR reactions involved a denaturing step at 95° C., annealing at 55° C. and extension step at 72° C. for 34 cycles. PCR products were analysed by electrophoresis on a 2% agarose gel.

Example 10 siRNA-based Suppression of Rhodopsin in Mice

To explore if siRNA Silencer B which demonstrated the best down-regulation of human rhodopsin in cell culture might function in vivo the Silencer B siRNA was sub-retinally injected into a mouse. The mouse carried a single copy of the wild type human rhodopsin gene (PhoNhr+/−) and a single copy of the endogenous mouse rhodopsin gene (rho+/−). Notably siRNA Silencer B targets a region of the rhodopsin sequence that is 100% homologous between mouse and human and therefore may suppress both human and mouse rhodopsin transcripts. Approximately 1 μg siRNA Silencer B in a 6 μl volume was sub-retinally injected into the left eye of this mouse in a 50% Xeragon buffer and 50% PBS buffer. The control right eye was sub-retinally injected solely with 6 μl of the 50% Xeragon: 50% PBS buffer. Mice were sacrificed 5 days subsequent to siRNA administration, retinal tissues isolated and RNA extracted from retinas for real-time RT PCR assays. Initial results from this preliminary experiment demonstrate that significant suppression of rhodopsin expression was obtained in the left eye (3.42%) when compared to the right eye control (100%) of the mouse (FIG. 23B).

Mouse Eye Subretinal Injection

The mouse was anaesthetized by means of Ketamine (2.08 mg per 15 gram body weight) and Xylazine (0.21 mg per 15 gram body weight) injected intraperitoneally. The eye was proptosed and maintained in position means of a loosely tied 10.0 nylon suture placed at the junction of the nasal $\frac{1}{3}^{rd}$ and temporal $\frac{2}{3}^{rd}$ of the upper and lower eyelids. Using a Leica Wild™ operating microscope the conjunctiva was reflected back to expose the sclera temporally. A puncture wound was made in the sclera approximately 1 mm behind the corneo-scleral limbus by means of a beveled 30-gauge needle. 3 μl of the solution to be injected was delivered subretinally by means of a 10 μl Hamilton syringe and a 30-gauge beveled needle to raise a subretinal bleb. The bleb could be visualized using the operating microscope after a drop of Vidisic™ and a small glass cover slip were placed over the cornea. The suture was removed and the eye gently replaced. The mouse was placed on a 37° C. heating pad until it recovered from the anaesthetic, after which it was replaced in the cage.

Retinal RNA Extraction

Mouse retinas were vortexed in a solution of 500 µl Guanidinium Thiocyanate and 7.1 µl/ml β-mercaptoethanol and left overnight at room temperature. 50 µl of 2M Sodium Acetate (pH4.0), 500 µl DEPC-treated $H_2O$ saturated Phenol and 2000 chloroform/Isoamyl alcohol (49:1) were added to the lysate and mixed gently by inversion. The solution was left on ice for 30 minutes and centrifuged at 13,200 rpm for 20 minutes. The supernatant was transferred to a new eppendorf 0.1µl Glycogen and 1 ml of cold isopropanol was added and mixed by inversion before being left at −20° C. for 2 hours. The supernatant from a 30 minutes spin discarded and the pellet washed in 5000 of 75% ethanol. Pellets were dried at 80° C. for 3 minutes. RNA was re-suspended in 30 µl depc-treated $H_2O$ and stored immediately at −70° C. The quality of the RNA was assessed by spectrophotometric reading of $OD_{260}/OD_{280}$ and also by examining 28S, 18S, and 5S bands on a 2% agarose gel.

siRNA was subretinally injected into a mouse eye and well tolerated in the tissue. Notably, sub-retinal injections into human eyes is an ophthalmological procedure that has previously been undertaken. Administration of therapeutic nucleotides into patients could follow multiple routes of administration including inter alia sub-retinal injection, intravitreal injection, intraocular implantation of a devise/drug factory and or systemic administration. Various carriers including viral and non-viral vectors or chemical or physical transfection agents may be used to aid in delivery of therapeutics/nucleotides.

REFERENCES

Akai J et al. (1999) Gene 239:65-73.
Antoniv T T et al. (2001) J. Biol. Chem. 276(24):21754-64.
Ayre B G et al. (1999) Proc. Natl. Acad. Sci. 96(7):3507-12.
Bahramian M B et al. (1999) Mol. Cell. Biol. 19(1):274-283.
Been and Cech (1986) Cell 47:207-216.
Bernoist and Chambon (1981) Nature 290:304-310.
Birikh K R et al. (1997) Eur. J. Biochem. 245(1):1-16.
Breault et al. (1997) J. Biol. Chem. 272(50):31241-50.
Brinster R L et al. (1982) Nature 296:39-42.
Brummelkamp T R et al. (2002) Science 296: 550-553.
Byers P H et al. (1997) Am. J. Med. Genet. 72(1):94-105.
Caplen N J et al. (2001) Proc. Natl. Acad. Sci. USA 98: 9742-9747.
Carter G and Lemoine N R (1993) Cancer Res. 67: 869-876.
Cazenave et al. (1989) Nucl. Acids Res. 17: 4255-4273.
Chadwick D R et al. (2000) Gene Ther. 7(16):1362-1368.
Chan P P et al. (1997) J. Mol. Med. 75(4):267-282.
Chang G Q et al. (1993) Neuron 11(4):595-605.
Chen C J et al. (1992) Nucleic Acids Res. 20(17)4581-4589.
Chinnery P F et al. (1999) Gene Ther. 6(12):1919-1928.
Clemens M J et al. (1997) J. Interferon Cytokine Res. 17: 503-524.
Clemens M J (1997) Int. J. Biochem. Cell Biol. 29:945-949.
Courvalin P et al. (1995) CR Acad. Sci. III 318(12):1207-12.
Daly A K et al. (1996) Pharmacogenetics 6:193-201.
Davidson F F and Steller H (1998) Nature 391(6667):587-91.
Davidson et al. (2000) Proc. Natl. Acad. Sci. USA 97:3428-3432.
D'Alessio M et al. (1991) Am. J. Hum. Genet. 49: 400-406.
Dosaka-Akita H et al. (1995) Cancer Res. 55: 1559-1564.
Dryja T P et al. (1990) Nature 343: 364-366.
Duval-Valentin et al. (1992) Proc. Natl. Acad. Sci. USA 89: 504-508.
Elbashir S M et al. (2001) Nature 411: 494-498.
Ellis and Rodgers (1993) Nucl. Acids Res. 21: 5171-5178.
Farrar G J et al. (1991) Nature 354: 478-480.
Farrar G J et al. (1991) Genomics 14: 805-807.
Farrar G J et al. (1995) Invest. Ophthamol. Vis. Sci. (ARVO) 36: (4).
Feldstein, P A et al. (1989) Gene 82(1):53-61.
Feng M et al. (1995) Cancer Res. 55: 2024-2028.
Filie et al. (1993) Hum. Mut. 2: 380-388.
Fire A et al. (1998) Nature 391:806-811.
Gaughan D J et al. (1995) FEBS Lett. 374: 241-245.
Gautier et al. (1987) Nucl. Acids Res. 15:6625-6641.
Gottesman et al. (1993) Ann. Rev. Biochem. 62: 385-427.
Hanvey J C et al. (1991) Antisense Res. Dev. 1:307-317.
Hanvey J C et al. (1992) Science 258: 1481-1485.
Hardenbol P and Van Dyke M W (1996) Proc. Natl. Acad. Sci. USA 93: 2811-2816.
Haseloff and Gerlach (1988) Nature 334:585-591
Haseloff J et al. (1989) Gene 82(1):43-52.
Heidenreich O and Eckstein F (1992) J. Biol. Chem. 267(3): 1904-9.
Helene C (1991) Anticancer Drug Des. 6(6):569-584.
Helene C et al. (1992) Ann NY Acad. Sci. 660:27-36.
Herschlag D et al. (1994) EMBO J. 13: (12) 2913-2924.
Herskowitz et al. (1987) Nature 329: 219-222.
Horster A et al. (1999) Gene Ther. 6(7):1231-1238.
Humphries P et al. (1992) Science 256: 804-808.
Humphries M et al. (1997) Nature Genet. 15: 216-219.
Inoue et al. (1987) Nucl. Acids Res. 15:6131-6148.
Jankowsky E and Schwenzer B (1996) Biochemistry 35(48): 15313-21.
Jankowsky E and Schwenzer B. (1996) Nucl. Acids Res. 24: (3) 423-429.
Jones J T et al. (1996) Nature Med. 2: 643-648.
Jorgensen R A et al. (1996) Plant Mol. Biol. 31(5): 957-973.
Kajiwara et al. (1991) Nature 354: 480-483.
Knudsen H and Nielsen P E (1996) Nucl. Acids Res. 24: (3) 494-500.
Krichevsky A M et al. (2002) Proc. Natl. Acad. Sci. USA 99:11926-11929.
Krol et al. (1988) BioTechniques 6:958-976.
Kuwabara T et al. (1996) Nucleic Acids Res. 24(12):2302-2310.
Kuwabara T et al. (1998) Mol. Cell. 2(5):617-27.
Lange W et al. (1993) Leukemia 7: 1786-1794.
Latchman D S (2000) Histol. Histopathol. 15(4):1253-1259.
Lemaitre et al. (1987) Proc. Natl. Acad. Sci. 84:648-652.
Letsinger R L et al. (1989) Proc. Natl. Acad. Sci. U.S.A. 86:6553-56.
Lewin A S et al. (1998) Nature Med. 4(8):967-71.
Lewis D L et al. (2002) Nat. Genet. 32:107-108.
Macejak D G et al. (1999) J. Virol. 73(9):7745-7751.
Maher L J et al. (1992) Bioassays 14(12):807-815.
Matsumoto T et al. (1994) Jpn. J. Hum. Genet. 39(1):205-206.
Mansergh F et al. (1995) J. Med. Genet. 32: 855-858.
Mansergh F et al. (1999) Am. J. Hum. Genet. 64(4):971-85.
Mashhour B et al. (1994) Gene Therapy 1: 122-126.
Maheshwari A et al. (2000) Mol. Ther. 2:121-130.
Martinez F D et al. (1997) J. Clin. Invest. 1200: 3184-3188.
McKay R A et al. (1996) Nucl. Acids Res. 24: (3) 411-417.
McCaffrey A P et al. (2003) Nat. Biotechnol. 21(6):639-44.
McManus M T et al. (2003) Nat. Genet. 33(3):401-6.
McNally et al. (1999) Hum. Mol. Genet. 8(7):1309-1312.
McWilliam P et al. (1989) Genomics 5: 612-619.

Miller V M et al. (2003) Proc Natl Acad Sci USA 10; 100 (12):7195-200.
Millington-Ward S and O'Neill B et al. (1997) Hum. Mol. Genet. 6: 1415-1426.
Millington-Ward S et al. (1999) Antisense Nucleic Acid Drug Dev. 9(6); 537-42.
Millington-Ward S et al. (2002) Hum Mol Genet. 11: 2201-2206
Miyagishhi M et al. (2002) Nature Biotechnol. 20:497-500.
Miyatake S et al. (1996) Jpn. J. Hum. Genet. 41(2):253-255.
Modlano D et al. (2001) Nature 414:305-308.
Muramatsu T et al. (2000) Int. J. Mol. Med. 7(1):61-66.
Nielsen P E (2000) Pharmacol. Toxicol. 86(1):3-7.
Ohkawa J et al. (1993) Proc. Natl. Acad. Sci. USA 90: 11302-11306.
Olsson J E et al. (1992) Neuron 9:815-30.
Ohkawa J et al. (1993) Proc. Natl. Sci. USA 90:11302-11306.
Ohta Y et al. (1996) Nucl. Acids Res. 24: (5) 938-942.
O'Neill B et al. (2000) Invest Ophthalmol Vis Sci. 2000 September; 41(10):2863-9.
Ortiz-Urda S et al. (2002) Nat. Med. 8:1166-1170.
Ott J et al. (1989) Proc. Natl. Acad. Sci. USA 87: 701-704.
Paddison P J et al. (2002) Proc. Natl. Acad. Sci. USA 99:1443-1448.
Paul C P et al. (2002) Nature Biotechnol. 20:505-508.
Phillips C L et al. (1990) J. Clin. Invest. 86: 1723-1728.
Postel et al. (1991) Proc. Natl. Acad. Sci. USA 88: 8227-8231.
Porumb H et al. (1996) Cancer Res. 56: 515-522.
Puttaraju M et al. (1999) Nat. Biotechnol. 17(3):246-252.
Quattrone A et al. (1995) Cancer Res. 55: 90-95.
Reaves P Y et al. (2000) Methods 22(3):211-218.
Redeker E et al. (1993) Hum. Mol. Genet. 2(6):823.
Rimsky et al. (1989) Nature 341: 453-456.
Rossi, G A et al. (1983) Boll. Soc. Ital. Biol. Sper. 59(6):806-812.
Rupert et al. (1995) Eur. J. Hum. Genet. 3(6):333-343.
Samson et al. (1996) Nature 382:722-725.
Sarver et al., 1990, Science 247:1222-1225.
Saville B J et al. (1990) Cell 61(4)685:696.
Sharp P A et al. (2003) RNA 9(4):493-501
Sizemore D R et al. (1995) Science 270 (5234):299-302.
Sokolov B P et al. (1995) J. Biol. Chem. 270 (16):9622-9629.
Stein et al. (1988) Nucl. Acids Res. 16:3209.
Stein et al., (1988) Cancer Res 48:2659-2668.
Strayer D S et al. (2000) Gene Ther. 7(10):886-895.
Sui G et al. (2002) Proc. Natl. Acad. Sci. USA 99:5515-5520.
Sullenger B A and Cech T R (1994) Nature 371:619-622.
Sun J S et al. (1989) Proc. Natl. Acad. Sci. USA 86: 9198-9202.
Taylor R W et al. (1997) Nature Genet. 15: 212-215.
Takahashi M et al. (1999) J. Virol. 73(9):7812-7816.
Tam P et al. (2000) Gene Ther. 7(21):1867-1874.
Trauger J W et al. (1996) Nature 382: 559-561.
Valera A et al. (1994) J. Biol. Chem. 269: 28543-28546.
Van der Krol et al. (1988) Biotechniques 6:958-976.
Van Soest S et al. (1994) Genomics 22:499-504.
Van Stijn T et al. (1995) Anim. Genet. 26(4):279.
Vasan N S et al. (1991) Amer. J. Hum. Genet. 48: 305-317.
Wagner et al. (1981) Proc. Natl. Acad. Sci. U.S.A. 78:1441-1445.
Wang F S et al. (1999) Int. J. Cancer 81(6):944-950.
Wei Z et al. (1996) Nucl. Acids Res. 24: (4) 655-661.
Westerhausen A I et al. (1990) Nucl. Acids Res. 18: 4968.
Wevrick R et al. (1994) Hum. Mol. Genet. 3(10):1877-1882.
Willing M C et al. (1993) Am. J. Hum. Genet. 45: 223-227.
Wu H N et al. (1989) Proc. Natl. Acad. Sci. USA 86(6):1831-1835.
Yamamoto et al. (1980) Cell 22:787-797.
Yang S et al. (2001) Mol. Cell. Biol. 21:7807-7816.
Yotnda P et al. (2001) Gene Therapy 8:930-937.
Zack D J et al. (1991) Neuron. 6(2):187-99.
Zamore P D (2001) Nature Struct. Biol. 8(9): 746-750.
Zaug A J et al. (1988) Biochemistry 27(25);8924-31.
Zaug et al. (1984), Science, 224:574-578.
Zaug and Cech (1986) Science, 231:470-475.
Zhuang J et al. (1996) Human Mut. 7: 89-99.
Zon (1988) Pharm. Res. 5:539-549.

---

What is claimed is:

1. A composition comprising:
   a) an RNAi suppression effector, or modified version thereof, or a suppression effector encoding an RNAi, that binds to mature RNA transcribed from DNA of a mutant allele of rhodopsin, thereby to inhibit the expression of the mutant allele, wherein said mature RNA comprises the nucleotide sequence CUCUACGUCACCGUC (SEQ ID NO: 176); and
   b) a replacement nucleic acid that encodes a wild-type or non-disease causing allele and that comprises five degenerate / wobble nucleotides that are altered so that the replacement nucleic acid is not suppressed, or is only partially suppressed, by the suppression effector.

2. The composition of claim 1, wherein the suppression effector is operatively linked to an expression vector.

3. The composition of claim 1, wherein the replacement nucleic acid is operatively linked to an expression vector.

4. A method for preparing a suppression effector and replacement nucleic acid, the method comprising the steps of:
   a) preparing an RNAi suppression effector, or modified version thereof, or a suppression effector encoding an RNAi, that binds to mature RNA transcribed from DNA encoding a mutant allele of rhodopsin, thereby to inhibit the expression of the mutant allele; wherein said mature RNA comprises the nucleotide sequence CUCUACGUCACCGUC (SEQ ID NO: 176) and
   b) preparing a replacement nucleic acid that encodes a wild-type or non-disease causing allele and that comprises five degenerate/wobble nucleotides that are altered so that the replacement nucleic acid is not suppressed, or is only partially suppressed, by the suppression effector.

5. A kit comprising:
   a) an RNAi suppression effector, or modified version thereof, or a suppression effector encoding an RNAi, that suppresses the expression of a mature RNA transcribed from a DNA encoding a mutant allele of rhodopsin wherein said mature RNA comprises the nucleotide sequence CUCUACGUCACCGUC (SEQ ID NO: 176); and
   b) a replacement nucleic acid that encodes a wild-type or non-disease causing allele that is not suppressed, or is only partially suppressed, by the suppression effector and that differs from the mutant allele in five degenerate/wobble nucleotides.

6. The composition of claim 1, wherein the suppression effector suppresses both alleles of an endogenous gene.

7. An isolated cell expressing (i) an RNAi suppression effector, or modified version thereof, or a suppression effector encoding an RNAi, that targets a mutant allele of rhodopsin, thereby inhibiting the expression of the mutant allele, wherein said suppression effector binds to the mature RNA transcribed from DNA encoding the mutant allele, wherein said mature RNA comprises the nucleotide sequence CUCUACGUCACCGUC (SEQ ID NO: 176); and (ii) a replacement nucleic acid that encodes a wild-type or non-disease causing allele and that comprises five degenerate/wobble nucleotides that are altered so that the replacement nucleic acid is not suppressed, or is only partially suppressed, by the suppression effector.

8. The composition of claim 1, wherein the replacement nucleic acid encodes mammalian rhodopsin.

9. The composition of claim 1, wherein the suppression effector encoding an RNAi and replacement nucleic acid are located on the same vector.

10. The method of claim 4, further comprising the step of transfecting the suppression effector and/or replacement nucleic into a cell using a lipofectamine or oligofectamine product.

11. The composition of claim 1, wherein the RNAi suppression effector or modified version thereof, or a suppression effector encoding an RNAi, and/or the replacement nucleic acid is naked nucleic acid.

12. The composition of claim 1, further comprising a lipid, a polymer, a nucleic acid, or another derivative that aids gene delivery or expression of the RNAi suppression effector or modified version thereof, or a suppression effector encoding an RNAi, and/or the replacement nucleic acid.

13. The method of claim 4, wherein the RNAi suppression effector or modified version thereof, or a suppression effector encoding an RNAi, and/or the replacement nucleic acid is naked nucleic acid.

14. The method of claim 4, further comprising providing a lipid, a polymer, a nucleic acid, or another derivative that aids gene delivery or expression of the RNAi suppression effector or modified version thereof, or a suppression effector encoding an RNAi, and/or the replacement nucleic acid.

15. The kit of claim 5, wherein the an RNAi suppression effector or modified version thereof, or a suppression effector encoding an RNAi, and/or the replacement nucleic acid is naked nucleic acid.

16. The kit of claim 5, further comprising a lipid, a polymer, a nucleic acid, or another derivative that aids gene delivery or expression of the RNAi suppression effector or modified version thereof, or a suppression effector encoding an RNAi, and/or the replacement nucleic acid.

17. The composition of claim 1, wherein the RNA is an mRNA.

18. The composition of claim 1, wherein said replacement nucleic acid comprises the nucleotide sequence CTGTATGTGACGGTG (SEQ ID NO: 175) or the corresponding mature RNA sequence thereof.

19. The method of claim 4, wherein said replacement nucleic acid comprises the nucleotide sequence CTGTATGTGACGGTG (SEQ ID NO: 175) or the corresponding mature RNA sequence thereof.

20. The kit of claim 5, wherein said replacement nucleic acid comprises the nucleotide sequence CTGTATGTGACGGTG (SEQ ID NO: 175) or the corresponding mature RNA sequence thereof.

21. The isolated cell of claim 7, wherein said replacement nucleic acid comprises the nucleotide sequence CTGTATGTGACGGTG (SEQ ID NO: 175) or the corresponding mature RNA sequence thereof.

* * * * *